US006476207B1

(12) United States Patent
Zhang et al.

(10) Patent No.: US 6,476,207 B1
(45) Date of Patent: Nov. 5, 2002

(54) GENES AND GENE EXPRESSION PRODUCTS THAT ARE DIFFERENTIALLY REGULATED IN PROSTATE CANCER

(75) Inventors: Jimmy Zhang, San Francisco, CA (US); Jon H. Astle, Taunton, MA (US); Eddie Carroll, III; Wilson O. Endege, both of Norfolk, MA (US); Donna M. Ford, Plainville, MA (US); John E. Monahan, Norfolk, MA (US); Robert Schlegel; Kathleen E. Steinmann, both of Middlesex, MA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/328,475

(22) Filed: Jun. 9, 1999

Related U.S. Application Data

(60) Provisional application No. 60/088,877, filed on Jun. 11, 1998.

(51) Int. Cl.[7] .............................. C12Q 1/68; C12P 19/34; C12N 15/63; C12N 15/85; C07H 21/04
(52) U.S. Cl. ..................... 536/23.1; 435/6; 435/91.1; 435/320.1; 435/325; 536/23.1; 536/24.3
(58) Field of Search ..................... 435/6, 91.1, 327.1, 435/325; 536/23.1, 24.3

(56) References Cited

FOREIGN PATENT DOCUMENTS

WO    WO 98/04689    2/1998

OTHER PUBLICATIONS

Sidransky, Int. J. Cancer, vol. 64, pp 1–2, 1995.*
Zhang et al., Mol. Endo. vol. 13, pp 156–166, 1999.*
Dominguez et al, Oncogene, vol. 17, pp 2187–2193, 1998.*
Pei et al., Mol. Endo. vol. 11, pp 433–411, 1997.*
Ishikawa et al., J. Clin Endo. Met. vol. 86, pp 867–874, 2001.*

EMBL Database Entry, Accession No. AA425141, Oct. 28, 1997.
EMBL Database Entry, Accession No. AA609384, Oct. 1, 1997.
EMBL Database Entry, Accession No. WO5287, May 8, 1996.
Heller et al., "Discovery and Analysis of Inflammatory Disease–Related Genes Using cDNA Microarrays," *Proc. Natl. Acad. Sci. USA* 94:2150–2155, 1977.
Brothman et al., "Phenotypic And Cytogenetic Characterization Of A Cell Line Derived From Primary Prostatic Carcinoma," *Int. J. Cancer* 44: 898–903, 1989.
Horoszewicz et al., "LNCaP Model of Human Prostatic Carcinoma," *Cancer Research* 43: 1809–1818, 1983.
Iizumi et al., "Establishment Of A New Prostatic Carcinoma Cell Line (TSU–PR1)," *The Journal of Urology* 137: 1304–1306, 1987.
Kaighn et al., "Establishment And Characterization Of A Human Prostatic Carcinoma Cell Line (PC–3)," *Investigative Urology* 17(1): 16–23, 1979.
Loop et al., "Human Primary Prostate Tumor Cell Line, ALVA–31: A New Model for Studying the Hormonal Regulation of Prostate Tumor Cell Growth," *The Prostate* 22: 93–108, 1993.
Muraki et al., "Establishment Of New Human Prostatic Cancer Cell Line (JCA–1)," *Urology* XXXVI(1): 79–84, 1990.
Stone et al., "Isolation Of A Human Prostate Carcinoma Cell Line (DU 145)," *Int. J. Cancer* 21:274–281, 1978.

* cited by examiner

*Primary Examiner*—W. Gary Jones
*Assistant Examiner*—Jehanne Souaya
(74) *Attorney, Agent, or Firm*—Jane E. R. Potter; Kimberlin L. Morley; Robert P. Blackburn

(57) ABSTRACT

This invention relates to novel human genes, to proteins expressed by the genes, and to variants of the proteins. The invention also relates to diagnostic and therapeutic agents related to the genes and proteins, including probes, antisense constructs, and antibodies. The invention further relates to polynucleotides differentially expressed in prostate cancer.

6 Claims, 5 Drawing Sheets

Sequence Range: 1 to 1383

```
              10          20          30          40          50          60
     TTA CTC ACT ATA GGG CTC GAG CGG CCG CCC GGG CAG GTG TAA AAA TAA AAT GAC AGT TTG AAC ATA CAA
     ATT GAG TGA TAT CCC GAG CTC GCC GGC GGG CCC GTC CAC ATT TTT ATT TTA CTG TCA AAC TTG TAT GTT
         <E   S   Y   P   E   L   P   R   G   P   L   H   L   F   L   I   V   T   Q   V   Y   L 70          80          90          100         110         120         130
 AAC CCA CCC CAT TCC TAT AGA GCC TAG TAC TAC ACT ACC CCC TCC CAA CTT TAG CCT CCA CAT ATA GTA
 TTG GGT GGG GTA AGG ATA TCT CGG ATC ATG ATG TGA TGG GGG AGG GTT GAA ATC GGA GGT GTA TAT CAT
 <V   W   G   M   G   I   S   G   L   V   V   S   G   G   G   L   K   L   R   W   M   Y   Y 140         150         160         170         180         190         200
 ATG TGC TTG GAA CAC AAA AAA CAC TTC ATA AAT TGT GCT GAA TGA AAT CAT TTC CAT GAG TGT TTA TGG
 TAC ACG AAC CTT GTG TTT TTT GTG AAG TAT TTA ACA CGA CTT ACT TTA GTA AAG GTA CTC ACA AAT ACC
 <H   A   Q   F   V   F   F   V   E   Y   I   T   S   F   S   I   M   E   M 210         220         230         240         250         260         270
 ATT TTG AGT TCA TTT GTA CCT TTT ACC TAA AAT TCT AGC CAC TTT AAT TTG GAG AGT TTC CAG AGC AAA
 TAA AAC TCA AGT AAA CAT GGA AAA TGG ATT TTA AGA TCG GTG AAA TTA AAC CTC TCA AAG GTC TCG TTT 280         290         300         310         320         330         340
     GGA CCT TTT ACC TAA AAT TCT AGC CAC TTT AAT TTG GAG AGT TTC CAG AGC AAA GGG CAC AGA TCC CAG
     CCT GGA AAA TGG ATT TTA AGA TCG GTG AAA TTA AAC CTC TCA AAG GTC TCG TTT CCC GTG TCT AGG GTC 350         360         370         380         390         400         410
     GCA TAA CAA CGC TTT GCG TAT ACA GCA ACC AAT ATC TTG TCA ACC CAA GAA AGT TCC TCC ATT GAT ACC
     CGT ATT GTT GCG AAA CGC ATA TGT CGT TGG TTA TAG AAC AGT TGG GTT CTT TCA AGG AGG TAA CTA TGG 420         430         440         450         460         470         480
     TAG TAG AAA TAG CCC AGT TTT TAA AGT CCT CAA AAC TGT AAC AAA TTA CTT GTT TTT AAA ATT TAA CTT
     ATC ATC TTT ATC GGG TCA AAA ATT TCA GGA GTT TGA CA TTG TTT AAT GAA CAA AAA TTT TAA ATT GAA 490         500         510         520         530         540         550
     AAA TTA ATA CAA TCA GAT TTT TGT GTT ATT TGG GTA TTA GAG TAT GTT AAA GCA CAT ATA TCC CAG AGA
     TTT AAT TAT GTT AGT CTA AAA ACA CAA TAA ACC CAT AAT CTC ATA CAA TTT CGT GTA TAT AGG GTC TCT 560         570         580         590         600         610         620
     CAT AGA GTT TCC GTT TCA AAA AGT CAT GCA TTC ATG TGT GCT AAT GAC AAT CCT ATC CTG ACC CGC TAT
     GTA TCT CAA GGC AAA GT TTT TCA GTA CGT AAG TAC ACA CGA TTA CTG TTA GGA TAG GAC TTG GCG ATA
```

*Fig. 1A*

```
      630         640         650         660         670         680         690
GTG ACT TGT ATC TCT AAA CCA TAG GCT TTC CTG AAT TTT ATC TGT TAA TTT AAC CCT GAT TTC TCA GCA
CAC TGA ACA TAG AGA TTT GGT ATC CGA AAG GAC TTA AAA TAG ACA ATT AAA TTG GGA CTA AAG AGT CGT 700         710         720         730         740         750
GCA GCT TCT CTT TGT AAA TAG ACT TGC CTC TTC TGT GTC TGA CCT CTG CTC CTC ATA ATC AGA TTA ACT
CGT CGA AGA GAA ACA TTT ATC TGA ACG GAG AAG ACA CAG ACT GGA GAC GAG GAG TAT TAG TCT AAT TGA 760         770         780         790         800         810         820
CAG ATA AAG CTG CTT CAG GGA AGA GGT CAA AAC CGT TGC CAA AAA TAG TAG TTG CCC TAC TTC AGT CTA
GTC TAT TTC GAC GAA GTC CCT TCT CCA GTT TTG GCA ACG GTT TTT ATC ATC AAC GGG ATG AAG TCA GAT 830         840         850         860         870         880         890
TTT TCA ACA GAG TAG CCA GGA GAT CCT GTT CAC ACC AAA GTC CAA TCA GCC CTA CTG TTA GCA CTC TGC
AAA AGT TGT CTC ATC GGT CCT CTA GGA CAA GTG TGG TTT CAG GTT AGT CGG GAT GAC AAT CGT GAG ACG 900         910         920         930         940         950         960
TCA CAA GCC TCC AGT GGC TTC CGA CCT CAC TCA CAG TAA AAG CCA AGT CAT CCT TTA GCC TAT GAT GTC
AGT GTT CGG AGG TCA CCG AAG GCT GGA GTG AGT GTC ATT TTC GGT TCA GTA GGA AAT CGG ATA CTA CAG 970         980         990        1000        1010        1020        1030
CTA CAT GAT TTG AAT TCC CTT CCA TTG ATT TTT GTC ACT GAT TTT TAA AAA TCC AAA TTC ATT CTC ATA
GAT GTA CTA AAC TTA AGG GAA GGT AAC TAA AAA CAG TGA CTA AAA ATT TTT AGG TTT AAG TAA GAG TAT 1040        1050        1060        1070        1080        1090        1100
CAG CTG AAT TGT CCT CTT TGC TTT AAG TAT GCC AGG ATT ATT TCT ACC TCA GGG CCT TTG CAC TTG ATA
GTC GAC TTA ACA GGA GAA ACG AAA TTC ATA CGG TCC TAA TAA AGA TGG AGT CCC GGA AAC GTG AAC TAT 1110        1120        1130        1140        1150        1160        1170
TTC CCT TCA CCT TTT CCA AGA TAG TTA TTC CCT CAC CTC AGT CAA GCC TTT ATT TAG ATG CCC CCT TCT
AAG GGA AGT GGA AAA GGT TCT ATC AAT AAG GGA GTG GAG TCA GTT CGG AAA TAA ATC TAC GGG GGA AGA 1180        1190        1200        1210        1220        1230        1240
CAT CAA GGC ATT CTC TGA TCT CCT TAT TTA AAT GTA TGA CAC CCC TTC TTT GCT TTA CAT TTA ATC AGA
GTA GTT CCG TAA GAG ACT AGA GGA ATA AAT TTA CAT ACT GTG GGG AAG AAA CGA AAT GTA AAT TAG TCT 1250        1260        1270        1280        1290        1300        1310
ACA TGT GTC ACT ATC TAG CAT ATA ATA CAT TTG CTT GAC CTC TTT TGT TTA CTG TCT ATG CCT CCT GAA
TGT ACA CAG TGA TAG ATC GTA TAT TAT GTA AAC GAA CTG GAG AAA ACA AAT GAC AGA TAC GGA GGA CTT 1320        1330        1340        1350        1360        1370        1380
TAC TGT GTA AGC TCC ACG ATA CAG GCA CTT TTC TCT ATT TCG AGC ACT GTT GTA TTA CAG AGC CTT AAA
ATG ACA CAT TCG AGG TGC TAT GTC CGT GAA AAG AGA TAA AGC TCG TGA CAA CAT AAT GTC TCG GAA TTT
```

*Fig. 1B*

Sequence Range: 1 to 1815

```
           10          20          30          40          50          60
  ACT TTT TGT TCA TTT TGA TTT TTG GAT AAT GCA AAA TTA TAG ATT TTT TAA AAA TTA TAT TCA AAG AAT
  TGA AAA ACA AGT AAA ACT AAA AAC CTA TTA CGT TTT AAT ATC TAA AAA ATT TTT AAT ATA AGT TTC TTA 70          80          90          100         110         120         130
  ACT GAG TGC AAG ACA ATC TTT CTA GGT TAA AAA ATA TCT TAT AAA CCT GAA TTG TCA ATT ATT ATT GTA
  TGA CTC ACG TTC TGT TAG AAA GAT CCA ATT TTT TAT AGA ATA TTT GGA CTT AAC AGT TAA TAA TAA CAT 140         150         160         170         180         190         200
  TCC CAG ATG TAT GGA AGT TAA TGG ATA GTC AGT AAC ATA CAG GAC TAG CAG AAG GTT TGT TGT TAT AGG
  AGG GTC TAC ATA CCT TCA ATT ACC TAT CAG TCA TTG TAT GTC CTG ATC GTC TTC CAA ACA ACA ATA TCC 210         220         230         240         250         260         270
  TAA TCT GGA GAG AAG CCA GGT AAG TGG AAT TTG GGA TTT GCT GCT GTT GCC AGA AAG CAG CAC AGA GAC
  ATT AGA CCT CTC TTC GGT CCA TTC ACC TTA AAC CCT AAA CGA CGA CAA CGG TCT TTC GTC GTG TCT CTG 280         290         300         310         320         330         340
  ATG GTA AGT GGC AAG ACC CAG GTA ACT AAA ACA ACC ATG TCT TAG TCC TTT TAT GCT GCT GTA ACA GAA
  TAC CAT TCA CCG TTC TGG GTC CAT TGA TTT TGT TGG TAC AGA ATC AGG AAA ATA CGA CGA CAT TGT CTT 350         360         370         380         390         400         410
  TAT CAC AGA CTG AGT AAT TTA TAA TGA ACA GAA CTT TAT TTG TCT TCT GGT TCT GGA GAC TGG GAA ATC
  ATA GTG TCT GAC TCA TTA AAT ATT ACT TGT CTT GAA ATA AAC AGA AGA CCA AGA CCT CTG ACC CTT TAG 420         430         440         450         460         470         480
  TAA GAG CGT GGC ATT GAC ATA TGG TGA GGG CAT TTG TGC CTC ATC ATC CCA TGA CAG AAG ATG GAA ATG
  ATT CTC GCA CCG TAA CTG TAT ACC ACT CCC GTA AAC ACG GAG TAG TAG GGT ACT GTC TTC TAC CTT TAC 490         500         510         520         530         540         550
  CAA GAG AGC TCA AAA GCA AGA GAG CAA ATG GGG CCA AAC TTG CTT TTT ATA ACA AGC CAC TCT TGT GAT
  GTT CTC TCG AGT TTT CGT TCT CTC GTT TAC CCC GGT TTG AAC GAA AAA TAT TGT TCG GTG AGA ACA CTA 560         570         580         590         600         610         620
  AAT GAA CCA ACT CAA ACA ATA AAG ACA TAA ATC CAT TCA TGA GGG CAG AGC CCT CAA GGA TGA ATC ACT
  TTA CTT GGT TGA GTT TGT TAT TTC TGT ATT TAG GTA AGT ACT CCC GTC TCG GGA GTT CCT ACT TAG TGA 630         640         650         660         670         680
   TCA CTT CTT A ATG GCC TCA GCT TCT AAT ACC ATC ACA ATA GTA ATT CAG TTT CAA CAT GGG TTT TAT
   AGT GAA GAA T TAC CGG AGT CGA AGA TTA TGG TAG TGT TAT CAT TAA GTC AAA GTT GTA CCC AAA ATA
                  M   A   S   A   S   N   T   I   T   I   V   I   Q   F   Q   H   G   F   Y>
```

*Fig. 2A*

```
      690          700         710         720         730         740         750
AGG GAC GTT GGA ACC ACA GCA AAC TGT AAC CAT TTT GAT TTC CTT ATT TGC ACC ATT TTA AAA AAA CCT
TCC CTG CAA CCT TGG TGT CGT TTG ACA TTG GTA AAA CTA AAG GAA TAA ACG TGG TAA AAT TTT TTT GGA
 R   D   V   G   T   T   A   N   C   N   H   F   D   F   L   I   C   T   I   L   K   K   P>

760         770         780         790         800         810         820
ATT TAT TTA ACG ACT GTT TAT TCA GTG CCT ATT CTG TTG TGT TGG GGA CTA GAG GTA ATT ACA AAG GGA
TAA ATA AAT TGC TGA CAA ATA AGT CAC GGA TAA GAC AAC ACA ACC CCT GAT CTC CAT TAA TGT TTC CCT
 I   Y   L   T   T   V   Y   S   V   P   I   L   L   C   W   G   L   E   V   I   T   K   G>

830         840         850         860         870         880         890
ATA AGA CAA ACA GTC ACC CAC TCT GGT GAT GCT TCC CTT ATC TTC ATA ATG CAT TTG ATC CTG TG ATT
TAT TCT GTT TGT CAG TGG GTG AGA CCA CTA CGA AGG GAA TAG AAG TAT TAC GTA AAC TAG GAC AC TAA
 I   R   Q   T   V   T   H   S   G   D   A   S   L   I   F   I   M   H   L   I   L>

900         910         920         930         940         950         960
CTT TGG CAC ATG AGT CCA TTG CAT CTT GCA TAT TAG TGT CCA GTA AGT TTT TCC TGA CCA ATT GAT AAT
GAA ACC GTG TAC TCA GGT AAC GTA GAA CGT ATA ATC ACA GGT CAT TCA AAA AGG ACT GGT TAA CTA TTA 970         980         990         1000        1010        1020        1030
ATA GAT ATA CAT TGG TAG CAG TTT TGT GTA TAT TTT TAT AGT TAG ATG TTG TTG GCA CAT GTG ACT TGT
TAT CTA TAT GTA ACC ATC GTC AAA ACA CAT ATA AAA ATA TCA ATC TAC AAC AAC CGT GTA CAC TGA ACA 1040        1050        1060        1070        1080        1090        1100
GTC TCA GAA AAA TAC AGA AAA TGG TTA AAG ACA GGA GGA TAC TAC CCT GAT TTC TCT GTT CAT TAA AGA
CAG AGT CTT TTT ATG TCT TTT ACC AAT TTC TGT CCT CCT ATG ATG GGA CTA AAG AGA CAA GTA ATT TCT 1110        1120        1130        1140        1150        1160        1170
ACA GCT ATT TGG GGG GAA AAC CTG ATA CAA TTA TTT GAG CAT GTG GCT TAA AGA TTA GAC CTA TAA ACA
TGT CGA TAA ACC CCC CTT TTG GAC TAT GTT AAT AAA CTC GTA CAC CGA ATT TCT AAT CTG GAT ATT TGT 1180        1190        1200        1210        1220        1230
ATT CAG GAG CAT CTT CCA GCA AAC TGT GTG AGA ATT CAC AGA AAT AAA CCT GGT AGG TTT GTG CTA TGT
TAA GTC CTC GTA GAA GGT CGT TTG ACA CAC TCT TAA GTG TCT TTA TTT GGA CCA TCC AAA CAC GAT ACA 1240        1250        1260        1270        1280        1290        1300
TAT TCA CAT GGG CTG TTA ACT CTT TTC CAT TCC TAG GTC CTT TAT TTC CCT GCC CTC CTC AAT CTC ATG
ATA AGT GTA CCC GAC AAT TGA GAA AAG GTA AGG ATC CAG GAA ATA AAG GGA CGG GAG GAG TTA GAG TAC 1310        1320        1330        1340        1350        1360        1370
CTC TTG AGA TTT TTA ACT ATA TTA CTT CTT TAC AAA GTC ATC TTC AAA ATG ATT CAT TTT GGA TAG CAA
```

SL5 Immunohistochemistry Comparison of Tumor vs Normal

| | 1 | 2 | 3 | 4 | 5 | 6 | 7 | 8 | 9 | 10 |
|---|---|---|---|---|---|---|---|---|---|---|
| A | Adrenal | Adrenal | Adrenal | Ovary | Ovary | Ovary | Ovary | Breast | Breast | Breast |
| Tumor | (+4) | (++4) | (+2) | (++4) | (++4) | (+4) | (++4) | (++4) | (+4) | (+1) |
| NC | (-) | (-) | (-) | wD | (-) | (-) | (-) | na | (-) | (-) |
| Normal | (+2) | (+2) | (+2) | (+1) | (+1) | na | | na | na | na |
| NC | (-) | (-) | (-) | (-) | (-) | na | | (++1) | | |
| B | Colon | Colon | Colon | Colon | Prostate | Prostate | Prostate | Prostate | Uterus | Cervical |
| Tumor | (++4) | (++4) | (+++4) | (+4) | (+2) | (++3) | (+3) | (++3) | (++4) | (+2) |
| NC | (-) | (-) | (-) | (-) | (-) | (-) | (-) | (-) | (-) | (-) |
| Normal | (+2) | (+1) | (+2) | (++3) | ? | (++2) | (+1) | (++2) | (+2) | (++2) |
| NC | (-) | (-) | (-) | (-) | (-) | (-) | (-) | (-) | (-) | (-) |
| C | Kidney | Kidney | Kidney | Kidney | Pancreas | Pancreas | Pancreas | Pancreas | Leiomyo- | Leiomyo- |
| Tumor | (+4) | (+4) | (+4) | (++4) | (+++4) | (++4) | (++4) | (+++4) | (+4) | (++4) |
| NC | (-) | (-) | (-) | (-) | (-) | (-) | (-) | (-) | (-) | (-) |
| Normal | ? | ? | | | (+1) | (+1) | (++2) | (+1) | EDG | |
| NC | (-) | (-) | | | (-) | (-) | (-) | (-) | | |
| D | Liver | Liver | Liver | Stomach | Stomach | Stomach | Lymphoma | Lymphoma | Lymphoma | Lymphoma |
| Tumor | (+4) | (+4) | (+4) | (-) | (-) | na | (+4) | (+2) | (+2) | (+1) |
| NC | (-) | (-) | (-) | (-) | (-) | na | (-) | (-) | ? | (-) |
| Normal | na | na | na | na | na | na | (+1) | (+1) | (-) | (-) |
| NC | na | na | na | na | na | na | (-) | na | | |
| E | Seminoma | Seminoma | Seminoma | Thyroid | Thyroid | Thyroid | Thyroid | Fibro- | Fibro- | Fibro- |
| Tumor | (+3) | (+4) | (++4) | (++4) | (+4) | (+4) | (+4) | (+4) | (+4) | (++4) |
| NC | (-) | (-) | (-) | (-) | (-) | (-) | (-) | (-) | (-) | (-) |
| Normal | (+2) | (+1) | (+2) | EDG | wD | EDG | EDG | (-) | (-) | (+2) |
| NC | (-) | (-) | (-) | (+1) | (+1) | (++2) | (-) | (-) | purk(+) | na |
| F | Melanoma | Melanoma | Melanoma | Chorio- | Carcinoid | Chorio- | Basal Cell | Basal Cell | Basal Cell | Germ Cell |
| Tumor | (++4) | (+4) | (++4) | (+4) | (+4)? | (+1) | (++3) | (++3) | (+1) | (++4) |
| NC | (-) | (-) | (-) | (-) | (-) | (-) | (+1) | (+1) | (-) | EDG |
| Normal | | | | | | | | | | (+1) |
| NC | | | | | | | | | | (-) |

Staining Intensity: - no staining; + weak; ++ medium; +++ strong staining
Staining Percentage: 1: 0-25%; 2: 26-50%; 3: 51-75%; 4: 76-100%
For example: (++3) stands for 51-75% of cells have medium staining
NC: Negative Control; na: no tissue materials on slides.

GENES AND GENE EXPRESSION PRODUCTS THAT ARE DIFFERENTIALLY REGULATED IN PROSTATE CANCER

This application claims priority to Provisional Application No. 60/088,877 filed Jun. 11, 1998.

FIELD OF THE INVENTION

This invention relates to the area of diagnosis, prognosis, and treatment of cancer, tumor progression, hyperproliferative cell growth, and accompanying physical and biological manifestations. More specifically, the invention includes polynucleotides that are differentially regulated in prostatic disorders, such as metastatic prostate cancer, localized prostate cancer, and benign prostate hyperplasia (BPH).

BACKGROUND OF THE INVENTION

Genes that are up- or down-regulated in cancer or tumor progression are useful for therapeutic and diagnostic purposes. For example, detection of genes or gene expression products up-regulated in hyperproliferative cells can be a predictive or diagnostic marker of the onset or the progression of cancer. Early diagnosis can be useful if the cancer, tumors, or hyperproliferating cells can be inhibited, removed, or terminated to prevent metastasis or recurrence of cancerous growth. Such early warning is of particular use to prostate cancer patients, where removal of the growth, tumor, or cells is beneficial if the disease is confined to the prostate. There is a need in the art for genes related to cancer and tumor progression.

SUMMARY OF THE INVENTION

The present invention provides methods and reagents for diagnosing cancer, tumor progression, hyperproliferative cell growth, and accompanying biological and physical manifestations. Reagents for such diagnostic kits include:
(a) polynucleotides comprising a sequence capable of hybridizing to one or more of SEQ ID NO: 1–339 or complement thereof;
(b) polypeptides comprising the amino acid sequence encoded by any one of SEQ ID NO: 1–339; and
(c) antibodies capable of binding polypeptides comprising the amino acid sequence of (b).

The methods of diagnosis of the present invention include both nucleic acid assays and immunoassays.

In another embodiment, the present invention provides both compositions and methods for treating or ameliorating cancer, tumor progression, hyperproliferative cell growth, and accompanying biological and physical manifestations. The compositions for treatment or amelioration include:
(a) polynucleotides comprising the sequence capable of hybridizing to one or more of the sequences shown in SEQ ID NO:1–339 and complement thereof, including antisense, ribozyme and gene therapy nucleic acid constructs;
(b) polypeptides comprising the amino acid sequence encoded by any one of SEQ ID NO: 1–339; and
(c) antibodies capable of binding polypeptides of polypeptides comprising the amino acid sequence (b).

Methods of treatment or amelioration include administering compositions of polynucleotides, polypeptides, antibodies, or combinations thereof and can be used
(a) to inhibit translation and/or transcription;
(b) to inhibit biological activity;
(c) as a vaccine antigen; and
(d) as an immune system inducer.

Such compositions can be administered systemically or locally to the desired site.

In one embodiment, the present invention provides a composition comprising an isolated polynucleotide selected from the group consisting of (a) any one of SEQ ID NOs:2, 5, 49, 50, 99, 100, 115, 116, 118, 130, 131, 140, 144, 145, 146, 157, 158, 159, 163, 164, 165, 166, 177, 178, 180, 211, 212, 213, 218, 219, 220, 221, 229, 232, 233, 242, 243, 248, 249, 254, 256, 257, 259, 272, 273, 277, 288, 289, 292, 293, 316, 317, and 330;

(b) a polynucleotide that encodes a variant of the polypeptide encoded by (a); and (c) a polynucleotide encoding a protein expressed by a polynucleotide having the sequence of any one of the sequences of (a).

Preferably, the nucleic acid obtained from the biological material of part (b) above is genomic DNA or mRNA. The nucleic acid can also be cDNA complementary to the mRNA.

Another embodiment of the invention is the use of the isolated polynucleotides or parts thereof as diagnostic probes or as primers.

In another embodiment, the present invention provides a composition comprising a polypeptide, wherein said polypeptide is selected from the group consisting of:

(a) a polypeptide encoded by any one of SEQ ID Nos:2, 5, 49, 50, 99, 100, 115, 116, 118, 130, 131, 140, 144, 145, 146, 157, 158, 159, 163, 164, 165, 166, 177, 178, 180, 211, 212, 213, 218, 219, 220, 221, 229, 232, 233, 242, 243, 248, 249, 254, 256, 257, 259, 272, 273, 277, 288, 289, 292, 293, 316, 317, and 330;

(b) a polypeptide encoded by full-length mRNA or cDNA corresponding to any one of SEQ ID NO: 1–339; and (c) a variant of the protein (a) or (b);

In certain preferred embodiments, the polynucleotide is operably linked to an expression control sequence. The invention further provides a host cell, including bacterial, yeast, insect and mammalian cells, transformed with the polynucleotide sequence. The invention also provides the fill-length cDNA and the full length human gene corresponding to the polynucleotide.

Protein and polypeptide compositions of the invention may further comprise a pharmaceutically acceptable carrier. Compositions comprising an antibody that specifically reacts with such protein or polypeptide are also provided by the present invention.

The invention further relates to a polypeptide or nucleic acid obtained by transforming a host cell with nucleic acid comprising at least one of SEQ ID NO: 1–339, culturing the host cell, and recovering the replicated nucleic acid, the expressed RNA, and/or the expressed polypeptide.

BRIEF DESCRIPTION OF THE FIGURES

FIG. 1 provides the open reading frame for clone SL 195.

FIG. 2 provides the open reading frame for clone SL 197.

FIG. 3 provides the immunohistochemistry staining results for clone SL 5 expression in a variety of normal and tumor tissues.

DETAILED DESCRIPTION OF THE INVENTION

Genes that are up- or down-regulated in cancer or tumor progression are useful for therapeutic and diagnostic purposes. For example, a diagnostic assay to determine the stage of the disease also is useful in tailoring treatment of aggressive versus more mild cancer or tumor progression. The polynucleotide sequences and encoded polypeptides of the present invention are useful for these diagnostic or prognostic purposes.

Further, modulation of genes or gene expression products that are mis-regulated can be used to treat or ameliorate cancer, tumor progression, hyperproliferative cell growth, and the accompanying physical and biological manifestations. For example, the polynucleotide sequences provided herein as SEQ ID NO:1–339, can be used to construct the following polynucleotide and polypeptide compositions that are useful for treatment: antisense; ribozymes; antibodies; vaccine antigens; and immune system inducers, to induce dendritic cells, for example.

Identified herein are polynucleotide sequences that are upregulated in a cancer cell line, more specifically in a prostate cancer cell line. Thus, the present invention relates to methods and reagents for diagnosis, and to methods and compositions for treatment.

I. Use of Polynucleotides Having a Sequence of One or More of SEQ ID NO: 1–339 to Obtain Full-Length cDNA and Full-Length Human Gene and Promoter Region Full-length cDNA molecules comprising the disclosed sequences are obtained as follows. The polynucleotide or a portion thereof comprising at least 12, 15, 18, or 20 nucleotides is used as a hybridization probe to detect hybridizing members of a cDNA library using probe design methods, cloning methods, and clone selection techniques as described in U.S. Pat. No. 5,654,173, "Secreted Proteins and Polynucleotides Encoding Them," incorporated herein by reference. Libraries of cDNA are made from selected tissues, such as normal or tumor tissue, or from tissues of a mammal treated with, for example, a pharmaceutical agent. Preferably, the tissue is the same as that used to generate the polynucleotides, as both the polynucleotides and the cDNA represent expressed genes. Most preferably, the cDNA library is made from the biological material described herein in the Examples. Alternatively, many cDNA libraries are available commercially. (Sambrook et al., *Molecular Cloning: A Laboratory Manual*, 2nd Ed. (Cold Spring Harbor Press, Cold Spring Harbor, N.Y. 1989).

Members of the library that are larger than the polynucleotide, and preferably that contain the whole sequence of the native message, are obtained. In order to confirm that the entire cDNA has been obtained, RNA protection experiments are performed as follows. Hybridization of a full-length cDNA to an mRNA will protect the RNA from RNase degradation. If the cDNA is not full length, then the portions of the mRNA that are not hybridized will be subject to RNase degradation. This is assayed, as is known in the art, by changes in electrophoretic mobility on polyacrylamide gels, or by detection of released monoribonucleotides. Sambrook et al., *Molecular Cloning: A Laboratory Manual*, 2nd Ed. (Cold Spring Harbor Press, Cold Spring Harbor, N.Y. 1989). In order to obtain additional sequences 5' to the end of a partial cDNA, 5' RACE (PCR Protocols: A Guide to Methods and Applications (Academic Press, Inc. 1990)) is performed.

Genomic DNA is isolated using polynucleotides in a manner similar to the isolation of full-length cDNAs. Briefly, the polynucldotides, or portions thereof, are used as probes to libraries of genomic DNA. Preferably, the library is obtained from the cell type that was used to generate the polynucleotides, but this is not essential. Most preferably, the genomic DNA is obtained from the biological material described herein in the Examples. Such libraries may be in vectors suitable for carrying large segments of a genome, such as P1 or YAC, as described in detail in Sambrook et al., 9.4–9.30. In addition, genomic sequences can be isolated from human BAC libraries, which are commercially available from Research Genetics, Inc., Huntville, Ala., USA, for example. In order to obtain additional 5' or 3' sequences, chromosome walking is performed, as described in Sambrook et al., such that adjacent and overlapping fragments of genomic DNA are isolated. These are mapped and pieced together, as is known in the art, using restriction digestion enzymes and DNA ligase.

Using the polynucleotides sequences of the invention, corresponding full length genes can be isolated using both classical and PCR methods to construct and probe cDNA libraries. Using either method, Northern blots, preferably, are performed on a number of cell types to determine which cell lines express the gene of interest at the highest rate.

Classical methods of constructing cDNA libraries are taught in Sambrook et al., supra. With these methods, cDNA can be produced from mRNA and inserted into viral or expression vectors. Typically, libraries of mRNA comprising poly(A) tails can be produced with poly(T) primers. Similarly, cDNA libraries can be produced using the instant sequences as primers.

PCR methods are used to amplify the members of a cDNA library that comprise the desired insert. In this case, the desired insert will contain sequence from the full length cDNA that corresponds to the instant ESTs. Such PCR methods include gene trapping and RACE methods. Gruber et al., PCT WO 95/04745 and Gruber et al., U.S. Pat. No. 5,500,356. Kits are commercially available to perform gene trapping experiments from, for example, Life Technologies, Gaithersburg, Maryland, USA. PCT Pub. No. WO 97/19110. (Apte and Siebert, *Biotechniques* 15:890–893, 1993; Edwards et al., *Nuc. Acids Res.* 19:5227–5232, 1991).

The promoter region of a gene generally is located 5' to the initiation site for RNA polymerase II, and can be obtained by performing 5' RACE using a primer from the coding region of the gene. Alternatively, the cDNA can be used as a probe for the genomic sequence, and the region 5' to the coding region is identified by "walking up." If the gene is highly expressed or differentially expressed, the promoter from the gene may be of use in a regulatory construct for a heterologous gene.

Once the full-length cDNA or gene is obtained, DNA encoding variants can be prepared by site-directed mutagenesis, described in detail in Sambrook et al., 15.3–15.63. The choice of codon or nucleotide to be replaced can be based on disclosure herein on optional changes in amino acids to achieve altered protein structure and/or function.

As an alternative method to obtaining DNA or RNA from a biological material, nucleic acid comprising nucleotides having the sequence of one or more polynucleotides of the invention can be synthesized. Thus, the invention encompasses nucleic acid molecules ranging in length from 15 nucleotides (corresponding to at least contiguous nucleotides of one of SEQ ID NO: 1–339) up to a maximum length suitable for one or more biological manipulations, including replication and expression, of the nucleic acid molecule. The invention includes but is not limited to (a) nucleic acid having the size of a full gene, and comprising at least one of SEQ ID NO:1–339; (b) the nucleic acid of (a) also comprising at least one additional gene, operably linked to permit expression of a fuision protein; (c) an expression vector comprising (a) or (b); (d) a plasmid comprising (a) or (b) and (e) a recombinant viral particle comprising (a) or (b).

The sequence of a nucleic acid comprising at least 15 contiguous nucleotides of at least any one of SEQ ID NO: 1–339, preferably the entire sequence of at least any one of SEQ ID NO: 1–339, is not limited and can be any sequence of A, T, G, and/or C (for DNA) and A, U, G, and/or C (for RNA) or modified bases thereof, including inosine and pseudouridine. The choice of sequence will depend on the desired function and can be dictated by coding regions desired, the intron-like regions desired, and the regulatory regions desired.

Where the entire sequence of any one of SEQ ID NO: 1–339 is within the nucleic acid, the nucleic acid obtained is referred to herein as a polynucleotide comprising the sequence of any one of SEQ ID NO: 1–339.

II. Expression of Polypeptide Encoded by Full-Length cDNA or Full-Length Gene

The polynucleotide, the corresponding cDNA, or the full-length gene is used to express the partial or complete gene product. Appropriate polynucleotide constructs are purified using standard recombinant DNA techniques as described in, for example, Sambrook et al., (1989) *Molecular Cloning: A Laboratory Manual*, 2nd ed. (Cold Spring Harbor Press, Cold Spring Harbor, N.Y.). The polypeptides encoded by the polynucleotides are expressed in any expression system, including, for example, bacterial, yeast, insect, amphibian and mammalian systems. Suitable vectors and host cells are described in U.S. Pat. No. 5,654,173.

Bacteria.

Expression systems in bacteria include those described in Chang et al., *Nature* (1978) 275:615, Goeddel et al., *Nature* (1979) 281:544, Goeddel et al., *Nucleic Acids Res.* (1980) 8:4057; EP 0 036,776, U.S. Pat. No. 4,551,433, DeBoer et al., *Proc. Natl. Acad. Sci.* (USA) (1983) 80:21–25, and Siebenlist et al., *Cell* (1980) 20:269.

Yeast.

Expression systems in yeast include those described in Hinnen et al., *Proc. Natl. Acad. Sci.* (USA) (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459, Roggenkamp et al., *Mol. Gen. Genet.* (1986) 202:302) Das et al., *J. Bacteriol.* (1984) 158:1165; De Louvencourt et al., *J. Bacteriol.* (1983) 154:737, Van den Berg et al., *Bio/Technology* (1990) 8:135; Kunze et al., *J. Basic Microbiol.* (1985) 25:141; Cregg et al., *Mol. Cell. Biol.* (1985) 5:3376, U.S. Pat. Nos. 4,837,148 and 4,929, 555; Beach and Nurse, *Nature* (1981) 300:706; Davidow et al., *Curr. Genet.* (1985) 10:380, Gaillardin et al., *Curr. Genet.* (1985) 10:49, Ballance et al., *Biochem. Biophys. Res. Commun.* (1983) 112:284–289; Tilburn et al., *Gene* (1983) 26:205–221, Yelton et al., *Proc. Natl. Acad Sci.* (USA) (1984) 81:1470–1474, Kelly and Hynes, *EMBO J.* (1985) 4:475479; EP 0 244,234, and WO 91/00357.

Insect Cells.

Expression of heterologous genes in insects is accomplished as described in U.S. Pat. No. 4,745,051, Friesen et al. (1986) "The Regulation of Baculovirus Gene Expression" in: The Molecular Biology Of Baculoviruses (W. Doerfler, ed.), EP 0 127,839, EP 0 155,476, and Vlak et al., *J. Gen. Virol.* (1988) 69:765–776, Miller et al., *Ann. Rev. Microbiol.* (1988) 42:177, Carbonell et al., *Gene* (1988) 73:409, Maeda et al., *Nature* (1985) 315:592–594, Lebacq-Verheyden et al., *Mol. Cell. Biol.* (1988) 8:3129; Smith et al., *Proc. Natl. Acad. Sci.* (USA) (1985) 82:8404, Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47–55, Miller et al., Generic Engineering (Setlow, J. K. et al. eds.), Vol. 8 (Plenum Publishing, 1986), pp. 277–279, and Maeda et al., *Nature*, (1985) 315:592–594.

Mammalian Cells.

Mammalian expression is accomplished as described in Dijkema et al., *EMBO J.* (1985) 4:761, Gorman et al., *Proc. Natl. Acad. Sci.* (USA) (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767, 704, 4,657,866, 4,927,762, 4,560,655, WO 90/103430, WO 87/00195, and U.S. Pat. No. RE 30,985.

Polynucleotide molecules comprising the polynucleotide sequence are propagated by placing the molecule in a vector. Viral and non-viral vectors are used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The polynucleotide is inserted into a vector typically by means of DNA ligase attachment to a cleaved restriction enzyme site in the vector. Alternatively, the desired nucleotide sequence may be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Polynucleotides are linked to regulatory sequences as appropriate to obtain the desired expression properties. These may include promoters (attached either at the 5' end of the sense strand or at the 3' end of the antisense strand), enhancers, terminators, operators, repressors, and inducers. The promoters may be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art may be used.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to the polypeptide is identified, its expression can be regulated in the cell to which the gene is native. For example, an endogenous gene of a cell can be regulated by an exogenous regulatory sequence as disclosed in U.S. Pat. No. 5,641,670, "Protein Production and Protein Delivery."

Ribozymes

Trans-cleaving catalytic RNAs (ribozymes) are RNA molecules possessing endoribonuclease activity. Ribozymes are specifically designed for a particular target, and the target message must contain a specific nucleotide sequence. They are engineered to cleave any RNA species site-specifically in the background of cellular RNA. The cleavage event renders the mRNA unstable and prevents protein expression. Importantly, ribozymes can be used to inhibit expression of a gene of unknown function for the purpose of determining its function in an in vitro or in vivo context, by detecting the phenotypic effect.

One commonly used ribozyme motif is the hammerhead, for which the substrate sequence requirements are minimal. Design of the hammerhead ribozyme is disclosed in Usman et al., *Current Opin. Struct. Biol.* (1996) 6:527–533. Usman also discusses the therapeutic uses of ribozymes. Ribozymes can also be prepared and used as described in Long et al., *FASEB J.* (1993) 7:25; Symons, *Ann. Rev. Biochem.* (1992) 61:641; Perrotta et al., *Biochem.* (1992) 31:16–17; Ojwang et al., *Proc. Natl. Acad. Sci.* (USA) (1992) 89:10802–10806; and U.S. Pat. No. 5,254,678. Ribozyme cleavage of HIV-I RNA is described in U.S. Pat. No. 5,144,019; methods of cleaving RNA using ribozymes is described in U.S. Pat. No. 5,116,742; and methods for increasing the specificity of ribozymes are described in U.S. Pat. No. 5,225,337 and Koizumi et al., *Nucleic Acid Res.* (1989) 17:7059–7071. Preparation and use of ribozyme fragments in a hammerhead structure are also described by Koizumi et al., *Nucleic Acids Res.* (1989) 17:7059–7071. Preparation and use of ribozyme fragments in a hairpin structure are described by Chowrira and Burke, *Nucleic Acids Res.* (1992) 20:2835. Ribozymes can also be made by rolling transcription as described in Daubendiek and Kool, *Nat. Biotechnol.* (1997) 15(3): 273–277.

The hybridizing region of the ribozyme may be modified or may be prepared as a branched structure as described in Horn and Urdea, *Nucleic Acids Res.* (1989) 17:6959–67. The basic structure of the ribozymes may also be chemically altered in ways familiar to those skilled in the art, and chemically synthesized ribozymes can be administered as synthetic oligonucleotide derivatives modified by monomeric units. In a therapeutic context, liposome mediated delivery of ribozymes improves cellular uptake, as described in Birikh et al., *Eur. J. Biochem.* (1997) 245:1–16.

Therapeutic and functional genomic applications of ribozymes proceed beginning with knowledge of a portion of the coding sequence of the gene to be inhibited. Thus, for many genes, a polynucleotide sequence as disclosed herein provides adequate sequence for constructing an effective ribozyme. A target cleavage site is selected in the target sequence, and a ribozyme is constructed based on the 5' and 3' nucleotide sequences that flank the cleavage site. Retroviral vectors are engineered to express monomeric and multimeric hammerhead ribozymes targeting the mRNA of the target coding sequence. These monomeric and multimeric ribozymes are tested in vitro for an ability to cleave the target mRNA. A cell line is stably transduced with the retroviral vectors expressing the ribozymes, and the transduction is confirmed by Northern blot analysis and reverse-transcription polymerase chain reaction (RT-PCR). The cells are screened for inactivation of the target MRNA by such indicators as reduction of expression of disease markers or reduction of the gene product of the target mRNA.

Antisense

Antisense nucleic acids are designed to specifically bind to RNA, resulting in the formation of RNA-DNA or RNA-RNA hybrids, with an arrest of DNA replication, reverse transcription or messenger RNA translation. Antisense polynucleotides based on a selected sequence can interfere with expression of the corresponding gene. Antisense polynucleotides are typically generated within the cell by expression from antisense constructs that contain the antisense EST strand as the transcribed strand. Antisense polynucleotides will bind and/or interfere with the translation of the corresponding mRNA. The expression products of control cells and cells treated with the antisense construct are compared to detect the protein product of the gene corresponding to the polynucleotide. The protein is isolated and identified using routine biochemical methods.

Antisense therapy for a variety of cancers is in clinical phase and has been discussed extensively in the literature. Reed reviewed antisense therapy directed at the Bcl-2 gene in tumors; gene transfer-mediated overexpression of Bcl-2 in tumor cell lines conferred resistance to many types of cancer drugs. (Reed, J. C., *N.C.L.* (1997) 89:988–990). The potential for clinical development of antisense inhibitors of ras is discussed by Cowsert, L. M., *Anti-Cancer Drug Design* (1997) 12:359–371. Additional important antisense targets include leukemia (Geurtz, A. M., *Anti-Cancer Drug Design* (1997) 12:341–358); human C-ref kinase (Monia, B. P., *Anti-Cancer Drug Design* (1997) 12:327–339); and protein kinase C (McGraw et al., *Anti-Cancer Drug Design* (1997) 12:315–326.

Given the extensive background literature and clinical experience in antisense therapy, one skilled in the art can use selected polynucleotides of the invention as additional potential therapeutics. The choice of polynucleotide can be narrowed by first testing them for binding to "hot spot" regions of the genome of cancerous cells. If a polynucleotide is identified as binding to a "hot spot", testing the polynucleotide as an antisense compound in the corresponding cancer cells clearly is warranted.

Ogunbiyi et al., *Gastroenterology* (1997) 113(3):761–766 describe prognostic use of allelic loss in colon cancer; Barks et al., *Genes, Chromosomes, and Cancer* (1997) 19(4):278–285 describe increased chromosome copy number detected by FISH in malignant melanoma; Nishizake et al., *Genes, Chromosomes, and Cancer* (1997) 19(4):267–272 describe genetic alterations in primary breast cancer and their metastases and direct comparison using modified comparative genome hybridization; and Elo et al., *Cancer Research* (1997) 57(16):3356–3359 disclose that loss of heterozygosity at 16z24.1-q24.2 is significantly associated with metastatic and aggressive behavior of prostate cancer.

Dominant Negative Mutations

Dominant negative mutations are readily generated for corresponding proteins that are active as homomultimers. A mutant polypeptide will interact with wild-type polypeptides (made from the other allele) and form a non-functional multimer. Thus, a mutation is in a substrate-binding domain, a catalytic domain, or a cellular localization domain. Preferably, the mutant polypeptide will be overproduced. Point mutations are made that have such an effect. In addition, fusion of different polypeptides of various lengths to the terminus of a protein can yield dominant negative mutants. General strategies are available for making dominant negative mutants. See Herskowitz, *Nature* (1987) 329:219–222. Such a technique can be used for creating a loss of function mutation, which is useful for determining the function of a protein.

Identification of Secreted and Membrane-Bound Polypeptides

Both secreted and membrane-bound polypeptides of the present invention are of interest. For example, levels of secreted polypeptides can be assayed conveniently in body fluids, such as blood, urine, prostatic fluid and semen. Membrane-bound polypeptides are useful for constructing vaccine antigens or inducing an immune response. Such antigens would comprise all or part of the extracellular region of the membrane-bound polypeptides.

Because both secreted and membrane-bound polypeptides comprise a fragment of contiguous hydrophobic amino acids, hydrophobicity predicting algorithms can be used to identify such polypeptides.

A signal sequence is usually encoded by both secreted and membrane-bound polypeptide genes to direct a polypeptide to the surface of the cell. The signal sequence usually comprises a stretch of hydrophobic residues. Such signal sequences can fold into helical structures.

Membrane-bound polypeptides typically comprise at least one transmembrane region that possesses a stretch of hydrophobic amino acids that can transverse the membrane. Some transmembrane regions also exhibit a helical structure.

Hydrophobic fragments within a polypeptide can be identified by using computer algorithms. Such algorithms include Hopp & Woods, *Proc. Natl. Acad. Sci. USA* 78: 3824–3828 (1981); Kyte & Doolittle, *J. Mol. Biol.* 157:105–132 (1982); and RAOAR algorithm, Degli Esposti et al., *Eur. J. Biochem.* 190: 207–219 (1990).

Another method of identifying secreted and membrane-bound polypeptides is to translate the present polynucleotides, SEQ ID NO:1–339, in all six frames and determine if at least 8 contiguous hydrophobic amino acids are present. Those translated polypeptides with at least 8; more typically, 10; even more typically, 12 contiguous hydrophobic amino acids are considered to be either a putative secreted or membrane bound polypeptide. Hydrophobic amino acids include alanine, glycine, histidine, isoleucine, leucine, lysine, methionine, phenylalanine, proline, threonine, tryptophan, tyrosine, and valine.

Putative secreted and/or membrane-bound polypeptides are encoded by the sequences of the following clones: SL-5, SL-6, SL-9, SL-11, SL-13, SL-90, SL-100, SL-107, SL-124, SL-135, SL-139, SL-143, SL-152, SL-153, SL-173, and SL-177.

Construction of Polypeptides of the Invention and Variants Thereof

The polypeptides of the invention include those encoded by the disclosed polynucleotides. These polypeptides can also be encoded by nucleic acids that, by virtue of the degeneracy of the genetic code, are not identical in sequence to the disclosed polynucleotides. Thus, the invention includes within its scope nucleic acids comprising polynucleotides encoding a protein or polypeptide expressed by a polynucleotide having the sequence of any one of SEQ ID NO: 1–339. Also within the scope of the invention are variants; variants of polypeptides include mutants, fragments, and fusions. Mutants can include amino acid substitutions, additions or deletions. The amino acid substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues that are not necessary for function. Conservative amino acid substitutions are those that preserve the general charge, hydrophobicity/hydrophilicity, and/or steric bulk of the amino acid substituted. For example, substitutions between the following groups are conservative: Gly/Ala, Val/Ile/Leu, Asp/Glu, Lys/Arg, Asn/Gln, Ser/Cys,Thr, and Phe/Trp/Tyr.

Cysteine-depleted muteins are variants within the scope of the invention. These variants can be constructed according to methods disclosed in U.S. Pat. No. 4,959,314, "Cysteine-Depleted Muteins of Biologically Active Proteins." The patent discloses how to substitute other amino acids for cysteines, and how to determine biological activity and effect of the substitution. Such methods are suitable for proteins according to this invention that have cysteine residues suitable for such substitutions, for example to eliminate disulfide bond formation.

The protein variants described herein are encoded by polynucleotides that are within the scope of the invention. The genetic code can be used to select the appropriate codons to construct the corresponding variants.

The invention encompasses polynucleotide sequences having at least 65% sequence identity to any one of SEQ ID NOs:1–339 as determined by the Smith-Waterman homology search algorithm as implemented in MSPRCH program (Oxford Molecular) using an affine gap search with the following search parameters: gap open penalty of 12, and gap extension penalty of 1.

Use of the Polynucleotides as Probes, in Mapping, and in Tissue Profiling

Probes

Polynucleotide probes comprising at least 12 contiguous nucleotides selected from the nucleotide sequence of a polynucleotide of SEQ ID NO:1–339 are used for a variety of purposes, including identification of human chromosomes and determining transcription levels.

The nucleotide probes are labeled, for example, with a radioactive, fluorescent, biotinylated, or chemiluminescent label, and detected by well known methods appropriate for the particular label selected. Protocols for hybridizing nucleotide probes to preparations of metaphase chromosomes are also well known in the art. A nucleotide probe will hybridize specifically to nucleotide sequences in the chromosome preparations which are complementary to the nucleotide sequence of the probe. A probe that hybridizes specifically to a polynucleotide should provide a detection signal at least 5-, 10-, or 20-fold higher than the background hybridization provided with other unrelated sequences.

In a non-limiting example, commercial programs are available for identifying regions of chromosomes commonly associated with disease, such as cancer. Polynucleotides of the invention can be used to probe these regions. For example, if through profile searching a polynucleotide is identified as corresponding to a gene encoding a kinase, its ability to bind to a cancer-related chromosomal region will suggest its role as a kinase in one or more stages of tumor cell development/growth. Although some experimentation would be required to elucidate the role, the polynucleotide constitutes a new material for isolating a specific protein that has potential for developing a cancer diagnostic or therapeutic.

Nucleotide probes are used to detect expression of a gene corresponding to the polynucleotide. For example, in Northern blots, mRNA is separated electrophoretically and contacted with a probe. A probe is detected as hybridizing to an mRNA species of a particular size. The amount of hybridization is quantitated to determine relative amounts of expression, for example under a particular condition. Probes are also used to detect products of amplification by polymerase chain reaction. The products of the reaction are hybridized to the probe and hybrids are detected. Probes are used for in situ hybridization to cells to detect expression. Probes can also be used in vivo for diagnostic detection of hybridizing sequences. Probes are typically labeled with a radioactive isotope. Other types of detectable labels may be used such as chromophores, fluors, and enzymes.

Expression of specific mRNA can vary in different cell types and can be tissue specific. This variation of mRNA levels in different cell types can be exploited with nucleic acid probe assays to determine tissue types. For example, PCR, branched DNA probe assays, or blotting techniques utilizing nucleic acid probes substantially identical or complementary to polynucleotides listed in the Sequence Listing can determine the presence or absence of cDNA or mRNA related to the polynucleotides of the invention.

Examples of a nucleotide hybridization assay are described in Urdea et al., PCT WO92/02526 and Urdea et al., U.S. Pat. No. 5,124,246, both incorporated herein by reference. The references describe an example of a sandwich nucleotide hybridization assay.

Alternatively, the Polymerase Chain Reaction (PCR) is another means for detecting small amounts of target nucleic acids, as described in Mullis et al., *Meth. Enzymol.* (1987) 155:335–350; U.S. Pat. No. 4,683,195; and U.S. Pat. No. 4,683,202, all incorporated herein by reference. Two primer polynucleotides nucleotides hybridize with the target nucleic acids and are used to prime the reaction. The primers may be composed of sequence within or 3' and 5' to the polynucleotides of the Sequence Listing. Alternatively, if the primers are 3' and 5' to these polynucleotides, they need not hybridize to them or the complements. A thermostable polymerase creates copies of target nucleic acids from the primers using the original target nucleic acids as a template. After a large amount of target nucleic acids is generated by the polymerase, it is detected by methods such as Southern blots. When using the Southern blot method, the labeled probe will hybridize to a polynucleotide of the Sequence Listing or complement.

Furthermore, mRNA or cDNA can be detected by traditional blotting techniques described in Sambrook et al., "Molecular Cloning: A Laboratory Manual" (New York, Cold Spring Harbor Laboratory, 1989). mRNA or cDNA generated from mRNA using a polymerase enzyme can be purified and separated using gel electrophoresis. The nucleic acids on the gel are then blotted onto a solid support, such as nitrocellulose. The solid support is exposed to a labeled probe and then washed to remove any unhybridized probe. Next, the duplexes containing the labeled probe are detected. Typically, the probe is labeled with radioactivity.

Mapping

Polynucleotides of the present invention are used to identify a chromosome on which the corresponding gene resides. Using fluorescence in situ hybridization (FISH) on normal metaphase spreads, comparative genomic hybridization allows total genome assessment of changes in relative copy number of DNA sequences. See Schwartz and Samad, *Current Opinions in Biotechnology* (1994) 8:70–74; Kallioniemi et al., *Seminars in Cancer Biology* (1993) 4:41–46; Valdes and Tagle, *Methods in Molecular Biology* (1997) 68: 1, Boultwood, ed., Human Press, Totowa, N.J.

Preparations of human metaphase chromosomes are prepared using standard cytogenetic techniques from human primary tissues or cell lines. Nucleotide probes comprising at least 12 contiguous nucleotides selected from the nucleotide sequence shown in the Sequence Listing are used to identify the corresponding chromosome. The nucleotide probes are labeled, for example, with a radioactive, fluorescent, biotinylated, or chemiluminescent label, and detected by well known methods appropriate for the particular label selected. Protocols for hybridizing nucleotide probes to preparations of metaphase chromosomes are also well known in the art. A nucleotide probe will hybridize specifically to nucleotide sequences in the chromosome preparations that are complementary to the nucleotide sequence of the probe. A probe that hybridizes specifically to a polynucleotide-related gene provides a detection signal at least 5-, 10-, or 20-fold higher than the background hybridization provided with non-EST coding sequences.

Polynucleotides are mapped to particular chromosomes using, for example, radiation hybrids or chromosome-specific hybrid panels. See Leach et al., *Advances in Genetics*, (1995) 33:63–99; Walter et al., *Nature Genetics* (1994) 7:22–28; Walter and Goodfellow, *Trends in Genetics* (1992) 9:352. Such mapping can be useful in identifying the function of the polynucleotide-related gene by its proximity to other genes with known function. Function can also be assigned to the related gene when particular syndromes or diseases map to the same chromosome.

Tissue Profiling

The polynucleotides of the present invention can be used to determine the tissue type from which a given sample is derived. For example, a metastatic lesion is identified by its developmental organ or tissue source by identifying the expression of a particular marker of that organ or tissue. If a polynucleotide is expressed only in a specific tissue type, and a metastatic lesion is found to express that polynucleotide, then the developmental source of the lesion has been identified. Expression of a particular polynucleotide is assayed by detection of either the corresponding mRNA or the protein product. Immunological methods, such as antibody staining, are used to detect a particular protein product. Hybridization methods may be used to detect particular mRNA species, including but not limited to in situ hybridization and Northern blotting.

Use of Polymorphisms

A polynucleotide will be useful in forensics, genetic analysis, mapping, and diagnostic applications if the corresponding region of a gene is polymorphic in the human population. A particular polymorphic form of the polynucleotide may be used to either identify a sample as deriving from a suspect or rule out the possibility that the sample derives from the suspect. Any means for detecting a polymorphism in a gene are used, including but not limited to electrophoresis of protein polymorphic variants, differential sensitivity to restriction enzyme cleavage, and hybridization to an allele-specific probe.

Use of Polynucleotides to Raise Antibodies

Expression products of a polynucleotide, the corresponding mRNA or cDNA, or the corresponding complete gene are prepared and used for raising antibodies for experimental, diagnostic, and therapeutic purposes. The polynucleotide or related cDNA is expressed as described above, and antibodies are prepared. These antibodies are specific to an epitope on the polynucleotide-encoded polypeptide, and can precipitate or bind to the corresponding native protein in a cell or tissue preparation or in a cell-free extract of an in vitro expression system.

Immunogens for raising antibodies are prepared by mixing the polypeptides encoded by the polynucleotide of the present invention with adjuvants. Alternatively, polypeptides are made as fusion proteins to larger immunogenic proteins. Polypeptides are also covalently linked to other larger immunogenic proteins, such as keyhole limpet hemocyanin. Immunogens are typically administered intradermally, subcutaneously, or intramuscularly. Immunogens are administered to experimental animals such as rabbits, sheep, and mice, to generate antibodies. Optionally, the animal spleen cells are isolated and fused with myeloma cells to form hybridomas which secrete monoclonal antibodies. Such methods are well known in the art. According to another method known in the art, the polynucleotide is administered directly, such as by intramuscular injection, and expressed in vivo The expressed protein generates a variety of protein-specific immune responses, including production of antibodies, comparable to administration of the protein.

Preparations of polyclonal and monoclonal antibodies specific for polynucleotide-encoded proteins and polypeptides are made using standard methods known in the art. The antibodies specifically bind to epitopes present in the polypeptides encoded by polynucleotides disclosed in the Sequence Listing. Typically, at least 6, 8, 10, or 12 contiguous amino acids are required to form an epitope. However, epitopes which involve non-contiguous amino acids may require more, for example at least 15, 25, or 50 amino acids. A short sequence of a polynucleotide may then be unsuitable for use as an epitope to raise antibodies for identifying the corresponding novel protein, because of the potential for cross-reactivity with a known protein. However, the antibodies may be useful for other purposes, particularly if they identify common structural features of a known protein and a novel polypeptide encoded by a polynucleotide of the invention.

Antibodies that specifically bind to human polynucleotide-encoded polypeptides should provide a detection signal at least 5-, 10-, or 20-fold higher than a detection signal provided with other proteins when used in Western blots or other immunochemical assays. Preferably, antibodies that specifically bind polypeptides do not detect other proteins in immunochemical assays and can immunoprecipitate EST-ncoded proteins from solution. For such immunoassays, any type of samples can be used, including tissue, organs, cells, urine, blood, prostatic fluid or semen.

Of interest are antibodies to the secreted polypeptides encoded by the present polynucleotide sequences, SEQ ID NO: 1–339. Antibodies to secreted polypeptides can be used to test body fluids, such as blood, urine, prostatic fluid and semen.

To test for the presence of serum antibodies to the polypeptide in a human population, human antibodies are purified by methods well known in the art. Preferably, the antibodies are affinity purified by passing antiserum over a column to which a protein, polypeptide, or fusion protein is bound. The bound antibodies can then be eluted from the column, for example using a buffer with a high salt concentration.

In addition to the antibodies discussed above, genetically engineered antibody derivatives are made, such as single chain antibodies or humanized antibodies.

Antibodies to the polypeptides encoded by one or more of SEQ ID NO: 1–339 also are contemplated for therapeutic compositions and uses. For example, antibodies directed to membrane-bound polypeptides that are up-regulated in cancer, tumor progression, hyperproliferative growth, and/or accompanying biological or physical manifestations can be constructed. Antibodies can provide a useful therapeutic in inhibiting cell growth or inducing an immune reaction to cancer, tumor, or hyperproliferating cells. Typically, such antibodies are directed the extracellular regions of the membrane-bound polypeptide. The borders of such regions can be determined by identifying the location of the hydrophobic transmembrane fragment(s) in the encoded polypeptides of the present invention.

Exemplary antibodies were prepared using two sequences from clone SL-5: $H_2N$-CGPRLPSFPCPTHEPSTGQLSK-$CONH_2$ (SEQ ID NO: 340) and $H_2N$-CKDSQGLSDFKR-NSRTTRRSYKCCONH$_2$ (SEQ ID NO: 341). Using polyclonal antibodies raised against a mixture of these polypeptides, immunohistochemistry was performed on a variety of tumor tissues and corresponding normal tissue. The results are shown in FIG. 3, and discussed in the Examples. These polypeptides are useful for detecting a higher level of expression of clone SL-5 in tumor tissues.

Use of Polynucleotides to Construct Arrays for Diagnostics

The present polynucleotide sequences and gene products are useful for determining the occurrence of cancer, tumor progression, hyperproliferative growth, and/or accompanying biological or physical manifestations. Specifically, the polynucleotides and encoded polypeptides of the instant invention can be utilized to determine the occurrence of prostatic disorders, such as BPH or localized prostate cancer.

A number of prostatic disorders exist, including adenocarcinoma, BPH, histologic prostate cancer, prostatic intraepithelial neoplasia, clinical prostate cancer, incidental prostate cancer, and localized prostate cancer. BPH is a common prostatic disorder in men which becomes clinically manifest usually after age fifty. In BPH, hyperplastic growth of prostatic cells in the periurethral glandular tissue in the central zone of the prostate gland cause an enlarged prostate which can compress or elongate the urethra and produce symptoms of urethral obstruction that may progress to urinary retention or to a constellation of symptoms known as prostatism. A host of physical manifestations can accompany prostatic disorders including: impotency, reduced urinary flow, hesitancy in initiating voiding, postvoid dribbling, a sensation of incomplete bladder emptying, and development of bladder or high urinary tract infections.

To determine the occurrence of cancer, tumor progression, hyperproliferative growth, and/or accompanying biological or physical manifestations, the levels of polynucleotides and/or encoded polypeptides of the present invention in a sample are compared to the levels in a normal control of body tissues, cells, organs, or fluids. The normal control can include a pool of cells from a particular organ or tissue or tissues and/or cells from throughout the body. Either the immunoassays described above or the nucleic acid assays described below can be used for such measurements.

Any observed difference between the sample and normal control can indicate the occurrence of disease or disorder. Typically, if the levels of the polynucleotides and the encoded polypeptides of the present invention are higher than those found in the normal control, the results indicate the occurrence of cancer, tumor progression, hyperproliferative growth, and/or accompanying biological or physical manifestations.

In addition, the present polynucleotides can be useful to diagnose the severity as well as the occurrence of cancer, tumor progression, hyperproliferative growth, and/or accompanying biological or physical manifestations, including prostatic disorders. For example, the greater the difference observed in the sample versus the normal control of the present polynucleotides or encoded polypeptides, the greater the severity of the disorder, in particular, when higher levels as compared to a normal control are observed.

The present polynucleotides, as shown in SEQ ID NO: 1–339, were expressed at higher levels in a prostate cancer cell line versus a normal prostate epithelial cell line.

Polynucleotide arrays provide a high throughput technique that can assay a large number of polynucleotide sequences in a sample. This technology can be used as a diagnostic and as a tool to test for differential expression to determine function of an encoded protein.

To create arrays, polynucleotide probes are spotted onto a substrate in a two-dimensional matrix or array. Samples of polynucleotides can be labeled and then hybridized to the probes. Double stranded polynucleotides, comprising the labeled sample polynucleotides bound to probe polynucleotides, can be detected once the unbound portion of the sample is washed away.

The probe polynucleotides can be spotted on substrates including glass, nitrocellulose, etc. The probes can be bound to the substrate by either covalent bonds or by non-specific interactions, such as hydrophobic interactions. The sample polynucleotides can be labeled using radioactive labels, fluorophors, etc.

Techniques for constructing arrays and methods of using these arrays are described in EP No. 0 799 897; PCT No. WO 97/29212; PCT No. WO 97/27317; EP No. 0 785 280; PCT No. WO 97/02357; U.S. Pat. No. 5,593,839; U.S. Pat. No. 5,578,832; EP No. 0 728 520; U.S. Pat. No. 5,599,695; EP No. 0 721 016; U.S. Pat. No. 5,556,752; PCT No. WO 95/22058; and U.S. Pat. No. 5,631,734.

Further, arrays can be used to examine differential expression of genes and can be used to determine gene function. For example, arrays of the instant polynucleotide sequences can be used to determine if any of the EST sequences are differentially expressed between normal cells and cancer cells, for example. High expression of a particular message in a cancer cell, which is not observed in a corresponding normal cell, can indicate a cancer specific protein.

Differential Expression

The present invention also provides a method to identify abnormal or diseased tissue in a human. For polynucleotides corresponding to profiles of protein families as described above, the choice of tissue may be dictated by the putative biological function. The expression of a gene corresponding to a specific polynucleotide is compared between a first tissue that is suspected of being diseased and a second, normal tissue of the human. The normal tissue is any tissue of the human, especially those that express the polynucleotide-related gene including, but not limited to, brain, thymus, testis, heart, prostate, placenta, spleen, small intestine, skeletal muscle, pancreas, and the mucosal lining of the colon.

The polynucleotide-related genes in the two tissues are compared by any means known in the art. For example, the two genes are sequenced, and the sequence of the gene in the tissue suspected of being diseased is compared with the gene sequence in the normal tissue. The polynucleotide-related genes, or portions thereof, in the two tissues are amplified, for example using nucleotide primers based on the nucleotide sequence shown in the Sequence Listing, using the polymerase chain reaction. The amplified genes or portions of genes are hybridized to nucleotide probes selected from the same nucleotide sequence shown in the Sequence Listing. A difference in the nucleotide sequence of the polynucleotide-related gene in the tissue suspected of being diseased compared with the normal nucleotide sequence suggests a role of the polynucleotide-encoded proteins in the disease, and provides a lead for preparing a therapeutic agent. The nucleotide probes are labeled by a variety of methods, such as radiolabeling, biotinylation, or labeling with fluorescent or chemiluminescent tags, and detected by standard methods known in the art.

Alternatively, polynucleotide-related mRNA in the two tissues is compared. PolyA$^+$ RNA is isolated from the two tissues as is known in the art. For example, one of skill in the art can readily determine differences in the size or amount of polynucleotide-related MRNA transcripts between the two tissues using Northern blots and nucleotide probes selected from the nucleotide sequence shown in the Sequence Listing. Increased or decreased expression of an polynucleotide-related mRNA in a tissue sample suspected of being diseased, compared with the expression of the same polynucleotide-related mRNA in a normal tissue, suggests that the expressed protein has a role in the disease, and also provides a lead for preparing a therapeutic agent.

Any method for analyzing proteins is used to compare two polynucleotide-encoded proteins from matched samples. The sizes of the proteins in the two tissues are compared, for example, using antibodies of the present invention to detect polynucleotide-encoded proteins in Western blots of protein extracts from the two tissues. Other changes, such as expression levels and subcellular localization, can also be detected immunologically, using antibodies to the corresponding protein. A higher or lower level of polynucleotide-encoded protein expression in a tissue suspected of being diseased, compared with the same polynucleotide-encoded protein expression level in a normal tissue, is indicative that the expressed protein has a role in the disease, and provides another lead for preparing a therapeutic agent.

Similarly, comparison of polynucleotide gene sequences or of polynucleotide gene expression products, e.g., mRNA and protein, between a human tissue that is suspected of being diseased and a normal tissue of a human, are used to follow disease progression or remission in the human. Such comparisons of polynucleotide-related genes, mRNA, or protein are made as described above.

For example, increased or decreased expression of the polynucleotide-related gene in the tissue suspected of being neoplastic can indicate the presence of neoplastic cells in the tissue. The degree of increased expression of the polynucleotide gene in the neoplastic tissue relative to expression of the gene in normal tissue, or differences in the amount of increased expression of the polynucleotide gene in the neoplastic tissue over time, is used to assess the progression of the neoplasia in that tissue or to monitor the response of the neoplastic tissue to a therapeutic protocol over time. The expression pattern of any two cell types can be compared, such as low and high metastatic tumor cell lines, or cells from tissue which have and have not been exposed to a therapeutic agent.

Screening for Peptide Analogs and Antagonists

Polypeptides encoded by the instant polynucleotides and corresponding full length genes can be used to screen peptide libraries to identify binding partners, such as receptors, from among the encoded polypeptides.

Such binding partners can be useful in treating cancer, tumor progression, hyperproliferative cell growth, and/or accompanying biological or physical manifestations. For example, peptides or other compounds that are capable of binding or interacting with membrane-bound polypeptides encoded by one or more of SEQ ID NO: 1–339, can be useful as a therapeutic. Also, peptides or other compounds capable of altering the conformation of any of the encoded polypeptides by one or more of SEQ ID NO: 1–339 can inhibit biological activity and be useful as a therapeutic.

A library of peptides may be synthesized following the methods disclosed in U.S. Pat. No. 5,010,175, and in PCT WO91/17823.

Peptide agonists or antagonists are screened using any available method, such as signal transduction, antibody binding, receptor binding, mitogenic assays, chemotaxis assays, etc. The methods described herein are presently preferred. The assay conditions ideally should resemble the conditions under which the native activity is exhibited in vivo, that is, under physiologic pH, temperature, and ionic strength. Suitable agonists or antagonists will exhibit strong inhibition or enhancement of the native activity at concentrations that do not cause toxic side effects in the subject. Agonists or antagonists that compete for binding to the native polypeptide may require concentrations equal to or greater than the native concentration, while inhibitors capable of binding irreversibly to the polypeptide may be added in concentrations on the order of the native concentration.

The end results of such screening and experimentation will be at least one novel polypeptide binding partner, such as a receptor, encoded by a cDNA polynucleotide or gene of the invention, and at least one peptide agonist or antagonist of the novel binding partner. Such agonists and antagonists can be used to modulate, enhance, or inhibit receptor function in cells to which the receptor is native, or in cells that possess the receptor as a result of genetic engineering. Further, if the novel receptor shares biologically important characteristics with a known receptor, information about agonist/antagonist binding may help in developing improved agonists/antagonists of the known receptor.

Therapeutics, whether polynucleotide or polypeptide or small molecule, can be tested, for example, in the mouse tumor assay described in Pei et al., *Mol. Endo.* 11: 433–441 (1997).

Other models for testing polynucleotides, polypeptides, antibodies, or small molecules useful for treatment include: animal models and cell lines disclosed in Bosland, *Encyclopedia of Cancer*, Volume II, pages 1283 to 1296 (1997) by Academic Press. Other useful cell lines are described in Brothman, *Encyclopedia of Cancer*, Volume II, pages 1303 to 1313 (1997) by Academic Press Pharmaceutical Compositions and Therapeutic Uses Pharmaceutical compositions can comprise polypeptides, antibodies, or polynucleotides of the claimed invention. The pharmaceutical compositions will comprise a therapeutically effective amount of either polypeptides, antibodies, or polynucleotides of the claimed invention.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgment of the clinician. Specifically, the compositions of the present invention can be used to treat, ameliorate, modulate, or prevent cancer, tumor progression, hyperproliferative cell growth and/or accompanying biological or physical manifestations, including prostatic disorders.

For purposes of the present invention, an effective dose will be from about 0.01 mg/kg to 50 mg/kg or 0.05 mg/kg to about 10 mg/kg of the polynucleotide, polypeptide or antibody compositions in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in *Remington's Pharmaceutical Sciences* (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Delivery Methods

Once formulated, the polynucleotide compositions of the invention can be (1) administered directly to the subject; (2) delivered ex vivo, to cells derived from the subject; or (3) delivered in vitro for expression of recombinant proteins.

Direct delivery of the compositions will generally be accomplished by injection, either subcutaneously, intraperitoneally, intravenously or intramuscularly, or delivered to the interstitial space of a tissue. The compositions can also be administered into a tumor or lesion. Other modes of administration include oral and pulmonary administration, suppositories, and transdermal applications, needles, and gene guns or hyposprays. Dosage treatment may be a single dose schedule or a multiple dose schedule.

Methods for the ex vivo delivery and reimplantation of transformed cells into a subject are known in the art and described in e.g., International Publication No. WO 93/14778. Examples of cells useful in ex vivo applications include, for example, stem cells, particularly hematopoetic, lymph cells, macrophages, dendritic cells, or tumor cells.

Generally, delivery of nucleic acids for both ex vivo and in vitro applications can be accomplished by, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

If a polynucleotide-related gene correlates with a proliferative disorder, such as neoplasia, dysplasia, and hyperplasia, the disorder may be amenable to treatment by administration of a therapeutic agent based on the polynucleotide or corresponding polypeptide.

Preparation of antisense polypeptides is discussed above. Neoplasias that re treated with the antisense composition include, but are not limited to, cervical cancers, melanomas, colorectal adenocarcinomas, Wilms' tumor, retinoblastoma, sarcomas, myosarcomas, lung carcinomas, leukemias, such as chronic myelogenous leukemia, promyelocytic leukemia, monocytic leukemia, and myeloid leukemia, and lymphomas, such as histiocytic lymphoma. Proliferative disorders that are treated with the therapeutic composition include disorders such as anhydric hereditary ectodermal dysplasia, congenital alveolar dysplasia, epithelial dysplasia of the cervix, fibrous dysplasia of bone, and mammary dysplasia. Hyperplasias, for example, endometrial, adrenal, breast, prostate, or thyroid hyperplasias or pseudoepitheliomatous hyperplasia of the skin, are treated with antisense therapeutic compositions. Even in disorders in which mutations in the corresponding gene are not implicated, downregulation or inhibition of gene expression can have therapeutic application. For example, decreasing gene expression can help to suppress tumors in which enhanced expression of the gene is implicated.

Both the dose of the antisense composition and the means of administration are determined based on the specific qualities of the therapeutic composition, the condition, age, and weight of the patient, the progression of the disease, and other relevant factors. Administration of the therapeutic antisense agents of the invention includes local or systemic administration, including injection, oral administration, particle gun or catheterized administration, and topical administration. Preferably, the therapeutic antisense composition contains an expression construct comprising a promoter and a polynucleotide segment of at least 12, 22, 25, 30, or 35 contiguous nucleotides of the antisense strand. Within the expression construct, the polynucleotide segment is located downstream from the promoter, and transcription of the polynucleotide segment initiates at the promoter.

Various methods are used to administer the therapeutic composition directly to a specific site in the body. For example, a small metastatic lesion is located and the therapeutic composition injected several times in several different locations within the body of tumor. Alternatively, arteries which serve a tumor are identified, and the therapeutic composition injected into such an artery, in order to deliver the composition directly into the tumor. A tumor that has a necrotic center is aspirated and the composition injected directly into the now empty center of the tumor. The antisense composition is directly administered to the surface of the tumor, for example, by topical application of the composition. X-ray imaging is used to assist in certain of the above delivery methods.

Receptor-mediated targeted delivery of therapeutic compositions containing an antisense polynucleotide, subgenomic polynucleotides, or antibodies to specific tissues is also used. Receptor-mediated DNA delivery techniques are described in, for example, Findeis et al., Trends in Biotechnol. (1993) 11:202–205; Chiou et al., (1994) Gene Therapeutics: Methods And Applications Of Direct Gene Transfer (J. A. Wolff, ed.); Wu & Wu, J. Biol. Chem. (1988) 263:621–24; Wu et al., J. Biol. Chem. (1994) 269:542–46; Zenke et al., Proc. Natl. Acad. Sci. (USA) (1990) 87:3655–59; Wu et al., J. Biol. Chem. (1991) 266:339–42. Preferably, receptor-mediated targeted delivery of therapeutic compositions containing antibodies of the invention is used to deliver the antibodies to specific tissue.

Therapeutic compositions containing antisense subgenomic polynucleotides are administered in a range of about 100 ng to about 200 mg of polynucleotides for local administration in a gene therapy protocol. Concentration ranges of about 500 ng to about 50 mg, about 1 $\mu$g to about 2 mg, about 5 $\mu$g to about 500 $\mu$g, and about 20 $\mu$g to about 100 $\mu$g of polynucleotides can also be used during a gene therapy protocol. Factors such as method of action and efficacy of transformation and expression are considerations which will affect the dosage required for ultimate efficacy of the antisense subgenomic polynucleotides. Where greater expression is desired over a larger area of tissue, larger amounts of EST antisense subgenomic polynucleotides or the same amounts readministered in a successive protocol of administrations, or several administrations to different adjacent or close tissue portions of, for example, a tumor site, may be required to effect a positive therapeutic outcome. In all cases, routine experimentation in clinical trials will determine specific ranges for optimal therapeutic effect. A more complete description of gene therapy vectors, especially retroviral vectors, is contained in U.S. Ser. No. 08/869,309, which is expressly incorporated herein, and in section G below.

For genes encoding polypeptides or proteins with anti-inflammatory activity, suitable use, doses, and administration are described in U.S. Pat. No. 5,654,173, incorporated herein by reference. Therapeutic agents also include antibodies to proteins and polypeptides, as described in U.S. Pat. No. 5,654,173.

Gene Therapy

The therapeutic polynucleotides and polypeptides of the present invention may be utilized in gene delivery vehicles. The gene delivery vehicle may be of viral or non-viral origin (see generally, Jolly, Cancer Gene Therapy (1994) 1:51–64; Kimura, Human Gene Therpay (1994) 5:845–852; Connelly, Human Gene Therapy (1995) 1:185–193; and Kaplitt, Nature Genetics (1994) 6:148–153). Gene therapy vehicles for delivery of constructs including a coding sequence of a therapeutic of the invention can be administered either locally or systemically. These constructs can utilize viral or non-viral vector approaches. Expression of such coding sequences can be induced using endogenous mammalian or heterologous promoters. Expression of the coding sequence can be either constitutive or regulated.

The present invention can employ recombinant retroviruses which are constructed to carry or express a selected nucleic acid molecule of interest. Retrovirus vectors that can be employed include those described in EP 0 415 731; WO 90/07936; WO 94/03622; WO 93/25698; WO 93/25234; U.S. Pat. No. 5, 219,740; WO 93/11230; WO 93/10218; Vile and Hart, Cancer Res. (1993) 53:3860–3864; Vile and Hart, Cancer Res. (1993) 53:962–967; Ram et al., Cancer Res. (1993) 53:83–88; Takamiya et al., J. Neurosci. Res. (1992) 33:493–503; Baba et al., J. Neurosurg. (1993) 79:729–735; U.S. Pat. no. 4,777,127; GB Patent No. 2,200,651; and EP 0 345 242. Preferred recombinant retroviruses include those described in WO 91/02805.

Packaging cell lines suitable for use with the above-described retroviral vector constructs may be readily prepared (see PCT publications WO 95/30763 and WO 92/05266), and used to create producer cell lines (also termed vector cell lines) for the production of recombinant vector particles. Within particularly preferred embodiments of the invention, packaging cell lines are made from human (such as HT1080 cells) or mink parent cell lines, thereby allowing production of recombinant retroviruses that can survive inactivation in human serum.

The present invention also employs alphavirus-based vectors that can function as gene delivery vehicles. Such vectors can be constructed from a wide variety of alphaviruses, including, for example, Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532). Representative examples of such vector systems include those described in U.S. Pat. Nos.

5,091,309; 5,217,879; and 5,185,440; and PCT Publication Nos. WO 92/10578; WO 94/21792; WO 95/27069; WO 95/27044; and WO 95/07994.

Gene delivery vehicles of the present invention can also employ parvovirus such as adeno-associated virus (AAV) vectors. Representative examples include the AAV vectors disclosed by Srivastava in WO 93/09239, Samulski et al., *J. Vir.* (1989) 63:3822–3828; Mendelson et al., *Virol.* (1988) 166:154–165; and Flotte et al., *PNAS* (1993) 90:10613–10617.

Representative examples of adenoviral vectors include those described by Berkner, *Biotechniques* (1988) 6:616–627; Rosenfeld et al., *Science* (1991) 252:431–434; WO 93/19191; Kolls et al., *PNAS* (1994) 91:215–219; Kass-Eisler et al., *PNAS* (1993) 90:11498–11502; Guzman et al., *Circulation* (1993) 88:2838–2848; Guzman et al., *Cir. Res.* (1993) 73:1202–1207; Zabner et al., *Cell* (1993) 75:207–216; Li et al., *Hum. Gene Ther.* (1993) 4:403–409; Cailaud et al., *Eur. J. Neurosci.* (1993) 5:1287–1291; Vincent et al., *Nat. Genet.* (1993) 5:130–134; Jaffe et al., *Nat. Genet.* (1992) 1:372–378; and Levrero et al., *Gene* (1991) 101:195–202. Exemplary adenoviral gene therapy vectors employable in this invention also include those described in WO 94/12649, WO 93/03769; WO 93/19191; WO 94/28938; WO 95/11984 and WO 95/00655. Administration of DNA linked to killed adenovirus as described in Curiel, *Hum. Gene Ther.* (1992) 3:147–154 may be employed.

Other gene delivery vehicles and methods may be employed, including polycationic condensed DNA linked or unlinked to killed adenovirus alone, for example Curiel, *Hum. Gene Ther.* (1992) 3:147–154; ligand linked DNA, for example see Wu, *J. Biol. Chem.* (1989) 264:16985–16987; eukaryotic cell delivery vehicles cells, for example see U.S. Ser. No. 08/240,030, filed May 9, 1994, and U.S. Ser. No. 08/404,796; deposition of photopolymerized hydrogel materials; hand-held gene transfer particle gun, as described in U.S. Pat. No. 5,149,655; ionizing radiation as described in U.S. Pat. No. 5,206,152 and in WO92/11033; nucleic charge neutralization or fusion with cell membranes. Additional approaches are described in Philip, *Mol. Cell Biol.* (1994) 14:2411–2418, and in Woffendin, *Proc. Natl. Acad. Sci.* (1994) 91:1581–1585.

Naked DNA may also be employed. Exemplary naked DNA introduction methods are described in WO 90/11092 and U.S. Pat. No. 5,580,859.

Further non-viral delivery suitable for use includes mechanical delivery systems such as the approach described in Woffendin et al., *Proc. Natl. Acad. Sci.* USA (1994) 91(24):11581–11585.

Computer-Related Embodiments

In general, a library of polynucleotides is a collection of sequence information, which information is provided in either biochemical form (e.g., as a collection of polynucleotide molecules), or in electronic form (e.g., as a collection of polynucleotide sequences stored in a computer-readable form, as in a computer system and/or as part of a computer program). The sequence information of the polynucleotides can be used in a variety of ways, e.g., as a resource for gene discovery, as a representation of sequences expressed in a selected cell type (e.g., cell type markers), and/or as markers of a given disease or disease state. In general, a disease marker is a representation of a gene product that is present in all cells affected by disease either at an increased or decreased level relative to a normal cell (e.g., a cell of the same or similar type that is not substantially affected by disease).

The nucleotide sequence information of the library can be embodied in any suitable form, e.g., electronic or biochemical forms. For example, a library of sequence information embodied in electronic form comprises an accessible computer data file (or, in biochemical form, a collection of nucleic acid molecules) that contains the representative nucleotide sequences of genes that are differentially expressed (e.g., overexpressed or underexpressed) as between, for example, a cancerous cell and a normal cell. Biochemical embodiments of the library include a collection of nucleic acids that have the sequences of the genes in the library, where the nucleic acids can correspond to the entire gene in the library or to a fragment thereof, as described in greater detail below.

The polynucleotide libraries of the subject invention generally comprise sequence information of a plurality of polynucleotide sequences, where at least one of the polynucleotides has a sequence of any of SEQ ID NOs: 1–339. By plurality is meant at least 2, usually at least 3 and can include up to all of SEQ ID NOs: 1–339. The length and number of polynucleotides in the library will vary with the nature of the library, e.g., if the library is an oligonucleotide array, a cDNA array, a computer database of the sequence information, etc.

Where the library is an electronic library, the nucleic acid sequence information can be present in a variety of media. "Media" refers to a manufacture, other than an isolated nucleic acid molecule, that contains the sequence information of the present invention. Such a manufacture provides the genome sequence or a subset thereof in a form that can be examined by means not directly applicable to the sequence as it exists in a nucleic acid. For example, the nucleotide sequence of the present invention, e.g., the nucleic acid sequences of any of the polynucleotides of SEQ ID NOs:1–339, can be recorded on computer readable media, e.g., any medium that can be read and accessed directly by a computer. Such media include, but are not limited to: magnetic storage media, such as a floppy disc, a hard disc storage medium, and a magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present sequence information. "Recorded" refers to a process for storing information on computer readable medium, using any such methods as known in the art. Any convenient data storage structure can be chosen, based on the means used to access the stored information. A variety of data processor programs and formats can be used for storage, e.g., word processing text file, database format, etc. In addition to the sequence information, electronic versions of the libraries of the invention can be provided in conjunction or connection with other computer-readable information and/or other types of computer-readable files (e.g., searchable files, executable files, etc, including, but not limited to, for example, search program software, etc.).

By providing the nucleotide sequence in computer readable form, the information can be accessed for a variety of purposes. Computer software to access sequence information is publicly available. For example, the BLAST (Altschul et al., supra.) and BLAZE (Brutlag et al. *Comp. Chem.* (1993) 17:203) search algorithms on a Sybase system can be used to identify open reading frames (ORFs) within the genome that contain homology to ORFs from other organisms.

As used herein, "a computer-based system" refers to the hardware means, software means, and data storage means used to analyze the nucleotide sequence information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means can comprise any manufacture comprising a recording of the present sequence information as described above, or a memory access means that can access such a manufacture.

"Search means" refers to one or more programs implemented on the computer-based system, to compare a target sequence or target structural motif, or expression levels of a polynucleotide in a sample, with the stored sequence information. Search means can be used to identify fragments or regions of the genome that match a particular target sequence or target motif A variety of known algorithms are publicly known and commercially available, e.g., MacPattern (EMBL), BLASTN and BLASTX (NCBI). A "target sequence" can be any polynucleotide or amino acid sequence of six or more contiguous nucleotides or two or more amino acids, preferably from about 10 to 100 amino acids or from about 30 to 300 nt A variety of comparing means can be used to accomplish comparison of sequence information from a sample (e.g., to analyze target sequences, target motifs, or relative expression levels) with the data storage means. A skilled artisan can readily recognize that any one of the publicly available homology search programs can be used as the search means for the computer based systems of the present invention to accomplish comparison of target sequences and motifs. Computer programs to analyze expression levels in a sample and in controls are also known in the art.

A "target structural motif," or "target motif," refers to any rationally selected sequence or combination of sequences in which the sequence(s) are chosen based on a three-dimensional configuration that is formed upon the folding of the target motif, or on consensus sequences of regulatory or active sites. There are a variety of target motifs known in the art. Protein target motifs include, but are not limited to, enzyme active sites and signal sequences. Nucleic acid target motifs include, but are not limited to, hairpin structures, promoter sequences and other expression elements such as binding sites for transcription factors.

A variety of structural formats for the input and output means can be used to input and output the information in the computer-based systems of the present invention. One format for an output means ranks the relative expression levels of different polynucleotides. Such presentation provides a skilled artisan with a ranking of relative expression levels to determine a gene expression profile.

As discussed above, the "library" of the invention also encompasses biochemical libraries of the polynucleotides of SEQ ID NOs: 1–339, e.g., collections of nucleic acids representing the provided polynucleotides. The biochemical libraries can take a variety of forms, e.g., a solution of cDNAs, a pattern of probe nucleic acids stably associated with a surface of a solid support (i.e., an array) and the like. Of particular interest are nucleic acid arrays in which one or more of SEQ ID NOs: 1–339 is represented on the array. By array is meant a an article of manufacture that has at least a substrate with at least two distinct nucleic acid targets on one of its surfaces, where the number of distinct nucleic acids can be considerably higher, typically being at least 10 nt, usually at least 20 nt and often at least 25 nt. A variety of different array formats have been developed and are known to those of skill in the art. The arrays of the subject invention find use in a variety of applications, including gene expression analysis, drug screening, mutation analysis and the like, as disclosed in the above-listed exemplary patent documents.

In addition to the above nucleic acid libraries, analogous libraries of polypeptides are also provided, where the where the polypeptides of the library will represent at least a portion of the polypeptides encoded by SEQ ID NOs: 1–339.

The present invention will now be illustrated by reference to the following examples which set forth particularly advantageous embodiments. However, it should be noted that these embodiments are illustrative and are not to be construed as restricting the invention in any way.

EXAMPLES

Example 1

ISOLATION OF THE POLYNUCLEOTIDES cDNA libraries were prepared from PrEC, normal human prostate epithelial cells, and LNCaP, a cell line derived from human lymph node metastasized prostate cancer. PrEC cells are available from Clonetics, San Diego, Calif., U.S.A. LNCaP cells are available from the ATCC, Manassas, Va., U.S.A.

Using a PCR technique and reagents available from Clontech, Palo Alto, Calif., USA (CLONTECH PCR-Select™), mRNA up-regulated in LNCaP was captured and amplified. The captured polynucleotide inserts were inserted in the pCR2. 1 vector, available from Invitrogen, Carlsbad, Calif., U.S.A. The vectors with the inserts were transformed into *E. coli* cells.

Example 2

CONFIRMATION OF DIFFERENTIAL DISPLAY

Ten clones were chosen at random, and up-regulation of the sequences of these clone inserts in LNCaP versus PrEC cells was confirmed by Northern blot. Dot blots were performed on 168 clones and up-regulation was confirmed.

Further, sequencing of the clones showed that prostate specific antigen (PSA) and prostate specific membrane antigen (PSMA) sequences were isolated by the process described in Example 1. A good correlation between increased serum PSA levels and prostate tumors has been observed. PSMA, a cell surface antigen, is another observed marker for prostate cancer. See Bosland, Encyclopedia of Cancer, Volume II, pages 1283–1296 (1997), Academic Press. Thus, the data confirm that up-regulated MRNA characteristic of gene expression in prostate cancer was cloned by the method of Example 1.

Example 3

POLYNUCLEOTIDE SEQUENCES

The sequence results are shown in SEQ ID NO:1–339. For the sequencing experiments, each clone was named SL-1 to SL-209. Inserts from some of the clones were sequenced more than once. Each sequence was designated a unique combination of two names. This unique combination is shown in Table 1 in columns 2 and 3, denoted as "Sequence Name" and "Other Seq Name."

Table 1 indicates all the sequences that correspond to each clone. Thus, all the sequences corresponding to clone SL-3, for example, are grouped together in Table 1.

Clones also were assigned cluster numbers. See column 4 of Table 1. Clones with the same cluster number generally comprise sequence derived from the same mRNA transcripts.

The last column of Table 1 indicates the nearest neighbor as determined by an alignment to sequences in a publicly available database.

A consensus for the sequence of each clone can be constructed by aligning the corresponding sequences or reverse complements thereof Table 1 lists the names of all the sequences that correspond to each clone, and Table 2 shows the specific sequence that corresponds to each unique combination of Sequence Name and/or "Other Seq. Name."

The entire insert of some clones may not be represented by the sequences presented in Table 2. For example, the 5' and 3' ends of a clone insert may have been sequenced, but the sequences do not overlap. Additional sequence corresponding to the clone insert can be isolated and determined by constructing probes or primers from the sequences presented in Table 2 and a library of mRNA or cDNA from a prostate cell or prostate cancer cell line using the methods described above.

Example 4

RESULTS OF PUBLIC DATABASE SEARCH

Both the nucleotide sequence and translations of masked sequences shown in the Sequence Listing were aligned with individual sequences that were publicly available. Similarity with individual sequences is used to determine the activity of the polypeptides encoded by genes corresponding to the sequences referred to in Table 2.

The sequences in SEQ ID NO: 1–333 first were masked to remove the pCR2. 1 vector sequences. Masking was performed by aligning the pCR2. 1 sequences with each of SEQ ID NO:1–333 using the BLASTN program. Any sequence that produced an alignment with a score of less that 0.1 was masked.

A BLASTN vs. Genbank search was performed using the masked sequences with search parameters of greater than 99% overlap, 99% identity, and a p value of less than $1 \times 10^{-40}$ and this resulted in discard of sequences. Sequences from this search also were discarded if the inclusive parameters were met, but the sequence was ribosomal or vector-derived.

The resulting sequences from the previous search were classified into three groups (1, 2 and 3 below) and searched in a BLASTX vs. NRP (non-redundant proteins) database search: (1) unknown (no hits in the Genbank search), (2) weak similarity (greater than 45% identity and p value of less than $1 \times 10^{-5}$), and (3) high similarity (greater than 60% overlap, greater than 80% identity, and p value less than $1 \times 10^{-5}$). This search resulted in discard of sequences as having greater than 99% overlap, greater than 99% identity, and p value of less than $1 \times 10^{-40}$.

The remaining sequences were classified as unknown (no hits), weak similarity, and high similarity (parameters as above). Two searches were performed on this set of sequences. First, a BLAST vs. EST database search resulted in discard of sequences with greater than 99% overlap, greater than 99% similarity and a p value of less than $1 \times 10^{-40}$; sequences with a p value of less than $1 \times 10^{-65}$ when compared to a database sequence of human origin were also excluded. Second, a BLASTN vs. Patent GeneSeq database resulted in discard of sequences with greater than 99% identity; p value less than $1 \times 10^{-40}$; greater than 99% overlap.

The masked sequences were translated in all six reading frames to determine the best alignment with the individual sequences. These amino acid sequences and nucleotide sequences are referred, generally, as query sequences, which are aligned with the individual sequences.

Query and individual sequences were aligned using the BLAST programs, available over the world wide web.

Table 2 shows the results of the alignments. Table 2 refers to each sequence by its Sequence Name and/or "Other Seq. Name" and includes the accession numbers and descriptions of nearest neighbors from the Genbank and Non-Redundant Protein searches.

The activity of the polypeptide encoded by the sequences referred to in Table 2 is expected to be the same or similar to the nearest neighbor reported in Table 2. The accession number of the nearest neighbor is reported, providing a reference to the activities exhibited by the nearest neighbor. The search program and database used for the alignment also are indicated as well as a calculation of the p value.

Full length sequences or fragments of the polynucleotide sequences of the nearest neighbors can be used as probes and primers to identify and isolate the full length sequence corresponding to sequence referred to in Table 2. Although full length sequences can be obtained from the cell lines described above, the nearest neighbors can indicate a tissue or cell type to be used to construct a library for the full-length sequences of those referred to in Table 2.

The sequences referred to in Table 2 and the translations thereof may be human homologs of known genes of other species or novel allelic variants of known human genes. In such cases, these new human sequences may be suitable as diagnostics, prognostics, or therapeutics. As diagnostics, the human sequences exhibit greater specificity in detecting and differentiating human cell lines and types than homologs of other species. The human polypeptides are less likely to be immunogenic when administered to humans than homologs from other species. Further, on administration to humans, the encoded polypeptides can show greater specificity or can be better regulated by other human proteins than are homologs from other species.

In the preferred embodiments of the invention, the sequences shown in SEQ ID NO:1–339 consisting of the unmasked regions should be considered as the source of probes and primers, as these sequences are most representative of the distinguishing portions of these polynucleotides.

Generally, the masking itself does not influence the search results as shown in Table 2, except to eliminate multiple "hits" based on similarity to repetitive regions common to more than one polypeptide.

Example 5

ANALYSIS OF CLONES SL-5, SL-9, SL-68, AND SL-173

Clone SL-5 (SEQ ID NO: 14 and 334)

By Northern Blot, a 4.1 kb band was observed in expressed in normal prostate, testis,and lymphoblasic leukemia. It was also expressed in the cell lines LNCaP, and MDA PCa 2A and 2B (metastatic prostate cells into bone, androgen sensitive). Additional sequence corresponding to SEQ ID NO: 14 is disclosed in SEQ ID NO:334.

Expression of SL-5 was investigated in normal and tumor tissues using immunohistochemistry. Antibody was prepared using two sequences from clone SL-5: $H_2N$-CGPRLPSFPCPTHEPSTGQLSK-CONH$_2$ (SEQ ID NO:

340) and H$_2$N-CKDSQGLSDFKRNSRTTR-RSYKCCONH$_2$ (SEQ ID NO: 341). Using polyclonal antibodies raised against a mixture of these polypeptides, immunohistochemistry (IHC) was performed on a variety of tumor tissues and corresponding normal tissue. The methods used were those described for the Manual IHC Protocol using BioGenex Reagents and Zymed AEC Solution, as known in the art. As shown in FIG. 3, SL-5 was detected in the following tumor tissue: adrenal, ovary, breast, colon, prostate, uterus, cervix, kidney, pancreas, liver, stomach, lymphoma, seminoma, thyroid, melanoma, basal cell carcinoma, and other tumor tissues. Where comparative normal tissue was available, expression in the corresponding normal tissue was lower than in the tumor tissue. Thus, SL-5 is a useful marker for cancer tissue including prostate.

Clone SL-9 (SEQ ID NO: 18)

By Northern Blot, sequences from SL-9 were specifically expressed in normal spleen and normal peripheral blood leukocyte. Expression of the SL-9 sequences was observed also in promyelocytic leukemia HL-60, chronic mylogenous leukemia K-562, lymphoblastic leukemia MOLT-4, Burkitt's lymphoma, and Raji cancer cell lines by Northern Blot.

Clone SL-173 (SEQ ID NO: 153 and 154)

By Northern Blot, SL173 was found in every cancer cell line tested. Sequence from SL-173 has similarity to and may be a human homologue of the rat tumor transforming gene, which was found in the pituitary and described in Pei et al., *Mol. Endo.* 11: 433–441 (1997) and Pei, *J. Biol. Chem.* 273(9): 5219–5225 (1998). When the rat tumor transforming gene was injected in NIH3T3cells, the cells became transformed and were able to form a tumor when injected into mice. (Pei et al., *Mol. Endo.* supra).

Clone SL-68 (SEQ ID NO:218 and 219)

Two transcripts, 2.6 kb and 4.3 kb, were observed in normal spleen, thymus and peripheral blood leukocytes, as well as in promyelocytic leukemia, chronic myelogenous leukemia and lymphoblastic leukemia. The 4.3 kb transcript was seen in normal testis, colon, Hela cell S3, colorectal adenocarcinoma and melanoma. The 2.6 kb band was found in the following prostate cell lines: PC-3 (metastatic to bone, androgen insensitive); DU-145 (metastatic to brain, androgen insensitive); FFpz (primary cells derived from normal prostate epithelium); Ffca (primary cells derived from Gleason Grade 3 prostate cancer epithelium); and WO-CA (primary cells derived from Gleason Grade 4 prostate cancer epithelium). However, higher expression was observed in LNCaP, MDA PCa 2A, HPV-7 and HPV-10. A 9.5 kb transcript was also observed in MDA PCa 2A and 2B. Additional sequence corresponding to this clone is disclosed in SEQ ID NO:335.

Clone SL69 (SEQ ID NO:220 and 221)

A weak 2.6 kb band was observed in normal testis as well as in chronic myelogenous leukemia and lymphoblastic leukemia. Additional sequence corresponding to this clone is disclosed in SEQ ID NO:336.

Clone SL86 (SEQ ID NO:242 and 243)

The sequence was expressed in normal prostate (2.7 kb and 1.1 kb) and testis (1.1 kb). Low expression was observed in a cancer cell line blot using the cell lines described above. 1.1 kb and 2.7 kb transcripts were observed in the cell lines LNCaP, and MDA PCa 2a and 2b (metastatic prostate cells into bone, androgen sensitive), and weak 1.1 kb transcript was seen in HPV-7 (immortalized normal prostate cells) and BPV-10 (immortalized prostate cancer cells). Additional sequence corresponding to this clone is disclosed in SEQ ID NO:337.

Clone SL195 (SEQ ID NO:288 and 289)

The sequence was expressed in normal prostate as a 1.9 kb transcript, and the same transcript also observed in all cell lines in the cancer cell line blot described above. It was more heavily expressed in HeLa cell S3 and chronic myelogenous leukemia, and was expressed in all prostate cell lines. Additional sequence corresponding to this clone is disclosed in SEQ ID NO:338.

Clone SL197 (SEQ ID NO:292 and 293)

Two transcripts, 2.4 kb and 4 kb, were observed in normal prostate and testis. Two very weak 2.4 kb signals were observed in Hela cell S3 and chronic myelogenous leukemia. The 2.4 kb transcript was expressed in all prostate cell lines. A 4kb transcript was found in LNCaP, MDA PCa 2A and 2B. Additional sequence corresponding to this clone is disclosed in SEQ ID NO:339.

Those skilled in the art will recognize, or be able to ascertain, using not more than routine experimentation, many equivalents to the specific embodiments of the invention described herein. Such specific embodiments and equivalents are intended to be encompassed by the following claims.

All patents, published patent applications and publications cited herein are incorporated by reference as if set forth fully herein.

TABLE 1

| Clone # | Sequence Name | Other Seq Name | Clone # Cluster # | Nearest Neighbor If Available |
|---|---|---|---|---|
| SL-001 | SL001 | 19sl1 | SL-001 | S60754 {VNTR locus DXZ4} |
|  | SL001M13 |  |  |  |
| SL-002 | SL002 | 20sl2 | SL-002 | L07935 HUMVNTRA |
| SL-003 | SL003 | 21sl3 | SL-003 | AB006625 - KIAA0287 gene |
|  | SL003 | 35-sl3-1m13 |  |  |
|  | SL003 | 35-sl3-1t7 |  |  |
|  | SL003 | 37-sl3-1m13 |  |  |
|  | SL003 | 39-sl3-1m13 |  |  |
| SL-004 | SL004 | 22sl4 | SL-004 |  |
|  | SL004M13 |  |  |  |
| SL-005 | SL005 | 23sl5 | SL-005 |  |
|  | SL005 | 30sl11b |  |  |
| SL-006 | SL006 | 24sl6 | SL-006 |  |
|  | SL006M13 |  |  | cosmid genomic clone |
| SL-007 | SL007 | 25sl7 | SL-003 | AB006625- KIAA0287 |
|  | SL007 | 28-sl7-1m13 |  |  |
|  | SL007 | 28-sl7-1t7 |  |  |

TABLE 1-continued

| Clone # | Sequence Name | Other Seq Name | Clone # Cluster # | Nearest Neighbor If Available |
|---|---|---|---|---|
| | SL007 | 30-sl7-1m13 | | |
| | SL007 | 30-sl7-1t7 | | |
| | SL007 | 32-sl7-1m13 | | |
| | SL007 | 32-sl7-1t7 | | |
| SL-008 | SL008 | 26sl8 | SL-008 | HUMP65 E=9e-62 |
| | | | | L-plastin, Phosphoprotein (p65) |
| SL-009 | SL009 | 27sl9 | | |
| | SL009M13 | | | |
| SL-010 | SL010 | 28sl10 | SL-005 | |
| SL-011 | SL011 | 29sl11a | SL-011 | HSU10685 - MAGE-10 Gene |
| SL-012 | SL012 | 31sl12 | SL-011 | HSU10685 - MAGE-10 Gene |
| SL-013 | SL013 | 32sl13 | | |
| SL-015 | SL015 | 34sl15 | SL-015 | HSU90336 - PEG3 mRNA |
| | SL015 | 46-sl15-2m13 | | |
| | SL015 | 47-sl15-2m13 | | HSMRNAEN - Enkephalinase |
| | SL015 | 47-sl15-2t7 | | |
| SL-016 | SL016 | 10-sl16-1m13 | SL-016 | |
| | SL016 | 10-sl16-1t7 | | |
| | SL016 | 11-sl16-1m13 | | |
| | SL016 | 18-sl16-2m13 | | |
| | SL016 | 18-sl16-2t7 | | |
| | SL016 | 19-sl16-2m13 | | |
| | SL016 | 19-sl16-2t7 | | |
| | SL016 | 20-sl16-2m13 | | |
| | SL016 | 20-sl16-2t7 | | |
| | SL016 | 35sl16 | | |
| | SL016 | 9-sl16-1t7 | | |
| SL-017 | SL017 | 36sl17 | SL-017 | HUMORF01 - KIAA0101 gene |
| SL-028 | SL028m13 | B1 | SL-028 | |
| | SL028t7 | B1 | | |
| SL-029 | SL029m13 | WE97.C1.M13 | SL-029 | |
| | SL029t7 | WE97.C1.T7 | | |
| SL-032 | SL032m13 | WE97.D1.M13 | SL-032 | HSTPI1G TPI1 gene |
| | SL032t7 | WE97.D1.T7 | | for triosephosphate isomerase. |
| SL-036 | SL036m13 | WE97.E1.M13 | SL-036 | HSU81599 homeodomain protein |
| | SL036t7 | WE97.E1.T7 | | HOXB13 |
| SL-037 | SL037m13 | C1 | SL-005 | |
| | SL037m13 | WE97.F1.M13 | | |
| | SL037t7 | C1 | | |
| SL-040 | SL040m13 | D1 | SL-040 | |
| | SL040t7 | D1 | | |
| SL-041 | SL041m13 | E1 | SL-016 | |
| | SL041m13 | WE97.H1.M13 | | |
| | SL041t7 | E1 | | |
| | SL041t7 | WE97.H1.T7 | | |
| SL-042 | SL042m13 | WE97.A2.M13 | SL-008 | HUMP65 phosphoprotein (p65) |
| | SL042t7 | WE97.A2.T7 | | HUMPLASTA L-plastin gene |
| SL-044 | SL044m13 | WE97.B2.M13 | SL-016 | |
| | SL044t7 | WE97.B2.T7 | | |
| SL-045 | SL045m13 | WE97.C2.M13 | SL-045 | |
| | SL045t7 | WE97.C2.T7 | | genomic DNA |
| SL-046 | SL046m13 | WE97.D2.M13 | SL-046 | |
| | SL046t7 | WE97.D2.T7 | | |
| SL-047 | SL047m13 | WE97.E2.M13 | SL-047 | |
| | SL047t7 | WE97.E2.T7 | | |
| SL-050 | SL050m13 | WE97.F2.M13 | SL-050 | |
| | SL050t7 | WE97.F2.T7 | | |
| SL-051 | SL051m13 | WE97.G2.M13 | SL-051 | |
| | SL051t7 | WE97.G2.T7 | | |
| SL-054 | SL054m13 | WE97.H2.M13 | SL-054 | |
| | SL054t7 | WE97.H2.T7 | | |
| SL-055 | SL055m13 | F1 | SL-050 | |
| | SL055t7 | F1 | | |
| | SL055t7 | WE97.A3.T7 | | |
| SL-057 | SL057m13 | WE97.C3.M13 | SL-057 | |
| | SL057t7 | WE97.C3.T7 | | |
| SL-058 | SL058m13 | WE97.D3.M13 | SL-058 | HSLRPR1GN leucine-rich primary |
| | SL058t7 | WE97.D3.T7 | | response protein 1. |
| SL-061 | SL061m13 | WE97.E3.M13 | SL-028 | |
| | SL061t7 | WE97.E3.T7 | | |
| SL-062 | SL062m13 | WE97.F3.M13 | SL-028 | |
| | SL062t7 | WE97.F3.T7 | | |
| SL-064 | SL064m13 | WE97.G3.M13 | SL-064 | |
| | SL064t7 | WE97.G3.T7 | | |
| SL-066 | SL066m13 | WE97.H3.M13 | SL-016 | |
| | SL066t7 | WE97.H3.T7 | | |

TABLE 1-continued

| Clone # | Sequence Name | Other Seq Name | Clone # Cluster # | Nearest Neighbor If Available |
|---|---|---|---|---|
| SL-067 | SL067m13<br>SL067t7<br>SL067t7 | H1<br>H1<br>WE97.A4.T7 | SL-067 | HUMKIAAP - KIAA0095 gene |
| SL-068 | SL068m13<br>SL068t7 | WE97.B4.M13<br>WE97.B4.T7 | SL-068 | |
| SL-069 | SL069m13<br>SL069t7 | WE97.C4.M13<br>WE97.C4.T7 | SL-069 | |
| SL-071 | SL071m13<br>SL071t7 | WE97.D4.M13<br>WE97.D4.T7 | SL-071 | |
| SL-072 | SL072m13<br>SL072t7 | WE97.E4.M13<br>WE97.E4.T7 | SL-015 | HSU90336 Human PEG3 mRNA<br>AB006625 KIAA0287 |
| SL-074 | SL074m13<br>SL074t7 | WE97.F4.M13<br>WE97.F4.T7 | SL-074 | |
| SL-075 | SL075m13<br>SL075t7 | WE97.G4.M13<br>WE97.G4.T7 | SL-075 | |
| SL-076 | SL076m13<br>SL076t7 | WE97.H4.M13<br>WE97.H4.T7 | SL-076 | |
| SL-077 | SL077m13<br>SL077t7 | WE97.A5.M13<br>WE97.A5.T7 | SL-077 | |
| SL-078 | SL078m13<br>SL078m13<br>SL078t7 | A2<br>WE97.B5.M13<br>A2 | SL-016 | BAC clone (with Alu) |
| SL-081 | SL081m13<br>SL081t7 | WE97.E5.M13<br>WE97.E5.T7 | SL-003 | AB006625 - KIAA0287 gene |
| SL-083 | SL083m13<br>SL083t7 | WE97.G5.M13<br>WE97.G5.T7 | SL-083 | |
| SL-084 | SL084m13<br>SL084t7 | WE97.H5.M13<br>WE97.H5.T7 | SL-084 | (HS295C6 Human DNA sequence) |
| SL-085 | SL085m13 | WE97.A6.M13 | SL-085 | |
| SL-086 | SL086m13<br>SL086t7 | WE97.B6.M13<br>WE97.B6.T7 | SL-086 | |
| SL-087 | SL087m13<br>SL087t7 | WE97.C6.M13<br>WE97.C6.T7 | SL-087 | EST and Mus musculus<br>ras-GTPase-activating protein |
| SL-088 | SL088m13<br>SL088t7 | WE97.D6.M13<br>WE97.D6.T7 | SL-015 | HSU90336 Human PEG3<br>& AB006625 - KIAA0287 gene |
| SL-089 | SL089m13<br>SL089t7 | WE97.E6.M13<br>WE97.E6.T7 | SL-089 | |
| SL-090 | SL090m13<br>SL090t7 | D2<br>D2 | SL-090 | |
| SL-091 | SL091m13<br>SL091t7 | WE97.G6.M13<br>WE97.G6.T7 | SL-091 | |
| SL-092 | SL092m13<br>SL092t7 | WE97.H6.M13<br>WE97.H6.T7 | SL-092 | HUMPRKACB testis-specific<br>cAMP-dependent protein kinase<br>catalytic subunit (C-beta isoform) |
| SL-093 | SL093m13<br>SL093t7 | E2<br>E2 | SL-008 | HUMLPLSTN2 L-plastin gene |
| SL-094 | SL094m13<br>SL094t7 | WE97.B7.M13<br>WE97.B7.T7 | SL-094 | |
| SL-095 | SL095m13<br>SL095t7 | WE97.C7.M13<br>WE97.C7.T7 | SL-003 | AB006625 - KIAA0287 |
| SL-096 | SL096m13<br>SL096t7 | WE97.D7.M13<br>WE97.D7.T7 | SL-096 | |
| SL-097 | SL097m13<br>SL097t7 | | SL-071 | |
| SL-098 | SL098m13<br>SL098t7 | | SL-098 | |
| SL-099 | SL099m13<br>SL099t7 | | SL-016 | |
| SL-100 | SL100m13<br>SL100m13<br>SL100t7<br>SL100t7 | F2<br>F2 | SL-085 | SL100m13 Alu - 2e-71 |
| SL-102 | SL102m13<br>SL102t7 | | SL-102 | HSRPL32 ribosomal protein L32 |
| SL-103 | SL103m13<br>SL103t7 | | SL-103 | |
| SL-105 | SL105m13<br>SL105t7 | | SL-105 | |
| SL-106 | SL106m13<br>SL106t7 | | SL-106 | |
| SL-107 | SL107m13<br>SL107t7 | | SL-016? | SL107m13 -Alu - 2e-78 |
| SL-110 | SL110m13<br>SL110t7 | | SL-003 | AB006625- KIAA0287 gene |
| SL-111 | SL111m13<br>SL111t7 | | SL-111 | |

TABLE 1-continued

| Clone # | Sequence Name | Other Seq Name | Clone # Cluster # | Nearest Neighbor If Available |
|---|---|---|---|---|
| SL-112 | SL112m13<br>SL112t7 | | SL-112 | |
| SL-115 | SL115m13<br>SL115t7 | | SL-115 | D86322 - calmegin |
| SL-116 | SL116m13<br>SL116t7 | | SL-116 | |
| SL-117 | SL117m13<br>SL117t7 | | SL-117 | HUMNUMB23 = HUMNPM<br>Human nucleolar protein (B23)<br>or Human nucleophosmin |
| SL-118 | SL118m13<br>SL118t7 | | SL-118 | |
| SL-119 | SL119m13<br>SL119t7 | | SL-119 | |
| SL-120 | SL120m13<br>SL120t7 | | SL-046 | |
| SL-121 | SL121m13<br>SL121t7 | | SL-016 | |
| SL-122 | SL122m13<br>SL122t7 | | SL-122 | HUMPRKACB testis-specific<br>cAMP-dependent protein kinase<br>catalytic subunit (C-beta isoform) |
| SL-124 | SL124m13<br>SL124t7 | | SL-016 | |
| SL-125 | SL125m13<br>SL125t7 | | SL-125 | HSU19145 GAGE-4<br>(U.S. Pat. No. 5,648,226) |
| SL-127 | SL127m13<br>SL127t7 | | SL-127 | |
| SL-128 | SL128m13<br>SL128t7 | | SL-005 | |
| SL-130 | SL130m13<br>SL130t7 | | SL-130 | |
| SL-132 | SL132m13<br>SL132t7 | | SL-011 | HSU10685 MAGE-10 gene<br>(U.S. Pat. No. 5,612,201) |
| SL-134 | SL134m13<br>SL134t7 | | SL-134 | HSC70P Hsc 70 pseudogene<br>(Heat Shock protein) |
| SL-135 | SL135m13<br>SL135t7 | | SL-135 | |
| SL-138 | SL138m13<br>SL138t7 | | SL-051 | |
| SL-139 | SL139m13<br>SL139t7 | | SL-139 | Homo sapiens cosmid |
| SL-142 | SL142m13<br>SL142t7 | | SL-005 | |
| SL-143 | SL143m13<br>SL143t7 | | SL-143 | Genomic clone<br>AC003978 |
| SL-144 | SL144m13<br>SL144t7 | | SL-144 | E= 3-81 |
| SL-145 | SL145m13 | | SL-003 | AB006625- KIAA0287 gene |
| SL-146 | SL146m13<br>SL146t7 | WE97.E7.M13<br>WE97.E7.T7 | SL-146 | |
| SL-147 | SL147m13<br>SL147m13<br>SL147t7 | G2<br>WE97.F7.M13<br>G2 | SL-147 | (1) HSCDC2R Human cell cycle<br>control gene CDC2<br>(2) HSU29091 selenium-binding |
| SL-148 | SL148m13<br>SL148t7 | WE97.G7.M13<br>WE97.G7.T7 | SL-016 | |
| SL-149 | SL149m13<br>SL149t7 | H2<br>H2 | SL-149 | |
| SL-150 | SL150m13<br>SL150t7 | A3<br>A3 | SL-150 | "Human DNA sequence" |
| SL-151 | SL151m13<br>SL151t7 | WE97.B8.M13<br>WE97.B8.T7 | SL-151 | Genomic frag |
| SL-152 | SL152m13<br>SL152t7 | WE97.C8.M13<br>WE97.C8.T7 | SL-152 | |
| SL-153 | SL153m13<br>SL153t7 | WE97.D8.M13<br>WE97.D8.T7 | SL-153 | |
| SL-154 | SL154t7 | WE97.E8.T7 | SL-154 | HUMPAR5R - PAR-5 mRNA |
| SL-155 | SL155m13<br>SL155t7 | WE97.F8.M13<br>WE97.F8.T7 | SL-028 | SL155m13 - EST only in Mouse |
| SL-156 | SL156m13<br>SL156t7 | WE97.G8.M13<br>WE97.G8.T7 | SL-016 | |
| SL-157 | SL157m13<br>SL157t7 | WE97.H8.M13<br>WE97.H8.T7 | SL-157 | |
| SL-158 | SL158m13<br>SL158t7 | WE97.A9.M13<br>WE97.A9.T7 | SL-011 | HSU10685 MAGE-10 gene<br>(U.S. Pat. No. 5,612,201) |
| SL-159 | SL159m13<br>SL159t7 | WE97.B9.M13<br>WE97.B9.T7 | SL-159 | Chromosome 11 pac |

TABLE 1-continued

| Clone # | Sequence Name | Other Seq Name | Clone # Cluster # | Nearest Neighbor If Available |
|---|---|---|---|---|
| SL-160 | SL160m13 | WE97.C9.M13 | SL-051 | |
| | SL160t7 | WE97.C9.T7 | | |
| SL-161 | SL161m13 | WE97.D9.M13 | SL-161 | HUMP65 phosphoprotein (p65) |
| | SL161t7 | WE97.D9.T7 | | HUMPLASTA L-plastin gene |
| SL-162 | SL162m13 | B3 | SL-162 | |
| | SL162t7 | B3 | | |
| SL-163 | SL163m13 | WE97.F9.M13 | SL-016 | HSU75330 -NCAM21 |
| | SL163t7 | WE97.F9.T7 | | |
| SL-164 | SL164m13 | WE97.G9.M13 | SL-016 | |
| | SL164t7 | WE97.G9.T7 | | |
| SL-165 | SL165m13 | WE97.H9.M13 | SL-165 | |
| | SL165t7 | WE97.H9.T7 | | (genomic seq) |
| SL-166 | SL166m13 | C3 | SL-166 | |
| | SL166t7 | C3 | | |
| | SL166t7 | WE97.A10.T7 | | |
| SL-167 | SL167m13 | WE97.B10.M13 | SL-167 | HUMLPACI09 lipoprotein-associated |
| | SL167t7 | WE97.B10.T7 | | coagulation inhibitor (LACI) gene |
| SL-168 | SL168m13 | WE97.C10.M13 | SL-168 | |
| | SL168t7 | WE97.C10.T7 | | |
| SL-169 | SL169m13 | WE97.D10.M13 | SL-169 | HUMNEUROF oligodendrocyte |
| | SL169t7 | WE97.D10.T7 | | myelin glycoprotein (OMG) |
| SL-170 | SL170m13 | WE97.E10.M13 | SL-170 | |
| | SL170t7 | WE97.E10.T7 | | |
| SL-171 | SL171m13 | WE97.F10.M13 | SL-171 | AB002374 - KIAA0376 gene |
| | SL171t7 | WE97.F10.T7 | | |
| SL-172 | SL172m13 | WE97.G10.M13 | SL-016 | |
| | SL172t7 | WE97.G10.T7 | | |
| SL-173 | SL173m13 | WE97.H10.M13 | SL-173 | |
| | SL173t7 | WE97.H10.T7 | | |
| SL-174 | SL174m13 | D3 | SL-174 | |
| | SL174t7 | D3 | | |
| SL-175 | SL175m13 | WE97.B11.M13 | SL-016 | |
| | SL175t7 | WE97.B11.T7 | | |
| SL-176 | SL176m13 | WE97.C11.M13 | SL-176 | |
| | SL176t7 | WE97.C11.T7 | | |
| SL-177 | SL177m13 | WE97.D11.M13 | SL-177 | |
| | SL177t7 | WE97.D11.T7 | | |
| SL-178 | SL178m13 | WE97.E11.M13 | SL-178 | |
| | SL178t7 | WE97.E11.T7 | | Human BAC clone |
| SL-179 | SL179m13 | WE97.F11.M13 | SL-179 | |
| | SL179t7 | WE97.F11.T7 | | |
| SL-181 | SL181m13 | WE97.H11.M13 | SL-181 | |
| | SL181t7 | WE97.H11.T7 | | |
| SL-182 | SL182m13 | F3 | SL-182 | HUMAPEA apurinic/apyrimidinic |
| | SL182m13 | WE97.A12.M13 | | endonuclease (HAP1h) |
| | SL182t7 | F3 | | HSHAP1MR Human HAP1 mRNA |
| SL-183 | SL183m13 | WE97.B12.M13 | SL-046 | |
| | SL183t7 | WE97.B12.T7 | | |
| SL-184 | SL184m13 | WE97.C12.M13 | SL-016 | |
| | SL184t7 | WE97.C12.T7 | | |
| SL-186 | SL186m13 | WE97.D12.M13 | SL-186 | |
| | SL186t7 | WE97.D12.T7 | | |
| SL-187 | SL187m13 | WE97.E12.M13 | SL-187 | |
| | SL187t7 | WE97.E12.T7 | | |
| SL-188 | SL188m13 | G3 | SL-188 | |
| | SL188t7 | G3 | | |
| | SL188t7 | WE97.F12.T7 | | |
| SL-191 | SL191m13 | WE97.H12.M13 | SL-181 | |
| | SL191t7 | WE97.H12.T7 | | |
| SL-192 | SL192m13 | H3 | SL-192 | |
| | SL192t7 | H3 | | "Human DNA sequence" |
| SL-193 | SL193m13 | A4 | SL-193 | |
| | SL193t7 | A4 | | |
| SL-194 | SL194m13 | B4 | SL-194 | HUMKG1DD - KIAA0098 gene |
| | SL194t7 | B4 | | |
| SL-195 | SL195m13 | C4 | SL-195 | |
| | SL195t7 | C4 | | |
| SL-196 | SL196m13 | D4 | SL-196 | HUMMAOAAA monoamine oxidase |
| | SL196t7 | D4 | | (MAOA) |
| SL-197 | SL197m13 | E4 | SL-197 | |
| | SL197t7 | E4 | | |
| SL-198 | SL198m13 | F4 | SL-198 | |
| | SL198t7 | F4 | | |
| SL-199 | SL199m13 | G4 | SL-016 | |
| | SL199t7 | G4 | | |

TABLE 1-continued

| Clone # | Sequence Name | Other Seq Name | Clone # Cluster # | Nearest Neighbor If Available |
|---|---|---|---|---|
| SL-201 | SL201m13<br>SL201t7 | A5<br>A5 | SL-028 | |
| SL-202 | SL202m13<br>SL202t7 | B5<br>B5 | SL-202 | (Mouse ESTs only)<br>mitochondrial genome & ESTs(?) |
| SL-203 | SL203m13<br>SL203t7 | C5<br>C5 | SL-040 | |
| SL-204 | SL204m13<br>SL204t7 | D5<br>D5 | SL-204 | |
| SL-205 | SL205m13<br>SL205t7 | E5<br>E5 | SL-205 | |
| SL-206 | SL206m13<br>SL206t7 | F5<br>F5 | SL-015 | AB006625 - KIAA0287 gene |
| SL-207 | SL207m13<br>SL207t7 | G5<br>G5 | SL-207 | HUMFOLMES - DHFR<br>dihydrofolate reductase gene |
| SL-208 | SL208m13<br>SL208t7 | H5<br>H5 | SL-208 | AB011165 - KIAA0593 |
| SL-209 | SL209m13<br>SL209t7 | A6<br>A6 | SL-209 | | batch 1
batch 2
batch 3
batch 4

TABLE 2

| Seq. Name and/or Other Seq. Name. | BlastN vs. Gb (nearest neighbor) | | | BlastX vs. NRPdb (nearest neighbor) | | |
|---|---|---|---|---|---|---|
| | Accession | Hit Description | P(V) | Accession | Hit Description | P(V) |
| 10-sl16-1t7 | <NONE> | <NONE> | <NONE> | <NONE> | <NONE> | <NONE> |
| 18-sl16-2t7 | <NONE> | <NONE> | <NONE> | MT_PLEPL | METALLOTHIONEIN (MT) ><br>PIR2:S30567 metallothionein - plaice ><br>GP:PPMMET_1 P; platessa mRNA for<br>metallolhionein | 0.32 |
| 22sl4 | AC004601 | *SEQUENCING IN<br>PROGRESS<br>*Human Chromosome 11p14.3<br>PAC clone pDJ939m16; HTGS<br>phase 1, 3 unordered pieces. | 0.016 | VP1_BPCHP | PROTEIN VP1 (ORF1) | 1.0 |
| 27sl9 | AF001549 | Homo sapiens chromosome 16<br>BAC clone CIT987SK-270G1<br>complete sequence. | 7.2e-28 | ALU6_HUMAN | !!!! ALU SUBFAMILY SP WARNING<br>ENTRY !!!! | 3.5e-07 |
| 32sl13 | AF006259 | Homo sapiens Rad51-interacting<br>protein mRNA, complete cds. | 1.2e-09 | MMU93583_1 | Mus musculus RAD51-binding protein<br>RAB22 mRNA, complete cds | 1.2e-13 |
| 39-sl3-1m13 | U07083 | Human prostatic acid phosphatase<br>(ACPP) gene, exon 1. | 1.1e-09 | MMU41047_1 | Mus musculus transcription factor<br>Genesis mRNA, complete cds;<br>A winged helix<br>retinoic-acid hepatocyte nuclear factor<br>3/forkhead transcription factor;<br>HNF3/FH transcription factor | 0.36 |
| 47-sl15-2t7 | I08056 | Sequence 2 from Patent EP<br>0272928. | 4.8e-52 | <NONE> | <NONE> | <NONE> |
| sl102m13 | AC004453 | Homo sapiens PAC clone<br>DJ0844F09 from 7p12-p13,<br>complete sequence. | 5.0e-50 | SIK1_YEAST | SIK1 PROTEIN > PIR2:S48550<br>hypothetical protein YLR197w - yeast<br>(Saccharomyces cerevisiae) ><br>GP:SCU20237_1 Saccharomyces<br>cerevisiae Sik1p (SIK1) gene, complete<br>cds; Possible microtubule binding<br>protein; similar to GenBank Accession<br>Number U14913 | 2.7e-09 |
| sl103m13 | AC002542 | Human BAC clone RG114A06<br>from 7q31, complete<br>sequence. | 0.78 | MUSIGHV01B_1 | Mouse CBA/J Ig heavy chain V1 region<br>pseudogene, 5' end; Ig heavy chain<br>precursor; Possible pseudogene | 0.30 |
| sl103t7 | AC002542 | Human BAC clone RG114A06<br>from 7q31, complete<br>sequence. | 7.0e-11 | MUSIGHV01B_1 | Mouse CBA/J Ig heavy chain V1 region<br>pseudogene, 5' end; Ig heavy chain<br>precursor; Possible pseudogene | 0.25 |
| sl106t7 | I48979 | Sequence 6 from U.S. Pat.<br>No. 5627054. | 4.3e-39 | Y694_METJA | HYPOTHETICAL PROTEIN<br>MJ0694 > PIR2:F64386 hypothetical<br>protein MJ0694 - Methanococcus<br>jannaschii >GP:U67516_8<br>Methanococcus jannaschii section 58 of | 1.5e08 |

TABLE 2-continued

| Seq. Name and/or Other | BlastN vs. Gb (nearest neighbor) | | | BlastX vs. NRPdb (nearest neighbor) | | |
|---|---|---|---|---|---|---|
| Seq. Name. | Accession | Hit Description | P(V) | Accession | Hit Description | P(V) |
| sl107t7.fsa | AL021395 | Human DNA Sequence*** SEQUENCING IN PROGRESS*** from clone 269M15; HTGS phase 1. | 2.6e-07 | ALU4_HUMAN | 150 of the complete genome; Conserved hypothetical protein; Similar to SP:Q12499 PID:1420682 PI !!!! ALU SUBFAMILY SB2 WARNING ENTRY !!!! | 0.45 |
| sl124t7 | B31344 | HS-1008-A2-A05-MF.abi CIT Human Genomic Sperm Library C Homo sapiens genomic clone Plate = CT 330 Col = 10 Row = A, genomic survey sequence. | 1.0e-55 | ALU7_HUMAN | !!!! ALU SUBFAMILY SQ WARNING ENTRY !!!! | 1.2e-14 |
| sl127t7 | Z83818 | Human DNA sequence from PAC 138A5 on chromosome X contains ESTs. | 2.8e-16 | YA3A_SCHPO | HYPOTHETICAL TRP-ASP REPEATS CONTAINING PROTEIN C18B11.10 IN CHROMOSOME I > PIR2:S58306 hypothetical protein SPAC18B11.10 - fission yeast (Schizosaccharomyces pombe) > GP:SPAC18B11_10 S; pombe chromosome I cosmid c18B11; Unknown; SPAC18B11; 10, Ie | 0.97 |
| sl135m13 | AC003959 | Homo sapiens chromosome 5, P1 clone 1029A7 (LBNL H15), complete sequence. | 1.8e-57 | AC004416_5 | Homo sapiens BAC clone RG013N12 from 7q31;2, complete sequence; H_RG013N12; gw; 1335199; a | 0.016 |
| sl135t7 | AC003044 | Human PAC clone DJ1055C04 from 7p15–7p21, complete sequence. | 3.8e-25 | ATTS0669_1 | A; thaliana transcribed sequence; clone VDV28-22792, 3' end; similar to nonspecitic lipid-transfer protein precursor | 0.77 |
| sl144m13 | AC003684 | Homo sapiens; HTGS phase 1, 53 unordered pieces. | 2.2e-10 | <NONE> | <NONE> | <NONE> |
| sl144t7 | AC004089 | *** SEQUENCING IN PROGRESS *** Human Chromosome 7 BAC Clone 155b01; HTGS phase 1, 11 unordered pieces. | 0.25 | <NONE> | <NONE> | <NONE> |
| SL149m13 WE97.H7.M13 | M87923 | Human carcinoma cell-derived Alu RNA transcript, clone CE12. | 7.2e-55 | ALU2_HUMAN | !!!! ALU SUBFAMILY SB WARNING ENTRY !!!! | 4.7e-17 |
| SL150m13 WE97.A8.M13 | AF019122 | Homo sapiens DNA polymerase gamma (POLG) gene, nuclear gene encoding mitochondrial protein, partial sequence, genomic survey sequence. | 5.5e-07 | <NONE> | <NONE> | <NONE> |
| SL152m13 | AF022186 | Cyanidium caldarium RK1 chloroplast sequence. | 0.11 | <NONE> | <NONE> | <NONE> |
| SL152t7 | AC002524 | Homo sapiens Xp22 BAC GSHB-257G1 (Genome Systems BAC Library) complete sequence. | 3.5e-28 | F40201 | artifact-warning sequence (translated ALU class F) - human | 1.2e-05 |
| SL153m13 | U29895 | Human 4-hydroxyphenylpyruvate-dioxygenase gene, complete cds. | 4.4e-15 | C40201 | artifact-warning sequence (translated ALU class C) - human | 0.49 |
| SL153t7 | U29895 | Human 4-hydroxyphenylpyruvate-dioxygenase gene, complete cds. | 5.1e-09 | A46010 | X-linked retinopathy protein (C-terminal, clone XEH.8c) - human (fragment) > GP:S58722_1 X-linked retinopathy protein {3' region, clone XEH; 8c} [human, mRNA Partial, 390 nt]; This sequence comes from FIG. 5 | 0.070 |
| SL155m13 | Z99286 | Caenorhabditis elegans sapiens cosmid Y7A9C, complete sequence. | 0.016 | POLG_PRSVH | GENOME POLYPROTEIN (CONTAINS: N-TERMINAL PROTEIN; HELPER COMPONENT PROTEINASE (EC 3.4.22.-) (HC-PRO); 42–50 KD PROTEIN; CYTOPLASMIC INCLUSION PROTEIN (CI); 6 KD PROTEIN; NUCLEAR INCLUSION PROTEIN A (NI- A) (EC 3.4.22.-) (49K PROTEINASE) (49 | 1.0 |
| SL157m13 | U91321 | Human Chromosome 16 BAC clone CIT9875K-A-363E6, complete sequence. | 6.0e-26 | ALU1_HUMAN | !!!! ALU SUBFAMILY J WARNING ENTRY !!!! | 4.5e-11 |

TABLE 2-continued

| Seq. Name and/or Other | BlastN vs. Gb (nearest neighbor) | | | BlastX vs. NRPdb (nearest neighbor) | | |
|---|---|---|---|---|---|---|
| Seq. Name. | Accession | Hit Description | P(V) | Accession | Hit Description | P(V) |
| SL160t7 | <NONE> | <NONE> | <NONE> | CA34_HUMAN | PROCOLLAGEN ALPHA 3(IV) CHAIN PRECURSOR > PIR1:CGHU3B collagen alpha 3(IV) chain precursor, long splice form-human > GPN:HSCOL4A3_1 H; sapiens COL4A3 mRNA; Type IV collagen alpha 3 chain > GP:HSCOL4A3_1 H; sapiens COL4A3 mRNA; Type IV collagen alp | 0.99 |
| SL162t7 WE97.E9.T7 | X58263 | Mouse microsatellite marker DNA D4SMH6b, 4. | 0.0029 | PRF1_LYCES | 36.4 KD PROLINE-RICH PROTEIN>PIR2:S19129 proline-rich protein TPRP-F1 - tomato > GP:LETPRPF1_1 L; esculentum TPRP-F1 gene for a proline rich protein | 0.99 |
| SL169t7 | AC004687 | *** SEQUENCING IN PROGRESS *** Homo sapiens chromosome 17, clone hRPC.1171_I_10; HTGS phase 1, 4 unordered pieces. | 2.5e-11 | <NONE> | <NONE> | <NONE> |
| SL174t7 | <NONE> | <NONE> | <NONE> | A54895 | mucin 21 intestinal/tracheal - rat (fragment) | 0.131 |
| SL176m13 | Z73424 | Caenorhabditis elegans cosmid C44B9, complete sequence. | 0.00084 | <NONE> | <NONE> | <NONE> |
| SL176t7 | Z83119 | Caenorhabditis elegans cosmid R05H10, complete sequence. | 0.38 | <NONE> | <NONE> | <NONE> |
| SL177m13 | AL022279 | Caenorhabditis elegans DNA *** SEQUENCING IN PROGRESS *** from clone Y43F11; HTGS phase 1. | 0.00064 | ANX7_BOVIN | ANNEXIN VII (SYNEXIN) (FRAGMENT) > PIR2:A27695 synexin - bovine (fragment) | 0.0018 |
| SL177t7 | AC002416 | Human Chromosome X, complete sequence. | 1.8e-17 | <NONE> | <NONE> | <NONE> |
| SL179m13 | AF039052 | Caenorhabditis elegans cosmid T22D1. | 0.030 | CMU23045_8 | Cepaea nemoralis complete mito-chondrial genome; ATPase subunit 8 > GP:CMU23045_8 Cepaea nemoralis complete mito-chondrial genome; ATPase subunit 8 | 0.98 |
| SL179t7 | L41631 | Mus musculus glucokinase gene, complete cds. | 0.017 | <NONE> | <NONE> | <NONE> |
| SL181m13 | Z98867 | Caenorhabditis elegans DNA *** SEQUENCING IN PROGRESS *** from clone Y52B11; HTGS phase 1. | 0.017 | PS0245 | hypothetical protein (cpcG4 region) - Anabaena sp. (strain PCC 7120) (fragment) > GP:ANARODCORA_6 Anabaena sp; cpcF gene, 3' end; cpcG1, cpcG2, cpcG3, and cpcG4 genes, complete cds; and unknown ORF, 3' end | 0.99 |
| SL181t7 | Z98867 | Caenorhabditis elegans DNA *** SEQUENCING IN PROGRESS *** from clone Y52B11; HTGS phase 1. | 0.018 | PS0245 | hypothetical protein (cpcG4 region) - Anabaena sp. (strain PCC 7120) (fragment) > GP:ANARODCORA_6 Anabaena sp; cpcF gene, 3' end; cpcG1, cpcG2, cpcG3, and cpcG4 genes, complete cds; and unknown ORF, 3' end | 0.99 |
| SL191m13 | Z98867 | Caenorhabditis elegans DNA *** SEQUENCING IN PROGRESS *** from clone Y52B11; HTGS phase 1. | 0.019 | <NONE> | <NONE> | <NONE> |
| SL195m13 | AC004626 | *** SEQUENCING IN PROGRESS *** Homo sapiens chromosome #16q12.1 + 16q22/23 + 1q11/12 BAC clone CIT987SK-A-427H10; HTGS phase 1, 15 unordered pieces. | 0.050 | HSU55091_1 | Human isolate HR015 T cell receptor V-beta complementarity determining region 3 mRNA, partial cds | 1.0 |
| SL195t7 | AC004626 | *** SEQUENCING IN PROGRESS *** Homo sapiens chromosome #16q12.1 + 16q22/23 + 1q11/12 BAC clone CIT9875K-A-427H10; HTGS phase 1, 15 unordered pieces. | 0.053 | S54078 | probable membrane protein YPR056w - yeast (Saccharomyces cerevisiae) > GP:SC9499X_12 S; cerevisiae chromosome sapiens XVI cosmid 9499; Unknown; YP9499;12, unknown, len:338, CAI: 0;12, similar to S44455, transcription factor BTF2 chain p34, (29;3% identit | 0.64 |

TABLE 2-continued

| Seq. Name and/or Other | BlastN vs. Gb (nearest neighbor) | | | BlastX vs. NRPdb (nearest neighbor) | | |
|---|---|---|---|---|---|---|
| Seq. Name. | Accession | Hit Description | P(V) | Accession | Hit Description | P(V) |
| SL197m13 | AF003134 | Caenorhabditis elegans cosmid ZC581. | 0.99 | <NONE> | <NONE> | <NONE> |
| SL197t7 | U43400 | Human herpesvirus-7 (HHV7) JI, complete virion genome. | 0.99 | <NONE> | <NONE> | <NONE> |
| SL19t7 | V00073 | Sindbis virus sequence complementary to 26S messenger RNA. | 3.2e-09 | <NONE> | <NONE> | <NONE> |
| SL201m13 | AB001684 | Chlorella vulgaris C-27 chloroplast DNA, complete sequence. | 0.0013 | SIU05069_1 | Simian immunodeficiency virus SIVRhE543 clone 5-4 envelope glycoprotein (env) gene, V1 region, partial cds | 1.0 |
| SL201t7 | AB001684 | Chlorella vulgaris C-27 chloroplast DNA, complete sequence. | 0.0014 | HUMLTBP_1 | Homo sapiens (clone H 4;4) latent transforming growth factor - beta binding protein (LTBP-1 L) gene, partial cds; Latent transforming growth factor-binding protein | 1.0 |
| SL204m13 | Z49910 | Caenorhabditis elegans cosmid F44G4, complete sequence. | 1.0e-11 | CEF44G4_1 | Caenorhabditis elegans sapiens cosmid F44G4, complete sequence; F44G4;1; Similarity to 35;1 KD hypothetical yeast protein (Swiss Prot accession number P38805); cDNA EST CEMSE65F comes from this | 5.6e-72 |
| SL204t7 | Z49910 | Caenorhabditis elegans sapiens cosmid F44G4, complete sequence. | 9.3e-12 | CEF44G4_1 | Caenorhabditis elegans sapiens cosmid F44G4, complete sequence; F44G4;1; Similarity to 35;1 KD hypothetical yeast protein (Swiss Prot accession number P38805); cDNA EST CEMSE65F comes from this | 2.3e-71 |
| SL28m13 | <NONE> | <NONE> | <NONE> | <NONE> | <NONE> | <NONE> |
| SL28t7 | Z84469 | Human DNA sequence *** SEQUENCING IN PROGRESS *** from clone 390O13; HTGS phase 1. | 2.9e-53 | <NONE> | <NONE> | <NONE> |
| SL29m13 | AC004465 | Homo sapiens 12q24 PAC RPCI3-363I18 (Roswell Park Cancer Institute Human PAC library) complete sequence. | 3.3e-09 | MCRA_METFE | METHYL-COENZYME M REDUCTASE ALPHA SUBUNIT (EC 1.8.-.-) > GP:MEFMCRC_5 M; fervidus sapiens methyl coenzyme M reductase component C genes mcrA, mcrB, mcrC, mcrD, and mcrG, complete cds; Methyl coenzyme M reductase alpha subunit | 0.95 |
| SL29t7 | AC004465 | Homo sapiens 12q24 PAC RPCI3-363I18 (Roswell Park Cancer Institute Human PAC library) complete sequence. | 0.97 | MCRA_METFE | METHYL-COENZYME M REDUCTASE ALPHA SUBUNIT (EC 1.8.-.-) > GP:MEFMCRC_5 M; fervidus methyl coenzyme M reductase component C genes mcrA, mcrB, mcrC, mcrD, and mcrG, complete cds; Methyl coenzyme M reductase alpha subunit | 0.97 |
| SL4M13 | D42085 | Human mRNA for KIAA0095 gene, complete cds. | 2.0e-27 | HUMKIMP_1 | Human mRNA for KIAA0095 gene, complete cds; KIAA0095 gene is related to S; cerevisiae NIC96 gene | 3.6e-12 |
| SL54m13 | Z68694 | Human DNA sequence from cosmid cU177E81 between markers DXS366 and DXS87 on chromosome X. | 4.9e-28 | HUMF8L1A_1 | Human factor VIII gene L1 element insertion DNA; Unknown protein; ORF; putative | 1.2e-12 |
| SL61t7 | AB001684 | Chlorella vulgaris C-27 chloroplast DNA, complete sequence. | 0.00083 | AF004841_1 | Homo sapiens CDO mRNA, complete cds; Immunoglobulin superfamily member; contains fibronectin type III-like domain | 1.0 |
| SL62t7 | AC004153 | *** SEQUENCING IN PROGRESS *** Plasmodium falciparum 3D7 chromosome 12 PFYAC812 genomic sequence; HTGS phase 1, 26 unordered pieces. | 1.0 | <NONE> | <NONE> | <NONE> |
| SL68m13 | AC004157 | *** SEQUENCING IN PROGRESS *** Plasmodium falciparum 3D7 chromosome 12 PFYAC293 genomic sequence; HTGS phase 1, 18 unordered pieces. | 0.00071 | <NONE> | <NONE> | <NONE> |

TABLE 2-continued

| Seq. Name and/or Other | BlastN vs. Gb (nearest neighbor) | | | BlastX vs. NRPdb (nearest neighbor) | | |
|---|---|---|---|---|---|---|
| Seq. Name. | Accession | Hit Description | P(V) | Accession | Hit Description | P(V) |
| SL68t7 | AJ226619 | Ciona intestinalis genomic fragment, clone 17H6, genomic survey sequence. | 0.064 | <NONE> | <NONE> | <NONE> |
| SL69m13.fsa | Z22789 | H. sapiens CNGT repeat polymorphism sequence. | 1.9e-22 | AE001179_2 | Borrelia burgdorferi (section 65 of 70) of the complete genome; Competence protein F, putative; Similar to GB:M59751 SP:P31773 PID:1573409 percent identity: 27;00; identified by sequence | 1.0 |
| SL69t7 | AL010138 | Plasmodium talciparum DNA *** SEQUENCING IN PROGRESS *** from config 3–66, complete sequence. | 0.21 | AE001179_2 | Borrelia burgdorferi (section 65 of 70) of the complete genome; Competence protein F, putative; Similar to GB:M59751 SP:P31773 PID:1573409 percent identity: 27;00; identified by sequence | 1.0 |
| SL75m13 | AC002536 | Human Chromosome 11 pac pDJ1075f20, complete sequence. | 1.0 | BTRNAT3_1 | B; taurus mRNA for complete thrombospondin | 0.0074 |
| SL77t7 | AF012886 | Buchnera aphidicola UDP-N-acetylmuramate: L-alanine ligase (murC157), D-alanine: D-alanine ligase (ddlB), cell division protein (ftsA), cell septation protein (ftsZ), and pfs genes, complete cds. | 0.40 | <NONE> | <NONE> | <NONE> |
| SL86m13 | Z69790 | Caenorhabditis elegans cosmid F33C8, complete sequence. | 0.020 | <NONE> | <NONE> | <NONE> |
| SL86t7 | U39368 | Acanthonevra sp. 16S ribosomal RNA gene, mitochondrial gene encoding mitochondrial RNA, partial sequence. | 0.054 | <NONE> | <NONE> | <NONE> |
| SL90m13 | <NONE> | <NONE> | <NONE> | <NONE> | <NONE> | <NONE> |
| SL94m13 | X95276 | P. falciparum complete gene map of plastid-like DNA (IR-B). | 0.0096 | SHFORF_1 | Shigella sonnei DNA for 26 ORFs, complete cds; ORF1 | 0.15 |
| SL94t7 | AL022313 | Human DNA sequence *** SEQUENCING IN PROGRESS *** from clone 1119A7; HTGS phase 1. | 6.0e-18 | A46010 | X-linked retinopathy protein (C-terminal, clone XEH.8c) - human (fragment) > GP:S58722_1 X-linked retinopathy protein {3' region, clone XEH; 8c} [human, mRNA Partial, 390 nt]; This sequence comes from FIG. 5 | 5.7e-07 |

We claim:

1. An isolated nucleic acid molecule selected from the group consisting of:
   (a) a polynucleotide consisting of the nucleotide sequence from the group consisting of SEQ ID NO: 153 and 154;
   (b) a polynucleotide that is a degenerate variant of SEQ ID NO: 153 or SEQ ID NO: 154; and
   (c) a polynucleotide that is the complement of (a) or (b).

2. A method of making a recombinant vector comprising inserting the nucleic acid molecule of claim 1 into a vector in operable linkage to a promoter.

3. A recombinant vector produced by the method of claim 2.

4. A method of making a recombinant host cell comprising introducing the recombinant vector of claim 3 into a host cell.

5. A recombinant host cell produced by the method of claim 4.

6. A diagnostic kit comprising:
   (a) a polynucleotide probe that consists of at least 12 contiguous nucleotides of the nucleotide sequence from the group consisting of SEQ ID NO: 153 and 154, or the complement thereof;
   (b) a normal biological sample; and
   (c) instructions for detecting differences that exist between the levels of hybridization between the probe and a test biological sample as compared to the level of hybridization between the probe and said normal biological sample.

* * * * *

SEQUENCE LISTING

<160> NUMBER OF SEQ ID NOS: 341

<210> SEQ ID NO 1
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 1

```
accgcctcgn atccctagta acggccgcca gtgtgctgga attcgccctt tcatgcctat      60
aatcccagca cttggggagg ccgaggatct cctctctggt ggatcacttg agggcaggag     120
ttaagagacc atcctggcca acatgatgaa accctgtctc tactaaaaat acaaaaagta     180
gctgggcgtg gtggcatact cttacaatcc cagctacttg ggaggctgag gcaggagaat     240
cacttgaacc taggaagcag aggttgcagt gggccaagat cacaccacta tactctagcc     300
tgggcgacag aggtggggaa aaagtagga cccctgtcct atattcaggt ttttctcaca     360
tatatgaacc catctaaatt ctacgttgtt aaaggtagct taggttaatt agtctatact     420
```

| | |
|---|---|
| tatttaagac caatatgggg tgagatggat ttttttttta aaaatcctac agtaaggctt | 480 |
| tctactttcc ttctaatgag gaaaaaggtg acaaaaattc aagtgtcaat gtccccttcc | 540 |
| tgggaagagg tttagaaaaa caacagctca ccttctgaac tctaccagtt ccttttgaag | 600 |
| ttaacgaagc attaaaatca gatgtaaaaa agaaaaaaa aaggcaggga aatatttaca | 660 |
| aaactggaca ttctttacag atatacaatc ttgctaatac tgggagaacc nttccaagga | 720 |
| tgtataaaga ggagacgnca ccttagtaat gccagggata gagaaaaccc nggatataat | 780 |
| atggggtttt taatgccgga acatggngga aactaggang agccgagatg ganctggtcc | 840 |
| ctgaagtgaa ctggttnagn tattctgggn accctcagga gggccttgca agtgtgtggg | 900 |
| taggnaaaaa actgggctgg gcaaactact tggntncaag ttttttttatg ggagaccgaa | 960 |
| caacctggga aggcttaaan gcaagnggtt cgncntttaa ttaaaaggct gggccaaatt | 1020 |
| accc | 1024 |

<210> SEQ ID NO 2
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 2

| | |
|---|---|
| gccgtcnaga cctgctcgag cggacgtcng tgcgatggat ntactgcaga nntctccctn | 60 |
| ncatcctaan acgactcact atagggcagt gacgaaaggt acnncgngga ngnttnntgg | 120 |
| ntangcgatc agctattgna cggaatctct gtganantga nnagctnana tcntctccan | 180 |
| ggaanaacag ntccncaang ctntattnga gacagagcta tgacannnnc ntntntactc | 240 |
| ngacagtcct taggaaccnc gcaantgana nngngngat gcnactagga nctgncncnn | 300 |
| ntagngagcg agcccggtgg ataactgccc tggtacncng nagctgnaaa gccgcctgca | 360 |
| gaccgaacct gagactgacg tcgcctcanc tatngacnnn nnnccnatnn tgagtgnaag | 420 |
| cgtnctnatg ngacactcgg ggnccacgat gcanancgct ancnnccnn ggngtgncan | 480 |
| tnagnnatcn ttgcncatat tncgnatntt gacatgtgta atgatngaga tctcatannt | 540 |
| gcactgtgct tctcatctat taacgctaaa ccatgacagt ttnctttcat tgccacntnc | 600 |
| tttcagtgac ccnanatntt atcgctanat attcnatcct tcaacngtag cattnttcct | 660 |
| gctnttcttt nccnaaagca tcttctttcc caactcactc cagggccaaa tactctcanc | 720 |
| cnnctcactn tangntctcn gntcacgtc tttcccgtga cacgtcattc aattcccctc | 780 |
| gnaagctanc ccaggcccaa ctttnntctt cttcaccggn nntaacttaa tcctggggga | 840 |
| aggnaangcn nggntctta gccttgntcc agaaccttng gtagcccgg ncacaaatcc | 900 |
| naaaaacctt tgcaggtttg ggggttggac cccgggncct ttttccgg gtngggttta | 960 |
| nggngggaac cgnattttta nnatngacca aggaaggctg gggtcctttg gaaagncccc | 1020 |
| cngg | 1024 |

<210> SEQ ID NO 3
<211> LENGTH: 1024
<212> TYPE: DNA
<213> ORGANISM: Homo Sapien
<220> FEATURE:
<221> NAME/KEY: misc_feature
<222> LOCATION: (1)...(1024)

<223> OTHER INFORMATION: n = A,T,C or G

<400> SEQUENCE: 3

| | | | | | |
|---|---|---|---|---|---|
| cttggtaccg | agctcggatc | cctagtaacg | gccgccagtg | tgctggaatt | cgcccttcca | 60 |
| tcctaatacg | actcactata | gggctcgagc | ggccgcccgg | gcaggtcact | gggttttct | 120 |
| cctttttgtag | ccttttcctt | tagtctcctc | ttcccggtgg | ttggtaaaaa | gaggtgaatt | 180 |
| gacagcctat | gttgaagaca | ctgtgctttt | ctcaagaagg | acatccaaac | agcaagtcta | 240 |
| cttctttctc | tttaacgatg | tgctcattat | caccaagaag | aagagtgaag | aaagttacaa | 300 |
| cgtcaatgat | tattccttaa | gagatcagct | attggtggaa | tcttgtgaca | atgaagagct | 360 |
| taattcttct | ccagggaaga | acagctccac | aatgctctat | tcaagacaga | gctctgccag | 420 |
| tcacctcttt | actctgacag | tccttagtaa | ccacgcgaat | gagaaagtgg | agatgctact | 480 |
| aggagctgag | acgcagagcg | agcgagcccg | ctggataact | gccctgggac | acagcagcgg | 540 |
| gaagccgcct | gcagaccgaa | cctcactgac | ccaggtggaa | atcgttaggt | catttactgc | 600 |
| taagcagcca | gatgaactct | ccctgcaggt | ggctgacgtc | gtcctcatct | atcaacgtgt | 660 |
| cagcgatggc | tggtatgagg | gggaacgact | acgagatgga | gaaagaagct | ggtttcctat | 720 |
| ggaatgtgcc | aaggagataa | catgtcaagg | ctacaattgn | ttaagaatgt | ggagagaatg | 780 |
| ggacgcttgc | taggactgga | gaanccacgt | gagnctttn | aangggcctt | tggtactgca | 840 |
| agaattgcac | cgacacttac | cgggcttggt | ggttctgggg | ctagtttaat | ggnaatttgg | 900 |
| cccagncttt | ttaattaaag | gaccggaaac | cntggccttt | aactttggcc | agtggtncgg | 960 |
| tntntnatgg | aaaaaacttt | gggtaccccg | gngttgccca | ggttagtttt | acctaacccc | 1020 |
| cccn | | | | | | 1024 |

<210> SEQ ID NO 4
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 4

| | | | | | |
|---|---|---|---|---|---|
| accgnnctcg | natccctagt | aacggccgcc | agtgtgctgg | aattcgccct | tgtatagtgg | 60 |
| tgtgatcttg | gctcactgct | acctccacct | cccaggctca | cacgatcctc | cagcctcagc | 120 |
| ctcccaagta | gctgcgacta | caggtgcacg | ccattgcagc | tggctaattt | ttgtattttc | 180 |
| agtagagatg | gggtttcccc | atgttggcca | ggctggtctt | gaactcctaa | gctcaagcaa | 240 |
| ttcacctgcc | tcagcctccc | agagtgctgg | gattactcct | aagctcaagc | aattcacctg | 300 |
| cctcagcctc | ccagagtgct | gggattactc | ctaagctcaa | gcaattcatc | tgcctcagcc | 360 |
| tcccagagtg | ctgggattac | tcctaaactc | aagcaattca | cctgcctcag | cctcccagag | 420 |
| tgctgggatt | actcctaagc | tcaagcaatt | cacctgcctc | agcctccag | agtgctggga | 480 |
| ttactcctaa | gctcaagcaa | ttcacctgcc | tcagcctccc | agagtgctgg | gattactcct | 540 |
| aagctcaagc | aattcacctg | cctcagcctc | ccagagtgct | gggattacag | gtgtgaagca | 600 |
| ctacacccag | cccattcttc | ccttttaacc | aaggaagaaa | ttacacaatg | aaacaaatac | 660 |
| cccgaatctt | aatatcactt | ttcctttgnc | ataattaaca | attagcgaca | cagaatcgag | 720 |
| gggaaaaaca | caggatccgt | ttacttctan | gaanggcgtt | tctgtgaatc | taagaagggg | 780 |
| cttttctgng | gtctcaaggn | cacgggtcaa | gccaggtggg | ccgcttgcgg | ggtgcgctgg | 840 |

```
ctggggagaa acttntcggg gatnggaagt gaaanngggtt ccgnctgggc cccttnttt    900 tgggaaaccc caggngngtn tngcaaaggc caagggaaag gcctcaaggg ggggcatgaa    960
ctttgnagct tccaactttg gttccnttan acnnggggg gccctatgg cccaaaaagg    1020 gctt                                                                1024
```

<210> SEQ ID NO 5
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 5

```
gccgtcnaga cncntgcngn agcgnncgnc ngtgggatgg nnanntgcng annncgcccn     60
tccntcctaa tacnactcac tataggcgnn agnggccacn tcnagctngn gnnngaagtt    120
ggnntgcngt gnagtctgtn cctgnggcan cgcgtcatgc atgactttgg gtcattgctg    180
ctctccttgc ctttagggga gggtcctggt gctctgtgag cagattngac cctaggggtg    240
aagtcatctn gccctgttc tgagccgaga gctggncagg gngcgtctca catcattcct    300
ctgcccctgt ngncgcatgg gaaatcctaa acaggctctg tggnaaangc tgnnccaagg    360
cgcctcctgg gcagncganc catcagnnga tcgnnagccn ngaancgatg gcccgggaaa    420
accaaaccag gaannaanca caccgtgcga aaggnattgg tgaacgaact gaaaaattgt    480
aaagctctta aggactttca tgcttgcnag nattnantga canaaaatca ctganncann    540
gaacataaag aaatagccat ggangattca cagtgtanct ngctgancng ctcatntggc    600
cncaagnnat gtttnactna cgnagncnca atgnactggt ccttgntnng gctggctttc    660
ttttctgngc aaaacttggn ggncccttaa ttgggcttan cccaacnaca agacttcctg    720
ggaaaacngg gnannntagga antttgnaag gacaaccaaa ggaaactgga agggaacaaa    780
ttttttggtt cccaaaaccg ggccaagatt gggcttcaaa aanccttttga accngggggn    840 ncaattnntn gggnttanat ccccgaaag gaanngggan ggtntttaag gnaaaancccn    900 nnccaaggaa cccngggttttn gggccntgga agggnccctg gncnnggttt cgagggnnttg    960 ncttaactgg aaggnccccna aagggaaaac cnnnnnttttt tnaagggntc cccggaaccc    1020
aaag                                                                  1024
```

<210> SEQ ID NO 6
<211> LENGTH: 957
<212> TYPE: DNA
<213> ORGANISM: Homo Sapien
<220> FEATURE:
<221> NAME/KEY: misc_feature
<222> LOCATION: (1)...(957)
<223> OTHER INFORMATION: n = A,T,C or G

<400> SEQUENCE: 6

```
acgcggggac acacagaggc gggcatttcc ctgacgactc gtgtgtgccg tgggggagcg     60
gtagatggcc cagccccaag tgttccgatc ttcctgccca acatattct gtgacgaaa    120 gcctatgttg acctcgtccg gcactcaagg cgtgggcagc ggcctaacgt ctgctgcggg    180
aacacagtcg cgttgaatgc tattctcaag acagacaaaa cagtgggaag acactacgcc    240
aagctgctaa ctccctggcc attgccggac tctttcaccc ccatggactt tccgctggca    300
```

-continued

```
ttttaaacaa catagtttct tttctctgtc tctttctctt tccctctctc tttctctttc        360
tctctctctc tctctctctc tctctctctc tctcaatctc ataatttctc tctctcgtgc        420
cacgttccca cccaacgctc tctcgcccac ttctactggg gcccacttcc tctcctgctc        480
tctctgtctc aacgtgattg actttcttgt gctgcncagg acttcttgcc cacgtgcgcc        540
ttcaanacgg taaagagctg caactgaacg tgtgagacat ggtgcanata aggctgagag        600
ggcggnggga gagatgccca tgaactcaag tacctgcccg ggcnggccgc tcgaaagggg        660
gaattccagc aaactggcgg ccgttactan tggattcgng ctccggtaca ngcttggggt        720
aatcatggtc aatanctggt ttcctgtggt naaattggtt ntccggctca nnaatttcaa        780
nannanatan naagcncggn aancataaan ttgttaaagc ccngggggttc cctnaatnan       840 tttgncctan tnnaacntta aattngngnt ttnncnncan anngncngnt ttttcaattc        900
cgggaaanct ngtcntnngn agctngcatt atcnanttcg ggccaaangc gcggggg          957
```

<210> SEQ ID NO 7
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 7

```
cttggcaccg ccctcggatc cctagtaacg gccgccagtg tgctggaatt cgcccttttag        60 agtatagtgg tgtgatcttg gctcactgca acctccacct cctgggttca agcaatgctg       120
cctcagcctc cccagtagtt gggactacag gcgtgtgcca ccacccggg ctaattttttg       180 tatttgcagt agagacgggg tttcatcatg ttggccaggc tggtctcgaa ctcctggcct       240
caagtgacac gcctgcctca acctcccaaa gtgctgggat tacaggcgtg agccaccgca       300
cctggcctct atgctcgaat ttctactctt agctaatctc tctaacacat atgcccttca       360
ttgggtaaag ctggctcagc agactaatta cacctgtcat gtaatacaag cctctccctg       420
gcctgtatta tctcatggtt gccttctatt tgtgacaagt gctatgaata ttccttttta       480
agaagtgata caaaatcttt tttttttttct tgaacaggat ttttaactca gacagtgtaa       540
acatcatgac aattctggaa tgtctgaagt ttgagataga agattgtcta agaaaagctg       600
agattgnctt agctgtttgt ggtatccgaa ttcctctgga acatgggcat caggaaccaa       660
gcgatgccac tgctactggg caggttttt atattttacc taaacagaga ccaatgacgc       720

tgacctacct taatgaaaat ttcagaaaaa ccatctggaa tcagccccat catgtccaga       780
attggaatgg aatctgggga tcaatggaac atacccggaa atacttttnt ttcccccaaa       840
ccaaggnaat ggaatgtcaa aagtattgga gcctaattta aaatggggnt tccntantaa       900
agntttgctt tcanttaatg ggancanttg gcnanntggt tttgggnacc ссттgcaтaaт      960

ttaaaccgng nggccagttg gccaaccaan atttcancng gaaagggggt aтттттaaaag      1020 cccg                                                                    1024
```

<210> SEQ ID NO 8
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 8

| | | | | | |
|---|---|---|---|---|---|
| tagangcatg | ctcgagcggn | ccgtcnggyt | gntgganctn | tgcgagactn | ngcccttnca | 60 |
| tactangacg | actnactata | ggnnnngtnc | agtgcgtcgc | gatcgggtgt | agggttatan | 120 |
| ngcngnnggn | ntnctnttgg | agagntnngn | ngctnanctg | ctatgntctc | ntggatnnnc | 180 |
| tntgcccgca | gaaaatnaat | gcgttttgaa | cagttttagn | tttgtgcctc | atanattgtg | 240 |
| tnantgctat | ncattatnnn | gnntgcatat | ntantctnna | nngccnncaa | ggcatcgcng | 300 |
| atggnctaac | atctcaaaac | nccttancct | acanntganc | nntgtggnan | actttgnngn | 360 |
| ggnantgtgg | ntaaaagnac | cangggnna | atcntggntc | agancnctan | aaagcattgn | 420 |
| ttactacaac | tggctcttga | atatcccctt | gcgctgatat | ttgtggtcag | ctgcctacag | 480 |
| ttgaatatgc | agcgtnacac | anncnaagct | gccagtgcta | caattaactg | aagcatnact | 540 |
| tantntgtaa | ncacnatcta | anttngcatc | agtnctcatg | acatncatta | catgggacag | 600 |
| gggcaagagc | agtagctctg | gtatgtgaca | ttgatcccca | gatgccttcc | caatctggac | 660 |
| atgatggggc | tgnnttccca | atggttacnc | tgaaaatgca | ttaagggagg | tcagcgtcat | 720 |
| ttgtctcatg | gatacgnaaa | aatctcttnc | accctgncca | tnaacaggng | gcaatcgctt | 780 |
| gnggncctga | tgnccatgtt | ccaaaaggaa | tccgatgcca | nnagcngctg | ggacagtctt | 840 |
| aagcttttct | tcnccaccct | tctatcttga | acttncanac | gtttccggaa | acnccaanga | 900 |
| nngttaccac | ttgccngacc | taaaaaacnc | tgttcacgaa | nttnaacttn | ggatttngga | 960 |
| acnctttctt | tanaaagggt | tatccattgc | nctttgtgnc | caaataggan | ggccncccct | 1020 |
| nnga | | | | | 1024 |

<210> SEQ ID NO 9
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 9

| | | | | | |
|---|---|---|---|---|---|
| accgccctcg | natccctagt | aacggccgcc | agtgtgctgg | aattcgccct | ttagagtata | 60 |
| gtggtgtgat | cttggcccac | tgcaacctct | gcttcctagg | ttcaagtgat | tctcctgcct | 120 |
| cagcctccca | agtagctggg | attgtaagag | tatgccacca | cgcccagcta | cttttttgtat | 180 |
| ttttagtaga | gacagggttt | catcatgttg | gccaggatgg | tctcttaact | cctgccctca | 240 |
| agtgatccac | cagagaggag | atcctcggcc | tccccaagtg | ctgggattat | aggcatgagc | 300 |
| caccgtgccc | agcctacttt | ctaattaacc | aaaaaaaaa | aaaaaaaaa | aaaaaagcg | 360 |
| gccgctgaat | tctattctag | aattaagcgg | ccgctgaatt | ctagacctgc | ccgggcggcc | 420 |
| gctcgagccc | tatagtgagt | cgtattagga | tggaagggcg | aattctgcag | atatccatca | 480 |
| cactggcggc | cgctcgagca | tgcatntaga | gggcccaatt | cgccctatag | tgagtcgtat | 540 |
| tacaattcac | tggccgtcgt | tttacaacgt | cgtgactggg | aaaaccctgg | cgttacccaa | 600 |
| cttaatcgcc | ttgcagcaca | tccccctttc | gccagctggc | gtaatagcga | agaggcccga | 660 |
| ccgatcgncc | ttccaacagt | tgcgcagcct | gaatggcgaa | tggacgcgcc | ctgtagcggc | 720 |
| gcattaancc | gccggcgggt | gtggtggtta | cnccgcancg | tgaaccgnta | cacttggcan | 780 |
| ggncctacgg | cccgntttcct | ttcgctttct | ttccttttcct | ttnttggnca | cgtttcggcc | 840 |

| | |
|---|---|
| gggttttccc cggtnaagct nttaaattng ggggcttccc ntttangggn tcccgaantt | 900 |
| anngcctta acgggaccnt ggancccaa aaaactttgg tttangggg angggttcac | 960 |
| cgtaangggg nccatttgcc ctggntaaac nggttttttc ccccnttgac nttgggnanc | 1020 |
| cccg | 1024 |

<210> SEQ ID NO 10
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 10

| | |
|---|---|
| gccgtcnaga nccatgcnnn agcgngcggc ngtgtnatgg nnanntgcag aanacgncct | 60 |
| ncnatcctaa tacgactcac tatagggctn gagcggncga ccggacagng ntnnnggtgg | 120 |
| ctnatgccta naatcccagn acttggggag gccnaggatc tcctntntgg tggatcactt | 180 |
| gagggcagga gttaanagac catcctggcc aacatgatga aaccctgtct ctactaaaaa | 240 |
| tacanaangt agctgggcgt ggtggcatac tcttacaanc ccagctactt ggaggctga | 300 |
| ggcaggagaa tcacttgaac ctaggaagca gaggttgcag tgggccaaga tcacaccact | 360 |
| atactctaaa gggcgaattc cagcacactg gcgnccgtta ctagaggatc cgngctcggt | 420 |
| nccaagcttg gcgtaatcat ggacanagct gttncctgtg tgaaatgggt aancgctnac | 480 |
| aanntnacac aacatacnag ccggaagcat aaagngtnaa gcctggggng cctaatgagt | 540 |
| gagctaactc acattaattg cgttgcgctc actgcccgct ttncagntcg ggaaacctgc | 600 |
| cgtgccagct gcattaatga atcggccacg cncngggag aggcggantg cgaatgggcg | 660 |
| cttcttncgn ttctcgctta ctgactngat gcggttcggc ccattgnntg cagcaaagcg | 720 |
| gnatcngctc acttnaaagg cnggnaatnc cggttntccc cntgaatccg ggggattacc | 780 |
| gcaggtnaag aaccatgggg anccaaaagg ccagctaaaa gggcccggga acccggaaaa | 840 |
| aaggcccngt tggttggcgt tttttcanaa ggttccgccc ccttgaccgn ngcnttacaa | 900 |
| aaattnggag gcnttaaggt cnnaantggg ggaaacccccc cgggaaattt caggntnccc | 960 |
| ngggggtttcc cctgggaagt tncttngggg gctttccnnt tcnaaacctg gcgnttaccg | 1020 |
| gnaa | 1024 |

<210> SEQ ID NO 11
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 11

| | |
|---|---|
| gtncgtctag atgcatgctc gagcggccgc cagtgtgatg gatatctgca gaattcgccc | 60 |
| ttgagcggcc gcccgggcag gtacgcgggg gggcatttcc ctgacgactc gtgtgtgccg | 120 |
| tggggagcg gtagatggcc cagccccaag tgttccgatc ttcctgccca aacatattct | 180 |
| gtgacggaaa gcctatgttg acctcgtccg gcactcaagg cgtgggcagc ggcctaacgt | 240 |
| ctgctgcggg aacacagtcg cgttgaatgc tattctcaag acagacaaaa cagtgggaag | 300 |
| acactacgcc aagctgctaa ctccctggcc attgccggac tctttcaccc ccatggactt | 360 |

```
tccgctggca ttttaaacaa catagtttct tttctctgtc tctttctctt tctctctctc      420
tttctctttc tctctctctc tctctctctc tctctctctg tcaatctcat aatttctctc      480
tctcgtgcca cgttcccacc caacgctctc tcgcccactt ctactggggc ccacttcctc      540
tcctgctctc tctgtctcaa cgtgattgac tttcttgtgc tgcccaggac ttcttgccca      600
cgtgcgcctt caaaacggta agagctgcaa ctgaacgtgt ganacatggt gcagataggc      660
tgagaggcng cgggaaaaat gcccatgaaa ctcaaagtac tccngccggc gancacgcta      720
angggngant ttcaagcaca nntggcgggc cgttactaan tggattcgaa cctccggtac      780
caaaagcttg ggcgttaatc atgncaanaa gccgttttcc ngtnttaaat ttgttnancc      840
gctcananat tccanacaan cnattacnan gccgggaaaa ccaanaaagt tgttaaaacc      900 ctggggttg ccnnaatgan ttgangctaa ntccnnttta atttncttg cnccnaaggg       960 ccggttttc cattcgggaa acctgtncgt nccaanctgn atttantgaa tcgggcaaac      1020
tccc                                                                  1024

<210> SEQ ID NO 12
<211> LENGTH: 957
<212> TYPE: DNA
<213> ORGANISM: Homo Sapien
<220> FEATURE:
<221> NAME/KEY: misc_feature
<222> LOCATION: (1)...(957)
<223> OTHER INFORMATION: n = A,T,C or G

<400> SEQUENCE: 12 acttttttt ttttttttt tttttttttt ttttagctt tatttttatt gttgacacta         60
ttacagatag aatgaccaca accatattaa caaaccaaaa acctgtgcac agaaacaaga     120
tgaagaaaat atatcaagat gttaaccaca ctctttggat ggtgaaaaca tgggtgagtt     180
tctcttctac atttctgtaa cttcaaagtt tctataatga acacatttca tatataatgg     240
aaatatatgt agtaaaggtg gactaccaaa acactagaat gatgaccttt caaggaaacc     300
gaaacaaaat aaccataatc ccacaacaac cacacaacta tttcttgttt ttcatctttc     360
ttcccatctt tgacatttat gcatacttat cactaacacc ctaataatca cagactagtg     420
cacagatcaa gatgttaaca gttaattgtt gttgggtgtt gggaatatgt gtgaatttc     480 tttactgaat ttccaaagtt ttgtatgagt atgtantata tttgtaatgg aaaatacata     540
cataagaatt tantaccaaa nacaccaaag attatttaag gaatttgaga caaaatatt     600 tanccaaatt cccacaatga caacaccaan tttaggtant ttccacatct ntttcaaatt     660
taanggcttt angcacacat attttaacac tggtanccac aagcngtgtt gcnccggaan    720
caanngntng agggaaacca ggtncaagga tggtnancan taagttgtta anggggttgg    780
gaanannggn aattttttaa acanattta cnttaantt ccaagttttn ccnccgggga      840 annttttng gccaccaatg ggggnnnccc nttatanccn ngtnaaccgg ggacatttt       900 tnnnggggaa atttnganaa atttagagtg ngaaangntt tttacccaan agtnccn        957

<210> SEQ ID NO 13
<211> LENGTH: 1020
<212> TYPE: DNA
<213> ORGANISM: Homo Sapien
<220> FEATURE:
<221> NAME/KEY: misc_feature
<222> LOCATION: (1)...(1020)
<223> OTHER INFORMATION: n = A,T,C or G
```

<400> SEQUENCE: 13

```
gtgngtctag atgcatgctc gagcggccgc cagtgtgatg gatatctgca gaattcgccc    60
ttcgagcggc cgcccgggca ggtacccagg attcaaaagt catcttcccc ggcgggaggc   120
aagggacgct tatggagaac ctcttaaaga tattgtgagc attctactca ttacttaggg   180
aaagagagcg ggtgttggtc caactctggc ttttgtgcca ggtaggagtt ggtcctgagg   240
ccgcccatct gaccatactg gacctgtttt aaggtttttc tctaaaaaaa ttttagattt   300
gtcaatctgt gctcctgcag gggatgctat gtccaaatgt cccaggattt gttttttttct   360
gtctttcctg agacattccc tgcccagcta cccaaggaat ccttcaaacg agcaaatctg   420
accatatctt ctatggtcag attaaaatct tccatggctc cctattgctt atgggacaaa   480
atcaaaattc ctgagtctgg tctaaaaggt gtttgatgat cttgacctgc tgactttgcc   540
agccttcttg tcagactctc gtgtcatgct ccgcctagac tatgagcctg ctatttcata   600
ctatgtagct ttgtaaagtc ccagaaaatg ctgggctctg actcttttat aactttacat   660
atactgttcc atctgcctgg aatgccttct acttgtctgt ccagcaaatt ctcaactcat   720
ctcttaaggg cccagcttca attgccgcct cctancataa gtcttcccctt gatttcccan   780
gcagnaatta nntcccgcgt accccgggga ntcccaatca gtttgtgctt tcaaaactga   840
tggnnngact tccctgaaat ttgggttacc ncaaaacgaa atgggtgaat ccnnttcccc   900
cggggggggct gcaattgcac ccttttttaa aggggaaccc tgnaantccc aatggnttaa   960
atttgacncc cttaanggcn tnanttcnat tgagcaactt naaaagggt tttttttttt  1020
```

<210> SEQ ID NO 14
<211> LENGTH: 1013
<212> TYPE: DNA
<213> ORGANISM: Homo Sapien
<220> FEATURE:
<221> NAME/KEY: misc_feature
<222> LOCATION: (1)...(1013)
<223> OTHER INFORMATION: n = A,T,C or G

<400> SEQUENCE: 14

```
gtgtcgatgc atgctcgagc ggccgccagt gtgatggata tctgcagaat tcgccctttc    60
gagcggccgc ccgggcaggt acctcattag taattgtttt gttgtttcat ttttttcnaa   120
ngtctcccct ctacnagctc acctgagata acagaatgaa aatggaagga cagccagatt   180
tctcctttgc tctcngctca ttctctctga ancctaggtt acccattttg gggacccatt   240
ataggcaata aacacagttc ccaaagcatt tggacagttt cttgttgtgt tttanaaggg   300
ttttccttttt tctnancctt ttcctgcaaa aggctcactc agtcccttgc ttgctcantg   360
gactgggctc cccagggcct aggctgcctt cttttccatg tcccacccat gagccctcna   420
ctagacagct cantaagcct ggcccttcat tctgcgctgt gttcttcctc ngtgaaaatc   480
caatacctct tacctcctct gcatgcaaag attctcaagg attgtcagac ttcaaacgta   540
acagcagaac caccagaagg tccnataaat gcagtagtga ccttctcaag ctgtcaggtc   600
tttaaatagg atttgggatt taatgcnatg tattttaaaa ggaaagaaat aagagttgcn   660
agtttaaaaa tgcatgtctt ttagccaatt cagaatcctg cccccaaact tttttaaaaa   720
gtcaagacag ataaagcttt gggggganacg gaaaaaaann gnnnaaaaaa anaaagtact   780
tcgggcggna acnacgctaa gggnnaattc agcananggg gggccgttac aagngggttc   840
nanncccggt acnaanccttt gggggtttaa caagggcnaa ancnggttnc cggggntnaa   900
aattgttacc cgcnaaaaat tccanaaaaa natncgaacc cggaaancca taaanttntn   960
```

```
aanccenggn ggccnaaggg agngnnnaac cccnaataaa tggnttggnc cnt          1013
```

<210> SEQ ID NO 15
<211> LENGTH: 951
<212> TYPE: DNA
<213> ORGANISM: Homo Sapien
<220> FEATURE:
<221> NAME/KEY: misc_feature
<222> LOCATION: (1)...(951)
<223> OTHER INFORMATION: n = A,T,C or G

<400> SEQUENCE: 15

```
accctagggc aaatactgag cagggtaaaa ttcccagaat acccactaga agcgtggaat    60
atatcaatat cctaggaaga agattcagca caccaaattt cccattactg ataacagctc   120
tgaaggcata ataagaaagt gagtgatcag aagagcagag aaatgacttg ttccagtcac   180
tgccatcttt tttacccttt cagtggttcc cttaccettt tccccactgg gcatacagct   240
catctctctc tgagtccttt tctgctttcc tcctttgctc taaacgttcg agtttcaaat   300
tcctcttacg accagactta tctcgaaata cggtttcagc atattgaaat tcagctgcaa   360
aggaaaatta tactcaaata tcaggatcaa aatcagaaat aacattctaa gagatcaaat   420
caaccgcttg ggattctaat gctagataag aacttctgca gccagaccaa agtagttcct   480
accaacatct tggtgcatat tggcactggg cccaagaaat ggcatttcc ttttttttt   540
ttttgagatg gagtctcact ctgttgccca ggttggagtg cantgggcgc gattttggct   600
cactgcaacc tccacctccc aaggttcaag cgattctcct gtctcaagcc tcctgagtna   660
gctggggaat acaggcata cnacancatg cctggctagt tttttttttg gaattttggn   720
tagagacagg ggtttcatca nggttngccc aggcctggtn cttggaactn anagaccctc   780
aggntggatt caaccccaact tccgggctac caaaaggtng ncgngggatt acangcattt   840
anncaacngn gccctnggge naaaatggna anttttcang aagggaaagc agcnntgggg   900
atcccnggnn naantttcac caaggcctta aaccagggnc gtaaatttgt t            951
```

<210> SEQ ID NO 16
<211> LENGTH: 1008
<212> TYPE: DNA
<213> ORGANISM: Homo Sapien
<220> FEATURE:
<221> NAME/KEY: misc_feature
<222> LOCATION: (1)...(1008)
<223> OTHER INFORMATION: n = A,T,C or G

<400> SEQUENCE: 16

```
gtgcgatgca tgctcgagcg gccgccagtg tgatggatat ctgcagaatt cgcccttteg    60
agcggccgcc cgggcaggta cattacttgg tgttaacatt gttggcagtg gtagccectt   120
ttcagaaagc aacttgctgt aagtcagggt gtccgttcca accttcagct agtgaaaagg   180
tagtaacaaa tggtaaacaa gagaatgatt gtttaaacct atctgtggac acttaatgca   240
actgtttaaa aatgataatc acgagttatg tagcaacgtg gaaatatatt tacagaacat   300
taagtggaga aagcaggaca cgaaagtata tttatactac agttataact caacagttca   360
tttatatgct gttcatttaa cagttcattt aaacagttca ttataactgt ttaaaaatat   420
atatgcttat agtcaaaagc tgttgtggtg ttgttgttgt aggcttatag ttgagcatta   480
ttttcttaaa tttcttgaat gttctttatg gtagtgttac taaaaagttt atgatcacat   540
tttcattgtg aacataattt gaactcatta tcacacactt ggaaaataca gaaagtggaa   600
```

| | |
|---|---|
| ggaaaaaaaa tcatatcccc ancatccaaa gacatatact ctcctcttat cctgttcaat | 660 |
| cctggtttcc ggtgcacaag gtttatgatt ataactgtgt caaatgtat aatcaaaata | 720 |
| gctgttacat taccttggtg gnantaaggg taaatacctt caccttaaat ttttcaaaan | 780 |
| gttcccaana ataaaggtcc ggataacagt ggtataagtg tgtcccaatt ggggtgcan | 840 |
| aatacattcc cangnnggaa aatttnnaaa tnaagttaaa ttattttaaa aaatttccaa | 900 |
| aattcccaan anctaanaac taangggnaa aaacctngat cgggntnccc caaacnngtt | 960 |
| taantgnnac nccttgggaa aanaagnttt aaaaanggtg gcaaaaag | 1008 |

<210> SEQ ID NO 17
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 17

| | |
|---|---|
| gtgnctctag atgcatgctc gagcggccgc cagtgtgatg gatatctgca gaattcgccc | 60 |
| tttnnanagg ncgncgggc angnantctt cccnccntg ccatnannca cggnnanaan | 120 |
| cngcagtggc actaantntg agacaatctt ncaaaccagc ttcatgtcgc tncacttntc | 180 |
| nnngtncaag angagggcca ggangggaaa catcacanct gcgctaagnc cngntccggg | 240 |
| nngtcagcat nngntctgtt ncaanncccn cgntcggtcc cctcatccta ctctgcctcc | 300 |
| natgactttg cnccctcagac ntcntggaac naaggnttcc nggggggcac accgcgtccg | 360 |
| gccgnnnntg tctcggggcc acttggcgtg tgtgataaat caatcaagct gttnanntcg | 420 |
| nacgagtctc nggtngcctg canannnaag cctcatcatc agagcctttc ctcaaaactg | 480 |
| gantcccana tgtcatcagg ttntggttnt tttcagccan naggaagccc tcngcattga | 540 |
| atccnagaac ttgggcatgg tnnaagatct acaagntnga atacgctgcc cgcnanaanc | 600 |
| nttcaaccct aacaggaagg tnggattcaa ggaaggtgta anggnncatt anccacncg | 660 |
| ggggnaccaa gggagntana antanncatn nntttgggtt cgcccnccga agggnnttaa | 720 |
| cccccggaat tnnntttnng ntnaagggg gnnnngggna aatcccngtt cnncatttgg | 780 |
| gaaagggann ccttnccttn cnntnggcct ntaaaagnnt tancaanacc cgnnatnntg | 840 |
| ttnanggccc cgnttttcaa nggggttaan nnnttnggn aaccccnnc cccaaagnng | 900 |
| gnnnaanggg ggnaattccc aanaaaacng ggggnncct tnnnnnangg gnttcgnnn | 960 |
| ccccnaaagg nnncntgggg ggnnannann gnncnaaaaa gggttcccnn nnnnaaattt | 1020 |
| tttc | 1024 |

<210> SEQ ID NO 18
<211> LENGTH: 981
<212> TYPE: DNA
<213> ORGANISM: Homo Sapien
<220> FEATURE:
<221> NAME/KEY: misc_feature
<222> LOCATION: (1)...(981)
<223> OTHER INFORMATION: n = A,T,C or G

<400> SEQUENCE: 18

| | |
|---|---|
| acgcgggaca gagagaaggt taagagcaac aagatgggag gcagctgcat ggaacctgtc | 60 |
| ccactgagga agtaaaacag agtttactc ttgttgccca ggctggagcg caatggtgcg | 120 |
| atctcggctc accgcaatct ctgcctcctg agttcaagcg aggagcaacc ctacctgatg | 180 |

```
gactggactt ctgcctggat tggagtttga tcatgcctcc atatgggtgt ttaccaggcg    240
tatgcattga acctgagttt gtctcttcaa tacaaggaaa atctctgccg cttagtgatt    300
ttccaagaaa catgagcttc tgcctttcaa tgaggaagat actcagaagt catgttcgag    360
cactccggaa aatgtccttg gagtttcaac atttctttgg tcttccacat ttcattttgt    420
cctgattaaa gaggaagcca agttgctgtt tgtgtggcca tgtgagcagg canggagatg    480
gtggctgcct agaagccaag agaagtggcc tcaagatgaa atctaccttg ctggtactgc    540
ccggggcggc cgcccgggca agtacnttt tttttttttt gtttttttttt ggcaaaaagg    600 ctgtaaagct tttttgggga gaaattttaa tgggncaaan tttccaacac aggnagcanc    660
cctgaaacca attttaagcg ggtccttccc ttttaaggct gtnnaattgc cccttcaanc    720
ttcctcaagg ngtttttcac cctcccnccg ggattttggn aaaggcccaa aantccntgg    780
gnnaanaagg gacaatctcc cggnnttaaa aaccaattnt ncggggngna accnggttcc    840
ctgggctann cnccttaan ggntccgggg gcccttttgn ggggnaatt ttcaaacggn    900 ncctncattt tctnaggggg naancnccct tngggtcann gggncannnn cccaagncttt   960 caaanccnaa ntcttttggg g                                              981

<210> SEQ ID NO 19
<211> LENGTH: 980
<212> TYPE: DNA
<213> ORGANISM: Homo Sapien
<220> FEATURE:
<221> NAME/KEY: misc_feature
<222> LOCATION: (1)...(980)
<223> OTHER INFORMATION: n = A,T,C or G

<400> SEQUENCE: 19
acttttttct tttttttttt tttttccgtc tccccaaagc tttatctgtc ttgacttttt      60 aaaaagttt ggggggcagat tctgaattgg ctaaaagaca tgcatttta aaactagcaa    120 ctcttatttc tttcctttaa aaatacatag cattaaatcc caaatcctat ttaaagacct    180
gacagcttga gaaggtcact actgcattta taggaccttc tggtggttct gctgttacgt    240
ttgaagtctg acaatccttg agaatctttg catgcagagg aggtaagagg tattggattt    300
tcacagagga agaacacagc gcagaatgaa gggccaggct tactgagctg tccagtggag    360
ggctcatggg tgggacatgg aaaagaaggc agcctaggcc ctggggagcc cagtccactg    420
agcaagcaag ggactgagtg aagcctttg caggaaaagg ctaagaaaaa ggaaaaccat    480
tctaaaacac aacaagaaac tgtccaaatg ctttgggaac tgtgtttaat gcctataatg    540
ggtccccaaa atgggtaac ctagacttca gagagatga gcanaganca nagggagaaa    600
tctggctgtc cttccaattt tcaatccgtn atcccaggtg aagctgggta ngaggggag    660 ancattngna naaaaatga aacaacanaa nccagtttac taaataaagg gaacctgccc    720
cngggcggcc cnccaanggg ccaaatttca ancaacanng gcgggcccg ttaccaantg    780 gnattccgaa gccncggta accaangcct nggngtnaat ccagngggnc aaancncgtt    840
tnccnggngt gnaaattggt tanccccgccc naanaattcc acancaacga atcngaagnc    900
cgggcnagca tnnangnnta aancccgngg ggggcncaaa agggaatgnn nccanaccnn   960
attaaatncg gttgccctg                                                 980

210> SEQ ID NO 20
<211> LENGTH: 1024
<212> TYPE: DNA
```

<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 20

| | | | | |
|---|---|---|---|---|
| cttggtaccg ngctcggatc cctagtaacg gccgccagtg tgctggaatt cgcccttcca | 60 |
| tcctaatacg actcactata gggctcgagc ggccgccggg caggtattca gcggccgctt | 120 |
| tttttttttt tttttttttt tttttttttt attgntgaca ctattacaga tagaatgacc | 180 |
| acaaccatat taacaaacca aaaacctgtg cacagaaaca agatgaagaa aatatatcaa | 240 |
| gatgttaacc acactntttg gatggtgaaa acatgggtga gtttctcttc tacatttctg | 300 |
| taacttcaaa gtttctataa tgaacacatt tcatatataa tggaaatata tgtagtaaag | 360 |
| gnggactacc aaaacactag aatgatgacc tttcaaggaa accgaaacaa aataaccata | 420 |
| atcccacaac aaccacacaa ctatttcttg gttttcatct ttcttcccat ctttgacatt | 480 |
| tatgcatact tatcactaac accctaataa tcacagacta gtgcacagat caagatgtta | 540 |
| acagttaatt gttgttgggt gttgggaata tgtgtgaatt ttctttactg aatttccaaa | 600 |
| gttttgtatg agtatgtatt atatttgtaa tggaaaatac atacataaaa tttattacca | 660 |
| aaacaccaaa gattatttaa ggaatttgag acaaaatatt taaccaaatt cccacaatga | 720 |
| caacactatt ttaggtatttt tccacatctt ttcatttaag actttatgcn cncatattta | 780 |
| acactggtat ccacaagcgt gtgccctgaa accaggatan ggggaaacn ngatcaagat | 840 |
| gttagccagt agtttggtag gnggttggga aatataggga atttttttnaa aaaaatttac | 900 |
| tttatttncn aaattttccc cttgggnaag ggattatggc ncnccaangg gngccccctt | 960 |
| aaanacnctg gttttcngga ccttttttttt ngggaccat ttggaaaaaa ttaangggga | 1020 |
| aggt | 1024 |

<210> SEQ ID NO 21
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 21

| | | | | |
|---|---|---|---|---|
| nagnngcang cncgagcgcg cgccagtgtg atggatatct gcngaattcg cccttcntan | 60 |
| cngnngncac tnaatgcang ngcnnaacca tgataacccg agttatgctn agcanaggaa | 120 |
| ctatatgtac agaaacatta agtgnngaaa gccnnacncn anggnanntg aatactacng | 180 |
| tnataactna ncagaccatt nanatgctgc acatttaaca nnncntncan acagnanatt | 240 |
| ataanngnnt ananntatat atgctnatng accaaagctg tngagggggtn gccgttgaag | 300 |
| gcnnnnngnt nagcattanc atnttacnnc acttgcctgn cctntatggc agggttacta | 360 |
| tctttgttac tgatcacgac atcantgcga acntaanacn aacncnntat nacacactng | 420 |
| nnanagcccg aatcgngnng gaacagtatc ntntcncnc canccnnaga catntncnnn | 480 |
| cctcttatcn tgancattcn agnttctgtg cacaggtnta tgatnntanc ngtgncaaan | 540 |
| tgnntcttna aantanttgc cacatnacct tngaggantt atggannaan actctcactt | 600 |
| taaanccnnc aancgacccc nanaaanctg tnctgntaac agtgcanaat gtgtgatttc | 660 |
| atagttntgc acacacatnc ccacnggaan cacaggcgtg tgcactgaac attntagagg | 720 |

-continued

```
ntacctatct gccgacacct aacactacng gtnacggcaa gatcggaacc tntaanngggg      780 ttaacncaaa cnctagggat acccngggaa atatgtggcc caccgtttaa accccccgaag      840 tgcccngtac ccnggacatt gttttcgtgn cggtanttgg gttaaanntg ggntnaaaac      900
cctaattccc cctgggggtt tgccactaaa tttgaaggac cttttggccc tgccaaaatc      960
annaaccctg gcncanaact ttgggggganc nggnnaggna gggtnncect ttttttccga     1020 aggc                                                                  1024
```

<210> SEQ ID NO 22
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 22

```
gtgcgatgca tgcncgagcg gccgccagtg tgatggatat ctgcagaatt cgcccttcg        60 agcggccgcc cgggcaggta cttttttttt ttttttttt ttttttttag attccacata       120
tgagtaaaat catgtggtat ttgacttgcc ttttaaaaca cagtgaagaa tctgtcttac      180
tttattcagg gtaggagaag ctacctgggc tccccataaa tgaggtgctc catcccatca      240
tacagcccca tcatattcag tgcttcccag atgacctcct cagggtgca gtagccctct      300 atgaagatta tgcttaggat aagtatgaga atgccagtct tgggcatgct ctggacatca      360
ctcagcatcc catcataggt gaggcccagg gaggtgacaa ggacaaagga gtggccagtg      420
ggatccactt cctttacatc aatgccaaag accagcagca tgcactcgga ggcttcacta      480
aacaacaaag ggaagtggtc ttcataattt tttatgacac tctccaagta tttctgcctt      540
tgtgatcggc tccttcattt gatacttgaa gagcagaaac tgcaccaaat cagtcacctt      600
ttcatctatc tcacttctgg gtaaagactc actgtctggc aaggacctgg tagggtgctt      660
gggactcccc tccttttggc tgcnggagnc ctcancagat tgatctaatg gaagggaaac      720
aacgacccna ggggaaggag cagggctatc tngagcaacn ctggggaagg atttggggtc      780
nccatcatca ngcagnaaac tccctcccgg gggtnccttg ggnanttaaa gggatnccca      840
ggaaggagga nggagggaan agggaggang agggaaaaac naggntngga aaaagggacn      900
cggngggaaa ttggggntta tacaccgccn ncnnnaannn ggggngagnc ngnngnccng      960
tcgnggncnn gnttccnntt gggngaagnn ggnttctcnn angggncgnn nnnnnnnnc     1020 cnnt                                                                  1024
```

<210> SEQ ID NO 23
<211> LENGTH: 948
<212> TYPE: DNA
<213> ORGANISM: Homo Sapien
<220> FEATURE:
<221> NAME/KEY: misc_feature
<222> LOCATION: (1)...(948)
<223> OTHER INFORMATION: n = A,T,C or G

<400> SEQUENCE: 23

```
acttttttct tttttttttt ttttccgtc tccccaaagc tttatctgtc ttgactttt         60 aaaaaagttt gggggcagat tctgaattgg ctaaaagaca tgcatttta aaactagcaa      120 ctcttatttc tttcctttaa aaatacatag cattaaatcc caaatcctat ttaaagacct      180
```

-continued

```
gacagcttga gaaggtcact actgcattta taggaccttc tggtggttct gctgttacgt    240
ttgaagtctg acaatccttg agaatctttg catgcagagg aggtaagagg tattggattt    300
tcacagagga agaacacagc gcagaatgaa gggccaggct tactgagctg tccagtggag    360
ggctcatggg tgggacatgg aaaagaaggc agcctaggcc ctggggagcc cagtccactg    420
agcaagcaag ggactgagtg agccttttgc aggaaaaggc taagaaaaag gaaaaccatt    480
ctaaaacaca acaagaaact gtccaaatgc tttgggaact gtgtttattg cctataatgg    540
gtccccaaaa tgggtaacct agacttcaga gagaatgagc agagnagcaa aggagaaatc    600
tgggctgtcc ttccattttc attccgttaa cctcaaggtg anctggtaaa aggggagaca    660
ttagaaaaaa aatgaancaa caancaatt actaatgang tacctgcccg gggcggccgc    720
aaagggcgaa ntccaagcac acngggcggg ccgttacaan tnggatttcg aacccggtac    780
caaancntgg gngtaaanca ngggncaana accggnttcc cggggtgaa antgttttat    840 ccgcccaaaa attccaaaaa ancaatanga aaccggaaan cataaagtnt taaaccctgg    900
ggggggccca aangantgag ccaaancca attnaattgg gttggncc                  948
```

<210> SEQ ID NO 24
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 24

```
taccgccctc gcatccctag taacggccnc cagtgtgctg gaattcgccc ttcctatctg     60
tggacactta atgcaactgt ttaaaaatga taatcacgag ttatgtagca acgtggaaat    120
atatttacag aacattaagt gggaaaagca ggacacgaaa gtatatttat actacagtta    180
taactcaaca gttcatttat atgctgttca tttaacagtt catttaaaca gttcattata    240
actgtttaaa aatatatatg cttatagtca aaagctgttg tggtgttgtt gttgtaggct    300
tatagttgag cattattttc ttaaatttct tgaatgttcc ttatggtagt gttactaaaa    360
agtttatgat cacattttca ttgtgaacat aatttgaact cattatcaca cacttggaaa    420
atacagaaaa gtggaggaaa aaaatcata tccccaccat ccaaagacat atactctcct    480
cttatcttgt tcattcttgt ttctgtgcac aggtttatga ttataactgt gtcaaaatgt    540
atattcaaaa tagctgttac attacctttg tggaattatg gttaaatact ttcactttaa    600 tttttttcaaa tgttccctat aataatgtcc tgataacagt gtattatgtg tgtctccatt    660
ggtgtgcata atacataccc agaggaaaaa ttagaaaata aagtaaatta ttttaaaaaa    720
ttacctatat tcccaacacc taacaactac tgnttaacca tcttgatctg nttcctctat    780
cttggttcag tgcacacgct ttgngaataa cagtggttaa atatgtgtgc cataaaggcc    840
ttaaatggaa aagatgtggg aaaaataact taanaataag ggtggccttt gggggggaaat    900 ttggttaaaa aattttgggc tcnaaaattc cnttaanaaa acctttgggg ggtttgggna    960
ataaaaatnt taanggangg aatnttcccn ttccanttt nattccttcc tcttcccaaa    1020
actt                                                                 1024
```

<210> SEQ ID NO 25
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 25

| | | | | | | |
|---|---|---|---|---|---|---|
| gccgtcnaga | cncatgcncn | agcgnncgnc | ngtgtgatgg | atatntgcng | aattcgncct | 60 |
| tccatcctaa | tacgactcac | tatagggctn | nagngngcca | ctattncnga | tngaangacc | 120 |
| acngccatat | taacaaacca | aaaacctgtg | cacagaaaca | agatgaagaa | aatatatcaa | 180 |
| gatgttaacc | acactctttg | gatggtgaaa | acatgggtga | gtttctcttc | tacatttctg | 240 |
| taacttcaaa | gnttctataa | tgaacacatt | tcatatataa | tggaantata | tgtagnaaag | 300 |
| gnggactacc | aaaacactag | aatgatgacc | tttcaaggaa | accgaaacaa | aataaccata | 360 |
| atcccacaac | aaccacacaa | ctatttcttg | gttntcatnt | ttcttcccat | ctttgacatt | 420 |
| tatgcatact | tatcactaac | accctaataa | tccagactag | tgcacagatc | aagatgttaa | 480 |
| cagttaattg | cngntgggtg | ttgggaatgn | gcgtgaattt | tctttactga | atttccaaag | 540 |
| ttttgtatga | gnntgtatna | natttgtaan | ggaaaatata | tacatnaaat | ttattaccaa | 600 |
| aacaccaaag | attatttaag | gaatttgaga | cnaaatattt | aacccaaatt | ccacaatgcc | 660 |
| aacactnttt | taggnatttt | ccacatcttt | tcntttaaga | ctttatgcnc | cccataatgt | 720 |
| aacactggta | tcacaaagcg | tgtgcactga | aaccagggat | nnagggaacc | gancaagatg | 780 |
| ttnncagnag | ttggtangng | gatnggaaaa | taggnaattt | ttaaannaat | tnacttttat | 840 |
| ttccnanatn | tccctttggg | gatgncttat | gcncccccat | ggggncccc | ctttanancc | 900 |
| ctggtaatca | nggccntttt | ttttgggggaa | cttttggaaa | aaanttnaag | gggaangttt | 960 |
| ttacccataa | tttccccaaa | ggnangggn | acncnttttt | ggaanatcct | ttnggcncct | 1020 |
| tttn | | | | | | 1024 |

<210> SEQ ID NO 26
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 26

| | | | | | | |
|---|---|---|---|---|---|---|
| gtgcgatgca | tgcncgagcg | gccgccagtg | tgatggatat | ctgcagaatt | cgcccttttcg | 60 |
| agcggccgcc | cgggcaggta | cttttttttt | tttttttttt | tttttttag | attccacata | 120 |
| tgagtaaaat | catgtggtat | ttgacttgcc | ttttaaaaca | cagtgaagaa | tctgtcttac | 180 |
| tttattcagg | gtaggagaag | ctacctgggc | tccccataaa | tgaggtgctc | catcccatca | 240 |
| tacagcccca | tcatattcag | tgcttcccag | atgacctcct | cagggtgca | gtagccctct | 300 |
| atgaagatta | tgcttaggat | aagtatgaga | atgccagtct | tgggcatgct | ctggacatca | 360 |
| ctcagcatcc | catcataggt | gaggcccagg | gaggtgacaa | ggacaaagga | gtggccagtg | 420 |
| ggatccactt | cctttacatc | aatgccaaag | accagcagca | tgcactcgga | ggcttcacta | 480 |
| aacaacaaag | ggaagtggtc | ttcataattt | tttatgcaca | tctccagtat | ttctgccttt | 540 |
| gtgatcggct | ccttcatttg | atacttgaag | agcagaaact | gcaccaaatc | agtcaccttt | 600 |
| tcatctatct | cacttctggg | gtaaagactc | actgtctggc | aggacctgta | gggtgcttgg | 660 |
| gactctcctc | cttttggctg | ctggagccct | caacaagatt | gatctaatgg | gaagggaaac | 720 |

| caaccnaccg | aanggggang | gagcaggctn | ttctgaagca | ctctggggga | aggattttgg | 780 |
| ngtncncnat | catncagcan | gnaaacctcc | cnccggggt | gccttggnna | ttananggtt | 840 |
| agcaaggang | gaggacgnag | gaananggan | gnangnaggg | aaaaagangg | attggaaaan | 900 |
| agggancctn | ggtgggaaat | tggggttttn | nagcaatccc | ccnccaaaaa | ncnaggggaa | 960 |
| ccctgttcaa | cccncanggc | cnggnttcca | cttttggaat | ttgaaanttt | cctcaaggaa | 1020 |
| ngaa | | | | | | 1024 |

<210> SEQ ID NO 27
<211> LENGTH: 935
<212> TYPE: DNA
<213> ORGANISM: Homo Sapien
<220> FEATURE:
<221> NAME/KEY: misc_feature
<222> LOCATION: (1)...(935)
<223> OTHER INFORMATION: n = A,T,C or G

<400> SEQUENCE: 27

| acgcggggtg | ggggggggtcc | tggtctttgg | cttctcgact | cggtcctgtt | tcgacagcga | 60 |
| acatgtcgcg | gcctgtcaga | aataggaagg | ttgttgatta | ctcacagttt | caggaatctg | 120 |
| atgatgcaga | tgaagattat | ggaagagatt | cgggccctcc | cactaagaaa | attcgatcat | 180 |
| ctccccgaga | agctaaaaat | aagaggcgat | ctggaaagga | ttcacaggaa | gatagtgagg | 240 |
| actcagaaga | caaagatgtg | aagaccaaga | aggatgattc | tcactcagca | gaggatagtg | 300 |
| aagatgaaaa | agagatcat | aaaaatgtgc | gccaacaacg | gcaggcggca | tctaaagcag | 360 |
| cttctaaaca | gagagagatg | ctcatggaag | atgtgggcag | tgaggaagaa | caagaagagg | 420 |
| aggatgaggc | accattccag | gagaattccg | gcagcgatga | agatttccta | atggaagatg | 480 |
| atgacgatag | tgactatggc | agttcgaaaa | agaaaaacaa | aaagatggtt | aagaagtcca | 540 |
| aacctgaaag | aaaagaaaag | aaaatgccca | aacccagact | aaaggctaca | gtgacgccaa | 600 |
| gtccagtgaa | aggcaaangg | aaaattnggt | cgccccacag | cttcaaaggc | atcaaanggg | 660 |
| aaagaatccn | tctccaaaag | aagaaagatg | agggaaccgg | aaaacccccc | agaaaaggaa | 720 |
| aacatctana | agccccccaa | cccagaaatc | tggggataaa | ggggctgaaa | aataaacccc | 780 |
| cntttgggga | agntttaaaa | ttatgaangg | nctggggaaa | aaatttttt | aaaaaannnn | 840 |
| nnnnnnnna | aaaaaantt | cctgcccggg | ggggcgccnc | naaagggga | anttcaanaa | 900 |
| aaangggggc | ggtttaaaaa | ggggtttcca | ccccn | | | 935 |

<210> SEQ ID NO 28
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 28

| cttggnaccg | ccctcggatc | cctagtaacg | gccgccagtg | tgctggaatt | cgcccttcct | 60 |
| atctgtggac | acttaatgca | actgttaaaa | aatgataatc | acgagttatg | tagcaacgtg | 120 |
| gaaatatatt | tacagaacat | taagtggaga | agcaggaca | cgaaagtata | tttatactac | 180 |
| agttataact | caacagttca | tttatatgct | gttcatttaa | cagttcattt | aaacagttca | 240 |
| ttataactgt | ttaaaaatat | atatgcttat | agtcaaaagc | tgttgtggtg | ttgttgttgt | 300 |
| aggcttatag | ttgagcatta | ttttcttaaa | tttcttgaat | gttctttatg | gtagtgttac | 360 |

```
taaaaagttt atgatcacat tttcattgtg aacataattt gaactcatta tcacacactt      420
ggaaaataca gaaaagtgga gaaaaaaaaa tcatatcccc accatccaaa gacatatact      480
ctcctcttat cttgttcatt cttgnttctg tgcacaggtt tatgattata actgtgtcaa      540
aatgtatatt caaaatagct gttacattac ctttgtggaa ttatggttaa atactttcac      600
tttaattttt tcaaatgttc cctataataa tgtcctgata acagtgtatt atgtgtgtct      660
ccattggtgt gcataataca tacccagagg aaaaattaga aaataaagta aattatttta      720
aaaaattacc tatattcccc aacacctaac aactactgnt aacatcttga nctggttcct      780
ctatcttggt tcaagtgcac accgcttgng aataacaagg gttaaaaatg ngngccataa      840
aggtcntaaa atggaaaagg atgtgggaaa aatnacctaa aaataggggt ggccattggg      900
gggnaatttg ggttaaaaaa tttgggctcn aaaatncctt aaaaaaaanc ctttgggggt      960
tttgggaaaa aaaaatttta ggggagggaa ttttccattt ccaaatntta ntccntactc     1020 ntta                                                                  1024
```

<210> SEQ ID NO 29
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 29

```
taggatncat gctcgagcgg ccgncagtgt gatggatatc tgcnagaata cgcccttcca       60
tcctaatacg actcactata gggctcgagc ggtcgcccag gcaggtgcta acaaaccaaa      120
aacctgtgca cagaaacang atgaagaaaa tatatcaaga tgtaaancac actctttggn      180
tggtgaaaac atgggtgagt ttctcttcta cntttctgcn antncanagn ttctataatg      240
aacacatttc atatgtaatg gannthtntg tagtgnaagg tggactaccg gaacactaga      300
atgatgacct ttcaaggaaa ccgaancaaa ntnaccntan tcccacaana accacannac      360
tattncntgg tnntnatgtt tcttcccatc tttgacattg atgcntactt aggactancg      420
ccctaataat cccagacttn ggcacagatc aaganggtaa cnggtgattg gaggtgggtn      480
gccggaantt ggggtgantg ttntttatgg anttnccann ttttggtang ngattgnnna      540
aaattngaan nggaaacnct tacttnaant tgnttaccnn aacnccnagg atnttttaag      600 gattngggggс cnaatttttt acccaaattc cnncaangcc ancnctgtnt aagtcatttt      660 caaantttt tcncttaaag accttaaggc cccctaaggt aacctgggaa tanaaggggg      720
ggcacntggn accaggntcc nagggaacng nnccaagant tttccccntt ntttgtttgg      780
gggttgggaa atnnnngnaa attttttaaa ggtaatcac ttaatttgcc aaaggaattc      840 ccttngggggg nggnnttatt gcncacccat gggagacccc cntaaggccc cnggaataag      900
ggcctttttt tttngggacc atttgggaaa aatttaaang ggaaggcnnt ttgnaccctt      960
aatttcccca aggnaaangg aaccncccnt tttgganatt gcattttngg ccccgttttt     1020
aagg                                                                  1024
```

<210> SEQ ID NO 30
<211> LENGTH: 1024
<212> TYPE: DNA
<213> ORGANISM: Homo Sapien
<220> FEATURE:

<221> NAME/KEY: misc_feature
<222> LOCATION: (1)...(1024)
<223> OTHER INFORMATION: n = A,T,C or G

<400> SEQUENCE: 30

```
gtgcgctcta gatgcatgct cgagcggccg ccagtgtgat ggatatctgc agaattcgcc       60
ctttcgagcg gccgcccggg caggtacttt aattttgctt gttcaaatga tctacactta      120
cattttgcaa atcttttttt ttaaattttt taaattttat attttttttc cagccaactc      180
aaggccaaaa aaatttctt aatatagtta ttatgcgagg ggaggggaag caaaggagca       240
caggtagtcc acagaataag acacaagaaa cctcaagctg tgaggtcaat ttgtaattaa      300
aagaatacta agattagatg aacacaacac tcagaaatac tctaggagag ctgaaaaaga      360
aggaacagat gttaacaaaa caaattaagg ctgctgggga acctgagtcc atgttaagct      420
tgggttgact gtaaagaatt tttttttttt taatgcaagt tagacatgga gttagagggt      480
cagataaata acgaagagaa ttaagttagc gatagaaaga tctaaggata ctagctcctg      540
ggcacctagg gtgcaaactg acttgtggca gcataagctg atgctgcaca ggggacccaa      600
gccatgttgc tacttgtcac ttaaggcang aagcgcacaa aggaagtgat gaaagggtat      660
tagcctgcaa cattatttac agcatganag cctctcctac gggtcccaac cttcattagg      720
cactactggt gattcaagtg aatgggttgt aacccantcc ttaaaaggca aaggatgtta      780
ggantttaca gggaaaaaag cttccggggt tttancaatt caccaatcan caaaccacat      840
attgaagttt ggttaaaaaa aaaaanannn anaaaaaagt nccctcggcc gngaaacanc      900
cctaaggggg naaattccag canactgggn gggccgntta caaaggggtt cgaaccncgg      960
taccaaacct tggggttaa ncaaggggca aaancgggtt nccgnnggg aaaattgttt      1020
nccg                                                                  1024
```

<210> SEQ ID NO 31
<211> LENGTH: 1019
<212> TYPE: DNA
<213> ORGANISM: Homo Sapien
<220> FEATURE:
<221> NAME/KEY: misc_feature
<222> LOCATION: (1)...(1019)
<223> OTHER INFORMATION: n = A,T,C or G

<400> SEQUENCE: 31

```
gtgngatgca tgctcgagcg gccgccagtg tgatggatat ctgcagaatt cgcccttttcg      60
agcggccgcc cgggcaggta ccatgctgac ttcttggtat cttttaaggc ctaattttcc      120
cttccttgag attactgtag tgtgttccag ctaatttcta tttggaaacg agttggaaca      180
gctgaaaact aggtattatt gaaggcaaag cagcctcacg tcagtttttt atcagctcat      240
ttgggaagtt tttttttttt ttttttttta attaattaga aagtaggctg ggcacggtgg      300
ctcatgccta taatcccagc acttggggag gccgaggatc tcctctctgg tggatcactt      360
gagggcagga gttaagagac catcctgcc aacatgatga aaccctgtct ctactaaaaa      420
tacaaaaagt agctgggcgt ggtggcatac tcttacaatc ccagctactt gggaggctga      480
ggcaggagaa tcacttgaac ctaggaagca gaggttgcag tgggccaaga tcacaccact      540
atactctagc ctgggcgaca gaggtgggga aaaaagtagg acccctgtcc tatattcagg      600
tttttctcac atatatgaac ccatctaaat tctacgttgt taaaggtanc ttaggttaat      660
taagtccata cttatttaag accaatatgg ggtgaaatgg gattttttttt taaaaatcct      720
acagntnagg ctttccnact ttccttcnaa atgaggaaaa aaaggtgaca aaaattcaag      780
```

```
tgtcaatgtc ccctcctggg gaaanaggtt tanaaaaaca acaggctcaa ccttctgaac      840
tnctaacaan ttcccttnga aanttaacga anccattaaa atcnngattt taaaagagga      900
aaanaaaaaa gttcctcggn cggnnacaan cctaagggng aaattccaca aaaanngggg     960
ggcctttana aagnggttcc nacccggtac aaaaccttgg gnttaaccan gggccaant     1019
```

<210> SEQ ID NO 32
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 32

```
accgccctcg natccctagt aacggccgcc agtgtgctgg aattcgccct tgttgttggg       60
tgttgggaat atgtgtgaat tttctttact gaatttccaa agttttgtat gagtatgtat      120
tatatttgta atggaaaata catacataaa atttattacc aaaacaccaa agattattta      180
aggaatttga gacaaaatat ttaaccaaat tcccacaatg acaacactat tttagttatt      240
ttccacatct tttcatttaa gactttatgc acacatattt aacactgtta tcacaagcgt      300
gtgcactgaa acaagataga ggaaacagat caagatgtta gcagtagttg ttaggtgttg      360
ggaatatagg taatttttta aaataattta ctttatttc taattttcc tctgggtatg      420 tattatgcac accaatggag acacacataa tacactgtta tcaggacatt attataggga      480
acatttgaaa aaattaaagt gaaagtattt aaccataatt ccacaaaggt aatgtaacag      540
ctattttgaa tatacatttt gacacagtta taatcataaa cctgtgcaca gaaacaagaa      600
tgaacaagat aagaggagag tatatgtctt tggatggtgg ggatatgatt ttttttcctc      660 cactttctg nattttccaa gtgtgtgata atgagttcaa attatgttca caatgaaaat      720
gtgatcatta aacttttag taacactacc aataaaggaa ccatttcaag aaaatttaag      780
gaaaaataat gctcaactat taagcctacc acaaccaaca cccacaacag cttttggact      840
attaagcnta tatattttta acnggtatta atggaactgg ttaaatgaac tggtaaaagg      900
aaccgcatnt taaatggact ggtgnggtta taaccggtgg tataaaaana cctttggggc      960 ctggttttc ccttaanggt ctgnaaanat attttcncgt ngtccanacc ncgggatatc     1020
aatt                                                                 1024
```

<210> SEQ ID NO 33
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 33

```
gccntcnaga cncatgctcg agcggncgnc agngtgatgg atatnnngca gagnncgccc       60
ttccanccna atacgacnca ctatagggcn nncnnnntng gcnnctttgn tgcccctccn      120
ctcgnataat anctatatta acgaaattgt nctggccttg agttggctgg agagaaatat      180
tnngagnnnn accngtnnnn ntnngnnatc ngtaaantgt aanagtagnt catttgaaca      240
agcaatnatt naantaccca ctggnggaaa ngngnctgaa tcttactctt ntggatctgc      300
```

| | | | | |
|---|---|---|---|---|
| aggantaggg | cttgtnagta | tgtcaaanat | gcnnncagtg | tcaangttta ngccnattgt | 360 |
| aganctngta | gcaggaancn | acnntgangg | ancnncagaa | nggagnccth anacatnncc | 420 |
| agatntacga | ggngagagga | gacanacnga | gaaagacacc | ntaggnncga nctgnagaag | 480 |
| gncaggattc | tgagaatgaa | ntgcncggnn | agtccnganc | agattggaaa aggagnttct | 540 |
| ganggnatgg | tgcacnngag | ggctgacngg | tangaggnac | tgntgttgga acgnacatag | 600 |
| cgaaagntgn | tgngcagtga | ggattactac | atgnngaaag | gactcttgaa acgaggaact | 660 |
| aactgtgatg | ncanggctga | agtttgggcn | nccatacttt | gnaggttaca attnttngca | 720 |
| gtggncgncc | cgtttaaana | gccnttttga | tggaaantca | agggtgnncg gtacnacctt | 780 |
| ccntttaggg | nacaaggcnt | tnccgantgg | gtngccagga | agaanganng ccnnanccct | 840 |
| annggnggg | cccccttaatn | gcacnggtg | aacaatgcna | accctcgggt tattggaacn | 900 |
| accgnggana | anatggttac | cgaaccatta | ngtggggnna | aacccggacc ccggaaggct | 960 |
| tttttnncct | cngggtaaaa | acttaacaga | ccnattttt | gcccgccntt taacangtct | 1020 |
| tttt | | | | | 1024 |

<210> SEQ ID NO 34
<211> LENGTH: 982
<212> TYPE: DNA
<213> ORGANISM: Homo Sapien
<220> FEATURE:
<221> NAME/KEY: misc_feature
<222> LOCATION: (1)...(982)
<223> OTHER INFORMATION: n = A,T,C or G

<400> SEQUENCE: 34

| | | | | |
|---|---|---|---|---|
| acaacaatct | aagcaaatct | caaatacaac | atacttgtaa | ttagaacaca atgcaatgac | 60 |
| ttgattttag | caagaactag | acacttaatt | tggtaaaaga | aaccaaacaa tgcattatat | 120 |
| tgaatactaa | gctaagttac | cataattagt | cttacaaatt | ctcaaatttc acaactactt | 180 |
| ttgaacatct | aaatttaaac | ctaaatttt | taattaaatg | cctgttcaac aaagctaatt | 240 |
| ggaacaaaca | catttatgta | aatttacatt | ctagaatacc | agggtaaaca aggagacgtt | 300 |
| attcaaagat | gaatgagaaa | gttctattct | ttttcatcat | ttgtgtgatc aggttgcaaa | 360 |
| ggacatgctc | tttcctcgat | gaaactgatg | tcgaattagt | ggcagaggtg gaagaaccaa | 420 |
| gcacctttct | ggggggctcga | gcagccacca | cttttctgta | agtgcctggg aacactgtct | 480 |
| gctttagtcc | gcaccatgtt | caaacaagaa | gagaggagag | gagagaacga actgacttcc | 540 |
| cagccgaagg | tgtttcactg | ggacaaggcc | ccgcgttacc | tgcccggggc gggccgctcg | 600 |
| aaangcgaa | ttccaagcaa | cactgggcgg | gccgtttacn | nagtgggatt cggngctcgg | 660 |
| gtancaaggc | ttgggggtaa | tcaagggca | atagccggtt | ttcccnggggg tgaaaaatgg | 720 |
| tnttccgngc | acaantccca | nacaancatt | ccgaagccgg | gaancntnaa agtgttaaaa | 780 |
| ncctgggggt | ngcccaaatg | angtggngct | naactcccat | ttaaattngc gnttgcgccc | 840 |
| nanggccng | cctttccaat | tncgggaaa | cctgttncgt | gccaagtcgg cantaaagaa | 900 |
| atcncggcna | antccccggg | gnaaagggcg | ggnttgccgt | nttgggggc gncttccggn | 960 |
| tttcccgggc | caaagggann | ng | | | 982 |

<210> SEQ ID NO 35
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 35

```
cttggcccgc cctcggatcc ctagtaacgg ccgccagtgt gctggaattc gcccttccat      60
cctaatacga ctcactatag ggctcgagcg gccgcccggg caggtataaa atttaaaaaa     120
tttaaaaaaa aagatttgca aaatgtaagt gtagatcatt tgaacaagca aaattaaagt     180
acccactggg ggaaatgtgt ctgaatctta ctcttctgga tctgcaggat tagggcttgg     240
aagtatgtca aagatgcagg gagtgtcaaa gtttaggaag attgtagagc tgagagcaag     300
aagcagaaat gagtgagtca agaagggag tcctaataca tcaccagatc taggagggga      360
gaggagacag acagaagaaa acaccagagg caagaactgt agaaggccag gtttctgaga     420
atgaattgag cggggtgtcc tgagcagttt ggaaaaggag tttttgatgg tatggtgtag     480
gtgagggctg gctgcatagg aaggactgag gttggagcgg acatcgggaa agctgagggg     540
cagtgaggtt tactacatgg gaaaaggact cttgaaacga gaatcagtgt tgatgtcagg     600
gtgaactttg tgggtacatt acttggtgtt aacattggtg gcagtggtaa gccccttttc     660
agaaagcaac ttgcttgtaa gtcanggtgt ccggtccaac ctttaactag tgaaaaggta     720
gtaaccaatg gtaaaccagg agaatgattg gttnaaccct atctgnggac acttaaatgc     780
cactggttta aaaatggnaa tcacgagttt tgtancaacc ggggnaatat atttaccgga     840
acctttantg ggnnaaagcc ggncnccnaa ggnttttat tncttcnggt tttaaccttta     900
acaggtncaa tttataatgc cgggccattt aacaggtcat ttttaacccg gtcnntttt     960
acccnggtta aaaaanntnt atgcctttag gncaaaanct ttttnggggg gnttnttgtt    1020
nang                                                                1024
```

<210> SEQ ID NO 36
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 36

```
taccgcctcg natccctagt aacggccgcc agtgtgctgg aattcgccct tccatcctaa      60
tacgactcac tatagggctc gagcggccgc ccggggcagg tagcaaatgt tgtggcattc     120
ctcctcctcc tcaagtcttt acccgaaact acttcccaag agaggttgct cttcccaaag     180
aatcacctgc cctgggacca tatggggcta ggctgagggt caggagccaa gagcctggtc     240
ccaactctgt ctgtggctta ctgtgagacc ctaggcaagt tgcttaccct ctctggggct     300
caaattcttc ctctttgaaa taggaataat aacttcatca ctagaattct tcacctggtt     360
gttgtgaagt taatcagaat aaatgtggag ataatacatg aatgagcgta cagaatatta     420
tttggctgtt ctgtggcatc gatataggtc atgatagtga caatagtgtc tgtcattgta     480
ttccacacca cttcttccct cagctaaagc aggaaaagaa aggaggtaag tctctctgtg     540
ttttttcttc ctttcccccaa gcccactttg ttaccttcct tggttgctgg atgagaaatt     600
agtcagaggg tcagagagga cctcaacttc atatgcttta aatagagcat atgcaatttt     660
aaaccatcct cttaaccaat ttttctttc ttttcagttt ttcccagtt atacttccac     720
atgatacacc agagaaggaa gatcctttct catactgaag aacacaagaa atttgaatag     780
```

-continued

| | |
|---|---|
| ttcctgctttc ctgnaccttc caccaaaaca aactttcaa tgatccaaaa aactggcttt | 840 |
| gnactgggga gtcacggaat gggccggctt ccanggaca tggcggnngg gcctttgcgg | 900 |
| ngtcgggcct gtggtggcgg cggaaaggna accgggggca tggnttnccg agcctggtct | 960 |
| tgcccccncg ggncatggtg tggaggcaaa gaanccctgaa gtccccacng gccccggga | 1020 |
| agna | 1024 |

<210> SEQ ID NO 37
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 37

| | |
|---|---|
| cttggcaccg cnctcggatc cctagtaacg gccgccagtg tgctggaatt cgcccttcca | 60 |
| tcctaatacg actcactata gggctcgagc ggccgcccgg gcaggtgaat tcagcggccg | 120 |
| cttttttttt tttttttttt tttttttttt acagggcggc ttttgttttt atttctgctt | 180 |
| ttttccctt tcttaaaaa aattaaataa agttctcatt atttcccaa tatacatcaa | 240 |
| atgagttttc atgcaaagca gcagtcacag aggcagaact gtccccagct cgtgcctntc | 300 |
| ggcttgaaga accaccttnt cccggccccg ggttctctgg ngttctcact gaggatggac | 360 |
| gacgcccact gtcntccca gctggaactg gctatgacga aacttggctg gcgtagggag | 420 |
| aggagtcctc ccctntcccc aggatggggt ctcaggggac agcaagctct ggggcctgat | 480 |
| ccccatcact tgnccttcca tctgagactc ccagtgtgac agcttggaca ggtccctctt | 540 |
| cccaggaatg cgaggctcct cctctcagct ctcaatggac atggcattaa tgagctgctc | 600 |
| caccttataa gccagccgnt gccgccgtgc ctgctcatcc tgctctaggg ccccgatgag | 660 |
| ctcctcacta tacttgctga cataggagta gatctcattg ggggcactca acatgttgaa | 720 |
| actccacggn gtgcaggcgg gactgctcgg cgagggtagg cattcatggc ctggtcactg | 780 |
| gatggctggg aaccttggcc aaggctgcgg nagnatcttt tcccccagc tnttggnaac | 840 |
| ttggggaagg cccttgggca taaaaagcaa cttggttgga angggaggn ctttgcccaa | 900 |
| cccgggggct ttggacgttg gaacaagagt nccttgaagg gtttgggncc cccncaaaaa | 960 |
| ngcangcntc cgggaaagcc gcccttgggg gtgncaaaac cccnaactgg ggggttnttn | 1020 |
| aanc | 1024 |

<210> SEQ ID NO 38
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 38

| | |
|---|---|
| taccgccctc gcatccctag taacggccgc cagtgtgctg gaattcgccc ttccatccta | 60 |
| atacgactca ctatagggct cggcggccgc ccgggcaggt gccgcttttt tttttttttt | 120 |
| tttttttttt tttttgcttc acaactgttt attttaagct gaaacttcaa tattcattga | 180 |
| ttacctataa taatagttac tcataaatgt agttaataat aaatataaa aattattatt | 240 |
| tttacattta tataaatctc tgaaaaatac caagttttga gagatagagc aagaaattgc | 300 |

```
ttanaaaatt gcaggaagcc tgaanaatct cagcatcagt caaagcaggt ncaacaaaaa      360
acaattttag acattcattt tttgctttaa gagtgcttaa aataaatgat cacagaatga      420
ataactgatg tatggcaaaa atgagtttaa aactatgtaa gctccaaggc cccaatgtgt      480
ataagaattc tttggaagga ttttgaagga ctgtaaatgt tgcaaataaa agtaaaaact      540
agtagttagg caatgngttt taaactatag ngtcacctac tgntcttctg gtgcctaact      600
gnattcttca acatcttctt ttcccttttg attagaaatc ctggtctacc tcaaaggttt      660
tgcattgntt tctagggaca tcagcaaact ggtagaccat atgagaaaca gaaataaaca      720
gtaatattat ctttagaaat taagcattat gtacncagtg agaaatggat tgacttgata      780
gaccttaaac cccttcttc ctttcacacc ctttntagna ccacctaang gtatccggat      840
tggggatggg gccccnctnt ggtaatcccc ctnnagtcag gacagggcc cctaagggcc      900 caattttntt tcgaattaga gaaatnccccc atttttggg gggttggcaa gtnttancccc      960 anggcttgca aaggcttntt tttgaagana cncccaaacc cggggncttn tttttcngga     1020
atca                                                                   1024

<210> SEQ ID NO 39
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 39
tcgcccgagc agnangcncn agcggncnnc agtgtgatgg ttatngtgnn gnnttcgcnc       60
tnccatncta atnctactca ctataggggnn cntgngncnc nnggcnagtn ntnacnnntn      120 anngtgtaa ctgatatcat ntcncnnana ccatggttac atnnanntag gtctcnnaang      180 nataccangc tntgagagnt ngaccnggaa ntcgnttnga aannttgngc gangccngat      240
caatatcccn atcgncaca gcggntccgc aagctgacaa tnctgnanat tnattnttgg      300 tttanngganc nnttacangn atggnncccn gagatgcatg nnggagtatg gcaaagatgn      360
ntgtaaaact atgtaagctc naaggcccca atgtgnataa cagttcntgg nanggantnt      420
ganggantgt aagngntnaa nntnaangnn anannnaaga ggtangncat gagcccnaaa      480
ctgtagnnnt anctacagng cttanggcgc ctacctggga caggcacgn cttcattaac      540 cttttgatta gaanncggg ggtaacncac nggttnngca tggtccagta ggngcattgn      600 ccngcnggc aaccatatgc tgngcncaaa taaacggtgc ttttanctca nnagattaaa      660 gcttttggc cacaggggna aaagnatggc ttganaggcc ttaaaccccc gtactcngtn      720 caccccttn gagaaccncc taacgggatc tggaaatgng atggcccct nttgggaaac      780 ncccctanaag anacctcngg ngaccccttg nggcccattt tgangtttag nacngcaatt      840
tncccatttt tgnggttttt gccaaccccta agncatggct tggcaatgga ntgnnttttc      900
caatagaanc aaaccccggn tnttttttgg ggggnatcag ggttaagggn nttggcaaaa      960 nnaaanngc ncnnggnaaa aattttccc nggtntatcn aaanncccca aagcttttng     1020 caan                                                                   1024

<210> SEQ ID NO 40
<211> LENGTH: 1024
<212> TYPE: DNA
```

<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 40

| | | | | | |
|---|---|---|---|---|---|
| nggacgcatg | ctcgagcggc | cgccagngng | atggatntng | tgcagaantc | gcccctttcat | 60 |
| gcctatgatc | ccngcacttg | gngaggccga | ggatctcctc | tctgggggat | cacttgaggg | 120 |
| caggagttaa | gagaccatcc | tggccaccat | gatgaaaccc | tgtcnctact | nnacatacag | 180 |
| gaagnagctg | gncgngntgg | catactctta | caatcccagc | tacttggnag | gntgangcag | 240 |
| ganaatcact | ngnacctang | aagcagaggn | tgcatntgnn | ccaanancac | accactatac | 300 |
| tntagcctgn | acgacagagg | tgntgataan | agcnggaccc | ctgactatat | ncaggntttt | 360 |
| ctgacntnna | nnancncatc | taaatnctac | gccgtntgag | gtcgcntagg | ttangtagnn | 420 |
| natnctnatt | tatgaccaat | atgntgtnan | acggcntnnt | gntnaaaant | tntacagnan | 480 |
| ggcngnctac | nttncttata | atgnggaaaa | cggtgnctga | natncangtg | nnnnngtccn | 540 |
| nttnntggna | agaggnttng | aaanncanca | gtgcaccttn | tgaactctac | nagnagcttn | 600 |
| tgaagctaac | naagcnttaa | natnagatgg | cntgntagga | ctgtacnngc | anggaaagat | 660 |
| tcacaaaact | ggacattctt | naccgagata | ngntcttgct | ttaccgggga | ggacnnntcc | 720 |
| aaggntgtnt | naagagggac | agtcagctta | gtnntgctng | ggtagagaaa | accangactt | 780 |
| natntgtgag | cttgatnggc | agaacctggn | nanccttgga | agagcntnga | ttgnccngat | 840 |
| ccctgaaagg | gcnnncttna | ccctatcggg | gaccttnnna | acctcttang | tggcacgcaa | 900 |
| ggcacnaacc | nggcncnttt | caagaatcnc | nggaatcnag | gccccttct | tgggntnanc | 960 |
| cngnnnnncc | cgttnagncc | cncgggnaaa | anntcttggg | nntttccaat | cccngnggnn | 1020 |
| nttt | | | | | | 1024 |

<210> SEQ ID NO 41
<211> LENGTH: 1004
<212> TYPE: DNA
<213> ORGANISM: Homo Sapien
<220> FEATURE:
<221> NAME/KEY: misc_feature
<222> LOCATION: (1)...(1004)
<223> OTHER INFORMATION: n = A,T,C or G

<400> SEQUENCE: 41

| | | | | | |
|---|---|---|---|---|---|
| ggtnnnntta | atcatcgccn | gcttggtacc | gagctcggat | ccctagtaac | ggccgccagt | 60 |
| gtgctggaat | tcgcccttag | cggccgcccg | ggcaggtact | tcccaccact | ggaaatgtta | 120 |
| gcataaaaga | acttggagag | gaaaaaagta | ttaacaaaac | tgcagtctgc | actctttaaa | 180 |
| cctgtttaag | gctcttcatc | ctggttagca | aaggtgtga | atgtaatgtg | atggaattta | 240 |
| aaagttttat | gagaccaggc | acagtggctc | acgactgtaa | ttccagcagt | ttaggaagcc | 300 |
| gaagtgtgca | gatcacctga | ggtccggaga | ccagcctggc | caacatggtg | aaaccctgtc | 360 |
| tctactagaa | atacaaaaat | tagccaggtg | tggtggcggg | cgcctgtaat | cccaactact | 420 |
| caggaggctg | aggctagaga | atcacttgaa | cccagcaggc | ggaggttgcg | gtgagtcgag | 480 |
| atcacgccat | tgcactccag | cctgtgcgac | aagagcgaaa | ctctgtctca | aaaagatttt | 540 |
| ataagaaagc | agagcttttc | cttgaagctc | ttttgaagtg | gtagcttaat | tagtattttg | 600 |
| ntgaaaatac | tttaaagatg | cctagtgaaa | agcctactaa | agtgctgtga | aaaatggggt | 660 |
| ttanaacatt | ttattttcan | gctttatggc | ctattttcca | ttgnggcaag | tgcaaaacta | 720 |

```
ccctggccca aangaagggc agagaacata attacctctt anggcacatt tcattctttg      780
cagctttgct taatccagtn gctaagttct ttacctnaac cctgnaggna ttgaacntta      840
ttnccatttn ngnaaaaggg tcaccctntt nnnacaatnt tncannanct ttttnggaag      900
ttanccnttg gccttaaaan ttnaaaantc cntntggnnt tccctttatn ccccnnangg      960
gnnnantang gnntggattt ttaanggncc ttggccngaa cccc                      1004
```

<210> SEQ ID NO 42
<211> LENGTH: 1020
<212> TYPE: DNA
<213> ORGANISM: Homo Sapien
<220> FEATURE:
<221> NAME/KEY: misc_feature
<222> LOCATION: (1)...(1020)
<223> OTHER INFORMATION: n = A,T,C or G

<400> SEQUENCE: 42

```
nnnnnnnnnn nnnnngattg ggccctctag atgcatgctc gagcggccgc cagtgtgatg       60
gatatctgca gaattcgccc ttagcgtggt cgcggccgag gtacctttga taattcctag      120
acctctattt tcattctgtg tattaatgtg ataacagat ggatatttta atatttaagg       180
cagatggtaa actttcctat aggtcttgtg agacttcgtc ttataggctg aacaccattc      240
acaaaatgta ataatgcttc attccttcag gttgaggtaa agaacttgag caactggatt      300
agcaaagctg caaagaatga aatgtggcct aagatgtaat tatgttctct gcccttcctt      360
tgggccaggg tagttttgca cttgacacaa tggaaaatag gccataaagc ctgaaaataa      420
aatgttctaa accccaatct cacagcactt tagtaggctt ttcactaggc atctttaaag      480
tattttcaac aaaatactaa ttaagctacc acttcaaaag agcttcaagg aaaagctctg      540 cttttcttata aaatcttttt gagacagagt ttcgctcttg tcgcacaggc tggagtgcaa      600
tggcgtgatc tcgactcacc gcaacctccg cctgctgggt tcaagtgatt ctctagcctc      660
agccttctgg agtaagttng gaatacaggc gccccgncaa cacacctggc taaattttgn      720
atttctagta naanaccagg ttttnancat gttggncaag gctggtcttc cggaaccttn      780
angtgatctg gacacctttg gntttcctaa actgggtgga aattancagc gggaaccnct      840
ggggcctggc tcattaaacc tttaaaatnc cttnccattc anttcncacc ttttggtaac      900
cccgnatgaa aacccttnaa ccgggttttta agnangcnna nnngggnnat ttgtaaaact      960 ttttcccnt tccaagtcnt ttaagccaan nntttnccng gnnnngggan ccctnccggc      1020
```

<210> SEQ ID NO 43
<211> LENGTH: 1020
<212> TYPE: DNA
<213> ORGANISM: Homo Sapien
<220> FEATURE:
<221> NAME/KEY: misc_feature
<222> LOCATION: (1)...(1020)
<223> OTHER INFORMATION: n = A,T,C or G

<400> SEQUENCE: 43

```
ggagnnnntt aaacgccagc ttggtaccga gctcggatcc ctagtaacgg ccgccagtgt       60
gctggaattc gcccttagcg tggtcgcggc cgaggtactg tttactgctt tgtcttcaag      120
gcctagtgta ataattaaca tctagtatgt gtttgatgga tagccaattt ttgcttcatt      180
ggtatgttgt taccacagtc attggtagag tcaatatatg aatgaagaaa gtataacaaa      240
tttgccctct agtagagtac ttttttttttt ttttttttt tttttgttttt tttttttttt      300
```

-continued

| | | | | | |
|---|---|---|---|---|---|
| tttttttttt | tttttttttt | tttttttttt | tttttttttt | tttttttttt | tttttttttt | 360
| tttttttttt | ngnnnttttn | ncntttttn | aannaaaaan | cggcccnann | accnnccnnc | 420
| nnntttttt | nncnggccnn | ccnggnttng | gggnnggggnn | cnttnngggc | cnnnnggncn | 480
| cttttttccn | naagggtttt | ggggttttng | gggnaantt | tnggnncnan | nnnggcccna | 540
| aaaaanttnn | gnccnanaan | cgcnntttcc | nannnnttnn | cnttgggcc | caaaaanttn | 600
| cgnaaccccn | tgggcnnaaa | gggcnttgnt | tttttgggg | nncccnaaac | cangggggg | 660
| cnnaaaaaat | gncccttgaa | nttttaaaa | aaccctntgg | naaaanccc | nngggttccc | 720
| ccnnnnnccc | ttantttn | acanaanggn | nnaaangggg | ncccnnaaaa | naccnttngg | 780
| ggccnttttt | tnacaaattt | gggntttnn | aaggggttt | tnggggggc | cctntatncc | 840
| ccnaaaaang | aaagggnnnc | ccccccnn | nnnnnnncc | cnaaaccccc | ggnnntttn | 900
| ccngggggg | cccnnaaaaa | ggggnaant | ttnggnaaan | nccnnnncn | gggggnccn | 960
| ttnaaanntc | nntttnanng | gggcccnnn | nncccnnn | anngggggn | nnaaaaaccn | 1020

<210> SEQ ID NO 44
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 44

| | | | | | |
|---|---|---|---|---|---|
| nnngnnnnn | nngattgggc | cctctagatg | catgctcgag | cggccgccag | tgtgatggat | 60
| atctgcagaa | ttcgccctt | cgagcggccg | cccgggcagg | tacgcgggc | tcggcgctgc | 120
| ctacggaggt | ggcagccatc | tccttctcgg | catcatggcc | gccctcagac | cccttgtgaa | 180
| gcccaagatc | gtcaaaaaga | gaaccaagaa | gttcatccgg | caccagtcag | accgatatgt | 240
| caaaattaag | cgtaactggc | ggaaacccag | aggcattgac | aacagggttc | gtagaagatt | 300
| caagggccaa | atcttgatgc | ccaacattgg | ttatggaagc | aacaaaaaaa | acaaagcaca | 360
| tgctgcccag | tggcttccgg | aagttcctgg | tccacaacgt | caaggagctg | gaagtgctgc | 420
| tgatgtgcaa | caaatcttac | tgtgccgaga | tcgctcacaa | tgtttcctcc | aagaaccgca | 480
| aagccatcgt | ggaaagagct | gcccaactgg | ccatcagagt | caccaacccc | aatgccaggc | 540
| tgcgcagtga | agaaatgag | taggcagctc | atgtgcacgt | tttctgttta | ataaatgta | 600
| aaaactgcaa | aaaaaaann | nnnnnnnn | nnnnnnnnn | nnnnnnnn | nnnnnnnn | 660
| nnnnnnnnn | nnnnnnnnn | nnnnnannna | aancccnnn | aaaananmn | nnnaaaaag | 720
| gctnttta | angggcaaat | tgggaaacct | ttttnattca | aaatggctt | ttnccangga | 780
| ctggggacca | nnttnccng | gggnccaaaa | ttgggntttc | ctttaanccc | nttncnnaan | 840
| gggaatttt | nccttgggc | cttgaaaaac | naagcnnna | aaaagnccct | tgggnnggaa | 900
| accccttng | ggggaatttc | cncncctttg | gggggcnnt | ntnnnnnggg | acccnanttg | 960
| gncccaantt | ttgggaaaaa | nnngggnnaa | aaagggnnnc | cctgggggaa | aatgttnccc | 1020
| ccca | | | | | | 1024

<210> SEQ ID NO 45
<211> LENGTH: 1024
<212> TYPE: DNA
<213> ORGANISM: Homo Sapien
<220> FEATURE:
<221> NAME/KEY: misc_feature

```
<222> LOCATION: (1)...(1024)
<223> OTHER INFORMATION: n = A,T,C or G

<400> SEQUENCE: 45
ggagnnnntn aatcatacgc cagcttggta ccgagctcgg atccctagta acggccgcca      60
gtgtgctgga attcgccctt tcgagcggcc gcccgggcag gtacggcgca ttttgtgcac     120
acaaaatgtg cgcacacaca cacacacaca cacacagaca ctcctgcaca tggcctgtta     180
aagaactaca agggaggtgg gacgcgggaa agtgtatggt gtgggtttgc atcgtctcat     240
cattgattct tctcatattt ttctctgatt agagaaacta aagagaattt tgtgagaaag     300
gcttgaaagt taatgagtta cttctaccaa agtgattaca agcagaaatc ctcagatgct     360
gtagagatgc tgacccacac atccttagct caaggaagcc cctcgcatta gtcaccttca     420
gccatcagca gcctccacca ttaaccccag tgtgctgtat aaaaaatact ttctacatgt     480
gcccaaattt gaaaagttag gaagcactga tttcaaagca aatcattcac atttgaactg     540
tcttcagtgt acctcggccg cgaccacgct aagggcgaat tctgcagata tccatcacac     600
tggcggccgc tcgagcatgc atctagaggg cccaattcgc cctatagtga gtcgtattac     660
aattcacttg ccgtcggttt tacaacgtcg tgactgggaa aaccctgcgt tacccaact      720
taatcgncnt ggagcacatt ccccntttgg ccnactggcg taattaacca aaaaggnccg     780
gaccgaatcg gccntttcca acaagttggg ccaacctgaa tnggcnaaan ggccccccc      840
tgtaaccggn gccattaaac ccccgncggg nnnntgggg taccccaac ggggaccggt       900
taacttggcc anggccttaa ggcccggtcc ttttggtttn ttnccttcn tttttngccc      960
ntttnccngg nttttcccgn aaagntntaa aagggggg tcccnttta ggggtcccaa       1020
taaa                                                                 1024

<210> SEQ ID NO 46
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 46
nnngnnnnnn nnnnnnngaa ttgggccctc tagatgcatg ctcgagcggc cgccagtgtg      60
atggatatct gcagaattcg cccttagcgt ggtcgcggcc gaggtacact gaagacagtt     120
caaatgtgaa tgatttgctt tgaaatcagt gcttcctaac ttttcaaatt tgggcacatg     180
tagaaagtat ttttttataca gcacactggg gttaatggtg gaggctgctg atggctgaag    240
gtgactaatg cgagggcgtt ccttgagcta aggatgtgtg ggtcagcatc tctacagcat     300
ctgaggattt ctgcttgtaa tcactttggt agaagtaact cattaacttt caagcctttc     360
tcacaaaatt ctctttagtt tctctaatca gagaaaaata tgagaagaat caatgatgag     420
acgatgcaaa cccacaccat acactttccc gcgtcccacc tcccttgtag ttctttaaca     480
ggccatgtgc aggagtgtct gtgtgtgtgt gtgtgtgtgt gtgcgcacat tttgtgtgca     540
caaaatgcgc cgtacctgcc cgggcggccg ctcgaaaggg cgaattccag cacactggcg     600
gncgttacta agtggatccc gagctcggta ccaagcttgg cgtaatcatg gncatagctg     660
nttcctgtgt gaaattggta tccgctcaca attccacaca acatacgagc ccggaagccn     720
taagtgtaaa agccctgggg tgcctnatga gtgagctaac tccattaaat tgcgttgccg     780
```

| | |
|---|---|
| ctcactggcc ggtttcagtc cggnaaanct gcggncnact gcantaatga atcggncaac | 840 |
| gcccccggga aaaaagcggt tgcgaattgg gccctntttc cctttcttgg ttaatggact | 900 |
| ccntnngnct tnggccnttc ggnttnggnn naacgggatt aanttnnntt naaagggggg | 960 |
| naanacgggt ttncccnana atcngggggn aaacccccng gaaanaaacn ttggncccaa | 1020 |
| nggc | 1024 |

<210> SEQ ID NO 47
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 47

| | |
|---|---|
| ggngnnnnnn aaacgccagc ttggtaccga gctcggatcc ctagtaacgg ccgccagtgt | 60 |
| gctggaattc gcccttagcg tggtcgcggc cgaggtgcat ctgaacattg ccaagcccta | 120 |
| ggacattccg tagagcttgg ggattctgga ccaattggtt cagacaggac acgaaatgcc | 180 |
| tgtttgatgg gttctgcaat taaacaccca actactctct tttcatcaga tataaaaaga | 240 |
| aaagttttta ttttgtttgg acatttagga acaacttgct ggaagcccaa ttcattatca | 300 |
| acaagttctt ggacatcttc tacctttttg atagcaaagc ttggatcatg tggcagaacc | 360 |
| aacacgattt tcccatccca aaactctgct actacacgtt ctttcttcca acccacatat | 420 |
| ttgattcctt ccagaaacct gtggtgatgc tgtacctgcc cgggcggcaa gggcgaattc | 480 |
| tgcagatatc catcacactg gcggccgctc gagcatgcat ctagagggcc caattcgccc | 540 |
| tatagtgagt cgtattacaa ttcactggcc gtcgttttac aacgtcgtga ctgggaaaac | 600 |
| cctggccgtt acccaactta atcgccttgc agcacatccc cctttcgcca gctggcgtaa | 660 |
| taagcgaaga ggcccgnacc gatcgcccct tccaacagtt gccgcagcct gaatggcgaa | 720 |
| tggacgcccc ctgtanccgg cgcattaaac cgccggcggg tnnttggggt accccncacg | 780 |
| gggaccggta cactttgnca agggccctaa cggcccggtc cntttcgctt tcttnccttt | 840 |
| cntttnttgg ccacgttngn ccgggttttc cccgtnaagc ttttaaaatn ggggcttcc | 900 |
| cnttttaggg gttccnaatt aanggcttta cgggacccctt gaccccnaaa aaactttnnn | 960 |
| tttnngggg gngggggntnc ccntaggggg ccattgnccc ttgnnaaaaa anggtttttn | 1020 |
| nncc | 1024 |

<210> SEQ ID NO 48
<211> LENGTH: 1017
<212> TYPE: DNA
<213> ORGANISM: Homo Sapien
<220> FEATURE:
<221> NAME/KEY: misc_feature
<222> LOCATION: (1)...(1017)
<223> OTHER INFORMATION: n = A,T,C or G

<400> SEQUENCE: 48

| | |
|---|---|
| gnnnnnnnga ntgggccctc tagatgcatg ctcgagcggc cgccagtgtg atggatatct | 60 |
| gcagaattcg cccttgccgc ccgggcaggt acagcatcac cacaggtttc tggaaggaat | 120 |
| caaatatgtg ggttggaaga aagaacgtgt agtagcagag ttttgggatg ggaaaatcgt | 180 |
| gttggttctg ccacatgatc caagctttgc tatcaaaaag gtagaagatg tccaagaact | 240 |
| tgttgataat gaattgggct tccagcaagt tgttcctaaa tgtccaaaca aaataaaaac | 300 |

```
ttttcttttt atatctgatg aaaagagagt agttgggtgt ttaattgcag aacccatcaa      360
acaggcattt cgtgtcctgt ctgaaccaat tggtccagaa tccccaagct ctacggaatg      420
tcctagggct tggcaatgtt cagatgcacc tcggccgcga ccacgctaag ggcgaattcc      480
agcacactgg cggccgttac tagtggatcc gagctcggta ccaagcttgg cgtaatcatg      540
gtcatagctg tttcctgtgt gaaattgtta tccgctcaca attccacaca acatacgagc      600
ccggaagcat aaagtgtaaa gcctggggt gcctaatgag tgagctaact cacattaatt       660
gcgttgcgct cactggccgc tttccagtcn ggaaacctgt cgtgccagct gcattaatga      720
atcggncaac gcgcggggga aaagcggtt gcgtaattgg cgctctttc cgctttcttg        780 nttacttgac tccttgggct tcggccgttc ggntgcggnn aacggnattc aacttactca      840
aaaggcggna atacggtatt cccngnaatc ngggataac ccccggaaan aactttgacc       900
naaaggcccc caaaaggccc ngaacccgna aaaagggcn cgnnnnnnnn gggtttcct        960 aaggttccgg ccccctggnn aggtttccca aaaatngnnn cctttnannn nnnnngg        1017
```

<210> SEQ ID NO 49
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 49

```
ggngnnnnnn anatnaaacg ccagcttggt accgagctcg gatccctagt aacggccgcc       60
agtgtgctgg aattcgccct tgagctggcc gcccgggcag gtactgaaat tactctgaat      120
tcagaaatgt aagtatatgc agctaggtca taaagacact gctttagaga agacatgtat      180
tagtggaatg gaacaggtaa catctttgag aagtcaatga gttctgcatg cagggatttc      240
accatcggaa tgatggcaag aatgatgcct gcctgtgtgc ttctcagagg acgtataaag      300
ccactgagga tgagtgctac agtgcttgtg aattgtgggg ccacagacat ttaagttggc      360
attgcttttc tcctcctctg cttaatccac ctttataaat atggcagatg gcttaagaca      420
ggcatcatca gcatctctgg agatgtgggc tcagagggca agtgggggcc gtggggtttt     480 ccactgagg gagggaagtt tctgtttccc atgtgttagt tgtagttgtc tttgtgcttc      540
accagaaaag aggtagagtg cgcaccttca cactaagagc ccgaaattgt gggtcagtac      600
tttttttttt ttnnnttttt tggtnntttt tnnnnnnnnn nnnntnnnn ngnnnnnnnt       660 tnnnttnnnn ngnnnnnnnn nnnnnnnnnn tttnntnngg nnnncncttn nnnnnnaann     720
nngnnnannn ncnnnnnnnn tngnnnnnnn nnnnncnttn ngggnnnang ncccnannnn      780
nccnnnnnnn nnnnnnnnnn nnnnnnnnn nnnnnnnnnn nnccnannn nnnnnnntnn       840 nnnaanncnn tnnnnnnnnn nnnggnnnnn nnnnttnnan nnnnnnnnnn nngnnnaann      900
nnnnnnnnnn nnnnnnnnna annnnnnnnn nnnnnnnnnn nnnnnnnnnn nnnnnnnnnn      960
nnnnnnannn nnnannggn nnncccnnn nnnnnnnnn nnnnnnnnnn nnnnnnnntt       1020 nngg                                                                  1024
```

<210> SEQ ID NO 50
<211> LENGTH: 1024
<212> TYPE: DNA
<213> ORGANISM: Homo Sapien
<220> FEATURE:

<221> NAME/KEY: misc_feature
<222> LOCATION: (1)...(1024)
<223> OTHER INFORMATION: n = A,T,C or G

<400> SEQUENCE: 50

```
ggagnnnntn nntncngant gggccctcta gatgcatgct cgagcggccg ccagtgtgat      60
ggatatctgc agaattcgcc cttagcgtgg tcgcggccga ggtacactga cttgagacca     120
gttgaataaa agtgcacacc ttaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaanaana ntaaaaaaaa tttnaaggta aagntnnccnn ntnaaaatct tttagggnna    300
tccntatann nntttcgnn tntttnnngg ntngncctct nntnccnnnt tttttnggna      360
ancccnaann cccngnctta ccnnatgngn cananttaaa anggtncntt nttnngngga     420
nctcannncc cccgccnttt tnntnngggg ggnttnncca nnggnggnna aatgcncngc     480
tnatnaanan gggnttnntc cnaaatnngn naaccctga ggnggnaanc ntnntggnct      540
tnntncngat tnngnnaccc ccncnngcag anntcnttgn nnccttantn ccggggnta      600
naccttcct ttaaaancnc nntgntntna aaaannnttt ncctgancna tcgggntaaa     660
ncnnntttt tgaaaaccnn ggctttttnn aanangctcc gntnggcnaa ctttggggaa     720
naaggnnttt tttaaggcct tgcttttag ggccanccta anggngannn ncngttgnct     780
tgnnngatgg tttttagggn ttcccgggtg ggaccnttnt tgggggaaa ttttggnccn     840
agggggntccc ctnnaagaaa tccnnnttcc nggncncnaa ttnccnnaaa aattnngggn   900
ccnaaanntt tnattgggaa ggnccttgg ttgcccnnt aaanggnccn naaaccttta     960
aanggggggn gcntttaatg gcnccttcn ggnccnaaa aaanggggnc ccccnntttt    1020
nagg                                                                1024
```

<210> SEQ ID NO 51
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 51

```
gngnnnnntt aactcccgct tggtaccgag ctcggatccc tagtaacggc cgccagtgtg     60
ctggaattcg cccttagcgt ggtcgcggcc gaggtacttt ttttttcttt tctttctttt    120
ttttttttt tttaattttt gagatggagt tttgctcttg ttgcccacgc tggagtgcaa    180
tggcgcaatc ttggctcatt gcaacctcca cctcccggat tcaagcgatc cttctgcctt    240
agcttcccaa gtagctggga ttatagacgt gtgccaccat tcccagctga ttttgtatt    300
tttagtagag atggggtttc accacgttgg ccaggctagt ctcgaactcc cgacctcatg    360
tgatcctccc accgcagcct cccaaagtgc tgggattaca ggcgtgagcc accatacccg    420
gttgattgta gacttttgat tggtatttac aaggacccat gagaggcaac aaagagaagt    480
tgtcaagaga acagaccctg agaccaatag tttggctcaa gctctggctc cctaacttcc    540
taccagtttg accttgggca agttacctaa catctttgtg cctccatttt ctatttgtaa    600
aaggaaacta atagtagtgc ctactttata atagagttat acaaatatt aaatgagtta    660
atatttgtaa agtaattaga aaaatgcctg gcacttcaaa agcagccttc atttattctt    720
tggaaataat tttaaatgaa ttcaagggtt atatgtagct tttaggcata tatncctaaa    780
```

| | |
|---|---|
| tggcactgta aaactgcana aatatccgat ctttaaaaat ttttgggtaa atttatcata | 840 |
| atatggnaac caaatcccat ttaatggctt ttaggggtan ccgatnaaaa ccngaagttt | 900 |
| gcagtttaag ccncttatgg aangggaccc gaaattccaa ggancccann gggaaaaaac | 960 |
| cccnngagga atnttggccg ntttaantta aanccttttgg gtnntttaag nncctaaaaa | 1020 |
| nttt | 1024 |

<210> SEQ ID NO 52
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 52

| | |
|---|---|
| gngnnnnnnt tnngnttcng antgggccct ctagatgcat gctcgagcgg ccgccagtgt | 60 |
| gatggatatc tgcagaattc gcccttcgag cggccgccg gcaggtact tcaaaactat | 120 |
| tcataagcaa aaatcagtgt caaaatatt tagtaactta aaaaaaacaa aaagtataag | 180 |
| tagagacgga caagaactcc tcctgctttc tcccactggg ctcatcgtat ttctgttcca | 240 |
| ttacataaga gactaaaact gacaaactct gttttatcgc taacacctaa aagcaataaa | 300 |
| tgtgatttgt taccatatta tgataaaatt taaccaaaaa attttaaaga tcggatattc | 360 |
| tgcagtttac agtgacattt atgtatatat gcctaaaagc tacatataaa ccttgaattc | 420 |
| atttaaaatt atttccaaag aataaatgaa ggctgctttt gaagtgccag gcatttttct | 480 |
| aattacttta caaatattaa ctcatttaat atttgtaata actctattat aaagtaggca | 540 |
| ctactattag tttccttta caaatagaaa atggaggcac aaagatgtta ggtaacttgc | 600 |
| ccaaggtcaa actggtagga agttagggag ccagagcttg agccaaacta ttggtctcag | 660 |
| gggtctgttc tcttgacaac ttctctttgn tgcctctcat gggtccttgt aaataccaat | 720 |
| caaaagtcta caatcaaacc gggtatgggg ctcacgcctg taatcccagc actttgggga | 780 |
| ggctgcggtg gggaggatcc ccatganggt ncggagttcg agactagcct gggccaacgt | 840 |
| ggnggaaacc ccatctntac taaaaattcc aaaatcanct ggggaaggng ggcacacgtc | 900 |
| tataatccca cttccttggg aagcttaagg ncnnaaggac gcttggaaac ccggaangggn | 960 |
| gnggttcaat ggancccaaa atgngccatt ggnctttcnc gnggggccaac angagccaaa | 1020 |
| ntcc | 1024 |

<210> SEQ ID NO 53
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 53

| | |
|---|---|
| gggnnnnnnn tnncttaacg cccgnttggt accgagctcg gatccctagt aacggccgcc | 60 |
| agtgtgctgg aattcgccct tagcgtggtc gcggccgagg tacattactt ggtgttaaca | 120 |
| ttgttggcag tggtagcccc tttttcagaaa gcaacttgct gtaagtcagg gtgtccgttc | 180 |
| caaccttcag ctagtgaaaa ggtagtaaca aatggtaaac aagagaatga ttgtttaaac | 240 |

-continued

```
ctatctgtgg acacttaatg caactgttta aaaatgataa tcacgagtta tgtagcaacg    300
tggaaatata tttacagaac attaagtgga gaaagcagga cacgaaagta tatttatact    360
acagttataa ctcaacagtt catttatatg ctgttcattt aacagttcat ttaaacagtt    420
cattataact gttaaaaaat atatatgctt atagtcaaaa gctgttgtgg tgttgttgtt    480
gtaggcttat agttgagcat tatttcttta aatttcttga atgttctttta tggtagtgtt    540
actaaaaagt ttatgatcac attttcattg tgaacataat ttgaactcat tatcacacac    600
ttggaaaata cagaaaagtg gaggaaaaaa aatcatatcc ccaccatcca aagacatata    660
ctctcctctt atcttgntca ttcttggttc tgngcacagg tttatgatta taactgngtc    720
aaaatgtata ttcaaaatag ctggtacatt acctttgngg nattatgggt aaatctttca    780
ctttaatttt ttcaaaggtc cctatnataa tggcccggat aaccgnggga tttaaggggg    840
ctcccatggn gggcataatn catacccnga ggaaaaattn naaaattaag gnaantatt     900
ttaaaaaatt ncctatattt cccaaaacct aacaactact ggtaaaaatn ttggaccggn    960
tccccctatt ntnggttaan ggcccaccct ttgggnaaaa ccggggtnaa aaattggggc   1020
ctaa                                                               1024
```

<210> SEQ ID NO 54
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 54

```
ggagnnnnnn ttnngtttgg gccctctaga tgcatgctcg agcggccgcc agtgtgatgg     60
atatctgcag aattcgccct ttcgagcggc cgcccgggca ggtactttt tttttttttt    120
tttttttttt ttacatttat gcatacttat cactaacacc ctaataatca cagactagtg    180
cacagatcaa gatgttaaca gttaattgtt gttgggtgtt gggaatatgt gtgaattttc    240
tttactgaat ttccaaagtt ttgtatgagt atgtattata tttgtaatgg aaaatacata    300
cataaaattt attaccaaaa caccaaagat tatttaagga atttgagaca aaatatttaa    360
ccaaattccc acaatgacaa cactatttta gttattttcc acatcttttc atttaagact    420
ttatgcacac atatttaaca ctgttatcac aagcgtgtgc actgaaacaa gatagaggaa    480
acagatcaag atgttagcag tagttgttag gtgttgggaa tataggtaat ttttaaaat    540
aatttacttt attttctaat ttttcctctg ggtatgtatt atgcacacca atggagacac    600
acataataca ctgttatcag acattatta tagggaacat ttgaaaaaat taaagtgaaa    660
gtatttaacc ataattccac aaaggtaatg taacagctat tttgaatata cattttgaca    720
cagttataat cataaacctg tgcacagaaa cnagaatgaa cnngattaga ngagagtata    780
tgtctttgga tggtggggat atgaattttt cctncacttt tctggatttt nccagtgtgn    840
gaaaaatgag ttccaaaata tggtcncaat ggnaaatgng ancntnaacc ttttagtanc    900
ccttnccttn aggaacattt caggaaantt tannaaaata anggctcaac ttttaggcct    960
acannancaa cccncaaaa ggnttttgac tntttanccn ntatattttt taaccggttt   1020
taan                                                               1024
```

<210> SEQ ID NO 55
<211> LENGTH: 1024

```
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 55
gnngnnnnnn ttaactccag cttggtaccg agctcggatc cctagtaacg gccgccagtg      60
tgctggaatt cgcccttagc ggccgcccgg gcaggtacct cacatgggaa acatgggaag    120
taaaaccacc tgaggagcct cttgatggtg agtcaggctg ttcctcgaag agtaggctgt    180
gactgccaaa ctttgtaggt taaggagtat ttataatgat ctttgaggaa actgcaactg    240
acaattgagg gaaaaaatg ttagttcatg actgcaaaat acatgacaga atcacaaaaa     300
ctattttaca agtttaaaaa acaaacctga tgctgatgca tggcaggcga accccaaagt    360
ggggcttagc ctgcaagggt tcttggcttc acccaggaaa ggattcaagg gcaagccagt    420
ggtaaggtgg aagaaaacac ctttatcaaa gcaacactgt tacagctcct gtggggtcac    480
agctcagtga ctgctcccag ggttgcccca taggcagggt gccgagagta gcagctgagc    540
ccagttttgc agtcatatgt atacctactt ttaattacat gcagattcag gggtggtttg    600
cgcagaaatt gttaggaaaa gggtggtaac ttttgggtca tcaggtcatt gccgcttaaa    660
gtggtggtaa tgcctgagtt ttgccatggc aatggtaaac tgacaaggca cgctgcttgg    720
tgtgtcttac agaaagctgc ttncgctctg nccttggtta nctagccctc ganncntttgg    780
ttgtaaatga accaagagaa gtcaccggcc cttggcgttt tcttcccaga agtacccttg    840
ggccgggaan cacgcttaag ggccaaattc ttgcagatat ccatnacact tggcnggncc    900
gnttcancct tgcatttaa aagggcccaa tttgncccctt taaanggagt cgantaccaa     960
ttnnnntggg ccgcgtttta acaacgtnnn ggacttggga aaaancccctg ggttaccccca  1020
antt                                                                 1024

<210> SEQ ID NO 56
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 56
gnagnnnnnn ttnngttnca gantgggccc tctagatgca tgctcgagcg gccgccagtg     60
tgatggatat ctgcagaatt cgcccttagc gtggtcgcgg ccgaggtact tctgggagaa    120
aacgccaagg ccgtgactct cttgctcatt tacaaacaaa agatcgaggg ctagctaaac    180
aaggacagag cggaagcagc tttctgtaag acacacccag cagcgtgcct tgtcagttta    240
ccattgccat ggcaaaactc aggcattacc accactttca gcggcaatga cctgatgacc    300
caaaagttac cacccttttc ctaacaattt ctgcgcaaac caccccctgaa tctgcatgta    360
attaaaagta ggtatacata tgactgcaaa actgggctca gctgctactc tcggcaccct    420
gcctatgggg caaccctggg agcagtcact gagctgtgac cccacaggag ctgtaacagt    480
gttgctttga taaaggtgtt ttcttccacc ttaccactgg cttgcccttg aatcctttcc    540
tgggtgaagc caagaaccct tgcaggctaa gccccacttt gggggttcgcc tgccatgcat    600
cagcatcagg tttgntttt aaacttgtaa aatagttttt gtgattctgt catgtatttt     660
```

```
gcagtcatga actaacattt tttttccctca attgcaagtt gcagtttcct tcaaagatca    720
ttataaatac tccntaaccc tacaaagttt ggcaagtcac agnctactct ttgaggaaca    780
agcctgactt accatcaaga agcttccttn angggntta cnttccatgg tttcccatgg    840
tgaaggancc tgncccgggc ggccgnttaa gggcgaaatt caacacactt gggnggccgn    900
tnnnttaang gatccnaact tggganccaa annnttgggg naaannatgg gnnnnnaact    960
ggnnnccggg ggggaaaatg gtatnccgnt tccaatttcc ccncnannnt tnnaancccg   1020 gaan                                                                1024
```

<210> SEQ ID NO 57
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 57

```
gngnnnnntt nantnaacgc cagcttggta ccgagctcgg atccctagta acggccgcca     60
gtgtgctgga attcgccctt agcgtggtcg cggccgaggt actcatcact gacttgaagc    120
ttagtatctg gcttccttaa ggatgtaact ttcatgtaac agattaataa cttatatgaa    180
aaccaacaca accatatgtt tagggctgga aagggccatg acgcctggtc atttttcctg    240
ttttacctta ctcttatgtg tgtcacactt catcaattcc ggaaacagtt tctggagatc    300
tcctcattac ctcttttaca atcacctcac tccagcatgg tgtctgttac ctcttcccac    360
ttgtgacaat gtccagtaag gtccactctc cattctgtgt gatgaccact tattacaacc    420
ctcagaatag gggacagtgg tgtgccccct gcaatacaat ggtttctatc tcctgatact    480
tttattacac ctctagcagg atgtcttgtg atcctcctta ttgattttct cctcacgatg    540
atgaacaatt atctcccgtt actcacctag cagtatctaa ctgtccctaa cacagcatgt    600
gggaatgccc tcaatacggt ggatgctgnt aactttcttc cttcccctca ggcaatggcg    660
gtgacttaca atgaaccata atggccacat ttcccaactg nattttggaa cctcttctgn    720 cccccttcttt ctaggancc agttaaaaaa aaaaaaccaa aactagcccc aatgnctgtg    780
atgcccatta atcacttacc cagggctgan ccctncatta aantttttgat gggatctctt    840 tggnttccca attggccgtt naacccaagn ctgntggatt cccaanttnc cccattgntt    900
taatgcgggt cccttaanca nccccttggnt actggacctg gccngggngg gcccttttaa    960
aaagggcaaa ttntggagaa aatnccttnc acttgggggg ccnttnnaac atggcntttt   1020 aang                                                                1024
```

<210> SEQ ID NO 58
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 58

```
gngnnnnntt nngtttggcc ctctagatgc atgctcgagc ggccgccagt gtgatggata     60
tctgcagaat tcgccctttc gagcggccgc ccgggcaggt acagtagcca aggtgactta    120
aggaaccgca tgaagcaatg tgggaaattg ggaatcagca gacattgggt taacgggaca    180
```

| atgggagcc aagagatacc atcaaaattt aatggagggg tcagacactg tgttagtgat | 240 |
| taatgggcat caacagacat tgggctagtt tttgttttt tttttaact ggggtcctag | 300 |
| aaagaagggg acagaagagg ttccaaaata cagttgggaa atgtggacat tatggttcat | 360 |
| tgtaagtcac cgccattgcc tgaggggaag gaagaaagtt aacagcatcc accgtattga | 420 |
| gggcattccc acatgctgtg ttagggacag ttagatactg ctaggtgagt aacgggagat | 480 |
| aattgttcat catcgtgagg gaaaaatcaa taaggaggat cacaagacat cctgctagag | 540 |
| gtgtaataaa agtatcagga gatagaaacc attgtattgc aggggcaca ccactgtccc | 600 |
| ctattctgag ggttgtaata agtggtcatc acacagaatg gagagtggac cttactagac | 660 |
| attgtcacaa gtgggaagag gtaacagaca ccatgctgga ntgaggtgat tgtaaaagag | 720 |
| gtaatgaaga gatcttccag aaactgtttc cggaattgat gantgtgacc nccttaaga | 780 |
| ntaaggtaaa acaggaaaaa tggnccaggc gtnatggcc cttttcagnc cttaacctt | 840 |
| attggtgggg tggtttcata taagttantt aatctggtnc cctgaaagtt tccttccttt | 900 |
| anggaaaccc gantcctaan cctttnaagt ccnnggatga gaccttggn ccgggaaccc | 960 |
| cccttaaggg cgaaattccn ncccacttgg gngggccntt nncttaaggg acccaacttg | 1020 |
| ggcc | 1024 |

<210> SEQ ID NO 59
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 59

| gagnnnnnnt taactcccgc ttggtaccga gctcggatcc ctagtaacgg ccgccagtgt | 60 |
| gctggaattc gcccttagcg tggtcgcggc cgaggtacct ggttttcttt caactcttca | 120 |
| atttcccatc ttccatcgta tattgaaatt tcctcatcca tgtcatcttt ctttgctttt | 180 |
| gataagaccc atccagccaa ccttccacta tcaaaagttt ctgcaaaata tacttctcct | 240 |
| ataggttgag gtgtcttata tttaatctct gaggaaagtt cactttcatt aacatcaatt | 300 |
| tcttctgaat tttcttcaaa gtcttccgtc tcaacatcat catccataaa ttctgcatta | 360 |
| attgagatga acagaagacc caaacataac caaaaggctt ggaaatgcat attgattatc | 420 |
| tctcttgcgg cctgttttcg gcagtgacag ctcagatgtc caagtcgttg ccacttggtc | 480 |
| cccgcgtctc ttcagaccag tccccccgc gtacctgccc gggcggccgc tcgaaagggc | 540 |
| gaattctgca gatatccatc acactggcgg ccgctcgagc atgcatctag agggcccaat | 600 |
| tcgccctata gtgagtcgta ttacaattca ctggccgtcg ttttacaacg tcgtgactgg | 660 |
| gaaaaccctg gcgttaccca acttaatcgc cttgcagcac atcccccttt cgccagctgg | 720 |
| cgtaataacg aaaagcccgc accgatcgcc ctttccacag ttgcgcagct gaatggcgaa | 780 |
| atggaccccn ccctgtancg gcgcattaan ccnccngcng gttnntgggg tacccccaac | 840 |
| ggggaccggt acactttgnc aagggcctaa cgnccggttc ntttggtttc ttnccttcn | 900 |
| ttnttngcac gttngnccgg ntttccccgt naagctttaa aatgggggc ttccccttt | 960 |
| angggtcccn aataaaggtt ttacggganc ttgaacccc aaaaaactt gnnttnaggg | 1020 |
| ggga | 1024 |

<210> SEQ ID NO 60
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 60

| | | | | | |
|---|---|---|---|---|---|
| gnnnnnnttn | ngttncngaa | ttgggccctc | tagatgcatg | ctcgagcggc | cgccagtgtg | 60 |
| atggatatct | gcagaattcg | cccttcgag | cggccgcccg | ggcaggtacg | cgggggggac | 120 |
| tggtctgaag | agacgcgggg | accaagtggc | aacgacttgg | acatctgagc | tgtcactgcc | 180 |
| gaaaacaggc | cgcaagagag | ataatcaata | tgcatttcca | agccttttgg | ttatgtttgg | 240 |
| gtcttctgtt | catctcaatt | aatgcagaat | ttatggatga | tgatgttgag | acggaagact | 300 |
| ttgaagaaaa | ttcagaagaa | attgatgtta | atgaaagtga | actttcctca | gagattaaat | 360 |
| ataagcacc | tcaacctata | ggagaagtat | attttgcaga | aacttttgat | agtggaaggt | 420 |
| tggctggatg | ggtcttatca | aaagcaaaga | aagatgacat | ggatgaggaa | atttcaatat | 480 |
| acgatggaag | atgggaaatt | gaagagttga | agaaaaacca | ggtacctcgg | ccgcgaccac | 540 |
| gctaagggcg | aattccagca | cactggcggc | cgttactagt | ggatccgagc | tcggtaccaa | 600 |
| gcttggcgta | atcatggtca | tagctgtttc | ctgtgtgaaa | ttgttatccg | ctcacaattc | 660 |
| cacacaacat | acgagcccgg | aagcataaag | tgtaaagccc | tggggtgcct | aatgagtgag | 720 |
| ctaactcaca | ttaaatgcgt | tgcgctcact | ggccgctttc | cagtcngaa | accctgtcgt | 780 |
| gccagctgca | ttaatgaatc | ggccaacgcc | cgggggaaaa | agcggnttg | cgtattgggc | 840 |
| gctcttccct | tcttgnttta | cttgactcgc | ttgggcttcg | tcgttcggct | gcggcnaacg | 900 |
| gnatcagctt | actcaaangc | gggaaatacg | gtantcccca | gaatccnggg | gattaccccn | 960 |
| ggaaaagaac | ctgtgagccn | aanggcccc | aaanggcccn | gaaccntaaa | aaanggcccg | 1020 |
| tnnn | | | | | 1024 |

<210> SEQ ID NO 61
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 61

| | | | | | |
|---|---|---|---|---|---|
| gggnnnnnnt | tncttacacg | cccgcttggt | accgagctcg | gatccctagt | aacggccgcc | 60 |
| agtgtgctgg | aattcgccct | ttcgagcggc | cgcccgggca | ggtacaaatg | gttttatgtc | 120 |
| accaattttg | ctgcaagaat | gggaactgct | tttaaatctg | taaatagctc | ttaacatttg | 180 |
| ttgtatgcac | tcttttctta | ctatggctgt | caacacttgt | gtagggttta | atttctaaat | 240 |
| tgttggcatg | ttcttttct | caggctattc | agaagtaaca | acattttca | tttcagacat | 300 |
| gcaatcacct | attaatgatg | aaatattta | ccactttggg | aatatttaat | tagtttagtc | 360 |
| atggagaata | cttcccacat | tttaagattt | ttcaaatatc | actgtcattt | ctattttagc | 420 |
| atttatcaa | attattgctt | ttttatttta | taataaggct | taagacagat | tatagacctc | 480 |
| cttaagagat | gagtttcttc | ttctaaaaat | gcatgttgat | agaggactat | ttaggctaat | 540 |
| cggaggaatc | attaagaaag | aaagttttaa | cactgtttat | ccctatctgc | tttccttgca | 600 |

| | |
|---|---|
| cttttctgt gaaaaatatt ttctgtttgc aaaatcttcc ctgagttctg aacccagcac | 660 |
| catcagtacc tcggccgcga ccacgctaag ggcgaattct gcagatatcc atcacactgg | 720 |
| cggccgctcg agcatgcatc tagagggccc aattcgccct atagtgagtc gtattacaat | 780 |
| tcactggccc gcgnttttac aacgtcgtga ctgggaaaac ccctgcgtta cccaacttaa | 840 |
| acgcccttgc agcacatccc cctttttgncc aantgcgtaa ttaccaaaaa ggcccgnacc | 900 |
| gaacggccnt ttcccaaagg tggcncaacc ctgaaatggc aaatgggccc cccccttgaa | 960 |
| ccggngccnt taanccccc nccgggnntt tnggggtccc cccacggnga nccgttaaac | 1020 |
| ttgc | 1024 |

<210> SEQ ID NO 62
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 62

| | |
|---|---|
| gnagnnnnnn ttnngnttgg gccctctaga tgcatgctcg agcggccgcc agtgtgatgg | 60 |
| atatctgcag aattcgccct tagcgtggtc gcggccgagg tactgatggt gctgggttca | 120 |
| gaactcaggg aagattttgc aaacagaaaa tatttttcac agaaaagtg caaggaaagc | 180 |
| agatagggat aaacagtgtt aaaactttct ttcttaatga ttcctccgat tagcctaaat | 240 |
| agtcctctat caacatgcat ttttagaaga agaaactcat ctcttaagga ggtctataat | 300 |
| ctgtcttaag ccttattata aaataaaaaa gcaataattt gataaaatgc taaaatagaa | 360 |
| atgacagtga tatttgaaaa atcttaaaat gtgggaagta ttctccatga ctaaactaat | 420 |
| taaatattcc caaagtggta aaatatttca tcattaatag gtgattgcat gtctgaaatg | 480 |
| aaaaatgttg ttacttctga atagcctgag aaaaagaaca tgccaacaat ttagaaatta | 540 |
| aaccctacac aagtgttgac agccatagta agaaaagagt gcatacaaca aatgttaaga | 600 |
| gctatttaca gatttaaaag cagttcccat tcttgcagca aaattggtga cataaaacca | 660 |
| tttgtacctg ccccgggcgg ccgctcgaaa gggcgaattc cagcacactg gccgnccgtt | 720 |
| acttagtgga tccgagctcg gtccaagcct tgcgtaaatc atggnccata ntggttcctg | 780 |
| nggtgaaatt ggtatcccgg tcacaatttc nccccancat acgaanccgg aagccntnaa | 840 |
| gngtaaaanc cctgggtggc ctaatgagtg aactaactca catttaaatg cgtgcgctta | 900 |
| ctggcccgtt ttccaatcng ggaaanctgt cgngcccact ggntttaang aatcggccan | 960 |
| gccccngg gaaaaagng gttgcnnatt gggccctttt tcggttcctt ggttantgga | 1020 |
| atcn | 1024 |

<210> SEQ ID NO 63
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 63

| | |
|---|---|
| gagnnnnnnt taancccgc ttggtaccga gctcggatcc ctagtaacgg ccgccagtgt | 60 |

-continued

```
gctggaattc gcccttagcg tggtcgcggc cgaggtacat tgacttcatt actaaagaac      120
aaaaatgttc atttttgtcc cagtaaattg agactgcttg tactttttt ttttttttt       180 tttttttttt ttattaaaat actgagtttt atttcacatg tatattttg tctcccccacc     240 atttccatgt ctgaccaccg ctactactat gtcctatcat aacattccat acatacttaa     300
aaccaagcaa agggtggagt tccatcttta aaaactaaac ggcattttgg acaacacatt     360
cttggcaata naacctggac aacatttatc aaacacggta gggaaagttc tcactctgca     420
ttataaaaag gacagccaga tatcaactgt tacagaaatg aaataagacg gaaattttt      480 taacaaattg tttaaactat tttcttaaag agacttcctc cattgccaga natcttgaat     540
agcctcttgg tcagtcatcc ggaagcaatt cttcacataa ttgatgaatt tggcttccac     600
tttgggaaga gaaccacctt tttctatact tgcttgcatt tttgctttaa tgncttctac     660
agaactaggt ccttttggng ttttaggagt tttttcctgn ttcttgaagg attcttggcc     720
ttttganctt ggggttgaaa ganggntttg agtctttca ttctgaattg acttttgggc     780 attttttggct ggagnatctc ggatagattt cttcactggg gctttttctt nagntttcct    840
catatcaaaa tcntcatcat catcancttt atnaaaatcc cctttaatna aatcggnat     900 tnatntttat tnagcngcaa ggtttacttt ttttctgggg gaancttgt tanccccttt      960 caggggcaa aaccggtttt ccaaaaatnc ccttaanaat ttnccaaanc cncncccntt    1020
ttaa                                                                  1024
```

<210> SEQ ID NO 64
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 64

```
ggagnnnnnn ttnngtttcc gaattgggcc ctctagatgc atgctcgagc ggccgccagt      60
gtgatggata tctgcagaat tcgcccttag cggccgcccg ggcaggtaca gccaacggtt     120
tcccttgggg gctttgaaat aacaccacca gtggtcttaa ggttgaagtg tggttcaggg     180
ccagtgcata ttagtggaca gcacttagta gctgtggagg aagatgcaga gtcagaagat     240
gaagaggagg aggatgtgaa actcttaagt atatctggaa agcggtctgc ccctggaggt     300
ggtagcaagg ttccacagaa aaaagtaaaa cttgctgctg atgaagatga tgacgatgat     360
gatgaagagg atgatgatga agatgatgat gatgatgatt ttgatgatga ggaagctgaa     420
gaaaaagcgc cagtgaagaa atctatacga gatactccag ccaaaaatgc acaaaagtca     480
aatcagaatg gaaagactc aaaaccatca tcaacaccaa gatcaaaagg acaagaatcc     540
ttcaagaaac aggaaaaaac tcctaaaaca ccaaaaggac ctagttctgt agaagacatt     600
aaagcaaaaa tgcaagcaag tatagaaaaa ggtggttctc ttcccaaagt ggaagccaaa     660
ttcatcaatt atgtgaagaa ttgcttccgg atgactgacc aagaggctat tcaagatctc     720
tggcaatggg agaagtctct ttaagaaaat agtttaaacc atttggtaaa aaattttccg     780
tcttatttca tttctgtacc agttgatatc ctgctgtcct ttttataatg cnaagtggag     840
aactttccct accggtttgg ataaatgttg gncaggttct attgcccaag aatgtgtgnc     900
ccaaaatgcc cgntagtttt tnaagatgga acttcacccn tttgcttggn tttaagtatg     960 nntngaagt ntgatnggac cntatnntna ccgnggncaa ccttggnaaa tggtggggag    1020
``` acaa 1024

<210> SEQ ID NO 65
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 65

| | | | | | |
|---|---|---|---|---|---|
| gggnnnnnnt | aactnnacgc | ccgcttggta | ccgagctcgg | atccctagta | acggccgcca | 60 |
| gtgtgctgga | attcgccctt | agcgtggtcg | cggccgaggt | actctgctga | tctctgcctt | 120 |
| gtaatggaaa | tgtttcattc | attaatgtta | ttgatatggt | tgcactatgt | ccgtaatttt | 180 |
| gcttttgtg | tatctgtcta | atgttttta | ttctccttt | tctcttttac | tattttcttt | 240 |
| taaattaagt | aaatagttcc | taacgtagta | ttttatttc | ttaaaataaa | tcaaactcac | 300 |
| ttataaaata | tatttcatat | tactttctta | tcgattgctg | tatgccttac | aacatacatc | 360 |
| ttatcagact | caacatttat | agtaacataa | atccattgag | acatagtaac | attaattctt | 420 |
| tataggtcta | tttattctac | ttattcaata | attgttatat | atatattaca | tctacatgtt | 480 |
| acaaacacaa | aaatatattg | ttataatgct | tgtttttatg | taattttatg | tctttaaag | 540 |
| aacatgagag | aagaaaggaa | agcaaagtaa | ctattagcat | tgttatgtta | acattattct | 600 |
| ttacaatttc | tggttctctt | cattttttc | ctgttgattc | aagttgtatc | ttagtgtcat | 660 |
| ttcatttctt | taatacaact | ttgctccaat | tatttcttt | gtgctcttaa | tgtcaaatat | 720 |
| attaagtttt | gnttgcatta | taggctcaac | actattatac | atatattggt | ttatgcattt | 780 |
| attttgaatt | aagagaaaat | aaaaatatgc | aatttaatgg | cttatatact | attcatataa | 840 |
| ttaccctcta | tgagggtnca | ttatatatgn | attccaaccn | tatttataaa | ntccaaanta | 900 |
| cctggtangt | gccnaaaggc | tcctaagcct | attagcccgg | aaaaaaaatc | cctgggtant | 960 |
| tccttggnaa | gggaggtttg | attgccacca | acctnttta | natngggttg | ggttttaata | 1020 | aacc 1024

<210> SEQ ID NO 66
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 66

| | | | | | |
|---|---|---|---|---|---|
| ggagnnnnnn | ttgngtnngg | gccctctaga | tgcatgctcg | agcggccgcc | agtgtgatgg | 60 |
| atatctgcag | aattcgccct | ttcgagcggc | cgcccgggca | ggtactccag | cctgggtaac | 120 |
| agagggagac | tctatgccaa | acaaacaaac | aaacaaacaa | acaacaatg | gagaccagaa | 180 |
| agcaatgaga | tgaaatgttc | aaagtgctga | agaaaaaaa | aaggtcaacc | aaaagtctta | 240 |
| tatccagaat | attttcaaa | gtataaaagc | aaaatacatt | ctcagataat | aaaaacaaaa | 300 |
| caaactaaaa | gagtttgttg | ctatcatacc | taccttacaa | gaaatactca | gtgattttt | 360 |
| tcaggctaat | aggctaggag | catttggcac | ctaacagtaa | tttgaattta | tatatatgtt | 420 |
| tgtatacata | tatatggaac | actcatagag | gtaattatat | gaatagttat | ataagacatt | 480 |

| | |
|---|---|
| aaattgcata tttttatttt ctcttaattc aaaataaatg cataaaacaa tatatgtata | 540 |
| atagtgttga gcctataatg caaacaaaac taatatattt gacattaaga gcacaaaaga | 600 |
| aataattgga gcaaagttgt attaaagaaa tgaaatgaca ctaagataca acttgaatca | 660 |
| acaggaaaaa aatgaagaga accagaaatt gtaaagaata atgntaacat aacaatgcta | 720 |
| atagttactt tgctttcctt tcttctctca tgntctttaa aagacataaa attacataaa | 780 |
| aaccaagcat tataacaata taattttggg tttggaacat ggtagatgta tatatatata | 840 |
| ccattattgg ataagtagaa taaataggac tattaaggaa ataatggtac tatggctcaa | 900 |
| tgggantaag gtacctataa ngtgagcct gganaggaag natgttgnaa ggcttccggc | 960 |
| aatcggttta gaaagtantt tggaaatata ttttnatnaa gngggttgga ttaatttagg | 1020 |
| aaaa | 1024 |

<210> SEQ ID NO 67
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 67

| | |
|---|---|
| gagnnnnnnt taactccagc ttggtaccga gctcggatcc ctagtaacgg ccgccagtgt | 60 |
| gctggaattc gcccttcga gcggccgcc gggcaggtac tttttttttt tttttttttt | 120 |
| ttttggaaaa tgagattttt gactttaaca aaacaaatac agattgaatt taccaaatat | 180 |
| tgataattca tgtanaacgg gtgccacaga ttttaaagta tcaaaaccaa gagggcatca | 240 |
| caaaataaac tttggtgaaa aatatcttca tcaagaaga aaatatgaga agagtagtcc | 300 |
| ttatgcagtg aggagaaata tatttggtaa agtaaatatg ggtagtagat actgaatcta | 360 |
| tagatagcat atattccaaa tgttttttag ggaatatcaa atcagatgat gcttanatgt | 420 |
| tatagtaata tcacttatct catttggaat gaaatttaat gttttttaat aaatagcaaa | 480 |
| ttttcatttt ttcactacct ttataaaaca aattaaatat ttagagtata actgatcata | 540 |
| actaacatca ccttgcattt actaataaat actctaaata catttggttt attattggaa | 600 |
| tttatatcct tataatttta cctgctagaa attagtgacc ttgtggcatt atgtttaaag | 660 |
| tttacattt cccagtgatg tgaacagtat ttatacntaa aatggatatc tgnccaatga | 720 |
| atagtaacca tgtttggtgg tttaaaaacc gnacatggtt tagtttgaca ttggcatgtc | 780 |
| tcttcagaaa ttnaaaaggt atcntttaag ggatggcttt tnggaaatca ttaataaact | 840 |
| accntctggg aaaangaatn ccaatttcaa gaagctacct aantagaact cagaccccn | 900 |
| gggcagggtn ttggnanaaa angctttcaa ttncaaattn nttntccgnn gnaaaccgaa | 960 |
| ngggacccctt annngnntgg accnccttttc cngnaaactg gttttaaaat aaaaatttcc | 1020 |
| gnnc | 1024 |

<210> SEQ ID NO 68
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 68

```
gnngnnnnnn ntnnnttcga attgggccct ctagatgcat gctcgagcgg ccgccagtgt      60
gatggatatc tgcagaattc gcccttagcg tggtcgcggc cgaggtacct agtagatcta     120
ctgagattaa acgggacctg tttggagcag aaccttttga cccatttaac tgtggagcag     180
cagatttccc tccagatatt caatcaaaat tagatgagat acaggagggg ttcaaaatgg     240
gactaactct tgaaggcaca gtattttgtc tcgacccgtt agacagtagg tgctgacatc     300
aagaacaaga aatcctgatt catgttaaat gtgtttgtat acacatgtca tttattatta     360
ttactttaag ataggtatta ttcatgtgtc aatgtttta aatattttaa tattttgaaa     420
atttttctcag ttaaatttcc tcaccttcac tattgatctg taatttttat tttaaaaaca     480
gcttactgta aagtagatca tacttttatg ttcctttctg tttctactgt agatgaattt     540
gtaattgaaa gacatattat acaaatacct gccttgtgtc tgagttctat ttagttagca     600
tcttgaaatt tgtattcatt ttccagatgg ctagtttatt aatgatttcc caaagccat      660
accttaaaga taactttta aattctgaag agacatgcca atggcaaact aaacatggtc      720
tggttttaaa ccaaccaaca tgttactatt cattgggaca gatatcattt tatggataaa     780
tctggtcaca tactggggaa atggaaactt taaacataat ggccccangg cactaatttc     840
ttaccggtaa aaatnttang ggtttaaant nccatattna acccnatggt tttaaaggat     900
ttattntaaa ngcnnggggga ngtannntttg acagtntncn ctaaaanttt aaatgggttn     960
ttaaaggtnt gaaaaaanga aaaattgctt tttttttnaaa accttttaant cntttccnag    1020
gggn                                                                  1024
```

<210> SEQ ID NO 69
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 69

```
gggnnnnnnnn tnncttanac gccnngcttg gtaccgagct cggatccta gtaacggccg       60
ccagtgtgct ggaattcgcc ctttcgagcg gccgcccggg caggtactcc ggtcggtgtc      120
agcagcacgt ggcattgaac attgcaatgt ggagcccaaa ccacagaaaa tggggtgaaa     180
ttggccaact ttctattaac ttatgttggc aattttgcca ccaacagtaa gctggcccct     240
ctaataaaag aaaattgaaa ggtttctcac taaacggaat taagtagtgg agtcaagaga     300
ctcccaggcc tcagcgtacc tcggccgcga ccacgctaag ggcgaattct gcagatatcc     360
atcacactgg cggccgctcg agcatgcatc tagagggccc aattcgccct atagtgagtc     420
gtattacaat tcactggccg tcgttttaca acgtcgtgac tgggaaaacc ctggcgttac     480
ccaacttaat cgccttgcag cacatccccc tttcgccagc tggcgtaata gcgaagaggc     540
ccgcaccgat cgcccttccc aacagttgcg cagcctgaat ggcgaatgga cgcgccctgt     600
agcggcgcat taagcgcggc gggtgtggtg gttacgcgca gcngtgaccg ctacacttgc     660
cagcgcccta gcccgtcct ttcgctttct cccttcctt tctcgccacg ttcgccggct      720
ttccccgtca gctctaaat cggggctcc cttttagggt tccgaattan tgctttacgg       780
accttgaccc caaaaaactt gantanggtg atgggtcacg taatgggccc atnggccttg     840
anaagacggt ttttcgccct tgacngttg gagtccacgt tctttaaaag gggactcttg     900
```

```
gttccaaact ggaacaaccn nttaancctt atttngggct aatcctttgg aattaatnag      960
ggattttgcc caatttgggc ccttnggtta aaaaagggg cttgntttaa ccaaaaattt     1020
aacc                                                                1024

<210> SEQ ID NO 70
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 70
ggagnnnnnn ttnngtttgg gccctctaga tgcatgctcg agcggccgcc agtgtgatgg       60
atatctgcag aattcgccct tagcgtggtc gcggccgagg tacgctgagg cctgggagtc     120
tcttgactcc actacttaat tccgtttagt gagaaacctt tcaattttct tttattagaa     180
gggccagctt actgttggtg gcaaaattgc caacataagt aatagaaag ttggccaatt      240 tcaccccatt ttctgtggtt tgggctccac attgcaatgt tcaatgccac gtgctgctga     300
caccgaccgg agtacctgcc cgggcggccg ctcgaaaggg cgaattccag cacactggcg     360
gccgttacta gtggatccga gctcggtacc aagcttggcg taatcatggt catagctgtt     420
tcctgtgtga aattgttatc cgctcacaat tccacacaac atacgagccg gaagcataaa     480
gtgtaaagcc tgggtgcct aatgagtgag ctaactcaca ttaattgcgt tgcgctcact     540
gcccgctttc cagtcgggaa acctgtcgtg ccagctgcat taatgaatcg gccaacgcgc     600
ggggagaggc ggtttgcgta ttgggcgctc ttccgcttcc tcgctcactg actcgctgcg     660
ctcggtcgtt cggctgcggc gagcggtatc aagctcactc aaaggcggta atacngttat     720
ccacagaatc aaggggatac gcaggaaaga acatgtgaac caaaaggcca caaaaggcca     780
ggaacccgta aaaaggccg cgttggctgg cgttttttcc atangcttcc ggccccttg      840 acgagcatta ccaaaaatcg acgctcaagt tcaaaggtgg cgaaanccccg accggactnt    900 taagaatccc agcgtttncc cctggaactt ccttgggcgc ttttctggtt ccaaccttgc    960
cgttaccgga tacctggncc gcnttttttcc ctttngggaa accngggcnt tntcaaaant  1020
taac                                                                1024

<210> SEQ ID NO 71
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 71
gagnnnnnnt taactcccgc ttggtaccga gctcggatcc ctagtaacgg ccgccagtgt       60
gctggaattc gcccttagcg tggtcgcggc cgaggtactt ttttttttc ttttttaca      120 tctgatttta atgcttcgtt aacttcaaaa ggaactggta gagttcagaa ggtgagctgt     180 tgttttcta aacctcttcc caggaagggg acattgacac ttgaattttt gtcacctttt      240
tcctcattag aaggaaagta gaaagcctta ctgtaggatt tttaaaaaaa aatccatctc     300
accccatatt ggtcttaaat aagtatagac taattaacct aagctacctt taacaacgta     360
gaatttagat gggttcatat atgtgagaaa aacctgaata taggacaggg gtcctacttt     420
```

```
tttccccacc tctgtcgccc aggctagagt atagtggtgt gatcttggcc cactgcaacc      480
tctgcttcct aggttcaagt gattctcctg cctcagcctc ccaagtagct gggattgtaa      540
gagtatgcca ccacgcccag ctacttttg tatttttagt agagacaggg tttcatcatg       600
ttggccagga tggtctctta actcctgccc tcaagtgatc caccagagag agatcctcg       660 gcctcccaa gtgctgggat tataggcatg agccaccgtg cccagcctac tttctaatta      720
attaaaaaaa aaaaaaaaac ttcccaaatg agctgataaa aaactgacgt gaggctgctt     780
tgccttcaat aatacctagt tttcagctgt tccaactcgt ttccaaattg gaaattanct    840
ggaacnccac tacagtaatc ttcanggaan gggaaaatta ggccttaaaa gaatccccag    900
aaagttcanc atnggnancc tgnccnggcc ggnccgttca aaangggcna aatttgcaga   960
aattccatna cacttggcgg gccgttcgan catggctttt aangggccca attgncccct   1020
aaag                                                                1024

<210> SEQ ID NO 72
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 72
gnagnnnnnn ttnnnttccg aattgggccc tctagatgca tgctcgagcg gccgccagtg    60
tgatggatat ctgcagaatt cgcccttcg agcggccgcc cgggcaggta ccatgctgac    120
ttcttggtat cttttaaggc ctaattttcc cttccttgag attactgtag tgtgttccag    180
ctaatttcta tttggaaacg agttggaaca gctgaaaact aggtattatt gaaggcaaag    240
cagcctcacg tcagtttttt atcagctcat ttgggaagtt tttttttttt ttttaattaa   300
ttagaaagta ggctgggcac ggtggctcat gcctataatc ccagcacttg gggaggccga   360
ggatctcctc tctggtggat cacttgaggg caggagttaa gagaccatcc tggccaacat   420
gatgaaaccc tgtctctact aaaaatacaa aaagtagctg ggcgtggtgg catactctta   480
caatcccagc tacttgggag gctgaggcag gagaatcact tgaacctagg aagcagaggt   540
tgcagtgggc caagatcaca ccactatact ctagcctggg cgacagaggt ggggaaaaaa   600
gtaggacccc tgtcctatat tcaggttttt ctcacatata tgaacccatc taaattctac   660
gttgttaaag gtagcttagg ttaattaagt ctatacttat ttaagaccaa tatggggtga   720
naatggattt ttttttaaaa atcctacagt aaggcttttct actttccttc taatgaggaa  780
aaaggtgacc aaaantcaag tggcaatggc ccctttctgg ggaaaagttt anaaaaacca   840
ccggttanct tntggaactt ttacccagtt ccctttttgaa gttaccgaag cctttaaaan  900
cagatgttaa aaaggaaan nnnaaaaagt nccttttggcc gggaaccccnc ttaagggcca  960 aattccacac acttgggggg ccgntnccnt anggatccca ncttgggncc aaanntttggg 1020 gnaa                                                                1024

<210> SEQ ID NO 73
<211> LENGTH: 1024
<212> TYPE: DNA
<213> ORGANISM: Homo Sapien
<220> FEATURE:
<221> NAME/KEY: misc_feature
<222> LOCATION: (1)...(1024)
```

<223> OTHER INFORMATION: n = A,T,C or G

<400> SEQUENCE: 73

| | | | | | |
|---|---|---|---|---|---|
| gagnnnnnnt | tnacttacac | gccngcttgg | taccgagctc | ggatccctag | taacggccgc | 60 |
| cagtgtgctg | gaattcgccc | ttagcgtggt | cgcggccgag | gtactgtgtt | atggcacaga | 120 |
| caatgcttgc | ttagcggtgc | cttgttacat | aggtggatgc | agagtgcgca | cacgggatga | 180 |
| tggcaataaa | gacctcactc | agtcgttgga | atgaaggaac | taggtaactg | cttcaacaag | 240 |
| gacggtctca | gctctacctt | atctctcaac | agagtgcaaa | cactgagtgt | gagctcagat | 300 |
| gtcatcttgt | tcctctttaa | aattcaccaa | attcttttgc | acattttct | gttatagaga | 360 |
| cacggatatc | ttcttcttca | tagtcatcaa | agttgctggt | atctccagag | cctctaaact | 420 |
| ttggtatgaa | tggagcttca | accttcctct | ggtaaatagc | aatccaatct | gtcgtggcaa | 480 |
| accacttgtg | agtttttata | tcactgacac | cattctttag | atttccaaat | ctcttgatca | 540 |
| aatccacctg | cagcaggttc | cgtagaaggt | ccttgagatc | tgaactgaag | tgggatggga | 600 |
| atcggacctt | tccagaaaca | atcttttcat | aaatctgaat | tggttggtct | gcaaagaatg | 660 |
| ggggatagcc | agctgccatt | tcatagatta | gcactcctaa | tgcccaccaa | tccactgcct | 720 |
| tattgnagcc | cttgctgaga | attatttctg | gagccaaata | cctctggagt | tccacataat | 780 |
| ggccaagttc | tgcctttaac | tcttttggca | accccaaaa | gtctgtgacc | cgggatatag | 840 |
| ccctgatggn | ccaatttaag | aagaattttc | angggtttaa | aaactctggt | aaatgaaggc | 900 |
| taanggaaat | ggaggnacct | tttttttttt | nnnnnnnttt | ttttttttaa | acnttgtaaa | 960 |
| aggccaaaat | tttggctana | anttantttc | aaagnttnaa | accntttcca | aattttttt | 1020 |
| taat | | | | | | 1024 |

<210> SEQ ID NO 74
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 74

| | | | | | |
|---|---|---|---|---|---|
| ggagnnnnnn | nttgagttcc | ggccctctag | atgcatgctc | gagcggccgc | cagtgtgatg | 60 |
| gatatctgca | gaattcgccc | tttcgagcgg | ccgcccgggc | aggtacagtc | aactgcattt | 120 |
| ttctctggtg | accaagcttc | cactgacaag | gaagaggatt | atattcgtta | tgcccatggt | 180 |
| ctgatatctg | actacatccc | taagaattta | agtgatgact | tatctaaata | cttaaagcct | 240 |
| ccagaacctt | cagcctcatt | gccaaatcct | ccatcaaaga | aataaagtt | atcagatgag | 300 |
| cctgtagaag | caaagaaga | ttacactaag | tttaatacta | agatttgaa | gactgaaaag | 360 |
| aaaaatagca | aaatgactgc | agctcagaag | gctttggcta | agttgacaa | gagtgggatg | 420 |
| aaaagtattg | atacctttt | tggggtaaaa | aataaaaaa | aaattggaaa | ggtttgaaac | 480 |
| tttgaaaata | aaatctagca | aaaatatttg | cttttacat | gtttaaaaa | aaaaaaaaa | 540 |
| aaaaaaaaaa | aagtacctcc | attcactaga | cctcatctac | agagatctaa | aacctgaaaa | 600 |
| tctcttaatt | gaccatcaag | gctatatcca | ggtcacagac | tttgggtttg | ccaaaagagt | 660 |
| taaaggcaga | acttggacat | tatgtggaac | tccagagtat | ttggctccag | aaataattct | 720 |
| cagcaagggc | tacaataagg | cagtgggatt | ggtgggcatt | aggagtgcta | atctatgaaa | 780 |
| tggcactggc | tatccccatt | cnttgcagac | ccacccattc | agaatttatt | gaaaagatg | 840 |

```
gttcttggaa ngnccgaatt cccattcccc ttcagntcna actcaagggc ccttttacgg    900
aancctggtt gcangggga ttgatccagg anaatttgga aatcttaaag aaaaggggnc     960
cggggtttta aaaacctcnc aagnggtttt gcccccancg naatgggatt ggttttcc     1020 ccna                                                                1024

<210> SEQ ID NO 75
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 75
gagnnnnnnt taactcccgc ttggtaccga gctcggatcc ctagtaacgg ccgccagtgt     60
gctggaattc gcccttagcg tggtcgcggc cgaggtacta tatgtatttt attaaaaatg    120
tggaagatta atctgtttct ctctgaatgt agattttcac caaaacatct cttaaaacag    180
cagggactca acacttaaaa atgaactaga agagctgggc acagtggctc acgcctgtaa    240
tcccagcact ttgggaggcc gagcgggca aatcacttga ggtcaggagt tcgagaccag     300
cctggccaac atggtgaaac cctgtctcta ctaaaaacac aaaaattaac tgggcatggc    360
ggcacacgcc tttaatccca gctactcaag aggctgaggc aggagaatcg ctttgaacct    420
gggaggcaga ggttgcagtg tgctgagatc ataccactgc attccagcct gggcgacaga    480
gcaagactcc acctcaaaaa aaaaagaag aaaagaaaat agtagtctca gccaggcgtg     540
atggctcaca cctgtaatcc cagcactttg ggaggccaag gtgggcagat cacctgaggt    600
caggagttcg agaccagcct ggcctacgtg gcaaaacctc atctctaata aaatacaaa     660 aattagcttg ggcgtggtgg catgcacctg tcatcccagc tatttgggag gctgagacag    720
gagaagtcgc tttgaacctg ggangcagaa aattgcggtg aagctaagat cgcacgactt    780
cacttccacc tgggcaaaag anggaactct atctcaaaaa aaaaaangg aaaaagtagt    840 ctntaagaca ctgggcaaac cttgaaagga attgagcagt cctcactttn ctgnagtcan    900
tttgntnaat gccacatggc tcttttgnaa gaaatttgag agcttttttc taatcccaat    960
ttttntaatt tgggaattcc ttttccgga ttttttcntt gccnggnggt gttcccaang   1020
gcct                                                                1024

<210> SEQ ID NO 76
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 76
gnngnnnnnn ttnnnttgng antngggccc tctagatgca tgctcgagcg gccgccagtg     60
tgatggatat ctgcagaatt cgccctttcg agcggccgcc cggcaggta ctctttgtgg    120 ctggcttctt tttctgcaca caatgcctat gagaccataa ctaaagtcaa attccatggt    180
cactaaccaa taatggcatc tcaaagaaat tccaacctag agaaattctg atgatgtggt    240
tagaacacca atcaggacac tcacttcatg gttgataatt cccgacatgc actgattcag    300
```

```
acccagctta ttgaattcat tgagtccaca ggccagcact ttgcctgact gggtcaacag    360
aaatgtccca tcacagccac attgaactgc aacaataatc aaggccttgg gaacatccac    420
ctgcaagaaa aaaatcagaa aaagaaatcc caaatatata attcgtatta gaaaaaaagc    480
tctcaaattc tttcaaaaga gacatgctgc atttagcaga atgactacag gaaagtgagg    540
actgctctat tcttttcagg tttgcccagt gtcttagaga ctactttttc tttttttttt    600
tttgagatag agtttccctc ttttgcccag gctggagtga agtccgtgcg atcttagctc    660
accgcaatct ctgcctccca ggttcaagcg acttctcctg tctcagcctc ccaaatagct    720
gggatgacag gtgcatgcca ccacgcccag ctaattttg gattttatt agagnatgag      780 gttttgccac gtaggccaag ctggncttga acttctgacc ctcaagtgac tggccaccct    840
tgggccttcc aaagtgctgg gaattacagg gngagccatt acgcctggnn tgaaactcca    900
atttcttttc ttcntttttt ttttggnggg gagcttgctn tgcncccaag ctgggaaagc    960 canggatga cttnnnncac tggaaccttg gcttcaggtt taaagggatt tctggcttaa    1020 nccc                                                                 1024

<210> SEQ ID NO 77
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 77
gagnnnnnnt aacttacacg cccgcttggt accgagctcg gatccactag taacggccgc     60
cagtgtgctg gaattcgccc ttagcgtggt cgcggccgag gtacttttt tttttttttt    120 tttttttac agaaggctgt aaagctttat gggagaatt ttaatgaaca aatttccaac     180
ataggagcag cctgcatcat ttcaacgtgc cttcttttaa cactgtgatt gcttttcacc    240
ttcttcaggc gttttcacct cctctggatt tgcgggtcc atctcctgcc catcaggacc    300
atcttcacac tcacacccag tctgtgggtg accctgttcc tggctatgag cttcaggctt    360
cggcccttga cctgcanatg ctccctcatc ctctccctcc tgagcagctg caggatcctg    420
acgttgagtt gctggttccc cttcttcagg tgttgctggt tccgcttcat cactgaactg    480
ctcgggccgc ataggcccaa tcatttcagg aggctgnacc tgcccgggcg gccgntcgaa    540
agggcgaatt ctgcagatat ccatcacact ggcggccgnt cgagcatgca tctagagggc    600
ccaattcgcc ctatagtgag tcgtattaca attcactggc cgtcgtttta caacgtcgtg    660
actgggaaaa ccctggcgtt acccaactta atcgccttgc agcacatccc ctttcgcca    720 gctggcgtaa taacgaaaag ccccgcaccg atcgcccttt ccaacagttg cgcancctga    780
aagggcnaaa tggacncccc tggaacggcc attaaccccc gcnggnnnnn gggtaccccn    840
caangngacc ggtacacttg gcaangccct aacgcccggt ccntttgntt ttctttcctt    900
tcnttttngc acgttnnncc gggttttccc ggnaagctnt naaatngggg ggtccccntt    960
tngggtccna ataaggcntt tagggnccctt ggnccccnaa aaatttgntt ttnnggggan   1020
ggtc                                                                1024

<210> SEQ ID NO 78
<211> LENGTH: 1024
<212> TYPE: DNA
<213> ORGANISM: Homo Sapien
```

<220> FEATURE:
<221> NAME/KEY: misc_feature
<222> LOCATION: (1)...(1024)
<223> OTHER INFORMATION: n = A,T,C or G

<400> SEQUENCE: 78

| | | | | | |
|---|---|---|---|---|---|
| gnagnnnnnn | ttgagtttgg | gccctctaga | tgcatgctcg | agcggccgcc | agtgtgatgg | 60 |
| atatctgcag | aattcgccct | ttcgagcggc | cgcccgggca | ggtacagcct | cctgaaatga | 120 |
| ttgggcctat | gcggcccgag | cagttcagtg | atgaagcgga | accagcaaca | cctgaagaag | 180 |
| gggaaccagc | aactcaacgt | caggatcctg | cagctgctca | ggagggagag | gatgagggag | 240 |
| catctgcagg | tcaagggccg | aagcctgaag | ctcatagcca | ggaacagggt | cacccacaga | 300 |
| ctgggtgtga | gtgtgaagat | ggtcctgatg | gcaggagat | ggacccgcca | aatccagagg | 360 |
| aggtgaaaac | gcctgaagaa | ggtgaaaagc | aatcacagtg | ttaaaagaag | gcacgttgaa | 420 |
| atgatgcagg | ctgctcctat | gttggaaatt | tgttcattaa | aattctccca | ataaagcttt | 480 |
| acagccttct | gtaaaaaaaa | aaaaaaaaa | aaaaagtac | ctcggccgcg | accacgctaa | 540 |
| gggcgaattc | cagcacactg | gcggccgtta | ctagtggatc | cgagctcggt | accaagcttg | 600 |
| gcgtaatcat | ggtcatagct | gtttcctgtg | tgaaattgtt | atccgctcac | aattccacac | 660 |
| aacatacgag | cccggaagca | taagtgtaa | agcctgggt | gcctaatgag | tgagctaact | 720 |
| cacattaatt | gcgttgccgc | tcactgcccg | ctttncagtc | gggaaacctg | tcgtgccagc | 780 |
| tgcattaatg | aatcggncaa | cgccccgggg | aaaaagcggt | ttgcgtattg | ggcgctcttc | 840 |
| gctttcttgg | ttacttgact | cnttgngcct | tggccgttcg | gttgcggnna | acggtttcag | 900 |
| cttacttcaa | angcgggaaa | tccggttttc | cncggaaatc | aggggaatac | ccnggaaaa | 960 |
| gaacttgtga | accnaaaggc | ccnccaaaag | gcccngnaac | cgtaaaaaan | ggcccntnn | 1020 |
| nntn | | | | | | 1024 |

<210> SEQ ID NO 79
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 79

| | | | | | |
|---|---|---|---|---|---|
| gngnnnnnnt | taacnccagc | ttggtaccga | gctcggatcc | ctagtaacgg | ccgccagtgt | 60 |
| gctggaattc | gcccttttcga | gcggccgccc | gggcaggtac | tgtttttgtc | atttgcacca | 120 |
| gcttctttct | ccaggaaaga | tcaaaacgat | gcactgcaag | gttaacatcc | aattttaat | 180 |
| acattgtgat | tggtccagat | agctgcctta | tccaactgcc | tcctttggac | cacttcatca | 240 |
| tgggacagct | tgatgcaatc | tacttgacaa | gaccctggaa | ccccacaccc | ctcatggaac | 300 |
| cagtgtccac | ctcccagtca | cagtgtgacc | ccagggaact | cttgcctgct | tgctttaaac | 360 |
| ccaccactta | aaagtctcca | cagaaaacct | gtttgaatag | tacctcggcc | gcgaccacgc | 420 |
| taagggcgaa | ttctgcagat | atccatcaca | ctggcggccg | ctcgagcatg | catctagagg | 480 |
| gcccaattcg | ccctatagtg | agtcgtatta | caattcactg | gccgtcgttt | tacaacgtcg | 540 |
| tgactgggaa | aaccctggcg | ttacccaact | taatcgcctt | gcagcacatc | cccctttcgc | 600 |
| cagctggcgt | aataagcgaa | gaggcccgca | ccgatcgccc | ttcccaacag | ttgcgcagcc | 660 |
| tgaatgggcg | aaatggacgc | gccctgtagc | ggcgcattaa | gcgcgggcgg | gtggtggtgg | 720 |

| | |
|---|---|
| ttacgccgca gcgtgaccgc tacacttgcc agcgcccttc cgcccgctcc tttcgctttc | 780 |
| ttcccttcct ttttngcacg ttcggccggc ttttcccgtc agctctaaat cgggggctcc | 840 |
| cctttagggt tccgaattan tgctttacgg gaccttganc cccaaaaact tggnttaggg | 900 |
| gtgagggtca cgtatgggcc attggccctg aaaanacggt ttttcgcccc tttgacccttt | 960 |
| ggaatcncgt nnttttaaaa ggggactttg gtcccaactg ggacaacnnt taacccctta | 1020 |
| ttng | 1024 |

<210> SEQ ID NO 80
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 80

| | |
|---|---|
| gnagnnnnnn ttnnnttgng aattgggccc tctagatgca tgctcgagcg gccgccagtg | 60 |
| tgatggatat ctgcagaatt cgcccttagc gtggtcgcgg ccgaggtact attcaaacag | 120 |
| gttttctgtg gagacttta agtggtgggt ttaaagcaag caggcaagag ttccctgggg | 180 |
| tcacactgtg actgggaggt ggacactggt tccatgaggg gtgtggggtt ccagggtctt | 240 |
| gtcaagtaga ttgcatcaag ctgtcccatg atgaagtggt ccaaggagg cagttggata | 300 |
| aggcagctat ctggaccaat cacaatgtat taaaaattga atgttaacct tgcagtgcat | 360 |
| cgttttgatc tttcctggag aaagaagctg gtgcaaatga caaaaacagt acctgcccgg | 420 |
| gcggccgctc gaaagggcga attccagcac actggcggcc gttactagtg gatccgagct | 480 |
| cggtaccaag cttggcgtaa tcatggtcat agctgtttcc tgtgtgaaat tgttatccgc | 540 |
| tcacaattcc acacaacata cgagccgaaa gcataaagtg taaagcctgg ggtgcctaat | 600 |
| gagtgagcta actcacatta ttgcgttgc gctcactgcc cgctttccag tcgggaaacc | 660 |
| tgtcgtgcca gctgcattaa tgaatcggcc aacgcgcggg gaaaagcggn ttgcgtattg | 720 |
| ggccgctctt ncgcttnctn gcttacttga ctcgcttgcg cttcgnccgt tcggcttgcg | 780 |
| gcnaagcggt attcagctta cttcaaaggc ggtaaatacn ggtattcccc agaaatcagg | 840 |
| gggatnaccc cnggaaaaga acatgtgaan ccaaaaggcc accaaaaagg ncnnggaacc | 900 |
| gtnaaaaang gccncnttnn nnctngtttt tccattaag gttcccgccc ccttgacagc | 960 |
| ctttccaaaa attcganncc ttcaaantnc aaagggggcn aaaaccccnc cggggctttt | 1020 |
| taag | 1024 |

<210> SEQ ID NO 81
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 81

| | |
|---|---|
| gngnnnnnnt taacttacac gccagcttgg taccgagctc ggatccctag taacggccgc | 60 |
| cagtgtgctg gaattcgccc tttcgagcgg ccgcccgggc aggtacctca ttagtaattg | 120 |
| ttttgttgtt tcattttttt ctaatgtctc ccctctacca gctcacctga gataacagaa | 180 |
| tgaaaatgga aggacagcca gatttctcct ttgctctctg ctcattctct ctgaagtcta | 240 |

```
ggttacccat tttggggacc cattataggc aataaacaca gttcccaaag catttggaca        300
gtttcttgtt gtgttttaga atggttttcc tttttcttag ccttttcctg caaaaggctc        360
actcagtccc ttgcttgctc agtggactgg gctccccagg gcctaggctg ccttcttttc        420
catgtcccac ccatgagccc tccactggac agctcagtaa gcctggccct tcattctgcg        480
ctgtgttctt cctctgtgaa aatccaatac ctcttacctc ctctgcatgc aaagattctc        540
aaggattgtc agacttcaaa cgtaacagca gaaccaccag aaggtcctat aaatgcagta        600
gtgaccttct caagctgtca ggtctttaaa taggatttgg gatttaatgc tatgtatttt        660
taaaggaaag aaataagaag ttgctagttt taaaaatgca tgtcttttaa ccaattcaga        720
atctgccccc aaacttttt naaaagtcaa gacagataaa gctttggggg agacngaaaa        780
aaaaaannnn nnnaaagagt accttnggcc gggaacacgc taagggcaa attctggcan        840 aaatncatta cactgggcgg gcggtttgag cattgcntnt ananggggccc aattngncct        900 ataangggggg cgattacaat tncctgggcc gcgttttaaa acgtnngaac tgggaaaanc        960
ctggggtncc cacnttaatg gccttggnga aatcccccct tttncccnan tggngnannn       1020 nncn                                                                    1024

<210> SEQ ID NO 82
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 82
gnagnnnnnn ttnngtttgg gccctctaga tgcatgctcg agcggccgcc agtgtgatgg         60
atatctgcag aattcgccct tagcgtggtc gcggccgagg tactcttttt tttttttttt        120
ttttccgtct ccccaaagct ttatctgtct tgactttta aaaaagtttg ggggcagatt        180
ctgaattggc taaaagacat gcatttttaa aactagcaac tcttatttct ttcctttaaa        240
aatacatagc attaaatccc aaatcctatt taaagacctg acagcttgag aaggtcacta        300
ctgcatttat aggaccttct ggtggttctg ctgttacgtt tgaagtctga caatccttga        360
gaatctttgc atgcagagga ggtaagaggt attggatttt cacagaggaa gaacacagcg        420
cagaatgaag ggccaggctt actgagctgt ccagtggagg gctcatgggt gggacatgga        480
aaagaaggca gcctaggccc tggggagccc agtccactga gcaagcaagg gactgagtga        540
gccttttgca ggaaaaggct aagaaaaagg aaaaccattc taaaacacaa caagaaactg        600
tccaaatgct ttgggaactg tgtttattgc ctataatggg tccccaaaat gggtaaccta        660
gacttcagag agaatgagca gagagcaaag gagaaatctg gctgtccttc catttttcatt       720 ctggtatctc aggtgaactg gtaaagggga gacatttgaa aaaaatgaaa cnaccaaaac        780
cattactaat gaggtacctg cccnggcngg ccgttcnaaa gggccaattc cacacactgg        840
gcggccgtta cttaatggat ccnaactcgg taccaancnt tgcgtaaatc atgggccnnt        900
actgggttnc ctgggggnaa atggtatncg gttaccaatt ccccccaann ttcgaccccg        960 gaancccctta agggtaaanc cctgggggcc ctnaagaggg gctaacttcc catttaaatg      1020
ggtt                                                                    1024

<210> SEQ ID NO 83
```

<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 83

| | | | | |
|---|---|---|---|---|
| gggnnnnnnt | taanttanac | gccnnncttg | gtaccgagct | cggatccta gtaacggccg | 60 |
| ccagtgtgct | ggaattcgcc | ctttcgagcg | gccgcccggg | caggtacact taaaattggt | 120 |
| gccgagcagg | gatataacct | gcagttaagt | gaaaagaaaa | tccagcctcc ccctccaaaa | 180 |
| aaaaaaaaaa | atttaatttt | taaaaattag | tggtatggca | ataagacact tcagaggcta | 240 |
| tcttaacctc | tgaataccca | tcttctagtt | taaagacaga | gacatcccat ctggaaaatg | 300 |
| ttaacttgtg | ttgtcatctc | gttgccggag | taagtagaca | taagacagag tttaagaagt | 360 |
| aaaaatatag | aaaaattttg | atggtcacaa | tgagataaat | attagaatat tactattcca | 420 |
| atgattaaat | gaggatcttg | aaataaattc | tgaagtcttc | caattttttac atttattgga | 480 |
| ggggtccctg | agttctgtca | acttttttat | ttaagtctct | tgctcttatt ttgtgcataa | 540 |
| atgttaaacc | ttccaaaaat | gaaatgttag | ctttctttct | tttactttttt attaaattta | 600 |
| atagaaaata | tgacctgagt | agttaaaaag | tattttgcat | tatttgcagt aagatgtctc | 660 |
| tagcactgct | caaagggcaa | attttaaaac | ttcagtctgg | gtgaaagatt ttgctagttt | 720 |
| tacagaaaga | tttgctatct | taaactcaaa | gctggttttt | cttttctcaa tgtaagtgac | 780 |
| tgggatgctg | gcttaagaat | tcttttccaag | gncatgtttg | tgaaataaac cttacatgag | 840 |
| agctttcctg | ncatctacnc | ctatatgtgg | cctngaggtt | gaccaaattt antttagntt | 900 |
| ctaagtgtaa | nctatcccaa | atgggctatc | caaatttgaa | tggngcccct catactgnga | 960 |
| aggaaaaang | tggnccctngg | ccgggaacac | ccttangggc | caattttgcg anttccntac | 1020 |
| aatt | | | | | 1024 |

<210> SEQ ID NO 84
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 84

| | | | | |
|---|---|---|---|---|
| gnagnnnnnn | ttgagntngg | ccctctagat | gcatgctcga | gcggccgcca gtgtgatgga | 60 |
| tatctgcaga | attcgccctt | agcgtggtcg | cggccgaggt | acagcattat catctcagta | 120 |
| tgtagtggca | cacattcaaa | atcgtataga | ccatatgagg | atagattaca acttagaaac | 180 |
| taaaataaat | ttgttcaaca | ctccagacaa | catatagtgt | agatgacagg aaagctctca | 240 |
| tgtaatgttt | atttcacaaa | catgaccttg | gaagaattca | taagacagca tcccagtcac | 300 |
| ttacatgaga | aaagaaaaac | cagcttgagt | ttaagatagc | aaatctttct gtaaaactag | 360 |
| caaatctttc | acccagactg | aagttttaaa | atttgccctt | tgagcagtgc tagagacatc | 420 |
| ttactgcaaa | taatgcaaaa | tacttttttaa | ctactcaggt | catattttct attaaattta | 480 |
| ataaaaagta | aaagaaagaa | agctaacatt | tcattttttgg | aaggtttaac atttatgcac | 540 |
| aaaataagag | caagagactt | aaataaaaaa | gttgacagaa | ctcagggacc cctccaataa | 600 |
| atgtaaaaat | tggaagactt | cagaatttat | ttcaagatcc | tcatttaatc attggaatag | 660 |

| | | |
|---|---|---|
| taatattcta atatttatct cattgtgacc atcaaaattt ttctatattt ttacttctta | 720 | |
| aactctgnct tatgnctact tactccggca acgagatgac caccacaagt taacattttc | 780 | |
| cagaanggat gtctctgnct ttaaactaga aagatgggta tttcagaggg taagaatacc | 840 | |
| ctctgaagtg gtcttaatgg catacccta atttttaaaa antaaaattt ttttttttt | 900 | |
| tgggangggg aaggctggat ttcctttcnc ttaacctnga gggtatatcc cctgnttggg | 960 | |
| acccaatttt aagngnacct ggcccgggcn ggccgttcaa aagggcgaat ttccgcncct | 1020 | |
| gggc | 1024 | |

<210> SEQ ID NO 85
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 85

| | | |
|---|---|---|
| gngnnnnnnt taacnccagc ttggtaccga gctcggatcc ctagtaacgg ccgccagtgt | 60 | |
| gctggaattc gccctttcga gcggccgccc gggcaggtac gcggggagag agaagcgagg | 120 | |
| ttctcgttct gagggacagg cttgagatcg gctgaagaga gcgggcccag gctctgtgag | 180 | |
| gaggcaagac acagtgggtc gcaggatctg acaagagtcc aggttctcag gggacaggga | 240 | |
| gagcaagagg tcaagagctg tgggacacca cagagcagca ctgaaggaga agacctgcct | 300 | |
| gtgggtcccc atcgcccaag tcctgcccac actcccacct gctaccctga tcagagtcat | 360 | |
| catgcctcga gctccaaagc gtcagcgctg catgcctgaa gaagatcttc aatcccaaag | 420 | |
| tgagacacag ggcctcgagg gtgcacaggc tccctggct gtggaggagg atgcttcatc | 480 | |
| atccacttcc accagctcct cttttccatc ctcttttccc tcctcctctt ttcctcctcc | 540 | |
| tcctcctgct atcctctaat accaagcacc ccagaggagg tttctgctga tgatgagaca | 600 | |
| ccaaatcctc cccagagtgc tcagatagcc tgctcctccc ctcggtcgtt gcttcccttc | 660 | |
| cattagatca atctgatgag ggctccagca gccaaaagga agagaagtcc cagcacccta | 720 | |
| caggtcctgc cagacagtga gtctttaccc agaagtgaga tgatgaaaag gngactggat | 780 | |
| tnggtgcagt ttctgntntt taagtntcaa atgaaggaa ccgatcncaa anggccgaaa | 840 | |
| tncttggaaa agtgncntna aaaaattatg aagaacnttt tcccttggng gttaangaaa | 900 | |
| cccctccaan gcnngcnngn nggnctttgg gcnttgangn nnaanggnaa gggatccccn | 960 | |
| ttgggccnnt tcntttggcc ttggnnncct ncctngggcc ctancttnng aagggaanc | 1020 | |
| cnnn | 1024 | |

<210> SEQ ID NO 86
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 86

| | | |
|---|---|---|
| gnagnnnnnn ttnngtttcn gaattgggcc ctctagatgc atgctcgagc ggccgccagt | 60 | |
| gtgatggata tctgcagaat tcgcccttag cgtggtcgcg gccgaggtac tccaggtagt | 120 | |

-continued

```
tttcctgcac ccaatcttgg gtgagcagct tcctgggctc cccataaatg aggtgctcca      180
tcccatcata cagccccatc atattcagtg cttcccagat gacctcctca ggggtgcagt      240
agccctctat gaagattatg cttaggataa gtatgagaat gccagtcttg ggcatgctct      300
ggacatcact cagcatccca tcataggtga ggcccaggga ggtgacaagg acaaaggagt      360
ggccagtggg atccacttcc tttacatcaa tgccaaagac cagcagcatg cactcggagg      420
cttcactaaa caacaaaggg aagtggtctt cataatttt tatgacactc tccagtattt      480
ctgcctttgt gatcggctcc ttcatttgat acttgaagag cagaaactgc accaaatcag      540
tcaccttttc atctatctca cttctgggta agactcact gtctggcagg acctgtaggg      600
tgcttggact ctcctccttt tggctgctgg agccctcatc agattgatct aatggaaggg      660
aagcaacgac cgagggggag gagcaggcta tctgagcact ctggggagg aattggtgtc      720 tcatcatcag cagaaacctt ctctggggtg cttggtatta gangatacag gaggaggagg      780
angaagaaga ngaagaagga aaagaggatg gaaaagaagg actgggtgga aatggatgat      840
gaagcatnct tcttcacagc ccaggggaac ctgtgcaccc ttnaagggcc tggggcttac      900
ttttgggaat tgaagaactt ntttaggcnt gccanngntt taccctttg ganccttnag      960 ggcctnaagn accttgganc angggnnncn nnnnnnngga attgggcncg gaaatttggg     1020 ccna                                                                 1024
```

<210> SEQ ID NO 87
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 87

```
gggnnnnnnt taactcatac gccagcttgg taccgagctc ggatcccta g taacggccgc       60 cagtgtgctg gaattcgccc ttagcgtggt cgcggccgag gtacattgag accagcaata      120
gttccagcat ctttggtagc ctgacgctga gagtcattaa agtaagctgg cactgtgacc      180
acagcattgg taacagtctt cccaaggtag gcttctgcaa tttccttcat ctttgtcaga      240
accatagaag acacctcctc tggatagaag cttttggtct ctcccttgta ttctacttgg      300
accttgggcc tgccagcatc attcaccacc ataaagggcc aatgtttcat atcagactgg      360
acaacagcat catcaaatct gcgtccaatc agacgtttgg catcaaaaac tgtgtcggtg      420
gggttcattg caacttgatt cttttgcggca tcaccgatca accgttcagt gtccgtaaag      480
gcgacatagc ttggagtggt tcggtttccc tgatcattgg caattatctc gacttttccg      540
tgctggaaaa cacccacaca agagtaggtg gtgccaagat caataccaac tgcaggtccc      600
ttggacatgg ttgctgggat gtaggcctgg ctccaataac gaaggaagcc acaaaaaccc      660
aagagctgca ggcgaagtcc aatgagaccc ccgcgg acc tgcccgggcg gccgctcgaa      720
agggcgaatt ctgcagatat ccatcacact ggcggccgnt cgagcatgca tctagang gc      780 ccaattcgcc ctataagnga gtcgnattac aatcacttgg ccgcgtttta caacgtcgtg      840
acttgggaaa accctgggg t acccaactta atcgncttgn agcacaatcc ccnttnnn cc      900 anctggcgga antnaccnaa aaggcccgna ccgaacggcc ntttccaaaa gttgcncaan      960
cctgaaangg caaaggacc ccccccttta acggggccat taaaccccc n ncgggnnnn     1020 nngg                                                                 1024
```

<210> SEQ ID NO 88
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 88

| | | | | | | |
|---|---|---|---|---|---|---|
| gnnnnnnttn | ngattgggcc | ctctagatgc | atgctcgagc | ggccgccagt | gtgatggata | 60 |
| tctgcagaat | tcgcccttcg | agcggccgcc | cgggcaggtc | cgcgggggggt | ctcattggac | 120 |
| tcgcctgcag | ctcttgggtt | tttgtggctt | ccttcgttat | tggagccagg | cctacatccc | 180 |
| agcaaccatg | tccaagggac | ctgcagttgg | tattgatctt | ggcaccacct | actcttgtgt | 240 |
| gggtgttttc | cagcacggaa | aagtcgagat | aattgccaat | gatcagggaa | accgaaccac | 300 |
| tccaagctat | gtcgccttta | cggacactga | acggttgatc | ggtgatgccg | caagaatca | 360 |
| agttgcaatg | aaccccaccg | acacagtttt | tgatgccaaa | cgtctgattg | gacgcagatt | 420 |
| tgatgatgct | gttgtccagt | ctgatatgaa | acattggccc | tttatggtgg | tgaatgatgc | 480 |
| tggcaggccc | aagtccaag | tagaatacaa | gggagagacc | aaaagcttct | atccagagga | 540 |
| ggtgtcttct | atggttctga | caaagatgaa | ggaaattgca | gaagcctacc | ttgggaagac | 600 |
| tgttaccaat | gctgtggtca | cagtgccagc | ttactttaat | gactcttcag | cgtcaggcta | 660 |
| ccaaagatgc | tggaactatt | gctggtctca | atgtacctcg | gcccgngacc | acgctaaggg | 720 |
| cgaattncag | cacactggcc | ggccgntact | taatggatcc | gaactcggta | ccaagccttg | 780 |
| cgtaatcatg | gnccatactg | gttnctgngg | tgnaattggt | attccggtca | caattncnca | 840 |
| caacattcca | anccggaagc | cttnagtgta | aagccctggg | tgcccttaag | agtgagctta | 900 |
| ctnncantta | aatgcgttgc | gcttnnttgg | ccgttttcca | tcgggnaaan | ctgcngccaa | 960 |
| ctggatttaa | ggaattggnc | aanncccccgg | ggaaaaaagn | gtttggtatg | gcgcttttnc | 1020 |
| gttt | | | | | | 1024 |

<210> SEQ ID NO 89
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 89

| | | | | | | |
|---|---|---|---|---|---|---|
| gggnnnnnnt | taaactccag | cttggtaccg | agctcggatc | cctagtaacg | gccgccagtg | 60 |
| tgctggaatt | cgcccttgag | cggccgcccg | ggcaggtaca | gttcagtaat | gttaagtgta | 120 |
| ttcacagtgc | tgtgcaaaac | atttctatct | tgcaaaaccg | aagttctata | tccactaaac | 180 |
| aactccgcat | tttccctctc | cccagccccct | gccaactgcc | attctacttt | ctgtttctct | 240 |
| atatttgact | acactagaca | cctcatacaa | gttaaatcag | agagtatttg | ttttttttgtg | 300 |
| actggtttct | ttaaacttag | cataacatcc | tcaagatcca | tcaatagtct | atcatgtatc | 360 |
| atgtattact | tcttttttaa | ggttgaacaa | tattccactg | tgtgtgtgtg | tgtgcacgtg | 420 |
| tataccacgt | tttgttttagc | cattcgtcca | tcaatggaac | ttgggttgct | tcgacccttt | 480 |
| ggctactgta | ttacgttgtt | ctagcattgc | tataaagacc | tgaggttggg | taatttataa | 540 |

-continued

```
agaaaagaag ttctgcaggc tatacaagca tggtgctggc atctgcctgg cttctgggga    600
ggcctcaggg acctttact catggtggaa ggtgaggcag gagcaggcat gccacatggt    660
gaaagcagga gcaagaaaga gtggggaggg tgccatcact taaaaaacca gatcccatga    720
gtattcatta ttgcaagaac agcatcaaac catgaggctt canccgtgg cccaaacacc     780 ttccaacang ccccaactcg cattaaggat accttcnaa nntaagggtt ggggggggacc    840 aaatntccca actatatcan tgnttttgaa cagggnctcc agttctttta aatcccgaaa    900
aaatttttaa aggantccca acccttttaa ngaactaaag gtttcccgna nnnngaaaag    960
tttttnnccc nggggnaaaa attnaatgnn tttncccnaa aaantaantt ttnaaagaaa    1020 nttt    1024
```

<210> SEQ ID NO 90
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 90

```
gnagnnnnnn ttnngttncg aattgggccc tctagatgca tgctcgagcg gccgccagtg     60
tgatggatat ctgcagaatt cgccttagc gtggtcgcgg ccgcggtaca tctcctaaag    120
actaatggtc atttacaaat tcaaacatga gataaagtat ttggtgatat gtccatcaag    180
tataactcag aaatcagtaa acaagtcttt tcccaaagta agttccttct aaatgtagct    240
aaaaagagcc actttgtcat taaagtgaat gagtatgcat ttttagaaca gacttgatgt    300
ttggattgtg ttaaacatat gtctgttagt gaaagtgtta gtcacaaaga taaaatttca    360
tctaaaaata atatatagag aaaaatgcaa taaatataca catggtaaaa tacttctctt    420
ttctgtaaac ttttagttct ttataagggt tgtgatatca tttaaaaatt tttctgtatt    480
gaaagaaact ggagacactg ttcatagcag ctgatatagt ttggatattt gtccccaccc    540
aaaccttata ttgaaatgta atccttaatg cggaggtggg gcctggtggg aggtgtttgg    600
gccacggggg tggagcctca tggtttgatg ctgttcttgc aataatgaat actcatggga    660
tctggttttt aaagtggatg gcaccctttc ccactctctc ttgctcctgc tttcaccatg    720
tggcatgcct gctcctgcct caccttcacc atgagtnaaa ggnctgang cctcccagaa    780 gccangcaga tgccancanc attgcttgga tagcctgcan aacttctttt ctttataaaa    840
taccccaacc tnaggcntta tgccatgctt gaacaaccgt aatncntanc ccaanggtcn    900
aaccaaccca ggtccattgg nngggcnaag gnttaacnaa acgnggnntc ccntgcncna    960 nnnnccccn ggggnaaatg gcaacccttn aaaanaagnn tncctgganc cngnnnnncc    1020 nttt    1024
```

<210> SEQ ID NO 91
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 91

```
gggnnnnnnt aattancgcc ngcttggtac cgagctcgga tccctagtaa cggccgccag    60
```

```
tgtgctggaa ttcgcccttt agcgtggtcgc ggccgaggta ccttggaagt tatgtcatta      120
atataggctg gttcatcaaa taaagcaaaa ccttgcaata tcagctagat ttacactccg      180
ggacgttgcc caaggtagg aagaaagcag agggaaatat ttcagtcatc atttccaaag       240
tcattatcaa aatctgtgag gaagtttaat cttccaaaga gtcaatgtca gacatcaggc      300
ctctgttgcc tgcttctctc gaggcactag attaggagtc ttcaataaga gacttaacat      360
gaggtatatg gaagatgagg caccgagata agttcatcat taggtgtgag cactgctcac      420
ccttgctggc aagttctcct taagggcctg aagcacaggt gtccaaagaa aagcgttaag      480
tccatcttaa tagaatctat gtggtatatg atgtggtcag cccctggtct gtgatcagca      540
agaacctaca gcacagatta tgccctgccc acttcaatga atacctactc tcctccattc      600
tccatcactt tttttgctat caagaactcc ggaccttgcc catgggagaa gtttagagag      660
gaactcttgt ggagaactgg tttatttct gccctgtgcc gacgagtttc agctggccaa       720
gaaaggagtc aagttattaa aaagcatcac aatggagatc ttccaggctg gttttttgg      780 ttttggtgg taaaactggg ggaaangggg actatttatt ctggccttaa atcaatnggc      840
aaattaagtc aagaagaccn ttttgggaat gtngactatg gatnccctcc taatngaatg      900
gagnagcctt aaaaagggg caangtaang gttttcnggt atggaagcca aaantttnc        960 cggctnaatg ggntggntnn ccaatattnn taccggcccn aaangggnnt tttncnnngg      1020
gtcc                                                                  1024
```

<210> SEQ ID NO 92
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 92

```
nngnnnnnnt tnngantggg ccctctagat gcatgctcga gcggccgccc gggcaggtac       60
tgcatccata atttatcgcc atgtgcaaca gctttgcgtt ttctaaggca caattttaa       120 tgaaatgatg tgtagatttc aatctaataa cagctcatcc aaatgacaaa tatggtcgaa      180
atccctccag tggctgagga aatttctgca cctatatgga acccacatgc aaagaaccca      240
tctagcatgt aataaataat cgctagccat actcaataag acacgaaaaa attattgctt      300
acataacaga aaaacatcta cttgaccccc ttttatgact acatcaatct attaggagtg      360
tatccatagt ctacattcac aaaatgtcat cttgacttat ttgccattga tttaaggcag      420
aataaatagt cccccttttcc ccagtcttaa caacaaaaaa caaaaaacca gcctggagat      480
ctacattgtg atgctttta ataacttgac tcctttcttg gccagctgaa actcgtcgca       540
cagggcagaa aataaaccag ctctccacaa gagttcctct ctaaacttct ccatgggcaa      600
ggtccggagt tcttgatagc aaaaaaagtg atgggagaat ggaggagaag taggtattca      660
ttgaagtggg cagggcataa tctgtgctgn aggttcttgc tgatcacaga ccaagggctg      720
accacatcat ataccacata gattctatta agaatggact taacgctttt ctttggacac      780
ctgtgcttta ngcccttttaa ggagaacttg ncanccangg gtgagcagtg cttcacacct      840
taaggatgaa ccttaatctc ggggcctcat cttccatata ncccctaaggg taagnctctt     900 taatggaaga ctcctnaatt agnggccttg aaaagaagca ggcacccgaa gggcctgagg      960
```

| | |
|---|---|
| ctgacattgg ctcttttnga agaataaact ttccttaccg naatttggaa aaggacctttt | 1020 |
| ggaa | 1024 |

<210> SEQ ID NO 93
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 93

| | |
|---|---|
| gngnnnnnnt taactccagc ttggtaccga gctcggatcc ctagtaacgg ccgccagtgt | 60 |
| gctggaattc gcccttagcg tggtcgcggc cgaggtactt tttcaaatgt cactgaaaga | 120 |
| attgttttg taacagtatg caaaatgata ctgtattgtt agaacaaaaa tctgtggagt | 180 |
| gttaatactt tgtaagccaa attaaagttt ctaagcagta taaaatgaga atgacatcat | 240 |
| cctttcctag tatttccaag tcttagagta ctctacaccc tgttggctat ttatctgggg | 300 |
| ttagacttct ggagactttt cagatagact tgaagtctct ggccttgcct gggaattact | 360 |
| ggctgcccaa ggaagcactg gagaaggcgg tggtctcctt gcccttgtgg tcctgctgtg | 420 |
| gcgcattttg attgagttcc tggttcggct ggtcagagtg gctggatagt gttggcccac | 480 |
| tccattcctc aggttttttt gaagcggtgg tcttttaggg agagcctttt gttcctggaa | 540 |
| cttccttgac gggtcccttt tcccttctgg gttgtcttgg gaacctcttt ggtgttgatg | 600 |
| ggttgttgtt ggaaaatggg ctggaggctc gtggtttcct ggacatcttc accagaccag | 660 |
| tgtctctcaa cagtctactc cagtccacct ggtctncccg agcttcccca ggacagtgaa | 720 |
| ngcaggccac aggctanaaa ctgtagtcnc ccgacattac aagccaattt gggnctgtgg | 780 |
| gctctgnttt ccaaatcaac cctttcanct tcatttggaa ncccattcag gaaanccccg | 840 |
| cgtaccttgc ccgggcgggc cgttcnaaag ggcgaattct gcanaaatcc cttanacttg | 900 |
| ggnggnccgt ttnaacctgc cttttaaagg gcccaattnn nccctntnna nnggagcgan | 960 |
| taccaattnn ntggnccgc gttttnaaaa cgnnnnnann tnggnaaaan ccctggggtn | 1020 |
| cccc | 1024 |

<210> SEQ ID NO 94
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 94

| | |
|---|---|
| ttnngaattg ggccctctag atgcatgctc gagcggccgc cagtgtgatg gatatctgca | 60 |
| gaattcgccc ttcgagcggc cgcccgggca ggtacgcggg gcttcctgga tggggatcca | 120 |
| gatggaggtg gagggttgat ttgggaagca gagcacagca gcacaaattt gcttgtaatg | 180 |
| tcggcgacta cagtttctag cctgctggcc tgccttcact gtcctggggg aagctcgggg | 240 |
| agaccaggtg gactggagta gactgttgag agacactggt ctggtgaaga tgtccaggaa | 300 |
| accacgagcc tccagcccat tttccaacaa ccacccatca acaccaaaga ggttcccaag | 360 |
| acaacccaga agggaaaagg gacccgtcaa ggaagttcca ggaacaaaag gctctcccta | 420 |
| aaagaccacc gcttcaaaaa aacctgagga atggagtggg ccaacactat ccagccactc | 480 |

```
tgaccagccg aaccaggaac tcaatcaaaa tgcgccacag caggaccaca agggcaagga      540
gaccaccgcc ttctccagtg cttccttggg cagccagtaa ttcccaggca aggccagaga      600
cttaagtcta tctgaaaagt cttccagaag tctaacccca gataaatagc cnaacagggt      660
ggagagtact tctaagactt ggaaatctta ggaaagggat gatgtcantc tcattttata      720
ctgnttaaaa actttaantt ggcttacaag tattaacccct tcacagaant ttgtctacca     780
tncagnatca atttggcatc tggtccaaaa ccatttttt agggcanttt gaaaagtcct       840
tnggccggga acaccttaag ggcgantcca gncacttggg nggncgtnan nnnaaggtcc      900
caactcgnnc caaannttgn gnaaacatgg gnnnanatgg gntcctgggg ggaaatgtat      960
ccgnttacaa nttcccncaa nntncnaanc cggannncnt taagggtaaa nnccctgggg     1020
gccc                                                                  1024
```

<210> SEQ ID NO 95
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 95

```
gggnnnnnnt taactccagc ttggtaccga gctcggatcc ctagtaacgg ccgccagtgt       60
gctggaattc gcccttcga gcggccgccc gggcaggtac tttttttttt ttttttttc       120 cgtctcccca aagctttatc tgtcttgact ttttaaaaaa gtttgggggc agattctgaa     180
ttggctaaaa gacatgcatt tttaaaacta gcaactctta tttctttcct ttaaaaatac    240
atagcattaa atcccaaatc ctatttaaag acctgacagc ttgagaaggt cactactgca    300
tttataggac cttctggtgg ttctgctgtt acgtttgaag tctgacaatc cttgagaatc    360
tttgcatgca gaggaggtaa gaggtattgg attttcacag aggaagaaca cagcgcagaa    420
tgaagggcca ggcttactga gctgtccagt ggagggctca tgggtgggac atggaaaaga    480
aggcagccta ggccctgggg agcccagtcc actgagcaag caagggactg agtgagcctt    540
ttgcaggaaa aggctaagaa aaaggaaaac cattctaaaa aacaacaaga aactgtccaa    600
atgctttggg aactgtgttt attgcctata atgggtcccc aaaatgggta acctagactt    660
cagagagaat gagcagagag caaaggagaa atctggctgc cttccatttt cattctgnta    720
tctcaggtga actggtanan gggagacatt ngaaaaaaat gaaacnacca aaaccattac    780
taatgaggta ccttnggncc gggaacacgc ttaaggcgaa ttttgcagaa atncattaca    840
ctggcggncc gttcagcatg cttttaaagg gcccaattnc cctttaaggg agtcgnatta    900
caatttnant gggccgcgtt ttacaacgtn nggaactggn aaaacccctg gggtnnccca    960
cttnaannnc cttggnnnan aatccccttt tnccnaantg gggnnnnnnn ccaaaggccc   1020 cnna                                                                1024
```

<210> SEQ ID NO 96
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 96

| | | |
|---|---|---|
| gngnnnnnnn tnngttncga ntgggccctc tagatgcatg ctcgagcggc cgccagtgtg | 60 |
| atggatatct gcagaattcg cccttagcgt ggtcgcggcc gaggtacctc attagtaatt | 120 |
| gttttgttgt ttcatttttt tctaatgtct cccctctacc agctcacctg agataacaga | 180 |
| atgaaaatgg aaggacagcc agatttctcc tttgctctct gctcattctc tctgaagtct | 240 |
| aggttaccca ttttggggac ccattatagg caataaacac agttcccaaa gcatttggac | 300 |
| agtttcttgt tgtttttag aatggttttc cttttctta gccttttcct gcaaaaggct | 360 |
| cactcagtcc cttgcttgct cagtggactg ggctccccag ggcctaggct gccttctttt | 420 |
| ccatgtccca cccatgagcc ctccactgga cagctcagta agcctggccc ttcattctgc | 480 |
| gctgtgttct tcctctgtga aaatccaata cctcttacct cctctgcatg caaagattct | 540 |
| caaggattgt cagacttcaa acgtaacagc agaaccacca gaaggtccta taatgcagt | 600 |
| agtgaccttc tcaagctgtc aggtctttaa ataggatttg ggatttaatg ctatgtattt | 660 |
| ttaaaggaaa gaaataagaa ttgctagttt taaaaatgca tgtcttttaa ccaattcaga | 720 |
| atctgccccc aaactttttt naaaagtcaa ggaccgataa agctttgggg agacngaaaa | 780 |
| aaaaaannnn aaaaagtacc tgcccgggcn ggccgttcna aagggcgaaa ttcaacacac | 840 |
| tgggcggccg gtacttaatg gatcccaact cggncccaac cttggggaaa ncatgggccn | 900 |
| taactgggtt cccgggggn aaatggtatt ccggttacaa attccccccc annttccana | 960 |
| cccggaaanc cnttaagggt aaaanccctg ggnggcccna anggggggct nacctcccct | 1020 |
| tnaa | 1024 |

<210> SEQ ID NO 97
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 97

| | | |
|---|---|---|
| gnngnnnnnn nttnnnttat acgccangct tggtaccgag ctcggatccc tagtaacggc | 60 |
| cgccagtgtg ctggaattcg cccttagcgt ggtcgcggcc gaggtacatc tgattttata | 120 |
| tgttgtccaa actggtcaat ccagttgctt aacacagaaa gcggacagat gatcagtgtt | 180 |
| gttcttggtc tctcctcaac atcagttttc tttgacccct ccactgcaca agctcccttt | 240 |
| ttcaacattt tcttttttgt tgtaggaaca gatgaagtta atgcacatgc aaatgccaca | 300 |
| tcttctataa ccttagaaga tcctttcgcc ctgcctttag tttcagactg tacagaggga | 360 |
| gagagagaga gaaagagagc acgccagtga gaaagcgagc gcgagcgcga gcgcaagggg | 420 |
| aggagagggt gggagagggc ggaaggggga aagctgtccg tgggagattg tgtcttcatg | 480 |
| tccacggggc tgcatctctt gatggtgcac tgaaaaagca gagctcacca gacagagtgg | 540 |
| aaaggcaggg ggaggggcag ggagcaacag aaggaagaga caacaagccc aagacagctt | 600 |
| ccatctcaga cggaaggccc ccagaagata gaattccagc cgactgaaaa accacccaat | 660 |
| gaacaaagaa gattctagaa aatagaagtg ttgggattac aaagttgngc gtttcatcgg | 720 |
| tacctgcccg ggcggncgnt caangggcga attctgcaga tatccatcac actggcggnc | 780 |
| gntcgagcat gcatntagan ggcccaantc gnccctataag ggagtcgnan tacaattcac | 840 |
| ttgggccgcg ttttacaacg tctgacttgg naaaanccct gnggttnccc aacnttaaac | 900 |

```
ggcnttggag nacaattccc cttttttncca anntggggna antnaccaaa agggccccnn      960
accgatggnc cttttncaaa aagttgggcc aaccttgaaa gggcaaaagg gccccccct       1020 ttaa                                                                  1024
```

<210> SEQ ID NO 98
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 98

```
gnngnnnnnn ttnngaatgg gccctctaga tgcatgctcg agcggccgcc agtgtgatgg        60
atatctgcag aattcgccct tgagcggccg cccgggcagg taccgatgaa acgcgcaact       120
ttgtaatccc aacactttct attttctaga atcttctttg ttcattgggt ggttttttcag      180 tcggctggaa ttctatcttc tgggggcctt ccgtctgaga tggaagctgt cttgggcttg      240
ttgtctcttc cttctgttgc tccctgcccc tccccctgcc tttccactct gtctggtgag      300
ctctgctttt tcagtgcacc atcaagagat gcagccccgt ggacatgaag acacaatctc      360
ccacggacag cttttcccct tccgccctct cccaccctct cctcccctttg cgctcgcgct      420 cgcgctcgct ttctcactgg cgtgctctct ttctctctct ctctccctct gtacagtctg      480
aaactaaagg cagggcgaaa ggatcttcta aggttataga agatgtggca tttgcatgtg      540
cattaacttc atctgttcct acaacaaaaa agaaaatgtt gaaaaaggga gcttgtgcag      600
tggagggtgc aaagaaaact gatgttgagg agagaccaag aacaacactg atcatctgtc      660
cgctttctgt gttaagcaac tggattgaca gtttggacaa catataaaaa tcagatgtac      720
ctcggncgcg accacgctta gggcgaattn cagcacactg ggcggccgtt acttaatgga      780
tccgaactcg naccaagcct tgcgtaaaca tgggcaatac tggnttcctg ngggggaaatg      840 gtaatccggt tacaaattcc ccacaacntt acaanccgga agcccttaag ngtaaaaccc      900
ctgggngccc caaagagtga gctaacttnc catttaaatg cgttngctca atggcccgtt      960
ttccatcggg naaaacctgn ngccantgga ttaangaatc ggncaaancc cccggggnaa      1020 aaan                                                                  1024
```

<210> SEQ ID NO 99
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 99

```
aacgccagct tggtaccgag ctcggatccc tagtaacggc cgccagtgtg ctggaattcg        60 cccttcgag cggccgcccg ggcaggtaca gataaatccg tgcatgcatt gagggagact       120
agagggtaaa atgaaatctg ccccatcctt cttacataca cagtgatagc attttgaatt      180
gttcttctac atttgaaatc ttagctgaaa gatcatcagc caccgacctt ttgtgaagct      240
agttctctag aacatacaat gttttttaaa aaattaaaaa cacagaagga aaaaagcaag      300
aaccaacgat aaatggagct tgtgcagaat ctggcagtgc tgtggacctg cccatctgtt      360
```

-continued

| | | |
|---|---|---|
| ctcccccgcg tactgactga acacactccc cgctttggtt cctgtaggac gggtgagata | 420 |
| ccacaccttg gcaaccacca gtaaaggctc atagtctagc ccttgggagg ccccgatttt | 480 |
| agggctgtgc tcggaggcga cctacgttag ggactgggag aagcgggtac ctcggccgcg | 540 |
| accacgctaa gggcgaattc tgcagatatc catcacactg gcggccgctc gagcatgcat | 600 |
| ctagagggcc caattcgccc tatagtgagt cgtattacaa ttcacttggc ccgtcgtttt | 660 |
| acaacgtcgt gactgggaaa accctgccgt tacccaactt aatcgccttg cagcacatcc | 720 |
| cccttcgcc agctgcgtaa taacgaaaag cccgnaccga tcgcccttc cacagttgcg | 780 |
| caacctgaat ggcnaatgga ccccccttg taccggcgca ttaaccnccn gccggntnnt | 840 |
| ggggtacccc cacgtggacc ggttcacttg gccaggggccc taangnccgg ttcntttggt | 900 |
| ttcttnccttt ccnttttttng cccgttngcc nggttttttcc cgtaagcttt taaannggggg | 960 |
| gcttcccctt ttangggtcc aaataangct ttacgggncc tttaaccccc aaaaaaattt | 1020 |
| nnnt | 1024 |

<210> SEQ ID NO 100
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 100

| | | |
|---|---|---|
| gggnnnnnnn ttnngttcng aattgggccc tctagatgca tgctcgagcg gccgccagtg | 60 |
| tgatggatat ctgcagaatt cgcccttagc gtggtcgcgg ccgaggtacc cgcttctccc | 120 |
| agtccctaac gtaggtcgcc tccgagcaca gccctaaaat cggggcctcc caagggctag | 180 |
| actatgagcc tttactggtg gttgccaagg tgtggtatct cacccgtcct acaggaacca | 240 |
| aagcggggag tgtgttcagt cagtacgcgg gggagaacag atgggcaggt ccacagcact | 300 |
| gccagattct gcacaagctc catttatcgt tggttcttgc tttttttcctt ctgtgttttt | 360 |
| aatttttttaa aaaacattgt atgttctaga gaactagctt cacaaaaggt cggtggctga | 420 |
| tgatcttttca gctaagattt caaatgtaga agaacaattc aaaatgctat cactgtgtat | 480 |
| gtaagaagga tggggcagat ttcatttttac cctctagtct ccctcaatgc atgcacggat | 540 |
| ttatctgtac ctgcccgggc ggccgctcga aagggcgaat tccagcacac tggcggccgt | 600 |
| tactagtgga tccgagctcg gtaccaagct tggcgtaatc atggtcatag ctgnttcctg | 660 |
| tgtgaaattg ntatccgctc acaattccac acaacatacg agcccggaag ccataaagtg | 720 |
| tnaaagccct ggggtgcctn atgagtgagc taactcacat ttaattgcgt tgcgctcact | 780 |
| ggcccgnttt cagtcgggaa aactgcntgc cactgcttaa tgaatcggcc acgcccggg | 840 |
| gaaaaagcgn ttgcgtantg ggcgctnttc cgctttcttg gttaactgac tcnttgggct | 900 |
| ttggccttng gnttnnggnn aacgggttna acttncnttn aaanggggggn naatccggtn | 960 |
| tncccccgaaa nncggggata accccccggaa anaactttgn ccnaaaggcc cccnaaaagg | 1020 |
| cccn | 1024 |

<210> SEQ ID NO 101
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 101

```
gggnnnnnnt tgaatnacac gccagcttgg taccgagctc ggatccctag taacggccgc    60
cagtgtgctg gaattcgccc ttagcgtggt cgcggccgag gtacgcggt attttcttaa   120
atttcttgaa tgttctttat ggtagtgtta ctaaaaagtt tatgatcaca ttttcattgt   180
gaacataatt tgaactcatt atcacacact tggaaaatac agaaaagtgg aggaaaaaaa   240
atcatatccc caccatccaa agacatatac tctcctctta tcttgttcat tcttgtttct   300
gtgcacaggt ttatgattat aactgtgtca aaatgtatat tcaaaatagc tgttacatta   360
cctttgtgga attatggtta aatactttca ctttaatttt ttcaaatgtt ccctataata   420
atgttctgat aacagtgtat tatgtgtgtc tccattggtg tgcataatac atacccagag   480
gaaaaattag aaaataaagt aaattatttt aaaaaattac ctatattccc aacacctaac   540
aactactgct aacatcttga tctgtttcct ctatcttgtt tcagtgcaca cgcttgtgat   600
aacagtgtta aatatgtgtg cataaagtct taaatgaaaa gatgtggaaa ataactaaaa   660
tagtgttgtc attgtgggaa tttggttaaa tattttgtct caaattcctt aaataatctt   720
tggtgttttg gtaataaatt ttaatgatgt attttccatt acaaatataa tacatactca   780
tacaaaactt tggaaaatta gtaaagaaaa ttcacacata ttcccacacc caacaccaat   840
ttaactggtn accatctgga ctgngcncta agctgggatt antttaggng tagtggataa   900
gtatgcctaa aggccaaaaa tgggaagaag gatgaaaanc cngaaaatan ttnccctggt   960
gtnnggggaa taagggggaat ttgggttcgg ttcctttgaa agggcatnnn tttcaagggg  1020
tttg                                                              1024
```

<210> SEQ ID NO 102
<211> LENGTH: 1020
<212> TYPE: DNA
<213> ORGANISM: Homo Sapien
<220> FEATURE:
<221> NAME/KEY: misc_feature
<222> LOCATION: (1)...(1020)
<223> OTHER INFORMATION: n = A,T,C or G

<400> SEQUENCE: 102

```
ggagnnnntt aaacgccagc ttggtaccga gctcggatcc ctagtaacgg ccgccagtgt    60
gctggaattc gccctttcga gcggccgccc gggcaggtac tctttctctc ccctcctctg   120
aatttaattc tttcaacttg caatttgcaa ggattacaca tttcactgtg atgtatattg   180
tgttgcaaaa aaaaagtgt ctttgtttaa aattacttgg tttgtgaatc catcttgctt   240
tttccccatt ggaactagtc attaacccat ctctgaactg gtagaaaaac atctgaagag   300
ctagtctatc agcatctgac aggtgaattg gatggttctc agaaccattt cacccagaca   360
gcctgtttct atcctgttta ataaattagt ttgggttctc tacatgcata acaaaccctg   420
ctccaatctg tcacataaaa gtctgtgact gaagtttag tcagcacccc caccaaactt   480
tattttctta tgtgttttt gcaacatatg agtgttttga aataaagta cctcggccgc    540
gaccacgcta agggcgaatt ctgcagatat ccatcacact ggcggccgct cgagcatgca   600
tctagagggc ccaattcgcc ctatagtgag tcgtattaca attcactggc cgtcgtttta   660
caacgtcgtg actgggaaaa ccctgcgtta cccaacttaa tcgccttgca gcacatcccc   720
ctttcgccag ctggcgtaat aacgaaaagc cccggaccga tcgcccttc caacaggtgc   780
```

| | |
|---|---|
| gcaacctgaa tggcgaaatg gaccccccct ggaaccggcg cantaaaccc ccgncgggnn | 840 |
| nntngggtac ccccacggg ganccgttca cttggccann gccctaangn cccgttcctt | 900 |
| tnggtttctt tccttccttt tgcccgttt gnccgggttt tcccggnaag ctttaaaaac | 960 |
| gggggcctcc cccttangg gtccnaataa nggcttttac gggnccttng aaccccaaan | 1020 |

<210> SEQ ID NO 103
<211> LENGTH: 1021
<212> TYPE: DNA
<213> ORGANISM: Homo Sapien
<220> FEATURE:
<221> NAME/KEY: misc_feature
<222> LOCATION: (1)...(1021)
<223> OTHER INFORMATION: n = A,T,C or G

<400> SEQUENCE: 103

| | |
|---|---|
| ggagnnnttn ngnngggccc tctagatgca tgctcgagcg ccgccagtg tgatggatat | 60 |
| ctgcagaatt cgcccttagc gtggtcgcgg ccgaggtact ttattttcaa aacactcata | 120 |
| tgttgcaaaa aacacataga aaataaagt ttggtgggg tgctgactaa acttcaagtc | 180 |
| acagactttt atgtgacaga ttggagcagg gtttgttatg catgtagaga acccaaacta | 240 |
| atttattaaa caggatagaa acaggctgtc tgggtgaaat ggttctgaga accatccaat | 300 |
| tcacctgtca gatgctgata gactagctct tcagatgttt ttctaccagt tcagagatgg | 360 |
| gttaatgact agttccaatg gggaaaaagc aagatggatt cacaaaccaa gtaattttaa | 420 |
| acaaagacac ttttttttt gcaacacaat atacatcaca gtgaaatgtg taatccttgc | 480 |
| aaattgcaag ttgaaagaat taaattcaga ggagggaga gaaagagtac ctgcccgggc | 540 |
| ggccgctcga aagggcgaat tccagcacac tggcggccgt tactagtgga tccgagctcg | 600 |
| gtaccaagct tggcgtaatc atggtcatag ctgnttcctg tgtgaaattg gtatccgctc | 660 |
| acaattccac acaacatacg agcccggaag cataaagtgt aaagccctgg ggtgcctaat | 720 |
| gagtgagcta actcacatta aatgcgttgc gctcactggc cgctttncag tccgggaaac | 780 |
| ctgtcgtgcc agctgcatta atgaatccgg ncaacgcccc ggggaaaaag cggttgcgta | 840 |
| ttgggcgctc ttncgctttc ttggttactg gctccttgng cctcggccgt tccggnttcg | 900 |
| gnnaaccggt atcagcttac ttcaaangcg gnaaatccgg tttncccnga aatccggggg | 960 |
| ttaacnccag gaaaanaacc tttgaaccna agggccccn aaaagggccc ggaaccctaa | 1020 |
| a | 1021 |

<210> SEQ ID NO 104
<211> LENGTH: 1017
<212> TYPE: DNA
<213> ORGANISM: Homo Sapien
<220> FEATURE:
<221> NAME/KEY: misc_feature
<222> LOCATION: (1)...(1017)
<223> OTHER INFORMATION: n = A,T,C or G

<400> SEQUENCE: 104

| | |
|---|---|
| ggagnnntta atcnacgccn gcttggtacc gagctcggat ccctagtaac ggccgccagt | 60 |
| gtgctggaat tcgcccttag cgtggtcgcg gccgaggtac tcagctgtct taataggatg | 120 |
| aagccttaag cagtggaaat ttcagttatt ttccacagta ttccattttg gaggatttgg | 180 |
| ggtgttact ttttaaattc ttgaacaact taacctccat gaggctttgt gaagtcagct | 240 |
| gtgaccaccc tcctcttact gtgttctcag tattcattca cttccaggga agaatgacag | 300 |
| ccacagggag atggtggtgg gcaagaatga gagtcccagg atccagattt agcctcagat | 360 |

```
cttccccatt caggaagggt tttccattta acaagagcac tagtatgaaa acattaggga        420
caaatctccc atgtctttga aattcggatt ctcctcttga gatccccttc ctcacctgcc        480
aatcaacttt ataaggccac aagtggtcac tggttttcct tccacaggtt tgaggttctc        540
agctttcctt aagcgaccca gcagctccgc tgttttcaga gtgaatatgt taagctttga        600
tgagattcta ttttcagtaa gttagtgctt ctggacacact tggagaaagc tgtgagagtc        660
attggctacg caagaacaa cgaaagctga tcctaaaagt gatccaatct aagaaaatgg        720
taaaacgagc tctggccaca gcacagaatt ttatgtgang aactcagatt tttgaagact        780
taacaattgc agaaaaaggn tgcagcctgn acacccatag cccaactttt ntgagccana        840
ctttgggttt tgggnggga cntggcacca tgtttgnacc tggccggccg gnccgttcna        900
aagggccaaa ttntggcnga aatnccttac actgggggc cgtttgagca tgcctntaaa        960
ngggcccaan tngnccctta aagggggcn nnttccaatt nnctgggccc ggttttn          1017

<210> SEQ ID NO 105
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 105
ggagnnnntt nnntnnngan tgggccctct agatgcatgc tcgagcggcc gccagtgtga         60
tggatatctg cagaattcgc cctttcgagc ggccgcccgg caggtacaaa catgtgccac        120
gtcaccacac aaaaccaaag tctgctcaga gaggtgggct atggtgtgca ggctgcaacc        180
tttctctgca attgttaagt cttcaaaaat ctgagttcct cacataaaat tctgtgctgt        240
ggccagagct cgttttacca ttttcttaga ttggatcact tttaggatca gcttcgttgt        300
tctttgcgta gacaatgact ctcacagctt tctccaagtg tcccagaagc actaacttac        360
tgaaaataga atctcatcaa agcttaacat attcactctg aaaacagcgg agctgctggg        420
tcgcttaagg aaagctgaga acctcaaacc tgtggaagga aaaccagtga ccacttgtgg        480
ccttataaag ttgattggca ggtgaggaag gggatctcaa gaggagaatc cgaatttcaa        540
agacatggga gatttgtccc taatgttttc atactagtgc tcttgttaaa tggaaaaccc        600
ttcctgaatg gggaagatct gaggctaaat ctggatcctg ggactctcat tcttgcccac        660
caccatctcc ctgtggctgt cattcttccc ctgaagtgaa tgaatactga gaacacagta        720
aggaaggagg gtggtcacaa gctgacttca caaagcccta atggangagtt aagttggtca        780 agaatttnaa aagtaaccc cccaaatcct ccaaaaatgg gaatactggt ggaaaataac        840
ctggaaattn ccctggttta aggcttcatt ctattaagac cgcttgagta cccttggccg        900
ngaaccccct taagggcgaa ntncaacaca ctgggngggc cggtacctaa nggatcccaa        960
ctnggnaccc aancnttggg gaaancatng ggccataact gggttcccgg ggggaaatgg       1020
taat                                                                    1024

<210> SEQ ID NO 106
<211> LENGTH: 1007
<212> TYPE: DNA
<213> ORGANISM: Homo Sapien
<220> FEATURE:
<221> NAME/KEY: misc_feature
<222> LOCATION: (1)...(1007)
```

<223> OTHER INFORMATION: n = A,T,C or G

<400> SEQUENCE: 106

| ggagnnnntt | aaacgccagc | ttggtaccga | gctcggatcc | ctagtaacgg | ccgccagtgt | 60 |
| gctggaattc | gcccttagcg | tggtcgcggc | cgaggtacac | agaatagctg | agcagttcac | 120 |
| ttcagggatc | aggtcatctc | tgctcctcct | agtttcacca | tgttctggca | ataaaaaaca | 180 |
| catattatat | cctggttttc | tctatccttg | cattactaag | gtgactgtct | ctctttatac | 240 |
| atccttgtat | ggttctccca | gtattagcaa | gattgtatat | ctgtaaagaa | tgtccagttt | 300 |
| tgtaaatatt | tccctgcctt | tttttttctt | tttttacatc | tgattttaat | gcttcgttaa | 360 |
| cttcaaaagg | aactggtaga | gttcagaagg | tgagctgttg | tttttctaaa | cctcttccca | 420 |
| ggaaggggac | attgacactt | gaattttgt | cacctttttc | ctcattagaa | ggaaagtaga | 480 |
| aagccttact | gtaggatttt | taaaaaaaaa | tccatctcac | cccatattgg | tcttaaataa | 540 |
| gtatagacta | attaacctaa | gctaccttta | acaacgtaga | atttaanatg | ggttcatata | 600 |
| tgtgagaaaa | acctgaatat | aggacagggg | tcctacttt | ttccccacct | ctgtcgccca | 660 |
| ggctagagta | ntaantggtg | gatcttggcc | cactgcaacc | tctgcttcta | gggtcaagtg | 720 |
| attctcctgc | tcagcctncc | aagtancccg | ggaattggaa | gagtatgcca | ccacgcccag | 780 |
| ctacttttg | gaattttagt | nnaaaacagg | ttcatcatgn | tggncccnga | agggcnctta | 840 |
| antcctgncc | ttnagngatc | ccccnnana | ngaaaccntg | gncnncccaa | nnncggnn | 900 |
| tntagcnnnn | ccnccgngcc | cannctactt | tnnnaannnn | nnnnnnnnnn | nnnnnnnnnn | 960 |
| nnnnnnnnaa | nnngnncnnn | nccngnnngn | ccnnnnnngg | gnaantc | | 1007 |

<210> SEQ ID NO 107
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 107

| gnagnnnnnn | nngattgggc | cctctagatg | catgctcgag | cggccgccag | tgtgatggat | 60 |
| atctgcagaa | ttcgcccta | gcggccgccc | gggcaggtac | ttttttttt | tttttttt | 120 |
| ttttttttt | aattaattag | aaagtaggct | gggcacgggng | gctcatgcct | ataatcccag | 180 |
| cacttgggga | ggccgaggat | ctcctctctg | gnggatcact | tgagggcagg | agttaagaga | 240 |
| ccatcctggc | caacatgatg | aaaccctgtc | tctactaaaa | atacaaaaag | tagctgggcg | 300 |
| tggtggcata | ctcttacaat | cccggctact | tgggaggctg | aggcaggana | atcacttgaa | 360 |
| cctaggaagc | agaggttgca | gtgggccaag | atcacaccac | tatactctag | cctgggcgac | 420 |
| agaggtgggg | aaaaaagtag | gacccctgtc | ctatattcag | gttttttctca | catatatgaa | 480 |
| cccatctaaa | ttctacgttg | ttaaaggtag | cttaggttaa | ttagtctata | cttatttaag | 540 |
| accaatatgg | ggtganatgg | attttttttt | aaaaatccta | cagtaaggct | ttctactttc | 600 |
| cttctaatga | ggaaaaaggt | gacaaaaatt | caagtgtcaa | tgcccttcc | ttggggaaga | 660 |
| ggtttagaaa | acaacagct | caccttntga | acttttacca | gttcctttt | gagttaaccg | 720 |
| aagcnttaaa | aatcagatgt | aaaaaangaa | aaaaaaggc | cgggaaattt | ttaccaaact | 780 |
| nggacattct | ttacagatat | acaatcttgc | taaaacctgg | gaaaaccctt | cccngggtgt | 840 |
| ttaaagggga | aacagtcccc | cttataatgc | ccgggggttna | gaaaanccccg | gatttttnnaa | 900 |

```
aaagggtttt tattgcccaa aactgggga accttnggg ggncccaaaa nnaacctgan      960 ccctgaagg naccgggtnn annnnntttt tgggaccttg gccgggaacc ccctttnggg    1020 ggna                                                                1024
```

<210> SEQ ID NO 108
<211> LENGTH: 470
<212> TYPE: DNA
<213> ORGANISM: Homo Sapien
<220> FEATURE:
<221> NAME/KEY: misc_feature
<222> LOCATION: (1)...(470)
<223> OTHER INFORMATION: n = A,T,C or G

<400> SEQUENCE: 108

```
actatgacca tgattacgcc aagcttggta ccgagctcgg atccactagt aacggccgcc     60
agtgtgctgg aattcgccct ttcgagcggc cgcccgggca ggtactattt tttttttttt    120
ttttcgtgtn tttgacattc cttgaatctg tttttattc cccttccaca gaacaggcct    180
gggactttcc aacaccctgc taaggaagtt ctgtgtccaa gtcccaccca ggctgggttg    240
tccccacctn ctncagccca cacagcccag gcagcatccg gccagtgcc ctgcatgaca    300 nagggtcttt gttgtgtaat gnttgttccc aagttgcatt ttctaaccga atcagtgtgt    360
tttcatgaaa ctgagtgtta ctgtggacca gtaagttnct ctgttgtctt cagtggtctt    420
cctgtgtggc tcaagggttc tctgtgagag tctggatttt catttctggg             470
```

<210> SEQ ID NO 109
<211> LENGTH: 808
<212> TYPE: DNA
<213> ORGANISM: Homo Sapien
<220> FEATURE:
<221> NAME/KEY: misc_feature
<222> LOCATION: (1)...(808)
<223> OTHER INFORMATION: n = A,T,C or G

<400> SEQUENCE: 109

```
gggcctctag angcatgctc gacggccgcc atgtgatgga tatctgcaga attcgccctt     60
agcgtggtcg cggccgaggt acaagtctgc ctaagagaca gaagtgagtn ttataatcta    120
cttggccatt cctcccagca gagaagcagc aggtagatat ggcatgcact gtgcctgctg    180
ctgctgctct tgtggcgaac actcagatgt ggaaccatag agggaccttg aggagctggg    240
acatgattct ttagagaaga gaagagacgg ggagcacagc atgagaatgg ccagtcaacc    300
catttcaaat tcttttatta aagtgccccc cgaggggcct tgcacaaaga tgatggggag    360
agcagaactg ctgctccttg acagaactct gatccttaca ctttgtttgg agtgggcttg    420
gggacagtca caagccatga acatgaatc caaaatggtc cccagatgag ccatggtgaa    480
ccaacagatg caagcaactt cttaaactgc tctattaaac actgctttat atgtgtcccc    540
atgatacaga aaagtgggat ggggccagcc attccagaaa tgaaaatcca gactctcaca    600
gagaaccctt gagccacaca ggaagaccac tgaagacaac agaggaacta ctggtccaca    660
gaaacactca gtttcatgaa aacacactga ttcgggtaga aaatgcaact tgggaacaaa    720
cattacacaa caaagacccct ctgtcatgca gggcactggc ccggatgctg ctgggctgtg    780
tgggctggaa gangtgggga caacccac                                       808
```

<210> SEQ ID NO 110
<211> LENGTH: 471
<212> TYPE: DNA

```
<213> ORGANISM: Homo Sapien
<220> FEATURE:
<221> NAME/KEY: misc_feature
<222> LOCATION: (1)...(471)
<223> OTHER INFORMATION: n = A,T,C or G

<400> SEQUENCE: 110
actatgacca tgattacgcc aagcttggta ccgagctcgg atccactagt aacgccccgc    60
cagtgtgctg gaattcgccc tttcgagcgg ccgcccgggc aggtacagcg acgtgatgat   120
gtagaggcgc ttcccatcca ggctgagctg gatcatctga gggcctncag ccacccgttt   180
tcccttgacc actaggggct ctggctggga ctttagttcc tcgtcctcca gcacttgcac   240
agggcctccc ttaacaatgc tgcctccgag gaagagctgt cctgtgaggc ggggtctctg   300
tgggtcagag atgtcatact gcctcaggtc cccatgcagc cagttgctga agtagaggaa   360
gcggtcgtcc aggagagca ggatgtcggt gatcaggcct ggcatttcgg gcagcagcca   420
gcccttcact ttcttggggg gcacctggat caccttctcc actgaccatg t            471

<210> SEQ ID NO 111
<211> LENGTH: 468
<212> TYPE: DNA
<213> ORGANISM: Homo Sapien
<220> FEATURE:
<221> NAME/KEY: misc_feature
<222> LOCATION: (1)...(468)
<223> OTHER INFORMATION: n = A,T,C or G

<400> SEQUENCE: 111
actatgacca tgattacgcc aagcttggta cccgagctcgg atccctagta acggccgcca    60
gtgtgctgga attcgcccctt agcgtggtcg cggccgaggt acttnnttnc tttntttaca   120
tctgatttta atgcttcgtt aacttcaaaa ggaactggta gagttcanaa ggtgagctgt   180
tgttttncta aacctnttcc caggaagggg acattgacac ttgaattttt gtcacctttt   240
tcctcattag aaggaaagta naaagcctta ctgtaggatt tttaaaaaaa aatccatctc   300
accccatatt ggtcttaaat aagtatagac taattaaccct aagctacctt taacaacgta   360
gaatttagat gggttcatat atgtgagaaa agcctgaata tangacaggg gtcctacttt   420
tttccccacc tctgtcgccc aggctggagt atagtggtgt gatcttng                468

<210> SEQ ID NO 112
<211> LENGTH: 813
<212> TYPE: DNA
<213> ORGANISM: Homo Sapien
<220> FEATURE:
<221> NAME/KEY: misc_feature
<222> LOCATION: (1)...(813)
<223> OTHER INFORMATION: n = A,T,C or G

<400> SEQUENCE: 112
attgggcctc tnnagcatgc tcgacggccg ccatgtgatg gatatctgca gaattcgccc    60
tttcgagcgg ccgcccgggc aggtaccatg ctgacttctt ggtatctttt anggcctaat   120
tttcccttcc ttgagattac tgtagtgtgt tccagctaat ttctatttgg aaacgagttg   180
gaacagctga aaactaggta ttattgaagg caaagcagcc tcacgtcagt tttttatcag   240
ctcatttggg aagttttnnt ttttttntn ttaattaatt agaaagtagg ctgggcacgg   300
nggctcatgc ctataatccc agcacttggg gaggccgagg atctcctctc tggtggatca   360
cttgagggca ggagttaaga gaccatcctg gccaacatga tgaaaccctg tctctactaa   420
aaatacaaaa agtagctggg cgtggtggca tactcttaca atcccagcta cttgggaggc   480
```

| | |
|---|---|
| tgaggcagga gaatcacttg aacccaggaa gcagaggttg cagtgggcca agatcacacc | 540 |
| actatactcc agcctgggcg acagaggtgg ggaaaaaagt nagacccctg tcctatattc | 600 |
| aggctttgct cacatatatg aacccatcta aattctacgt tgttaaaggt agcttaggtt | 660 |
| aattagncta tacttattta agaccaatat ggggtganat ggattttttt ttaaaaatnc | 720 |
| tacagtaagg ctttctactt tccttctaat gaggaaaang gtgacaaaaa ttcaagtgtc | 780 |
| natgcccctt cctggggaag aggtttaaaa aat | 813 |

```
<210> SEQ ID NO 113
<211> LENGTH: 506
<212> TYPE: DNA
<213> ORGANISM: Homo Sapien
<220> FEATURE:
<221> NAME/KEY: misc_feature
<222> LOCATION: (1)...(506)
<223> OTHER INFORMATION: n = A,T,C or G

<400> SEQUENCE: 113
```

| | |
|---|---|
| nccaacttgg taccganctc ggatccctag taacggcana cattganctg atacgccaag | 60 |
| cttggtaccg agctcggatc cactagtaac ggncgccagt gtgctggaat tcgcccttcg | 120 |
| agcggccgcc cggcaggta cgcggggcct ctggcgctac catggcgttt ggcaagagtc | 180 |
| accgggatcc ctacgcgacc tccgtgggcc acctcataga aaaggctaca tttgctggag | 240 |
| ttcagactga agattgggc cagttcatgc acatctgtga cataattaac actacccagg | 300 |
| atgggccaaa agatgcagtg aaagctttga agaaaangat ttncaaaaac tacaatcata | 360 |
| aagaaatcca acttaccttg tcacttattg acatgtgtgt gcagaactgt ggtccaagtt | 420 |
| tccagtctct gattgtgaag aaggaatttg ttaaagagaa tttagttaag ctactgaatc | 480 |
| ccagatacaa cttgccatta gacatt | 506 |

```
<210> SEQ ID NO 114
<211> LENGTH: 813
<212> TYPE: DNA
<213> ORGANISM: Homo Sapien
<220> FEATURE:
<221> NAME/KEY: misc_feature
<222> LOCATION: (1)...(813)
<223> OTHER INFORMATION: n = A,T,C or G

<400> SEQUENCE: 114
```

| | |
|---|---|
| gggcccntnn agctgctcga gcggccgcca gtgtgatgga tatctgcaga attcgccctt | 60 |
| agcgtggtcg cggccgaggt acaacttatt ctaaatattt tcattttctg tgttctaaat | 120 |
| agaaatatta agttgcagta aaagagaaa aaaggctat ttagcattac aaagaatcat | 180 |
| atttaaaggc tgcccaatgt agagtctagt gacctgttca ggacacctga aatataatta | 240 |
| aatgacaatt atcaaggttt taacaattta taattctaaa ccagaggatt ataaagaagt | 300 |
| gcaaattgac ttttacattc aactttagtt aaatgaaggc actcagtatt cttcctgaat | 360 |
| aatacattca gtttctcaca tttatgctt tcatctattc agaattattt catagtaaaa | 420 |
| taatctactc ttatcacagc tgtgtgacga tttctaaatg taggaaggcc tgtgaaacat | 480 |
| gacactgcag ttaaattggt tggcctaagg actaagtaat ttttcttctg ctgaagttt | 540 |
| aagtgagtat tgttccaaa caagttctgt tgaaatctca cgctgttgtc aggaatcagt | 600 |
| gttatcctgg aactgttatt ctatttaatc ttcattatag cagaaatgtg ccaccatggc | 660 |
| tttgacatgt tggtaggtat tgtcttccag gcttcaaagc tgcacagagt ctacgtttta | 720 |

| | |
|---|---|
| gagagttggc acctttgatg tggtagtgag ctgatcatnc actttcttct cagtcaccat | 780 |
| cattttgagc tcctttgtgc tggtgagcat can | 813 |

<210> SEQ ID NO 115
<211> LENGTH: 471
<212> TYPE: DNA
<213> ORGANISM: Homo Sapien

<400> SEQUENCE: 115

| | |
|---|---|
| accagctatg acctgattac gccaagcttg gtaccgagct cggatccact agtaacggcc | 60 |
| gccagtgtgc tggaattcgc ccttagcgtg gtcgcggccg aggtaccatg attttgtgtt | 120 |
| caggaaacaa agaacatgaa atattacatt cttcagaatg ttttcttgt gccattaaat | 180 |
| gaatcaagta aatgaggcaa tgaggcacaa ataaggaatt tagatttcag caatattttg | 240 |
| atccactgta gctttcagtt tctgaaactt tggaagggcc tacatacttt gtaagaattt | 300 |
| ttggcttata ttgttaataa tcaacagagc caagaaaaca tttcttagaa tgttcaaaga | 360 |
| caccaccta gccttccttc cctgcagcta taacattatt tttctaagag aaaaggcaga | 420 |
| gagtcttcac aaagccatac cagacttaaa attaccagag aacattttgg t | 471 |

<210> SEQ ID NO 116
<211> LENGTH: 818
<212> TYPE: DNA
<213> ORGANISM: Homo Sapien
<220> FEATURE:
<221> NAME/KEY: misc_feature
<222> LOCATION: (1)...(818)
<223> OTHER INFORMATION: n = A,T,C or G

<400> SEQUENCE: 116

| | |
|---|---|
| ttncannggg cccctagagc atgctcgacg gccgccatgt gatggatatc tgcagaattc | 60 |
| gcccttcga gcggccgccc gggcaggtac tttttttttt tttttttttt ttttttttgtg | 120 |
| tgtggtcttg aactcctggc ctcaaatgat cttcctgcct cagcctccca aagtcctggg | 180 |
| attactggca tgagtcacca cacctggctc attctttttc ttaatatggc tctaaatggc | 240 |
| tttttatttt ttttgctttg gcaatttatt tctaggaaat taaataattc tttcattata | 300 |
| atcaagggaa tgaaagactt caggaggtcc atagtggagt tcaaaaccat atggagttca | 360 |
| ctattctaca agattataca ggcaataata taagtattct aaggtgtttt aggtagattt | 420 |
| atagatgtta gatttcaaaa tgggttaata agtgtttatg aatttccaag gtgtatcact | 480 |
| aacttctcaa gatgaaatca tatatagaaa ctatcaaaat tttccttgtt ctgctgtcaa | 540 |
| gaaatgaata atatacactg atataactgt aactcacatc taaagggata gtgcttgaat | 600 |
| aagctaattt acaatgagtt caaggtatta ttttaaaatt cttattgncc ttagacaata | 660 |
| attatgccaa caaatgtgaa aaatattaaa tctccttctg ntaattttc cagttttatt | 720 |
| acccaaaagt cacacaggta atgcaagtca tgaaataaat caaatgagcc cttcctggag | 780 |
| agcctacttt atttaccttg ggaaaatgga tgacatnt | 818 |

<210> SEQ ID NO 117
<211> LENGTH: 467
<212> TYPE: DNA
<213> ORGANISM: Homo Sapien
<220> FEATURE:
<221> NAME/KEY: misc_feature
<222> LOCATION: (1)...(467)
<223> OTHER INFORMATION: n = A,T,C or G

<400> SEQUENCE: 117

```
accactatga cctgattacg ccaagcttgg taccgagctc ggatccacta gtaacggccg    60
ccagtgtgct ggaattcgcc ctttcgagcg gccgcccggg caggtactac tggttttctc   120
cctggcttca cgtgtctctg tgttccccta tgctggggtg tcctcccagt gctttcaggc   180
ttcatctcct tcctaacctc tcctttctat tttttttttt tttttttgaga tggagtcttg   240 ctcagtcgcc cangctggag tgctaacctc tcctttcatg tggagatgga cagggatggc   300
aggagcactg agtgctcttg acaacaccat tgaagatgat gctgacgatc agctaccctg   360
tggagaaggc aggccaggct gggtgagagg ggagctcctt ggaagtcagg gggtctgtaa   420
ggacagcaag gatctctttg tcccaacctc cagcagcctt tatgggt                 467
```

```
<210> SEQ ID NO 118
<211> LENGTH: 815
<212> TYPE: DNA
<213> ORGANISM: Homo Sapien
<220> FEATURE:
<221> NAME/KEY: misc_feature
<222> LOCATION: (1)...(815)
<223> OTHER INFORMATION: n = A,T,C or G

<400> SEQUENCE: 118
```

```
gggcctctna agcatgctcg acggccgcca tgtgatggat atctgcagaa ttcgccctta    60
gcgtggtcgc ggccgaggta cctggggtct cagggttgct ctgggcctga tcatccactc   120
agatctgtaa ggaggatttg caggatccat ttagaaagat cctcccttac ttccacaagc   180
atggcctttg gctcttaaat acctgtgctg gggttttgta attatagaaa caacaggaac   240
caaaactcat taatgttgag ctacaaacca gaggaagctc tctttctcaa acagggctc    300 aggcctagaa aaatctagtt ttctgaaatc gctagccagc aacagcactg agatggccat   360
cccagaaaca aggccaacac agaagcaccc ataaaggctg ctggaggttg ggacaaagag   420
atccttgctg tccttacaga cccctgact tccaaggagc tccctctca cccagcctgg    480 cctgccttct ccacagggta gctgatcgtc agcatcatct tcaatggtgt tgtcaagagc   540
actcagtgct cctgccatcc ctgtccatct ccacatgaaa ggagaggtta gcactccagc   600
ctgggcgact gagcaagact ccatctcaaa aaaaaaaaa aaaatagaaa ggagaggtta   660
ggaaggagat gaagcctgaa agcactggga ggacacccca gcataggga acacagagac   720 acgtgaagcc agggagaaaa ccagtagtac ctgcccggcg ccgntcgaa agggcgaatt    780 ccagcacact ggcgggccgt tactagtgga tccct                              815
```

```
<210> SEQ ID NO 119
<211> LENGTH: 811
<212> TYPE: DNA
<213> ORGANISM: Homo Sapien
<220> FEATURE:
<221> NAME/KEY: misc_feature
<222> LOCATION: (1)...(811)
<223> OTHER INFORMATION: n = A,T,C or G

<400> SEQUENCE: 119
```

```
gggcctctnn agctgctcga cggccgccat gtgatggata tctgcagaat tcgcccttag    60
cgtggtcgcg gccgaggtac tctattttt gcttgtatga ttgatgggtc tttcattatc    120
tgtgattgac attctatgag taggtgcttt tgctttgcct ataagtcgtt attatgaagg   180
aggaatggtg aataagaagg taatttagaa aagcctatat taaatatacc atgaacattg   240
aatatagcaa gatcttattc tctagttgtt atcttagttg ataaattctg tatgtgttat   300
```

| | |
|---|---|
| gtgtttgtgt atacatatgt acttaatctg atcggtatct aaaagaagga aaggatggtc | 360 |
| aggaaacatt tatcataaat gtagccaagg atatcaatta gggtagacaa gaataggaca | 420 |
| aaaataggcc agagctcctg aggaggtgat atgggtccct tgatttgcag aaaatgacag | 480 |
| cctatccaag tggcccagtg tatgcctccc agtagcagtg ggcatgtaaa ctgcagcgac | 540 |
| cttatttta aaaccaaaaa cctagtatgt ggacaaagaa catgacaata tttggtacct | 600 |
| gcccgggcgg ccgctcgaaa gggcgaattc cagcacactg gcggccgtta ctagtggatc | 660 |
| cgagctcggt ccaagcttgg cgtaatcatg gtcatagctg gttcctgtgt gaaattggta | 720 |
| tcccgctcac aattnccaca cacatacgaa cccggaagca ttaaagtgta aaagcctggg | 780 |
| gtgcctaatg aagtgagcta ctcacattaa a | 811 |

<210> SEQ ID NO 120
<211> LENGTH: 466
<212> TYPE: DNA
<213> ORGANISM: Homo Sapien
<220> FEATURE:
<221> NAME/KEY: misc_feature
<222> LOCATION: (1)...(466)
<223> OTHER INFORMATION: n = A,T,C or G

<400> SEQUENCE: 120

| | |
|---|---|
| anttgacctg attacgccaa gcttggtacc gagctcggat ccactagtaa cggccgccag | 60 |
| tgtgctggaa ttcgcccttt cgagcggccg cccgggcagg tacccacgtt ttgctccaca | 120 |
| ctccttgacc acagggctc ggacacaaac ccctgtcacc aggagagtca gtcagcacta | 180 |
| cttgggaggg ctaaagggaa atttggaaat aaaattccaa agtttggagt aaaaaaattc | 240 |
| aagtgttgat tttatattct ttcccttct gacacagcct aaagcgtagg gggaacatgt | 300 |
| gtttatctgt gggagataaa caagatggag tcccaaagac tttaacaaaa tattttttta | 360 |
| aaaatccact agaatagaaa atacattatt tagatatact ttatgctgag agtgagtata | 420 |
| tatgcttgtc ctatttaaac ttgtgagaaa aagtggtatc ccttng | 466 |

<210> SEQ ID NO 121
<211> LENGTH: 812
<212> TYPE: DNA
<213> ORGANISM: Homo Sapien
<220> FEATURE:
<221> NAME/KEY: misc_feature
<222> LOCATION: (1)...(812)
<223> OTHER INFORMATION: n = A,T,C or G

<400> SEQUENCE: 121

| | |
|---|---|
| ttgggcccnt nnagcatgct cgagcggccg ccagtgtgat ggatatctgc agaattcgcc | 60 |
| cttagcgtgg tcgcggccga ggtacaactc tccagggcac aatacgttta cagctgcctt | 120 |
| tccttcacat acttttctaa ttcagaacta ctcacaattc taagcaaatt cccattcacg | 180 |
| aagtctgtcc ataatgcgac cttctctttt tttaacatat acatcttaaa aaacaaatat | 240 |
| ataaaaaatt cttattttgc tggaatgctt tcaattttc acattttaca tgatcatcac | 300 |
| atttatttct tatattgaaa ggcatggttt ctgttgacat gtcgtgcaaa gccaaaaaaa | 360 |
| aaaaaaaaaa aaagggctgg attgcttttc aattggtcta acacttttcc ttgtctaggc | 420 |
| tttggatttt aaagttcatg acagccccac caccagtaga accccaagg cttgcatttc | 480 |
| ctggtaatcg actggaaacg tcccctgttg gccatgctaa gattccttca acagggtcat | 540 |
| cctgcattta ttctccttct gccccacccc cacaatgaaa caagatagcc cccatatttc | 600 |
| taaatgtatc aagggatacc acttttctc acaagtttaa ataggacaag catatatact | 660 |

-continued

```
cactctcagc ataaagtata tctaaataat gtattttcta ttctagngga tttttaaaaa      720
aatattttgg taaagtcttt ggggactcca tcttggttat cttccacaga taaaccatgt      780 tcccctacg ctttaggctg tggtcagaaa gg                                    812
```

<210> SEQ ID NO 122
<211> LENGTH: 467
<212> TYPE: DNA
<213> ORGANISM: Homo Sapien

<400> SEQUENCE: 122

```
actatgacca tgattacgcc aagcttggta ccgagctcgg atccactagt aacggccgcc       60
agtgtgctgg aattcgccct tagcgtggtc gcggccgagg taccatgctg acttcttggt      120
atcttttaag gcctaatttt cccttccttg agattactgt agtgtgttcc agctaatttc      180
tatttggaaa cgagttggaa cagctgaaaa ctaggtatta ttgaaggcaa agcagcctca      240
cgtcagtttt ttatcagctc atttgggaag tttttttttt tttttttttt ttttaattaa      300
ttagaaagta ggctgggcac ggtggctcat gcctataatc ccagcacttg gggaggccga      360
ggatctcctc tctggtggat cacttgaggg caggagttaa gagaccatcc tggccaacat      420
gatgaaaccc tgtctctact aaaaatacaa aaagtagctg ggcgtgg                   467
```

<210> SEQ ID NO 123
<211> LENGTH: 864
<212> TYPE: DNA
<213> ORGANISM: Homo Sapien
<220> FEATURE:
<221> NAME/KEY: misc_feature
<222> LOCATION: (1)...(864)
<223> OTHER INFORMATION: n = A,T,C or G

<400> SEQUENCE: 123

```
gggcctctng agcatgctcg agcggccgcc atgtgatgga tatctgcaga attcgccctt       60
tcgagcggcc gcccgggcag gtacttttt tttttttttt tcttttttta catctgattt      120
taatgcttcg ttaacttcaa aaggaactgg tagagttcag aaggtgagct gttgttttc      180 taaacctctt cccaggaagg ggacattgac acttgaattt ttgtcacctt tttcctcatt      240
agaaggaaag tagaaagcct tactgtagga tttttaaaaa aaaatccat ctcaccccat      300 attggtctta aataagtata gactaattaa cctaagctac ctttaacaac gtagaattta      360
gatgggttca tatatgtgag aaaaacctga atataggaca ggggtcctac tttttccc      420 acctctgtcg cccaggctag agtatagtgg tgtgatcttg gcccactgca acctctgctt      480
cctaggttca agtgattctc ctgcctcagc ctcccaagta gctgggattg taagagtatg      540
ccaccacgcc cagctacttt ttgnattttt agtagagaca gggtttcatc atgttggcca      600
ggatggnctc ttaactcctg ccctcaagtg gatccaccag agaaggagat cccttggnct      660
tccccaagtg cctggggatt attaggcatt gaagcccacc cgtggcccca agccctacnt      720
tttcttaaat taaatttaaa aaaaaanaan nnnnnnnnn nnaaaaaaaa ccttttcccc      780 aaattggganc ctgggtttaa aaaaacctgg acccttnaan gggcntggnt tttggcccctt     840 tnaaataaat tnccctaag gnnt                                             864
```

<210> SEQ ID NO 124
<211> LENGTH: 467
<212> TYPE: DNA
<213> ORGANISM: Homo Sapien
<220> FEATURE:

<221> NAME/KEY: misc_feature
<222> LOCATION: (1)...(467)
<223> OTHER INFORMATION: n = A,T,C or G

<400> SEQUENCE: 124

```
antatgacct gattacgcca agcttggtac cgagctcgga tccactagta acggccgcca      60
gtgtgctgga attcgccctt tcgagcggcc gcccgggcag gtacatgcac acacacacac     120
acacacacac acgtgtctac tgggctcctt ttggattttt tagttcaatc agaaatcacc     180
aaacagatca ataaagaggc aatgttaaat gaccgggaaa ttggtaatgt gacatcacaa     240
cactgccttt aaggtgccat atctaaatcc aggtagcact gctgctagca gaatctgttg     300
ttttaggaga caagggtggg ctgggtatgc tggctcgtgc ctataattcc agcactttga     360
gagggcaagg caggagaacc acattaggct aggagtttan gaccagcctg gcaacatag      420
tgagatccca tctctacaaa aataaaaaaa ttagctttcc agctgct                   467
```

<210> SEQ ID NO 125
<211> LENGTH: 833
<212> TYPE: DNA
<213> ORGANISM: Homo Sapien
<220> FEATURE:
<221> NAME/KEY: misc_feature
<222> LOCATION: (1)...(833)
<223> OTHER INFORMATION: n = A,T,C or G

<400> SEQUENCE: 125

```
gnnnnnnnnn ngnnttnnnn ntttaataga tgagcgtacg gngcctgtaa agcatgctcg      60
agcggccgcc atgtgatgga tatctgcaga attcgccctt agcgtggtcg cggccgaggt     120
acctgatatc gtttaacttt cctctttatc tttcttagag atacttcaca tgtgggacag     180
attatatttt ggaaagatgt ccacaacaat attgcccatc ccacattgct catcttacaa     240
tgtgatctca agactcctcc cactgagtgg gtgagaaggg acttatacca ctttcatttg     300
aatctaggca gatctgtgtg acagccttga ccaatagagt atggttaaag tgatgccccc     360
aggcatggtg gcccatacct ggaatcctgg ttttccgggg aggcccaggt gggggtagag     420
gtgaggggga tgattgtttg aacacacgag tttgagacta ccctgagcaa cacaatgaga     480
ccctatttt ttttaatgat ttctgaagca gaatcacaaa tagccgtgcg tttttttctt      540
gcgcttttag gatacttact tttaaaaccc agtcaccata ttgttaggaa gcccaaacag     600
cacacataga gagacatacg gagaagccaa ccatagaggt tcctgttgac agctcantcg     660
aggtcttaac caacagtcat acttagctgc cagccatatg agtgaagggc ttncagatga     720
ttctaacgcc cagcagttgg gtcccccag cctgtaagcc ttcccagctg aggcctnaca     780
atgatggagc anagaaaagt gtccctgtcc aaattctgac ccatgataaa atg            833
```

<210> SEQ ID NO 126
<211> LENGTH: 788
<212> TYPE: DNA
<213> ORGANISM: Homo Sapien
<220> FEATURE:
<221> NAME/KEY: misc_feature
<222> LOCATION: (1)...(788)
<223> OTHER INFORMATION: n = A,T,C or G

<400> SEQUENCE: 126

```
nnnnnnntnn nnacanttga ctgatacccca acttggtacc gactcggatc cactagtaac     60
ggccgccagt gtgctggaat tcgcccttag cgtggtcgcg gccgaggtac gcggggatc      120
agagagaagc gaggttctcg ttctgaggga caggctcgag atcggctgaa gagagcgggc    180
```

```
ccaggctctg tgaggaggca agggaggtga gaaccttgct ctcagagggt gactcaagtc    240
aacacaggga accoctcttt tctacagaca cagtgggtcg caggatctga caagagtcca    300
ggttctcagg ggacagggag agcaagaggt caagagctgt gggacaccac agagcagcac    360
tgaaggagaa gacctgcctg tgggtcccca tcgcccaagt cctgcccaca ctcccacctg    420
ctaccctgat cagagtcatc atgcctcgag ctccaaagcg tcagcgctgc atgcctgaag    480
aagatcttca atcccaaagt gagacacagg gcctcgaggg tgcacaggct cccctggctg    540
tggaggagga tgcttcatca tccactttca ccagctcctc ttttccatcc tcttttcctt    600
ctccttcntt ttctnctnct nctnctgcat ctntaatacc aagcacccca naggaggttt    660
ctgctgatga tgagacaccc aaatncttcc anagtgctna anatagcctg ntncttcccc    720
cttnggncnt gctttccctt ncnttanatt naatnctgat taagggttc cancanncca    780 aaaggaat                                                              788

<210> SEQ ID NO 127
<211> LENGTH: 766
<212> TYPE: DNA
<213> ORGANISM: Homo Sapien
<220> FEATURE:
<221> NAME/KEY: misc_feature
<222> LOCATION: (1)...(766)
<223> OTHER INFORMATION: n = A,T,C or G

<400> SEQUENCE: 127
gggcctctna agcatgctcg acggccgcca tgtgatggat atctgcagaa ttcgcccttt     60
cgagcggccg cccgggcagg tactccaggt agttttcctg cacccaatct tgggtgagca    120
gcttcctggg ctccccataa atgaggtgct ccatcccatc atacagcccc atcatattca    180
gtgcttccca gatgacctcc tcaggggtgc agtagccctc tatgaagatt atgcttagga    240
taagtatgag aatgccagtc ttgggcatgc tctggacatc actcagcatc ccatcatagg    300
tgaggcccag ggaggtgaca aggacaaagg agtggccagt gggatccact tcctttacat    360
caatgccaaa gaccagcagc atgcactcgg aggcttcact aaacaacaaa gggaagtggt    420
cttcataatt ttttatgaca ctctccagta tttctgcctt tgtgatcggc tccttcattt    480
gatacttgaa gagcagaaac tgcaccaaat cagtcacctt ttcatctatc tcacttctgg    540
gtaaagactc actgtctggc aggacctgta gggtgcttgg actctcctcc ttttggctgc    600
tggagccctc atcagattga tctaatggaa gggaagcaac gaccganggg gaggagcagg    660
ctatctgagc actctgggga ggatttggtg tctcatcatc agcagaaacc tnctctgggg    720
tgcttgggta ttagangatg gcaggaagaa gaagangaag aggaag                   766

<210> SEQ ID NO 128
<211> LENGTH: 779
<212> TYPE: DNA
<213> ORGANISM: Homo Sapien
<220> FEATURE:
<221> NAME/KEY: misc_feature
<222> LOCATION: (1)...(779)
<223> OTHER INFORMATION: n = A,T,C or G

<400> SEQUENCE: 128
gnnnnntnnn nacactantt tnngacccgn canctggtac cgactcggac cactagtaac     60
ggccgccagt gtgctggaat tcgcccttc gagcggccg cccgggcagg tactcctcat     120
cctgcgtttg gtctccaggt gtcgcctttc tgccgtgttc ctaatatttt gattcctgtc    180
```

```
ttgaaaaaag cacctgctgc acagtaagcc cagggatgtg gcagctgcag cgggcttggc      240
tttgtgagga accgggtgtg tccacgttgg gggaacatca tacttgatac acacgttttt      300
atttgcacaa agaaaatgct attttttggag ccagaatttt catgtctgat ttatggtgat     360
tttcttaaga accagaactg ctggcagaaa gggggcaccc acacgcttag atagccgatg      420
tcttattaga gggcagtttg tggttcctga tttggaaatt aatattctcc aaacattcca      480
gtccaatgaa agttttatcc gctttcccat gtaaaaattc ttcccatgag agtgacttga      540
tcctcacaat cccgttgaag tcgtgtgtga gtcctacagt attaggttca gcattgccgt      600
ctncaagtgc tctttgtagg gaaacagttt ctggtcatga caagcttcca cttccatctg      660
atcctggcct ggcctggaaa cagagcacat gtgtttgagg atggcngtgt ttggggacag      720
gacatgancg tattgtgtgg ggctgctagg acangcgtgg tgtggtgggg gantgtccn      779

<210> SEQ ID NO 129
<211> LENGTH: 774
<212> TYPE: DNA
<213> ORGANISM: Homo Sapien
<220> FEATURE:
<221> NAME/KEY: misc_feature
<222> LOCATION: (1)...(774)
<223> OTHER INFORMATION: n = A,T,C or G

<400> SEQUENCE: 129
ttnnnantgg gcccntngag catgctcgac ggccgccatg tgatggatat ctgcagaatt       60
cgcccttagc gtggtcgcgg ccgaggtacc tgggtgggac tgggaaactg tgaaacaagt      120
agactgactt ggacactccc ccaccacacc acgcctgtcc tagcagcccc acacaatacg      180
ctcatgtcct gtccccaaac accgccatcc tcaaacacat gtgctctgtt tccaggccag      240
gccaggatca gatgggaagt ggaagcttgt catgaccaga aactgtttcc ctacaaagag      300
cacttggaga cggcaatgct gaacctaata ctgtaggact cacacacgac ttcaacggga      360
ttgtgaggat caagtcactc tcatgggaag aattttttaca tgggaaagcg ataaaacttt     420
tcattggact ggaatgtttg gagaatatta atttccaaat caggaaccac aaactgccct      480
ctaataagac atcggctatc taagcgtgtg ggtgccccct ttctgccagc agttctggtt      540
cttaagaaaa tcaccataaa tcagacatga aaattctggc tccaaaaata gcattttctt      600
tgtgcaaata aaaacgtgtg tatcaagtat gatgttcccc caacgtggac acacccggt      660 tcctnacaaa gccaagcccg ctgcagctgc acattcctg ggcttactgt gcacangtgc       720
tttttttaag acaggatcaa atnttaggac ccngnanaan gcaacacctg gaga            774

<210> SEQ ID NO 130
<211> LENGTH: 803
<212> TYPE: DNA
<213> ORGANISM: Homo Sapien
<220> FEATURE:
<221> NAME/KEY: misc_feature
<222> LOCATION: (1)...(803)
<223> OTHER INFORMATION: n = A,T,C or G

<400> SEQUENCE: 130
ggnnnnttnn anacgnatcn gacctganta cgccaacttg gtaccgagct cggatccact       60
agtaacggcc cgccagtgtg ctggaattcg cccttagcgt ggtcgcggcc cgaggtacct      120
tggaagttat gtcattaata taggctggtt cgtcaaataa agcaaaacct tgcaatatca      180
gctagattta cactccggga cgttgcccaa aggtaggaag aaagcagagg gaaatatttc      240
agtcatcatt tccaaagtca ttatcaaaat ctgtgaggaa gtttaatctt ccaaagagtc      300
```

-continued

```
aatgtcagac atcaggcctc tgttgcctgc ttctctcgag gcactagatt aggagtcttc      360
aataagagac ttaacatgag gtatatggaa gatgaggcac cgagataagt tcatcattag      420
gtgtgagcac tgctcaccct tgctggcaag ttctccttaa gggcctgaag cacaggtgtc      480
caaagaaaag cgttaagtcc atcttaatag aatctatgtg gtatatgatg tggtcagccc      540
ccggtctgtg atcagcaaga acctacagca cagattatgc cctgcccact tcaatgaata      600
cctactctcc tncattctcc atcacttttt ttgctatcaa gactccggac cttgcccatg      660
gagaagttta gagaggaact cttgtggaga gctggtttat tttctgccct gtgcgacgag      720
tttcagcttg gccaaagaaa ggagtcaagg ttattaaaaa gcatcacaat ggtagatctt      780
ccaggcttgg ntttttttgt ttt                                              803
```

<210> SEQ ID NO 131
<211> LENGTH: 818
<212> TYPE: DNA
<213> ORGANISM: Homo Sapien
<220> FEATURE:
<221> NAME/KEY: misc_feature
<222> LOCATION: (1)...(818)
<223> OTHER INFORMATION: n = A,T,C or G

<400> SEQUENCE: 131

```
antgggcctc tnnagcatgc tcgacggccg ccatgtgatg gatatctgca gaattcgccc       60
ttngcccgct ttccagncgg gaaacctgtc ntgccagntg cattaatgaa tcngccaacg      120
cgcggngaga ggcggnttgc gtattgggcg ctcttccgct tcctcgctca ctgactcgct      180
gcgctcggcc gttcngctgc ggcgagcggt atcagctcac tcaaaggcgg taatacngtt      240
atccacagat caggggatan cggcaggaaa gaacatgtga ncaaaaggcc agcaaaaggc      300
caggaaccga aaaaaggccg ctttgttggc gtntnaccat aggctcnncc cccttgacna      360
gcttcacaaa aatctacgct cagntcccag gtgcnaaatc ccganaggac tntaangatt      420
cnnggnnttt ccccctgaan nctncctant gcgctctcct gtnccaacct tgccgtttac      480
cggatacctg nccgcctnna tnccttcgng aagcntggct tttnaatngg ctcacttttt      540
gggnatctaa aancggnnta ggcngnncgt tnnaaantng nnttttttgcn caaaccccct      600 gtttaaactn acccatgngc attatcccgg aaacttttgg tnttngaatc caaccnggna      660
aanacacnan ttaatnngcc nttggcntga aacccacttg ggtnaaccat ggattttggc      720
ncnaccnagg gtnnttttnn nggcnggtnc ntacccggag ttctttnaaa acngggtggg      780
cncttanacc tatcnggnnt tcccctttan aaaaaaat                              818
```

<210> SEQ ID NO 132
<211> LENGTH: 777
<212> TYPE: DNA
<213> ORGANISM: Homo Sapien
<220> FEATURE:
<221> NAME/KEY: misc_feature
<222> LOCATION: (1)...(777)
<223> OTHER INFORMATION: n = A,T,C or G

<400> SEQUENCE: 132

```
acnntatgac ntgantaccc aacttggtac cgactcggac cactagtaac ggccgccagt       60
gtgctggaat tcgcccttcg gcccgcccgg gcaggtacct ggaaaataac ttctttcttt      120
tcctctagat tttcgaagaa gcaaataaat caagaataga aacctatata taggaggttg      180
ggcctcctgc aaagaatgaa gcacttttg ttaaatacag gagaggctac ttggctgcac      240
```

```
taatatgtgc tttttggaat cttatagagt gtcaccaagt tgaactttgg aatggcttga    300
atcatccctg gagcatctgt gccgggcagt caggagtgag tgcaccgcct cccacccagc    360
cccattgggc ctcacaccct cttcattcct ttccccatga ggcaggcaaa cacggtcatg    420
accattttgg ggttcacttc aaccaggtct tctggcaggg catacactct tgctccaatt    480
tttcgggcca tagagatggc atattttgca ttgttgagtt tctcatcatc attcagattt    540
tctgtcttca gaaggtcata gttaatggaa cctggttgga tggcatcgat gangtccaga    600
acaggcagac ttgtacctcg gccgcgacca cgctaagggc gaattctgca gatatncatc    660
acactggcgg gccgntcgag catgcatcta ganggcccaa ttcgccctat agtgagtcgt    720
attacaattc actgggccgt cgttttacaa cgtcgtgact gggaaaaccc tgcgttn       777
```

<210> SEQ ID NO 133
<211> LENGTH: 775
<212> TYPE: DNA
<213> ORGANISM: Homo Sapien
<220> FEATURE:
<221> NAME/KEY: misc_feature
<222> LOCATION: (1)...(775)
<223> OTHER INFORMATION: n = A,T,C or G

<400> SEQUENCE: 133

```
ntgggcctct nnagcatgct cgacggccgc catgtgatgg atatctgcag aattcgccct     60
tagcgtggtc gcggccgagg tacaagtctg cctgttctgg acctcatcga tgccatccaa    120
ccaggttcca ttaactatga ccttctgaag acagaaaatc tgaatgatga tgagaaactc    180
aacaatgcaa aatatgccat ctctatggcc cgaaaaattg gagcaagagt gtatgccctg    240
ccagaagacc tggttgaagt gaaccccaaa atggtcatga ccgtgtttgc ctgcctcatg    300
gggaaaggaa tgaagagggt gtgaggccca atggggctgg gtgggaggcg gtgcactcac    360
tcctgactgc ccggcacaga tgctccaggg atgattcaag ccattccaaa gttcaacttg    420
gtgacactct ataagattcc aaaaagcaca tattagtgca gccaagtagc ctctcctgta    480
tttaacaaaa agtgcttcat tctttgcagg aggcccaacc tnctatatat aggtttctat    540
tcttgattta tttgcttctt cgaaaatcta gaggaaaaga aagaagttat tttccaggta    600
cctgcccggg cggccgaang gcgaattcca gcacactggc ggccgttact agtggatccg    660
agctcggtac caagcttggc gtaatcatgg tcatagctgt ttcctgtgtg aaattgntat    720
ccggtcacaa ttcccacaca tacgaacccg gaagcataaa gtgtaaagcc tgggg         775
```

<210> SEQ ID NO 134
<211> LENGTH: 772
<212> TYPE: DNA
<213> ORGANISM: Homo Sapien
<220> FEATURE:
<221> NAME/KEY: misc_feature
<222> LOCATION: (1)...(772)
<223> OTHER INFORMATION: n = A,T,C or G

<400> SEQUENCE: 134

```
acnnttgacc tgatacccag ctggtccgac tcggacccta gtaacggccg ccatgtgctg     60
gaattcgccc ttgagcggcc gccgggggcag gtctataagt cttttaaattg ggtcgtgttt    120 ttagcaggta agactaattt atctcttctc cagtgaattg atgctggtgg gattcgattt    180
cacatcacaa cttatattga tagggatttc cttcccaaga gtaataaatt gtttggtttg    240
atataaactt gggggcatat tcaatatcaa ggtactttt tttttttttt aagttttagt    300
tcagaataac attaattttg agagattgag gtaaagaacc ttaactaatg ctaaggagtt    360
```

```
tattttgatt aacataggtt attctgacca ccacctcttc cttccttaat ctccttagaa    420
tctgacagtc tcaaagctgt cacacaaatt agactaattt tgacactttg aaatgaaaac    480
ttcaaggaag aagtagccac ggacagttat gtttataatc agtaggtggc actctttcct    540
caggtagccc cccatttca catgatgtgt ttgaaggtta aatgcccaa aagtgctgag      600 tcagctataa aactaagtcc ctgaattcca tggccctttt aaatatgtaa tcattcaaga    660
ttgaaaaaaa aaattaagca tttttgntt gnttgcttgg ttggttttga gacngagttt     720
cactcttgnt ggccaggctg gagtgcaatg gcgccatctn actcactgna ag            772

<210> SEQ ID NO 135
<211> LENGTH: 784
<212> TYPE: DNA
<213> ORGANISM: Homo Sapien
<220> FEATURE:
<221> NAME/KEY: misc_feature
<222> LOCATION: (1)...(784)
<223> OTHER INFORMATION: n = A,T,C or G

<400> SEQUENCE: 135
ntgggcctct nnagcatgct cgacggccgc catgtgatgg atatctgcag aattcgccct     60
tagcgtggtc gcggcccgag gtacttcttt tgaataattc agtattttaa aaatgcaagc   120
caggcacagt ggctcacgcc tgtaatccag cactttggaa ggccgaggtg ggggatcac    180 gaggtcagga gttcaagacc agcctggcca acatggtgaa acctcatctc tactaaaaat   240
acaaaaacta gctgggcatg gtggcgggca cctgtaaccc cagctacttg agggctgaa    300 ggagaattgc ttgaatccgg gaggcagagg ttgcagtgag ctgagatggc gccattgcac    360
tccagcctgg ccaacaagag tgaaactccg tctcaaaaac aaacaagcaa acaaacaaaa    420
aatgcttaat ttttttttc aatcttgaat gattacatat ttaaaagggc catggaattc     480
agggacttag ttttatagct gactcagcac ttttggtggc atttaacctt caaacacatc    540
atgtgaaaat gggggctac ctgaggaaag agtgccacct actgattata aacataactg     600
tccgtggcta cttcttcctt gaagttttca tttcaaagtg tcaaaattag tctaatttgt    660
gtgacagctt tgagactgtc agattctaag gagattaaag gaanggaaga ggtggtggtc    720 agaataaacct atgttaatca aaaataaact tccttagcat taagttaang gtctttacct   780 caan                                                                784

<210> SEQ ID NO 136
<211> LENGTH: 768
<212> TYPE: DNA
<213> ORGANISM: Homo Sapien
<220> FEATURE:
<221> NAME/KEY: misc_feature
<222> LOCATION: (1)...(768)
<223> OTHER INFORMATION: n = A,T,C or G

<400> SEQUENCE: 136
acnttgantg nacccacttg tccgactcgg atccctagta acggcgcagt gtgctggaat     60
tcgccctttg agcggccgcc gggcaggtac ttttttttt ctttttttac atctgatttt    120
aatgcttcgt taacttcaaa agggaactgg gtagagttca gaaggtgagc tgttgttttt   180
ctaaacctct tcccaggaag gagacattga cacttgaatt tttgccacct ttttcctcat    240
tagaaggaaa gtagaaagcc ttactgtagg attttttaaa aaaaatccat ctcacccccat    300 attggtctta aataagtata gactaattaa cctaagctac ctttaacaac gtagaattta    360
```

| | |
|---|---:|
| gatgggttca tatatgtgag aaaaacctga atataggaca ggggtcctac ttttttcccc | 420 |
| acctctgccg cccaggctag agtatagtgg tgtgatcttg gcccactgca acctctgctt | 480 |
| cctaggttca agtgattctc ctgcctcagc ctcccaagta gctgggattg taagagtatg | 540 |
| ccaccacgcc cagctacttt tgtattttt agtagagaca gggtttcatc atgttggcca | 600 |
| ggatggtctc ttaactcctg ccctcaagtg atccaccaga gaggagatcc tcggccttcc | 660 |
| caagtgctgg gattataggc atgagccacc gtacccagcc tactttctaa ttaattaaaa | 720 |
| aaaaannnnn nnnnaaaaaa acttnccaaa tgactgataa aaaactgc | 768 |

<210> SEQ ID NO 137
<211> LENGTH: 777
<212> TYPE: DNA
<213> ORGANISM: Homo Sapien
<220> FEATURE:
<221> NAME/KEY: misc_feature
<222> LOCATION: (1)...(777)
<223> OTHER INFORMATION: n = A,T,C or G

<400> SEQUENCE: 137

| | |
|---|---:|
| ttgggcctct ngagcatgct cgacggccgc catgtgatgg atatctgcag aattcgccct | 60 |
| tagcgtggtc gcggccgagg taccatgctg acttcttggt atcttttaag gcctaatttt | 120 |
| cccttccttg agattactgt agtgtgttcc agctaatttc tatttggaaa cgagttggaa | 180 |
| cagctgaaaa ctaggtatta ttgaaggcaa agtagcctca cgtcagtttt ttatcagctc | 240 |
| atttgggaag ttttttttt tttttttttt tttttaatt aattagaaag taggctgggt | 300 |
| acggtggctc atgcctataa tcccagcact ggggaggcc gaggatctcc tctctggtgg | 360 |
| atcacttgag ggcaggagtt aagagaccat cctggccaac atgatgaaac cctgtctcta | 420 |
| ctaaaaatac aaaaagtagc tgggcgtggt ggcatactct tacaatccca gctacttggg | 480 |
| aggctgaggc aggagaatca cttgaaccta ggaagcagag gttgcagtgg gccaagatca | 540 |
| caccactata ctctagcctg ggcggcagag gtggggaaaa aagtaggacc cctgtcctat | 600 |
| attcaggttt ttctcacata tatgaaccca tctaaattct acgttgttaa aggtagctta | 660 |
| ngttaattag tctatactta tttaagacca atatggggtg agatggattt ttttttaaaa | 720 |
| atcctacant aaggctttct actttccttc taatgaggaa aaaagtggca aaaattt | 777 |

<210> SEQ ID NO 138
<211> LENGTH: 950
<212> TYPE: DNA
<213> ORGANISM: Homo Sapien
<220> FEATURE:
<221> NAME/KEY: misc_feature
<222> LOCATION: (1)...(950)
<223> OTHER INFORMATION: n = A,T,C or G

<400> SEQUENCE: 138

| | |
|---|---:|
| nnnnnnnnnn nnnnnnnnnn nttnnnnnnn nnnnnaaanc cnnnnnttna nnngnnaaac | 60 |
| cccattggna aanttaaccn nccccaaaa gcccttttngg ggtttaaccc ccgaaagcct | 120 |
| tccgggggna atccccaact ttaagttaaa acngggggccc cgggcccaag ttggttggcc | 180 |
| tttgggggaa aatttcgcc cccttttccga agccgggccc ggccccgggg gccagggta | 240 |
| ccatgggaat ggttaccttt tggcaagaac tggtcaaacc ctggaaattt tggtatttt | 300 |
| gctttggaca ttggccctaa attaattaag tttcaaggtg gtcaggcttt acccactttt | 360 |
| tggtctggca acatgcagaa gagacagtgc cctttttagt gtatcatatc aggaatcatc | 420 |
| tcacattggt ttgtgccatt actggtgcag tgactttcag ccacttgggt aaggtggagt | 480 |

```
tggccatatg tctccactgc aaaattgctg attttccttt tgtaattaat aagtgtgtgt      540
gaagattctt tgagatgagg tatatatctc actcttcatc aaactataag tttttttaag      600
taaaagaaaa tttattatga aactaaagga ataaaagaat gaccactcca taggcagaga      660
aacgtcactt taaggttttg acgtcaattg attttttgtcc aaatcaataa ttactgcaat     720
gattgaaaaa tgattattac taagtttgtt ttcattgtct caaggtctgc tgaactctgg      780
atccaggctg tgtcaacagg gtagtgtggt gcctcctgta cctcggccgc gaccacgcta      840
agggcgaatt ctgcagatat ccatcacact ggcggccgtt cgagcatgca tctagagggc      900
ccaattcgcc tatagtgagt cgtattacaa ttcactggcc cgcgttttag                 950
```

<210> SEQ ID NO 139
<211> LENGTH: 779
<212> TYPE: DNA
<213> ORGANISM: Homo Sapien
<220> FEATURE:
<221> NAME/KEY: misc_feature
<222> LOCATION: (1)...(779)
<223> OTHER INFORMATION: n = A,T,C or G

<400> SEQUENCE: 139

```
ttgggcccnt agagctgctc gagcggccgc catgtgatgg atatctgcag aattcgccct       60
tagcgtggtc gcggccgagg tacaggaggc accacactac cctgttgaca cagcctggat      120
ccagagttca gcagaccttg agacaatgaa aacaaactta gtaataatca ttttttcaatc     180 attgcagtaa ttattgattt ggacaaaaat caattgacgt caaaaccttaa aagtgacgtt     240 tctctgccta tggagtggtc attcttttat tccttttagtt tcataataaa ttttctttta    300
cttaaaaaaa cttatagttt gatgaagagt gagatatata cctcatctca aagaatcttc     360
acacacactt attaattaca aaaggaaaat cagcaatttt gcagtggaga catatggcca     420
actccacctt acccaagtgg ctgaaagtca ctgcaccagt aatggcacaa accaatgtga    480
gatgattcct gatatgatac actaaaaagg gcactgtctc ttctgcatgt tgcagacaaa    540
aagtgggtaa gctgacactg aaactaataa ttaggcaatg tcaagcaaat acaaattcag    600
gttgacagtc tgcaaagtaa catccatgta cctgcccggg cngnccgctc gaagggcgaa    660
ttccagcaca ctggcggccg ttactagtgg atccgagctc ggtaccaagc ttggcgtaat    720
catgggcata gctggttcct gtgtgaaatt ggtatncgct cacaattncc acaacatag     779
```

<210> SEQ ID NO 140
<211> LENGTH: 779
<212> TYPE: DNA
<213> ORGANISM: Homo Sapien
<220> FEATURE:
<221> NAME/KEY: misc_feature
<222> LOCATION: (1)...(779)
<223> OTHER INFORMATION: n = A,T,C or G

<400> SEQUENCE: 140

```
gcccntagag catgctcgac ggccgccagt gtgatggata tctgcagaat tcgcccttag       60
cgtggtcgcg gccgaggtac caggtgggct gacgcacatc ccctaaacat tctggatctc      120
ttactcatcg tgaaaggcag acgctctaag tctaaagtct agggtaggag tttccattct      180
ttggaaaacc aaagatggtt actcttctta atgaaactga gaagaaggta tctacagaaa     240
acactgaatt taaacaaatt atgaccttgt ttgttgaagc catcaaggac ccaagatata     300
tcaaagaaca acatctctgt attggcctac aggttcagag tgttttgagg tctgtttaag     360
```

-continued

| | |
|---|---|
| cactaatagg attttaggcc agcatccagt cagaagagat agttcacaga ctcagagttg | 420 |
| gaaacagatt aaaaaaaaaa agatgtcaac atagaaaatg atgatagagt ttagttaaaa | 480 |
| aaattcacac ataaaattac agttaaaaaa attcacacat aaaatagagt gtttgcatag | 540 |
| caagacatta ttgcccttca gcctggcaga aaaacataaa ctcaggtgta tattttataa | 600 |
| taaacattgt attgaatgct aagaatgata cactgttgaa catctcctga atggtttgcc | 660 |
| ttcttgtaaa tcataccaat tgtttagaca attgaaattc caagctcttt ctcttctccc | 720 |
| atataaaaac caacagaaac anggaggctg ttagtagcaa gctcctcatg ggaaanggt | 779 |

<210> SEQ ID NO 141
<211> LENGTH: 986
<212> TYPE: DNA
<213> ORGANISM: Homo Sapien
<220> FEATURE:
<221> NAME/KEY: misc_feature
<222> LOCATION: (1)...(986)
<223> OTHER INFORMATION: n = A,T,C or G

<400> SEQUENCE: 141

| | |
|---|---|
| aanccnnnnn ntttatttgg gnaaacccaa ttgggnaaaa ttnaacccgn cccccnaaa | 60 |
| ngccctttn gggggttnaa ccccccggaa aaccctttcc ggggggaaat tccccaacct | 120 |
| ttaaagnttt aaaaacccgg gggccccggg ccccaaagt ttgggttggc cnttggggga | 180 |
| aaaattttt ccgggccccc cnttttaaag cccggttggg gtttccggcc nggggccc | 240 |
| gggaaagggt tnaccctttt ttttttaact ttttttnnntt tccttttttn nttccttttt | 300 |
| tttctttttt tttttctttg gtntnnnttt tttttcaat tttttggttt ttggttttg | 360 |
| gttatggttt tttagaaca ggggtcccac tctgtcaccc aggctggagt gcagtggtgc | 420 |
| aatcacaggt cactgaaacc tcccacctag ctgggactag aggtgcaggc caccacacca | 480 |
| gctaatttat gtaatttttg tagagacgag tttcaccacg ttacctaggc ttgtcttgaa | 540 |
| cacctgggct caagcaatct tccagcccca gcctcccaaa gtgctgggat tacaggtata | 600 |
| aaccacaatg ccccgtttt tactctttac tgcatccttc ccatcagtat taattcctca | 660 |
| gaaatttagt accctgtgc ttcattcagt atcagtaacc ctgcaatgat ttttacaaat | 720 |
| atctttttct agtgggtttt ttacttagag gaaagaactt tgtaatagct cttaatgttt | 780 |
| atatataaga gaagacagaa tggaaaatgt ttttgaagt caaatattgc atgatgtaaa | 840 |
| gaaaaaactt taaacttaaa tgagtanggt tgtcctgaat tacactggta actctctact | 900 |
| tctttattaa agaagttata gtaagatgcc tttggntacc tgatttcagt gtacctgccc | 960 |
| gggccggccg ntcaaaaggg cgaant | 986 |

<210> SEQ ID NO 142
<211> LENGTH: 780
<212> TYPE: DNA
<213> ORGANISM: Homo Sapien
<220> FEATURE:
<221> NAME/KEY: misc_feature
<222> LOCATION: (1)...(780)
<223> OTHER INFORMATION: n = A,T,C or G

<400> SEQUENCE: 142

| | |
|---|---|
| gggcccgtan agcatgctcg agcggccgcc atgtgatgga tatctgcaga attcgccctt | 60 |
| tcgagcggcc gcccggggcag gtacactgaa atcaggtaac aaaggcatct tactataact | 120 |
| tctttaataa agaagtagag agttaccagt gtaattcagg acaacctact catttaagtt | 180 |
| taaagttttt tctttacatc atgcaatatt tgacttcaaa aaacatttc cattctgtct | 240 |

```
tctcttatat ataaacatta agagctatta caaagttctt tcctctaagt aaaaaaccca    300
ctagaaaaag atatttgtaa aaatcattgc agggttactg atactgaatg aagcacaggg    360
gtactaaatt tctgaggaat taatactgat gggaaggatg cagtaaagag taaaaacggg    420
ggcattgtgg tttatacctg taatcccagc actttgggag gctggggctg aagattgct     480 tgagcccagg tgttcaagac aagcctaggt aacgtggtga aactcgtctc tacaaaaatt    540
cataaattag ctggtgtggt ggcctgcacc tctagtccca gctaggtggg aggtttcagt    600
gacctgtgat tgcaccactg cactccagcc tgggtgacag agtgggaccc tgtctaaaaa    660
aaacataaca naacanaacn naatgaaaaa aaaaacaaga aaaagaata gaaaagaaa      720 aaagtnaaaa gtncctcggn cgcgaccacg ctaagggcga attccagcac actgcggccn    780
```

<210> SEQ ID NO 143
<211> LENGTH: 794
<212> TYPE: DNA
<213> ORGANISM: Homo Sapien
<220> FEATURE:
<221> NAME/KEY: misc_feature
<222> LOCATION: (1)...(794)
<223> OTHER INFORMATION: n = A,T,C or G

<400> SEQUENCE: 143

```
nnnnnnnnnn nnnacnnttg actgataccc aacttggtac cgactcggac cactagtaac    60
ggccgccagt gtgctggaat tcgccctttc gagcggccgc ccgggcaggt acagaaagaa    120
gagccaggat attctttgtt ttcctaagcg tagctgtgag caacattatc tctcctactg    180
gcttctttga ggtatgagag tcatcattac atctgtgtgc tttgtcaagt tatatgtcac    240
aattccacct gtgggtagag aacaagcaca agagtcacat caactgtgtg ctgggccagg    300
gttatgtcac aatcttccct gagagcatgc accaggcaga agagtcacat cacagggttc    360
tcaaccagag atgttacaat cctctcctga aagcaggaca caggaaaaag agtaagatca    420
cctgcatgct gggctcagat atatgtcaca agactcactg tgggcaaagt ccagaaggac    480
agacagaaca gctggttgct tgacccagca atatgtcaca atcttctcta tgggcagaat    540
gcaggcagaa gtagagggct tcatcttcca ggtgatggat taaaaaaata catcccaagg    600
ctctctgtgg gaaagggctc angcagaaac tttccaaccc ctangtgttt gcttcagtga    660
tatgtcacaa ttaaccaaaa tatgcaggtt tcaagcaagt gagtnaagtc atatcaccta    720
nggtgcttgg tccanaaatc tgncacaatc tttttttttt ttttggcatg cccagcngaa    780
ttgaaaagtc ncan                                                      794
```

<210> SEQ ID NO 144
<211> LENGTH: 782
<212> TYPE: DNA
<213> ORGANISM: Homo Sapien
<220> FEATURE:
<221> NAME/KEY: misc_feature
<222> LOCATION: (1)...(782)
<223> OTHER INFORMATION: n = A,T,C or G

<400> SEQUENCE: 144

```
cnanngggcc cntagagcat gctcgacggc cgccagtgtg atggatatct gcagaattcg    60
cccttagcgt ggtcgcggcc gaggtacaat cttggctcac tgcaacctcc acctcccggg    120
ttcaagcaat tctcctggct cagcctcctg agtgctggga ctacaggcat gcaccaccac    180
tcccacctaa ttttgtattt ttgatagaga cggggcttct ccatgttggt caggctgttc    240
```

```
tcaaactcct gacctcaggt gatttgactg tcttagcctc ccacagtgct gagcttatag    300
gcaggtgcca cgacacctgg ctggaatcat ttatttcaac atatctctgg gtccaacaac    360
atggtgatgc aactttcctg catgggcccc cccacagaaa tactctaata catcttttca    420
ttcattatct tggtgatgtg acttttctat tctgcttggg cactgccaaa aaaaaaaaaa    480
aagattgtga cagatttctg gaccaagcac ctaggtgata tgactttact cacttgcctg    540
aaacctgcat attttggtta ttgtgacata tcactgaagc aaacacctag gggttggaaa    600
gtttctgcct gagcccttcc acagagagcc ttgggatgta tttttttaat ccatcacctg    660
ggagatgaaa ccctctactt tgcctgcat tctgcccata gagaagattg tgacatattg    720
ctgggtcaag caacccagct ggtctgctgt ccttntggac tttgcccaca agtgagtttt    780 gn    782
```

<210> SEQ ID NO 145
<211> LENGTH: 780
<212> TYPE: DNA
<213> ORGANISM: Homo Sapien
<220> FEATURE:
<221> NAME/KEY: misc_feature
<222> LOCATION: (1)...(780)
<223> OTHER INFORMATION: n = A,T,C or G

<400> SEQUENCE: 145

```
annnttgacc tgatacccag cttggtaccg agctcggatc cactagtaac ggccgccagt    60
gtgctggaat tcgcccttc gagcggccgc ccgggcaggt acttttttta cttttttttt    120
cttttttttt ttggacatct gttttcactc ttaggctttt aaacaatagt tattgctttt    180
atccctctca gattctaata actgagagcg atggggctat attgaatctc tgtatgcact    240
gagaactgag ctatgaagag gatcttatta aactgctggt ctgactttat ggattgacac    300
tgttcctttc ttttattgtg aaaaaaaaaa aaacccctga agtcttggg accccctaa    360 agtcttttgg gaatcctcaa aaagcatggg aagttaagta tttagctaca taaatgttgt    420
aagatcatat cttatgtata gaagtaataa gaccatttgg aattactgga ctaattgaat    480
agttaagggt tctattcggg acaataaaat gtattttgaa agtgctgcta actattgatg    540
ctgacagtgt tcactccta tgagtgaccc aaacatatta taaatatgtg gtaaagggaa    600
tggagcctgt ggggttgagc agaatgttgg acttttttt tnnnnnnnnn nttttttgnc    660
ttnctattng atngataacg atttcnggat tnccttaaa nncncngang gtttggaaac    720
tttggactgg attctggttc ccngaaacag gttcactggg nnccggggga cacttttaan    780
```

<210> SEQ ID NO 146
<211> LENGTH: 778
<212> TYPE: DNA
<213> ORGANISM: Homo Sapien
<220> FEATURE:
<221> NAME/KEY: misc_feature
<222> LOCATION: (1)...(778)
<223> OTHER INFORMATION: n = A,T,C or G

<400> SEQUENCE: 146

```
ttgggcccnt agagcatgct cgacggccgc catgtgatgg atatctgcag aattcgccct    60
tagcgtggtc gcggccgagg tacatggagg cctggactgt aaagagacta cggaaggggc    120
agcatgtgtg ttttgcttct cagattcatt gtcactcacg ttgcataaag tcctcagttg    180
tttttaagta attgttttac tatggatata ttaaacatac agaataaaaa agggaataaa    240
catacaattt ggcaaacccc ctactgagcc tttaaaaata ttagaaggtt ggtattaaac    300
```

| | |
|---|---|
| caggtaactt acggatttgg aaaaaaaaaa aaaaagaaag cattgaatat ggctgggcgg | 360 |
| ttctctgggg atccttgggc agacccagtt tgccccgatt tctcactgta gttttcaaga | 420 |
| ataactgtag gaggcggtgg gagtgcagca tcctgagata agggagacga gccagaacag | 480 |
| cgcgggcact gttccagccc ccctagaaat gggttgatct tcagtgcttc agctcagtgt | 540 |
| gtcatgcttc acccacgatg taaaagccta ggatcggagg cttccccagg gttcgtcagc | 600 |
| tgtggcacaa tagggcccgt tgcaaataag attctattcc tgtcagacag tttcgtgagt | 660 |
| ttgtggggga acactcaccc tagcttctgn tgnctcttca tgcctgtgtg ttcctaatca | 720 |
| acttttttgn gtaacttggt gttttgaaag tgtcaccagc acacaatgga acctgtcn | 778 |

```
<210> SEQ ID NO 147
<211> LENGTH: 784
<212> TYPE: DNA
<213> ORGANISM: Homo Sapien
<220> FEATURE:
<221> NAME/KEY: misc_feature
<222> LOCATION: (1)...(784)
<223> OTHER INFORMATION: n = A,T,C or G

<400> SEQUENCE: 147
```

| | |
|---|---|
| acnntatgac ctgattacgc caacttggta ccgactcgga ccactagtaa cggccgccag | 60 |
| tgtgctggaa ttcgcccttt cgagcggccg cccgggcagg tacttttttt tttttttttt | 120 |
| ttttttttg ggattgaatc aacatgcttt aataggaaaa gatgtatggg ctatatatgn | 180 |
| atcaatctgg ngaancctcg ntctaataaa gggtcttttt cttttctatg atacacacag | 240 |
| ncacgctgat aatatgcnaa tgaacatttt cctttatgnc tctncanata atggttattg | 300 |
| gctgaggnaa attaaattcc caccanggnt tgctgncagt attttaacac ccacattagt | 360 |
| atatgcntnc agggtcataa ccccctaaaa tccatnatgc aaccttatta atctggcttg | 420 |
| ggantccngg ttaatgcttg gatttanttc ctgattacac tncntngaaa agtgagacat | 480 |
| ttgncattcc caactttggg aaaaccaact tatattcaac cntntnaatg aaggccatct | 540 |
| tgatggnctc aacactaatt tttatgatgc aaatttatac acngattttt gtaaagggca | 600 |
| aagtttaaaa agcgtattta acttgatggt ttctatcagc attaatnaaa tggncatgaa | 660 |
| taggcattaa aaacagttgc cagtgatnat ctgcatgaaa ggaaaagaa ccctgcaaat | 720 |
| ggctattgaa nttggaaata ttggntttga natgtaagaa aatntttaga aagctcncnc | 780 |
| tgng | 784 |

```
<210> SEQ ID NO 148
<211> LENGTH: 775
<212> TYPE: DNA
<213> ORGANISM: Homo Sapien
<220> FEATURE:
<221> NAME/KEY: misc_feature
<222> LOCATION: (1)...(775)
<223> OTHER INFORMATION: n = A,T,C or G

<400> SEQUENCE: 148
```

| | |
|---|---|
| gggcccntan agcatgctcg acggccgcca gtgtgatgga tatctgcaga attcgccctt | 60 |
| agcgtggtcg cggccgaggt acaaagcact gtttaaaacc agtccaagat acttaatcca | 120 |
| aactgtatca tgattcttca ttagaaatct agacaccact catggtggtt tcttacactt | 180 |
| taaaagttg aggcattttc agtgtgagca ttctgaatat ctcttacata tcaaaaacaa | 240 |
| tacttccaac tcaatagcca tttgcagggt tctttttcct tcatgcagat tatcactggc | 300 |

-continued

```
aactgttttt aatgactatt catgaccatt ttatttatgc tgatagaaaa catcaagtta      360
aatacgcttt taaaactttg tcctttacaa aaatcagtgt ataaatttgc atcataaaaa      420
ttagtgttga gaccatcaag atggccttca tttatatgt tgtatattag ttggttttcc      480
cagagttggg aatggcagat gtctcacttt tctatgtagt gtaatcagga aataaatcca      540
agcactaaac aggaatccca agacagatta ataaggttgc atgatggatt ttaggggtt      600 atgaccctgg acgcatatac taatgtgggt gttaaaatac tgacagcaag ccctggtggg      660
aattaattta cctcagacaa taaacattat ctggagagac ataaaggaaa atgttcattt      720
gcatattatc agcgtggctg ggtgtatcat agaaaaagaa aagaacctt tttan           775
```

```
<210> SEQ ID NO 149
<211> LENGTH: 783
<212> TYPE: DNA
<213> ORGANISM: Homo Sapien
<220> FEATURE:
<221> NAME/KEY: misc_feature
<222> LOCATION: (1)...(783)
<223> OTHER INFORMATION: n = A,T,C or G

<400> SEQUENCE: 149
```

```
acnntatgac ctgatacgcc aagcttggta ccgagctcgg atccactagt aacggccgcc      60
agtgtgctgg aattcgccct tagcgtggtc gcggccgagg tacccgatta accagagca     120 aaaactacct tctgcaggtc agggagctaa tgacatggca ttggccaaac gttcccgcag    180
tcgaactgct acagaatgtg acgttcgtat gagcaagtct aagtcagaca atcagatcag    240
tgacagagct gctttggagg ccaaagtgaa ggatcttctc acgctggcaa aaaccaaaga    300
cgtagaaatt ttacatttga gaaatgaact gcgagacatg cgtgcccagc tgggcattaa    360
tgaggatcat tctgagggtg atgaaaaatc tgagaaggaa actattatgg ctcaccagcc    420
gactgatgtg gagtccactt tattgcagtt gcaggaacag aatactgcca tccgtgaaga    480
actcaaccag ctgaaaaatg aaaacagaat gttaaaggac aggttgaatg cattgggctt    540
ttccctagag cagaggttag acaattctga aaaactgttt ggctatcagt ccctgagccc    600
agaaatcacc cctggtaacc agagcgatgg aggaggaact ctgacttctt cagtggaang    660 ctctgccct ggctcantgg gaggatctct tgagtcagga tgaaaataca ctaatggacc    720
attagcacag tacttcatgg caatttagac agtgagtgca atgaggtcta ccagcccctt    780 ann                                                                   783
```

```
<210> SEQ ID NO 150
<211> LENGTH: 771
<212> TYPE: DNA
<213> ORGANISM: Homo Sapien
<220> FEATURE:
<221> NAME/KEY: misc_feature
<222> LOCATION: (1)...(771)
<223> OTHER INFORMATION: n = A,T,C or G

<400> SEQUENCE: 150
```

```
gggcccntan agcatgctcg acggccgcca tgtgatggat atctgcagaa ttcgcccttt      60
cgagcggccg cccgggcagg tactgtgttg gttctcttcc atctggtgta tccgttcagt    120
caggcaagcc acggacactt cactggcatt cccgctgctc cccttccggg agcgctctat    180
gctggggatg ccttccgact ctgaggagga tggtgcatcc agcgcatcat cgctcgatgt    240
gaggggctgg tagacctcac tgcactcact gtctaaattg tccatggagt tactgtgctg    300
atggtccatt agtgtatttt catcctgact caagagatcc tccactgagc caggggcaga    360
```

```
gccttccact gaagaagtca gagttcctcc tccatcgctc tggttaccag gggtgatttc      420
tgggctcagg gactgatagc caaacagttt ttcagaattg tctaacctct gctctaggga      480
aaagcccaat gcattcaacc tgtcctttaa cattctgttt tcattttcca gctggttgag      540
ttcttcacgg atggcagtat tctgttcctg caactgcaat aaagtggact ccacatcaag      600
tcggctggtg agccataata gtttccttct cagatttttc atcaccctca gaatgatcct      660
cattaatgcc cagctgggca cgcatgtctc gcagttcatt tctcaaatgt aaaatttcta      720
cgtctttggt ttttggcagc gtgagaagat ccttncttgg nctcnaagcn g              771
```

<210> SEQ ID NO 151
<211> LENGTH: 778
<212> TYPE: DNA
<213> ORGANISM: Homo Sapien
<220> FEATURE:
<221> NAME/KEY: misc_feature
<222> LOCATION: (1)...(778)
<223> OTHER INFORMATION: n = A,T,C or G

<400> SEQUENCE: 151

```
acnntatgac ctgatacgcc agcttggtac cgactcggat ccactagtaa cggccgccag       60
tgtgctggaa ttcgcccttt gagcggccgc ccgggcaggt actttttttt ttctttttt      120 acatctgatt ttaatgcttc gttaacttca aaggaactg gtagagttca aaggtgagc      180 tgttgttttt ctaaacctct tcccaggaag gagacattga cacttgaatt tttgccacct      240
ttttcctcat tagaaggaaa gtagaaagcc ttactgtagg atttttaaaa aaaatccat      300 ctcaccccat attggtctta aataagtata gactaattaa cctaagctac ctttaacaac      360
gtagaattta gatgggttca tatatgtgag aaaaacctga atataggaca ggggtcctac      420
ttttttcccc acctctgccg cccaggctag agtatagtgg tgtgatcttg gcccactgca      480
acctctgctt cctaggttca agtgattctc ctgcctcagc ctcccaagta gctgggattg      540
taagagtatg ccaccacgcc cagctacttt ttgtattttt agtagagaca gggtttcatc      600
atgttggcca ggatggtctc ttaactcctg ccctcaaagt gatccaccag agaggagatc      660
ctcggcctnc ccaagtgctg ggattatagg catgagccac cgtacccagc ctactttcta      720
attaattaaa aaaaaannnn nnnnaaaaaa aacttnccaa atgagctgat aaaaacng       778
```

<210> SEQ ID NO 152
<211> LENGTH: 772
<212> TYPE: DNA
<213> ORGANISM: Homo Sapien
<220> FEATURE:
<221> NAME/KEY: misc_feature
<222> LOCATION: (1)...(772)
<223> OTHER INFORMATION: n = A,T,C or G

<400> SEQUENCE: 152

```
gggcccntag agctgctcga cggccgccat gtgatggata tctgcagaat tcgcccttag       60
cgtggtcgcg gccgaggtac catgctgact tcttggtatc ttttaaggcc taattttccc      120
ttccttgaga ttactgtagt gtgttccagc taatttctat ttggaaacga gttggaacag      180
ctgaaaacta ggtattattg aaggcaaagt agcctcacgt cagttttta tcagctcatt      240 tgggaagttt ttttttttt tttttttttt tttaattaat tagaaagtag gctgggtacg      300
gtggctcatg cctataatcc cagcacttgg ggaggccgag gatctcctct ctggtggatc      360
acttgagggc aggagttaag agaccatcct ggccaacatg atgaaaccct gtctctacta      420
```

| | |
|---|---|
| aaaatacaaa aagtagctgg gcgtggtggc atactcttac aatcccagct acttgggagg | 480 |
| ctgaggcagg agaatcactt gaacctagga agcagaggtt gcagtgggcc aagatcacac | 540 |
| cactatactc tagcctgggc ggcagaggtg gggaaaaaag taggacccct gtcctatatt | 600 |
| caggttttc tcacatatat gaacccatct aaattctacg ttgttaaagg tagcttaagt | 660 |
| taattagtct atacttattt aagaccaata tggggtgaga tggattttt tttaaaaaat | 720 |
| cctacagtaa ggntttctac tttccttcta atgaggaaaa angnggcaaa at | 772 |

<210> SEQ ID NO 153
<211> LENGTH: 780
<212> TYPE: DNA
<213> ORGANISM: Homo Sapien
<220> FEATURE:
<221> NAME/KEY: misc_feature
<222> LOCATION: (1)...(780)
<223> OTHER INFORMATION: n = A,T,C or G

<400> SEQUENCE: 153

| | |
|---|---|
| acnntatgac ntgaatacgn ccaagcttgg taccgagctc ggatccacta gtaacggccg | 60 |
| ccagtgtgct ggaattcgcc cttagcgtgg tcgcggccga ggtacttttt tttttttttt | 120 |
| tttttttttt tttagttaaa gaatgcttta ttaatacaaa tacacacaaa ctctgaagca | 180 |
| ctaagaaatt taaatatcta tgtcacagca aacaggtggc aattcaacat ccagggtcga | 240 |
| cagaatgctt gaaggagact gcaacagatt ggattcccat ggtggagagg gcatnttcac | 300 |
| aggtgaaggg gggcccagct gaaacagctt ttcaagctct ctctcctcgt caaggatcat | 360 |
| gagaggcact ccactcaagg ggaggtgcgc aatctggtgc tcttcaggca ggtcaaaact | 420 |
| ctcaaagtct agaggattga agggaaagaa tttttctatt tctggatagg catcatctga | 480 |
| ggcaggaaca gagcttttg ctttaacagt cttctcagtc atctttttgg cagaaaagct | 540 |
| tggctgtttt tgtttgaggg gtcccttggt ctttacagac ttttctgtag ctctgttgac | 600 |
| agttcccaaa gccttctag tagctttagg taaggctggt ggggcatcga acgttttgcc | 660 |
| aaaacgtggt gttgaaactt gagatctccc atctaagct tgattgaan gtccagaccc | 720 |
| cagcttcagc ccatccttag caaccacacn ggtgcctggg tctncatttt ccttatnang | 780 |

<210> SEQ ID NO 154
<211> LENGTH: 770
<212> TYPE: DNA
<213> ORGANISM: Homo Sapien
<220> FEATURE:
<221> NAME/KEY: misc_feature
<222> LOCATION: (1)...(770)
<223> OTHER INFORMATION: n = A,T,C or G

<400> SEQUENCE: 154

| | |
|---|---|
| gncctgtnna gctgctcgag cggccgccat gtgatggata tctgcagaat tcgccctttc | 60 |
| gagcggccgc ccgggcaggt acgcggggac cgcggcctca gatgaatgcg gctgttaaga | 120 |
| cctgcaataa tccagaatgg ctactctgat ctatgttgat aaggaaaatg gagaaccagg | 180 |
| cacccgtgtg gttgctaagg atgggctgaa gctgggggtct ggaccttcaa tcaaagcctt | 240 |
| agatgggaga tctcaagttt caacaccacg ttttggcaaa acgttcgatg ccccaccagc | 300 |
| cttacctaaa gctactagaa aggctttggg aactgtcaac agagctacag aaaagtctgt | 360 |
| aaagaccaag ggaccctca aacaaaaaca gccaagcttt tctgccaaaa agatgactga | 420 |
| gaagactgtt aaagcaaaaa gctctgttcc tgcctcagat gatgcctatc cagaaataga | 480 |
| aaaattcttt cccttcaatc ctctagactt tgagagtttt gacctgcctg aagagcacca | 540 |

```
gattgcgcac ctcccttga gtggagtgcc tctcatgatc cttgacgagg agagagagct    600
tgaaaagctg tttcagctgg gccccccttc acctgtgaag atgccctctt caccatggga    660
atccaatctg gtgcagtctc ttcaagcatt ctgtcgaccc tggatgttga attgccacct    720
gtttgctgtg acatagatat ttaaatttct tagtgcttca gagtttgngg               770
```

<210> SEQ ID NO 155
<211> LENGTH: 767
<212> TYPE: DNA
<213> ORGANISM: Homo Sapien
<220> FEATURE:
<221> NAME/KEY: misc_feature
<222> LOCATION: (1)...(767)
<223> OTHER INFORMATION: n = A,T,C or G

<400> SEQUENCE: 155

```
acattatgac tgatacgcca gcttggtacc gactcggatc cactagtaac ggccgccagt     60
gtgctggaat tcgcccttag cgtggtcgcg gccgaggtac gcgggcccgc tggataactg    120
ccctgggaca cagcagcggg aagccgcctg cagactgaac ctcactgacc caggtggaaa    180
tcgttaggtc atttactgct aagcagccag atgaactctc cctgcaggtg gctgacgtcg    240
tcctcatcta tcaacgtgtc agcgatggct ggtatgaggg ggaacgacta cgagatggag    300
aaagaggctg gtttcctatg gaatgtgcca aggagataac atgtcaagct acaattgata    360
agaatgtgga gagaatggga cgcttgctag gactggagac caacgtgtag tctctcagat    420
ggtcttttgt tactgcaaga tttgcacgac acttaccggg ctggttggtt ctgggctagt    480
tttattgnta attttgtcac agcctattta attaaaagaa cgaaaacact tgcctttaag    540
cttgccaggt tgttctgctc tctcatgaga agagcttgga tacagtgagt ttgcacagct    600
cagtttttac ctaaccacac acttgcagac ctnctgaggt acctgcccgg gcggccgctc    660
gaaanggcga attctgcaga tatccatcac acttggcggn cgctcgaaca tgcatctaga    720
nggcccaatt cgncctatag tgagtcgtat tacaattcac tggncgc                  767
```

<210> SEQ ID NO 156
<211> LENGTH: 827
<212> TYPE: DNA
<213> ORGANISM: Homo Sapien
<220> FEATURE:
<221> NAME/KEY: misc_feature
<222> LOCATION: (1)...(827)
<223> OTHER INFORMATION: n = A,T,C or G

<400> SEQUENCE: 156

```
attgggcccc tagatgcatg ctcgacggcc gccagtgtga tggatatctg cagaattcgc     60
cctttcgagc ggccgcccgg gcaggtacct caggaggtct gcaagtgtgt ggttaggtaa    120
aaactgagct gtgcaaactc actgtatcca agctcttctc atgagagagc agaacaacct    180
ggcaagctta aaggcaagtg ttttcgttct tttaattaaa taggctgtga caaaattaac    240
aataaaacta gccagaacc aaccagcccg gtaagtgtcg tgcaaatctt gcagtaacaa     300
aagaccatct gagagactac acgttggtct ccagtcctag caagcgtccc attctctcca    360
cattcttatc aattgtagct tgacatgtta tctccttggc acattccata ggaaaccagc    420
ctctttctcc atctcgtagt cgttccccct cataccagcc attggctgac acnttgattg    480
gatgaaggcc ancttanncc nactngcagg gagaagtcaa tttgnttgnt taaccnntna    540
atggancctt accnanttnc acctgggtgc aagtgagggt tcaagtctgc angcggcttc    600
```

| | |
|---|---|
| ccgctgctgt ggtcccaagg gcaagttatn cagcggggcc cgcgttacct tgggccgggg | 660 |
| accaacgcct taangggccg aaatttccaa gcacacttgg ccggcccgtt acctagtggg | 720 |
| atnccgaact tcgggtaccc aaagccttgg gcgttaatca atgggtcaat aggcttggtt | 780 |
| tcctggtgtg naaaattggt aatccggttc acaanttccc cacaaca | 827 |

<210> SEQ ID NO 157
<211> LENGTH: 818
<212> TYPE: DNA
<213> ORGANISM: Homo Sapien
<220> FEATURE:
<221> NAME/KEY: misc_feature
<222> LOCATION: (1)...(818)
<223> OTHER INFORMATION: n = A,T,C or G

<400> SEQUENCE: 157

| | |
|---|---|
| aaacactatga cctgatacgc cancttggta ccgnctcgga tccctagtaa cggccgccag | 60 |
| tgtgctggaa ttcgcccttt cgagcggccg ccgggcaggt acataatctg gaaatttatg | 120 |
| ttacaggtat gcatatttgt atatgaaaaa tattaactga gaaattactg agcttcttag | 180 |
| caaaaaatat aattatttca gagatatgat acagtttaat atctgccttc ctcaaaaagt | 240 |
| cagaaaataa aaagttttaa attgcatata ttttcatttc ttacatatgt cagaacactc | 300 |
| agaatttta ataaaatgtt ttaaaacata attataagtt gttactttta tttctatggt | 360 |
| tagtggaacc cacagggtcc tgtatctgat taaatggagg atatattagg agaattttt | 420 |
| agaagaatga cacatgtgac ataccaccat atttgcaaga aaatataact tgatagtaga | 480 |
| gtaagttagc tgctttatat gatgaattaa aggcactagc tcttagaaaa aaaggatta | 540 |
| aaatgctgac ttcagtaata atgtaaggag ctctgctctt taacatttcc taattaggta | 600 |
| taaactatga tggaagggaa aggtggaatg gaagtntcta cntnttacca ttggcttctcn | 660 |
| ttcatgaaat tggcagnnag cctnccattt cnnnaggnct ttaatnaaaa antttttccc | 720 |
| aactttnct tttcnaaaaa nttnttnncc nnatngnnaa ctggnggtna aaacccggct | 780 |
| tttttggggg gaaancctac ctggntnggg naaaaant | 818 |

<210> SEQ ID NO 158
<211> LENGTH: 772
<212> TYPE: DNA
<213> ORGANISM: Homo Sapien
<220> FEATURE:
<221> NAME/KEY: misc_feature
<222> LOCATION: (1)...(772)
<223> OTHER INFORMATION: n = A,T,C or G

<400> SEQUENCE: 158

| | |
|---|---|
| ntgggcccnt nnagcatgct cgacggccgc cagtgtgatg gatatctgca gaattcgccc | 60 |
| ttagcgtggt cgcggccgag gtacttcaac caccctcct acaaaactct ataccttgt | 120 |
| catattaaaa ttgtatgtta tgccaggctt ccctaataca acaaaatctc tgaataaaac | 180 |
| ctattaaata tacaatttct atcaacatgc ctgccacaca tgcttaataa ttgcttagtg | 240 |
| aatacaagat taatgcatga gtgcctaagt tacttcatct agtataacaa atgacaatat | 300 |
| ctcatttgtt tcccgaagta tccttattcc attcaagctc tgaagaaagt attaatgata | 360 |
| ttcgtcctta agtaattttt tctgcattca aatctcacca ttcaaatgat tttccaacag | 420 |
| tagtttcccc aaaagcagtt tacacagtta catttgttat aattttttgaa agaaaagttg | 480 |
| ggaaaatttt attaagactc tgaatgtagc ttactgccaa ttcatgaaga aagcaatgta | 540 |
| atacgtagat acttcattcc accttttccct tcatcatagt ttataactaa ttaggaaatg | 600 |

| | |
|---|---|
| ttaaagagca gagctcctta cattattact gaagtcagca tttatacttt ttttctaag | 660 |
| agctagtgcc tttaattcat catataaagc agctaactta ctctactatc aagttatatt | 720 |
| ttcttgcaaa tatggtggta tgtcacatgt gtcattcttc taaaaaattc tg | 772 |

<210> SEQ ID NO 159
<211> LENGTH: 1024
<212> TYPE: DNA
<213> ORGANISM: Homo Sapien
<220> FEATURE:
<221> NAME/KEY: misc_feature
<222> LOCATION: (1)...(1024)
<223> OTHER INFORMATION: n = A,T,C or G

<400> SEQUENCE: 159

| | |
|---|---|
| ttgggnaaaa ttttaaaccg gccccccaa angnccctt ttgggggntt aaacccccg | 60 |
| gnaangcccc tttccggggg gggaaattcc ccccaaccct ttaaaggttt aaaaacccgg | 120 |
| gggccnccgg gcccccaaa ggtttgggtt tgggccctt ggggggaaaa aatttttcc | 180 |
| gggcccccc nttttaaag gccgggttgg ggggtttccc gggcccgggg gcccccgga | 240 |
| aaagggttt aaccccctn aatttttttn gggttttcc ccccaaatn gggtttccaa | 300 |
| tttttttt tttaaaaaac ccaaaanggg aaaaaaggg gttggcccaa aatttaaggg | 360 |
| cctttctttc aaagggttt cctttgggaa aaaaaacct tgggttgggg gaaaaggttt | 420 |
| ncccaaaaat ttaaacctgg gaaaaccttc tttgggnaac ccactttaaa aatttaaant | 480 |
| taaanttaaa tttaaattta aanttaagga atgggnttgg aaaaaaaag gaatattccn | 540 |
| ttaatttggc cttaattttt taatttgntn atttgactgg tnatgnnttt acttttnaaa | 600 |
| aacntnctnn ccaaaaacca attttacntg gncnngtggg atttaccntn ttcnattacc | 660 |
| ngggagttaa cccaactnga acntttngga gggnccagtc ctccataggg acctccntca | 720 |
| nttntgatnc caactgcaag ttcagggaaa ttctcacatc ccccttgggc natatatctc | 780 |
| tttaaaagcn cctcacagca ctcactgaan tctattatat tatagatang gtntattatg | 840 |
| ggaaangggt nacanntcaa natnncccaa cgcgggggana cacanngngc agngcccgat | 900 |
| gatnttccna nacacagant ttggtgttct ctggagncgt ttccccncta gnaaaatgtt | 960 |
| gacacntgga cagagttttt accccagggg gaacgtnaat caatctttgg aagtttcaaa | 1020 |
| tcag | 1024 |

<210> SEQ ID NO 160
<211> LENGTH: 771
<212> TYPE: DNA
<213> ORGANISM: Homo Sapien
<220> FEATURE:
<221> NAME/KEY: misc_feature
<222> LOCATION: (1)...(771)
<223> OTHER INFORMATION: n = A,T,C or G

<400> SEQUENCE: 160

| | |
|---|---|
| gggcctctnn agcatgctcg agcggccgcc agtgtgatgg atatctgcag aattcgccct | 60 |
| ttcgagcggc cgcccgggca ggtactgtaa gttatttct tccttatctc ccaatgacac | 120 |
| tgttttctac atgaaaaata ccattttggc tttatcaaca tgttattaat tcataatatg | 180 |
| agagatctat cagcactatt tgtaaaaata ttcaattaaa aaaattaaga tgatttatag | 240 |
| ttgtgtggta aagaatttga ccttacccaa aggaggtcag gcttttgccc tcagccttaa | 300 |
| ggagataatc ttgtcatacc caataaaagt gttatttaa agtgaggctg actacacctg | 360 |

```
ataatccagc ttgagggaca gttatgccag tttgaccaac tagatgattt agggagcttt        420
ctctcccaac ttcaaagctg tgatgaatca acaggtaat taatcgatca tgcttatgta         480
atgaagcctt gattgaaact tcaaagattg attgacgttc cttggttggt aatactctgt        540
catgtgtcaa ttctagaagg gtaatacgtc ctgaggataa cagaagctct gtgtttggaa        600
tcatcctgga ctctgcactt tgnttctcct gctttggctg attttgatct gtaacctta         660 cctataataa accataacta taatataata gatttcagtg agtgctgtga ngctttctag        720
tgatttattg aacctaaggg tggatgtgag aatttnctga acttgcagtt g                 771

<210> SEQ ID NO 161
<211> LENGTH: 771
<212> TYPE: DNA
<213> ORGANISM: Homo Sapien
<220> FEATURE:
<221> NAME/KEY: misc_feature
<222> LOCATION: (1)...(771)
<223> OTHER INFORMATION: n = A,T,C or G

<400> SEQUENCE: 161
acncttgacc tgatcgccag cttggtaccg actcggaccc tagtaacggc cgccagtgtg         60
ctggaattcg cccttagcgt ggtcgcggcc cgaggtacag aatttattat gaaatagctt        120
aatggcaagt ggtaatttag aagaattaag ttatcagata ggagatatat taaaatattt        180
aaaaattgga tatattcttg aagccctttt acacaagtaa tttctataat ttgattgtaa        240
tgaaagtata atataccttg ttactattat cagattaatt tttgaaagta gaattcctta        300
atcaagccaa ggttatgctg ctttataaga aattaatcag gtagtttaac actagagctc        360
attagccaac ctgtatgtag cacaaaataa tcatctctga taaataccta taatatatt         420 ttattcatac ttttaaatat tttacaattc aaataaaaac cttatatgta gacaatctgg        480
gctaaatttc catgtatgtt ttgaaaaata atgttagcat gaatagattc atatttaaat        540
atgattttaa atactcttaa tagaggagac ataagaaata tttacataaa agctaagtag        600
catgatacag ctcatggtta ttttcctcat aggaaaacaa ttacttgatt ttttttttgca       660 taggattaaa gactgagtat cttttctaca ttcttttaac tttctaaggg gcacttctca        720
aaacacagac caggtagtaa atctncactg ntctaaggtc tcaccccact t                 771

<210> SEQ ID NO 162
<211> LENGTH: 768
<212> TYPE: DNA
<213> ORGANISM: Homo Sapien
<220> FEATURE:
<221> NAME/KEY: misc_feature
<222> LOCATION: (1)...(768)
<223> OTHER INFORMATION: n = A,T,C or G

<400> SEQUENCE: 162
gggcccctnn agctgctcgn cggccgccag tgtgatggat atctgcagaa ttcgcccttta        60 gcggccgccc gggcaggtac tacaaaaaca gaataatttt gaagttttag aataaatgta       120
atatatttac tataattcta aatgtttaaa tgcttttcta aaaatgcaaa actatgatgt       180
ttagttgctt tatttttacct ctatgtgatt attttttctta attgttattt tttataatca     240 ttattttttct gaaccattct tctggcctca gaagtaggac tgaattctac tattgctagg     300
tgtgagaaag tggtggtgag aaccttagag cagtggagat ttactacctg gtctgtgttt      360
tgagaagtgc cccttagaaa gttaaaagaa tgtagaaaag atactcagtc ttaatcctat       420
gcaaaaaaaa atcaagtaat tgttttccta tgaggaaaat aaccatgagc tgtatcatgc      480
```

| | |
|---|---|
| tacttagctt ttatgtaaat atttcttatg tctcctctat taagagtatt taaaatcata | 540 |
| tttaaatatg aatctattca tgctaacatt atttttcaaa acatacatgg aaatttagcc | 600 |
| cagattgtct acatataagg ttttttatttg aattgtaaaa tatttaaaag tatgaataaa | 660 |
| atatatttat aggtatttat cagagatgat tattttgtgc tacatacagg ttgggctaat | 720 |
| gagctctagt ggtaaactac ctgataattt cttataaagc agcatacc | 768 |

<210> SEQ ID NO 163
<211> LENGTH: 776
<212> TYPE: DNA
<213> ORGANISM: Homo Sapien
<220> FEATURE:
<221> NAME/KEY: misc_feature
<222> LOCATION: (1)...(776)
<223> OTHER INFORMATION: n = A,T,C or G

<400> SEQUENCE: 163

| | |
|---|---|
| nantatgacc tgatacgcca acttggtacc gactcggatc cactagtaac ggccgccagt | 60 |
| gtgctggaat tcgcccttag cgtggtcgcg gccgaggtac tcttccgcag agggaaggct | 120 |
| gtagaagtct ttgcaagctt catacagaga aatacaaaag gtgtgatgcc attaactggt | 180 |
| cctttctaaa gcattaggaa tttagtgaaa ctctcaaaca caaaactgaa aagccatttg | 240 |
| aacaaatctc atatacttgt agataagctt ttttttattt aaagcataca aattcaaatc | 300 |
| tttcaagcag aaaattcagt caagtgagat ccattggtgg tttgagttca aagtcagtga | 360 |
| gcaaatggaa atcattgcgg catctctctc atttccctag tggacattag accactcaaa | 420 |
| atgtgtcaca taatttacag ccccttggta gtaattgaat atacacgttg agagtgcact | 480 |
| ggcagaacac ttaagaaaga ttgaatgcag gaggaccagc ttacgttatt tttggctcta | 540 |
| ctctggtttt tgcttttaat gttttttctt gagattaatt tcaattgggt tgttccatcc | 600 |
| tattcaaaca aatgctttga gagaagagat gaacagcagc atcaaataaa attgtgatat | 660 |
| ttagttttnag agacatcang tgttgtaatc aaataagaca gaaggccaa gttaaaatct | 720 |
| gtgattngca taaatgaatt taactgttag aatagcanaa ttgagaggtn gattan | 776 |

<210> SEQ ID NO 164
<211> LENGTH: 773
<212> TYPE: DNA
<213> ORGANISM: Homo Sapien
<220> FEATURE:
<221> NAME/KEY: misc_feature
<222> LOCATION: (1)...(773)
<223> OTHER INFORMATION: n = A,T,C or G

<400> SEQUENCE: 164

| | |
|---|---|
| cgggcctcta gatgctgctc gacggccgcc atgtgatgga tatctgcaga attcgccctt | 60 |
| tcgagcgccg cccgggcagg tacacagtgg ataccacata ctcgctctga ggaagaagga | 120 |
| ggaggagaaa gaggagaagg aaggaaattt tcaaatgaca atttctatca ggactcattt | 180 |
| tcctattata agttcagaat acttggacgt ctttataaaa tcaagttgaa atctctacta | 240 |
| ttttgatctg tattctctta aatattaaag gttataccta gggagattcc atgttgactg | 300 |
| gcaaacaaag cataccattt taagaataac tcttcataaa atatgtgtct aagaattaaa | 360 |
| agtgtctagt aacagataca caaagagag atttagaata attaatattt aaagacagat | 420 |
| aatttttaatg tttcacactt ttaactacaa aattctttgt tttcctaaat attagcaaaa | 480 |
| atgttatata ttaaaataaa tcttgaaaat ctcaccctac atttagataa tagttcaaaa | 540 |

```
gtcatattgc taatctacct ctcaattctg ctattcttac agcttaaatt catttatggc      600
aaatcacaga ttttactttg tccttctgtc ttatttgatt acaacacctg atgtctctga      660 aactaaaatat ccaatttatt tgatgctgct gttcatctct tctctcaaag cattngtttg     720
aatangatgg aacaacccaa ttgaaattaa tctcaaggaa aaacattaaa ant             773
```

<210> SEQ ID NO 165
<211> LENGTH: 783
<212> TYPE: DNA
<213> ORGANISM: Homo Sapien
<220> FEATURE:
<221> NAME/KEY: misc_feature
<222> LOCATION: (1)...(783)
<223> OTHER INFORMATION: n = A,T,C or G

<400> SEQUENCE: 165

```
tnnnnnacac tatgacctga ttacgccanc ttggtaccga ctcggatcca ctagtaacgg      60
ccgccagtgt gctggaattc gcccttagcg tggtcgcggc cgaggtacag taggaaaata     120
agaataacaa cgggcaaaat ctttttagaa catttatgct ttatctgttt tagcttctaa     180
aacaatcctg aaggatgaat aattatcatg agtatagcag aatttaattt tccctgttgc     240
tccaaaattt taatgaaaac tttacggttg agagaaatag gtaaataaaa aaacttccta     300
aaattctaaa gacaattgtt gaataaaatt taagtgaatg agtttgtgct tcatatttaa     360
cttttaactt tccataggc tttattaaat ggaaaactga aatttacaaa gtcttagagt      420
agaagcattt ttatcctggc tagggattct ctaagagaac cagtagcacc aagatgcact    480
ggaacagtgc aacgagagag ttcatgcctt agggtttaga agcatacaag caaagggaat    540
ggtgcccact tcttactaga aaatttcac aggctggagt ctgggcggag gagcctggga     600
tgacagtaga agtgtgcagg aagcactaag tctagcctgt acctgcccgg gcggccgctc    660
gaaaggcgaa ttctgcagat atncatcaca ctggccggcc gntcgagcat gcatntagag    720
ggcccaattc gccctatagtg ancgtattac aattcactgg ccgcgtttta caacgtnnng   780 cnn                                                                   783
```

<210> SEQ ID NO 166
<211> LENGTH: 775
<212> TYPE: DNA
<213> ORGANISM: Homo Sapien
<220> FEATURE:
<221> NAME/KEY: misc_feature
<222> LOCATION: (1)...(775)
<223> OTHER INFORMATION: n = A,T,C or G

<400> SEQUENCE: 166

```
attgggcctc tnnagcatgc tcgagcggcc gccagtgtga tggatatctg cagaattcgc      60
ccttcgagcg gccgcccggg caggtacagg ctagacttag tgcttcctgc acacttctac     120
tgtcatccca ggctcctccg cccagactcc agcctgtgaa attttttctag taagaagtgg    180 gcaccattcc ctttgcttgt atgcttctaa accctaaggc atgaactctc tcgttgcact     240
gttccagtgc atcttggtgc tactggttct cttagagaat ccctagccag gataaaaatg    300
cttctactct aagactttgt aaatttcagt tttccattta ataaagccta ttggaaagtt    360
aaaagttaaa tatgaagcac aaactcattc acttaaattt tattcaacaa ttgtctttag    420 aatttttagga agttttttta tttacctatt tctctcaacc gtaaagtttt cattaaaatt   480
ttggagcaac agggaaaatt aaattctgct atactcatga taattattca tccttcagga    540
ttgttttaga agctaaaaca gataaagcat aaatgttcta aaaagatttt gcccgttgtt   600
```

```
attcttattt tcctactgna cctcggccgc gaccacgcta agggcgaatt ccagcacact      660
ggcggccgtt actagtggat ccgagctcgg taccaanctt ggcgtaatca tggtcatagc      720
tggttcctgt gtgaaantgt atccgntcac aattcacaca acatacganc cggag           775
```

<210> SEQ ID NO 167
<211> LENGTH: 797
<212> TYPE: DNA
<213> ORGANISM: Homo Sapien
<220> FEATURE:
<221> NAME/KEY: misc_feature
<222> LOCATION: (1)...(797)
<223> OTHER INFORMATION: n = A,T,C or G

<400> SEQUENCE: 167

```
ttgnaacnat tntgacctga ttacgccaac ttggtaccga gctcggatcc actagtaacg       60
gccgccagtg tgctggaatt cgcccttagc gtggtcgcgg ccgaggtact tcagaaggt       120 aaatcagtag atcacccatg tgtatctgca ccttctcaac tgagagaaga accacagttg      180
aaacctgctt ttatcatttt caagatggtt atttgtagaa ggcgaggaac caattatgct      240
tgtattcata agtattactc taaatgtttt gttttttgtaa ttctgactaa gaccttttaa     300
ccatggttag ttgctagtac ccttccttgt ccgaaggagc tgaccagtat tgatgagaga      360
gtccaggcag ctcctgaagt tcagctggta gtttgttctc tgaacatttg gtctcttgaa      420
ggcacagtat atctggggct tcttcctttta cccaatctaa tcctttcttc ttaatccagg     480
ctcgaagccc atncacattc aagagcagaa tcttgagtgt ggcaggtttg ccactgggtg     540
aggttttctg atctgggggg tcctcataca gggctggggc cctntcctgc tgcctctttg     600
tcattttctt tgcgggccgt cttactcttc ttggcctctg gcttctgtcc tgagctcatc     660
cccgtctttc ggccaccngt tcccctttttt tacacgcctt cggcatttcc cgttaccgaa    720
cgccctttgg gcagctgtac ctgccccngg cggccgttcg aaaaggccna attcttgcag     780
aatttccatc ncaccnn                                                     797
```

<210> SEQ ID NO 168
<211> LENGTH: 780
<212> TYPE: DNA
<213> ORGANISM: Homo Sapien
<220> FEATURE:
<221> NAME/KEY: misc_feature
<222> LOCATION: (1)...(780)
<223> OTHER INFORMATION: n = A,T,C or G

<400> SEQUENCE: 168

```
acantatgac ctgatacgcc aacttggtac cgactcggat ccactagtaa cggccgccag       60
tgtgctggaa ttcgccctta gcgtggtcgc ggccgaggta ctccggtcgg tgtcagcagc      120
acgcggcatt gaacattgca atgtggagcc caaaccacag aaaatggggt gaaattggcc      180
aactttctat taacttatgt tggcaatttt gccaccaaca gtaagctggc ccttctaata      240
aaagaaaatt gaaaggtttc tcactaaacg gaattaagta gtggagtcaa gagactccca      300
ggcctcagcg tacctgcccg ggcggccgct cgaaagggcg aattctgcag atatccatca      360
cactggcggc cgctcgagca tgcatctaga gggcccaatt cgccctatag tgagtcgtat      420
tacaattcac tggccgtcgt tttacaacgt cgtgactggg aaaaccctgg cgttacccaa      480
cttaatcgcc ttgcagcaca tccccctttc gccagctggg gtaatagcga agaggcccgc      540
accgatcgcc cttcccaaca gttgcgcagc ctgaatggcg aatggacgcg ccctgtaacg      600
```

```
gcgcattaag cgcggcgggt gtggtggtta cgcgcagcgt gacccgtaca cttgccagcg      660
ccctancgcc cgctncttc gctttcttcc ctttctttct tngcacgttc gccggctttt      720
cccgtcaagc tctaaatcgg gggctccttt tanggttccg atttantgct ttacngnacn      780
```

<210> SEQ ID NO 169
<211> LENGTH: 771
<212> TYPE: DNA
<213> ORGANISM: Homo Sapien
<220> FEATURE:
<221> NAME/KEY: misc_feature
<222> LOCATION: (1)...(771)
<223> OTHER INFORMATION: n = A,T,C or G

<400> SEQUENCE: 169

```
gggccnctng agcatgctcg acggccgcca tgtgatggat atctgcagaa ttcgcccttt      60
cgagcggccg cccgggcagg tacgctgagg cctgggagtc tcttgactcc actacttaat     120
tccgtttagt gagaaacctt tcaattttct tttattagaa gggccagctt actgttggtg     180
gcaaaattgc caacataagt taatagaaag ttggccaatt tcaccccatt ttctgtggtt     240
tgggctccac attgcaatgt tcaatgccgc gtgctgctga caccgaccgg agtacctcgg     300
ccgcgaccac gctaagggcg aattccagca cactggcggc cgttactagt ggatccgagc     360
tcggtaccaa gcttggcgta atcatggtca tagctgtttc ctgtgtgaaa ttgttatccg     420
ctcacaattc cacacaacat acgagccgga agcataaagt gtaaagcctg gggtgcctaa     480
tgagtgagct aactcacatt aattgcgttg cgctcactgc ccgctttcca gtcgggaaac     540
ctgtcgtgcc agctgcatta atgaatcggc caacgcgcgg ggagaggcgg tttgcgtatt     600
gggcgctctt ccgcttnctc gctcactgac tcgctgcgct cggtcgttcn gctgcggcga     660
gcggtatcaa gctactcaaa ggcngtaata ccgntatcca cagaatcagg ggataacgca     720
ggaaagaaca ttgtgagcaa aaggcancaa aagggcagga accgtaaaaa n              771
```

<210> SEQ ID NO 170
<211> LENGTH: 777
<212> TYPE: DNA
<213> ORGANISM: Homo Sapien
<220> FEATURE:
<221> NAME/KEY: misc_feature
<222> LOCATION: (1)...(777)
<223> OTHER INFORMATION: n = A,T,C or G

<400> SEQUENCE: 170

```
acacttgacc tgatacgcca acttggtacc gagctcggac cactagtaac ggccgccagt      60
gtgctggaat tcgcccttag cgtggtcgcg gccgaggtac acagaatagc tgagcagttc     120
acttcaggga tcaggtcatc tctgctcctc ctagtttcac catgttctgg caataaaaaa     180
cacatattat atcctggttt tctctatcct tgcattacta aggtgactgt ctctctttat     240
acatccttgt atggttctcc cagtattagc aagattgtat atctgtaaag aatgtccagt     300
tttgtaaata tttccctgcc ttttttttc ttttttttaca tctgatttta atgcttcgtt     360
aacttcaaaa ggaactggta gagttcagaa ggtgagctgt tgttttcta aacctcttcc     420 caggaagggg acattgacac ttgaattttt gtcacctttt tcctcattag aaggaaagta     480
gaaagcctta ctgtaggatt tttaaaaaaa aatccatctc accccatatt ggtcttaaat     540
aagtatagac taattaacct aagctacctt taacaacgta gaatttagat gggttcatat     600
atgtgagaaa aacctgaata taggacaggg gtcctacttt tttcccccacc tctgtcgccc     660 aggctagagt atagtggtgt gatcttggcc cactgnaacc tctgcttcct anggtcaagt     720
```

```
gattcttcct gcctcacctt ccaagtagct gggattggaa gaatatgccn ccccccg        777
```

<210> SEQ ID NO 171
<211> LENGTH: 782
<212> TYPE: DNA
<213> ORGANISM: Homo Sapien
<220> FEATURE:
<221> NAME/KEY: misc_feature
<222> LOCATION: (1)...(782)
<223> OTHER INFORMATION: n = A,T,C or G

<400> SEQUENCE: 171

```
nngggcccnt agagcatgct cgacggccgc cagtgtgatg gatatctgca gaattcgccc     60
tttcgagcgg ccgcccgggc aggtactttt tttttttttt tttttttttt tttaattaat   120
tagaaagtag ctgggcacg gtggctcatg cctataatcc cagcacttgg ggaggccgag    180
gatctcctct ctggtggatc acttgagggc aggagttaag agaccatcct ggccaacatg   240
atgaaaccct gtctctacta aaaatacaaa aagtagctgg gcgtggtggc atactcttac   300
aatcccagct acttgggagg ctgaggcagg agaatcactt gaacctagga agcagaggtt   360
gcagtgggcc aagatcacac cactatactc tagcctgggc gacagaggtg gggaaaaaag   420
taggaccct gtcctatatt caggtttttc tcacatatat gaacccatct aaattctacg    480
ttgttaaagg tagcttaggt taattagtct atacttattt aagaccaata tggggtgaga   540
tggattttttt tttaaaaatc ctacagtaag gctttctact ttccttctaa tgaggaaaaa   600
ggtgacaaaa attcaagtgt caatgtcccc ttcctgggaa gaggtttaga aaacaacag    660
ctcaccttct gaactctacc agttcctttt tgaaagttaa ccgaagcatt aaaatcagat   720
gttaaaaaag aaaaaaaaaa ggcnggaaa atatttacaa aactgggaca ttctttacag    780
an                                                                    782
```

<210> SEQ ID NO 172
<211> LENGTH: 773
<212> TYPE: DNA
<213> ORGANISM: Homo Sapien
<220> FEATURE:
<221> NAME/KEY: misc_feature
<222> LOCATION: (1)...(773)
<223> OTHER INFORMATION: n = A,T,C or G

<400> SEQUENCE: 172

```
canttgacct gatacgccaa cttggtaccg actcggacca ctagtaacgg ccgccagtgt     60
gctggaattc gcccttttcga gcggccgccc gggcaggtac catcctgtgg ctccttaagg  120
aggcttctct ctttaattct ccatgaggca tccaggtgtgg tctgggctat gggaagaacc   180
cttcaacttg ggagtagaca ggtgctccaa ttcatagtgc ccattctcag aggccttgtg    240
tgtgagtttc tccttcatgc cttccttctg gctcttcttg tgctccataa tctgctggag   300
ctggtgccca gcatagtctg gcttggtggt cagcgggcca gccggcacag ctacaccaag   360
gacatctgac accatgtagg ggcgcagcca gcccaccaag ggagtgcttc cggggctgta   420
gtgggtctgt ttgtggtaga agagaagtcc atctacctca aaagggaaat ccatagatag   480
cacatcacac aggctttcgg gagtgcaagg gaagttcttt agcccacaa atttaaaagg    540
attaagcttg gttttctctc ccagtccttc ttcttctggt aactttgaat gcatccagta   600
gaatcggaaa tcaagtctgg caatcataaa agggtgtcc ccgccagcac atcacattca    660
gaacgtagta ggtctggttt acctcattgt aaatgcaatc tagaatggtg taagcttttg   720
```
ctgntgaagt ttccctgtgc ctctggcaga atgaagaaan ctgttgacac aac        773

<210> SEQ ID NO 173
<211> LENGTH: 772
<212> TYPE: DNA
<213> ORGANISM: Homo Sapien
<220> FEATURE:
<221> NAME/KEY: misc_feature
<222> LOCATION: (1)...(772)
<223> OTHER INFORMATION: n = A,T,C or G

<400> SEQUENCE: 173
ntgggcctct nnagctgctc gacggccgcc atgtgatgga tatctgcaga attcgccctt        60
agcgtggtcg cggccgaggt acagttcctt ggagcagagt gagcgccgcc ggaggttact       120
ggaactgcag aaatccaagc ggctggatta tgtgaaccat gccagaagac tggctgaaga       180
tgactggaca gggatggaga gtgaggaaga aaaataagaa agatgatgaa gaaatggaca       240
ttgacactgt caagaagtta ccaaaacact atgctaatca attgatgctt tctgagtggt       300
taattgacgt tccttcagat ttggggcagg aatggattgt ggtcgtgtgc cctgttggaa       360
aaagagccct tatcgtggcc tccagggggtt ctaccagtgc ctacaccaag agtggctact       420
gtgtcaacag gttttcttca cttctgccag gaggcaacag gcgaaactca acagcaaaag       480
actacaccat tctagattgc atttacaatg aggtaaacca gacctactac gttctggatg       540
tgatgtgctg gcggggacac cctttttatg attgccagac tgatttccga ttctactgga       600
tgcattcaaa gttaccagaa gaagaaggac tgggagagaa aaccaagctt aatccttta       660 aatttgtggg gctaaagaac ttcccttgca ctcccgaaag cctgtgtgat gtgctatcta       720
tggatttcct tttgaggtag atggacttct cttctaccac aaacagaccc ac             772

<210> SEQ ID NO 174
<211> LENGTH: 780
<212> TYPE: DNA
<213> ORGANISM: Homo Sapien
<220> FEATURE:
<221> NAME/KEY: misc_feature
<222> LOCATION: (1)...(780)
<223> OTHER INFORMATION: n = A,T,C or G

<400> SEQUENCE: 174
acactatgac ctgatacgcc aagcttggta ccgagctcgg atccactagt aacggccgcc        60
agtgtgctgg aattcgccct tagcgtggtc gcggccgagg tacaaaaata cattttcca       120 catacaaaag agagaaaaaa acaaagacat gtggcgggtg gcgaggggag gcccaatccc       180
aacaccctac aaggttccat ggaatggaga aggaacaaaa aaatccccaa ttattttggg       240
gtaagatgtg ccccagaaaa ggtgaaatct atgcaataaa acccaggttt tcttcaaatc       300
tagcatctag gatttctatc agagtttcaa ataatcagaa tttctatcag aatttctacc       360
ctgaggtgac acctactaac tgtaggttct ttcattaaaa atgaagacat cttttcaccag       420 aatgtatcaa gctataaaac tggcttcaga gcctacactt agccagagtg gaaaaaaaat       480
agtgcatatt ttcgacagca attttgaatt gatgcttgag gtctcaatcc accagcaccc       540
agatatcatg ttacctccct cagttgaata caagttaaaa tgatgatctt atcgagatct       600
caatagagca cagtgcccct catgtttcgg gtaagaaggt gggaggagga atgaagccgg       660 gtattcacacc cagcccaatg acagcttaag ccttaacatg cnggcatctt acaatgacca       720
taaacaaggg angggccaag canggctngc gatcattact ttgcgcacag aatgccatgt       780

<210> SEQ ID NO 175
<211> LENGTH: 771
<212> TYPE: DNA
<213> ORGANISM: Homo Sapien
<220> FEATURE:
<221> NAME/KEY: misc_feature
<222> LOCATION: (1)...(771)
<223> OTHER INFORMATION: n = A,T,C or G

<400> SEQUENCE: 175

```
gggcctctag agcatgctcg agcggccgcc atgtgatgga tatctgcaga attcgccctt    60
tcgagcggcc gccgggcagg tactaaaaca gctttgctta tgttggccag gggaaaacat   120
ggcattctgt gcgcaaagct aatgatcgcc agccctgcct tggcccctcc cttgtttatg   180
gtcattgtaa gatgcccgca tgttaaggct taagctgtca ctgggctggg tgtaataccc   240
gcttcattcc tcctcccacc ctcttacccg aaacatgaag ggcactgtgc tctattgaga   300
tctcgataag atcatcattt taacttgtat tcaactgagg gaggtaacat gatatctggg   360
tgctggtgga ttgagacctc aagcatcaat tcaaaattgc tgtcgaaaat atgcactatt   420
ttttttccac tctggctaag tgtaggctct gaagccagtt ttatagcttg atacattctg   480
gtgaaagatg tcttcatttt taatgaaaga acctacagtt agtaggtgtc acctcagggt   540
agaaattctg atagaaattc tgattatttg aaactctgat agaaatccta gatgctagat   600
ttgaagaaaa cctgggtttt attgcataga tttcaccttt tctgggcac atcttacccc    660
aaaataattg gggattttt tgntccttct ccattccatg gaaccttgta gggtgtttgg   720
gattgggcct tccctngcca cccgccacat gtctttggtt ttttctctct t           771
```

<210> SEQ ID NO 176
<211> LENGTH: 773
<212> TYPE: DNA
<213> ORGANISM: Homo Sapien
<220> FEATURE:
<221> NAME/KEY: misc_feature
<222> LOCATION: (1)...(773)
<223> OTHER INFORMATION: n = A,T,C or G

<400> SEQUENCE: 176

```
atngggcctc tagagcatgc tcgagcggcc gccatgtgat ggatatctgc agaattcgcc    60
cttagcgtgg tcgcggccga ggtactcatg tattttttt ttttttccaga tctctttccc   120
caagttgcta ttgtaagagt attctgctgc gtgtggatgc agttatacac attaaagcag   180
atctggagtc tgaagtagct ataaagcagc tataaaacag aaatacatgc atagctgcaa   240
aaaccatgat aggtagagga cttttctttt ggttttgttt tgttttgttt tgttttgttt   300
ttggttttac agagaagaga ttttattac aaagaaaaaa attccagtga attgtgcaga   360
aatgctggtt tttacaccat cctaaagaaa aactttacaa gggtgttttg gagtagaaaa   420
aaggttataa agttggaatc ttaaattgta aaattaacca ttgagtgtca aagttctaaa   480
agcagaactc attttgtgca atgaacataa ggaaagacta ctgtataggt ttttttttc    540
tccttttaaa tgaagaaaag ctttgcttaa gggttgcata cttttattgg agtaaatctg   600
aatgatccta ctcctttgga gtaaactag tgcttaccag tttccaattg tatttagctt    660
ctggttggaa tttgaaaaaa aagaaaaaa agaaaagaa aacctaaata aaataggtga   720
aagttccctg actattcagg tgaatacnca aaaanaaaan nnnnnaann nnt          773
```

<210> SEQ ID NO 177
<211> LENGTH: 772
<212> TYPE: DNA

<213> ORGANISM: Homo Sapien
<220> FEATURE:
<221> NAME/KEY: misc_feature
<222> LOCATION: (1)...(772)
<223> OTHER INFORMATION: n = A,T,C or G

<400> SEQUENCE: 177

```
acattngacc tgatacgcca gcttggtacc gagctcggat ccactagtaa cggccgccag      60
tgtgctggaa ttcgccctta gcgtggtcgc ggccgaggta cagtaggaaa ataagaataa     120
caacgggcaa atcttttta gaacatttat gctttatctg ttttagcttc taaaacaatc     180
ctgaaggatg aataattatc atgagtatag cagaatttaa ttttccctgt tgctccaaaa     240
ttttaatgaa aactttacgg ttgagagaaa taggtaaata aaaaaacttc ctaaaattct     300
aaagacaatt gttgaataaa atttaagtga atgagtttgt gcttcatatt taactttaa      360
ctttccaata ggctttatta aatggaaaac tgaaatttac aaagtcttag agtagaagca     420
tttttatcct ggctagggat tctctaagag aaccagtagc accaagatgc actggaacag     480
tgcaacgaga gagttcatgc cttanggttt agaagcatac aagcaaaggg aatggtgccc     540
acttcttact agaaaaattt cacaggctgg agtctgggcg gaggagcctg ggatgacagt     600
agaagtgtgc aggaagcact aagtctagcc tgtacctgcc cgggcggncg ctcgaagggc     660
gaattctgca gatatccatc acactggcgg ccgctcgagc atgctctana gggcccaatt     720
cgccctatag tgagtcggat tacanttnaa tggccgncgt tttacaacgt cc             772
```

<210> SEQ ID NO 178
<211> LENGTH: 770
<212> TYPE: DNA
<213> ORGANISM: Homo Sapien
<220> FEATURE:
<221> NAME/KEY: misc_feature
<222> LOCATION: (1)...(770)
<223> OTHER INFORMATION: n = A,T,C or G

<400> SEQUENCE: 178

```
attgggcccc tnnagcatgc tcgngcggcc gccagtgtga tggatatctg cagaattcgc      60
ccttcgagcg gccgcccggg caggtacagg ctagacttag tgcttcctgc acacttctac     120
tgtcatccca ggctcctccg cccagactcc agcctgtgaa attttctag taagaagtgg      180
gcaccattcc ctttgcttgt atgcttctaa accctaaggc atgaactctc tcgttgcact     240
gttccagtgc atcttggtgc tactggttct cttagagaat ccctagccag gataaaaatg     300
cttctactct aagactttgt aaatttcagt tttccattta ataaagccta ttggaaagtt     360
aaaagttaaa tatgaagcac aaactcattc acttaaattt tattcaacaa ttgtctttag     420
aattttagga agttttttta tttacctatt tctctcaacc gtaaagtttt cattaaaatt     480
ttggagcaac agggaaaatt aaattctgct atactcatga taattattca tccttcanga     540
ttgttttaga agctaaaaca gataaagcat aaatgttcta aaaagatttt gcccgttggt     600
attcttattt tcctactgta cctcggccgn gaccacgcta agggcgaatt ccagcacact     660
ggcggccgnt actagtggat ccgagctcgg tacccaanct tggcgtaatc atggncatag     720
ctgttcctgn gngaaatngn natncgntna caattnccac acatacnann                770
```

<210> SEQ ID NO 179
<211> LENGTH: 502
<212> TYPE: DNA
<213> ORGANISM: Homo Sapien
<220> FEATURE:
<221> NAME/KEY: misc_feature
<222> LOCATION: (1)...(502)
<223> OTHER INFORMATION: n = A,T,C or G

<400> SEQUENCE: 179

| | | | | | |
|---|---|---|---|---|---|
| cnnnttgacn | tgattcgcca | acttggtacc | gagctcggat | ccctagtaac | ggccgccagt | 60 |
| gtgctggaat | tcgcccttag | cgtggtcgcg | gccgaggtac | ctggccccca | acttctcgaa | 120 |
| taaaatgaaa | ctatgattct | tggcctcact | cactaccatg | tgacattgat | caaatcactt | 180 |
| cacctctcca | aacctcagag | tctttatctg | taagatggaa | aaagtaacac | ctacttcagg | 240 |
| ggctgtcatg | aggattaaat | aaatgtgccc | agcaggtagt | aagtatacaa | cacaaagcat | 300 |
| ctaatggttc | attcatacat | ttgcttattt | tgcaattatt | ggccacctgc | caatgttggg | 360 |
| cactgttcta | ggcacagggg | atacagcaag | ggcaaacacc | taactactgg | tggagggaag | 420 |
| acgataaaca | aatacgtaaa | gatttgtgcc | aggtagtgat | aaaagcaaag | aatgactcat | 480 |
| ggagagggtc | agctggggag | ac | | | | 502 |

<210> SEQ ID NO 180
<211> LENGTH: 823
<212> TYPE: DNA
<213> ORGANISM: Homo Sapien
<220> FEATURE:
<221> NAME/KEY: misc_feature
<222> LOCATION: (1)...(823)
<223> OTHER INFORMATION: n = A,T,C or G

<400> SEQUENCE: 180

| | | | | | |
|---|---|---|---|---|---|
| gggccttnna | gcatgctcga | cggccgccat | gtgatggata | tctgcagaat | tcgcccttc | 60 |
| gagcggccgc | ccgggcaggt | actgcgtggt | ctccccagct | gaccctctcc | atgagtcatt | 120 |
| ctttgctttt | atcactacct | ggcacaaatc | tttacgtatt | tgtttatcgt | cttccctcca | 180 |
| ccagtagtta | ggtgtttgcc | cttgctgtat | ccctgtgcc | tagaacagtg | cccaacattg | 240 |
| gcaggtggcc | ataattgca | aaataagcaa | atgtatgaat | gaaccattag | atgctttgtg | 300 |
| ttgtatactt | actacctgct | gggcacattt | atttaatcct | catgacagcc | cctgaagtag | 360 |
| gtgttacttt | ttccatctta | cagataaaga | ctctgaggtt | tggagaggtg | aagtgatttg | 420 |
| atcaatgtca | catggtagtg | agtgaggcca | agaatcatag | tttcatttta | ttcgagaagt | 480 |
| tgggggccag | gtacctcggc | cgcgaccacg | ctaagggcga | attccagcac | actggcggcc | 540 |
| gttactagtg | gatccgagct | cggtaccaag | cttggcgtaa | tcatggtcat | agctgtttcc | 600 |
| tgtgtgaaat | tgttatccgc | tcacaattcc | acacaacata | cgagccggaa | gcataaagtg | 660 |
| taaagcctgg | ggtgcctaat | gagtgagcta | actcacatta | attgcgttgc | gctcactgcc | 720 |
| cgcttttcag | tcgggaaacc | tgtcgtgcca | gctgcattaa | tgaatcggcc | aacgcgcgg | 780 |
| gaaaagcngn | ttgcgtattg | gggcgctctt | ncgctttctt | gcn | | 823 |

<210> SEQ ID NO 181
<211> LENGTH: 501
<212> TYPE: DNA
<213> ORGANISM: Homo Sapien
<220> FEATURE:
<221> NAME/KEY: misc_feature
<222> LOCATION: (1)...(501)
<223> OTHER INFORMATION: n = A,T,C or G

<400> SEQUENCE: 181

| | | | | | |
|---|---|---|---|---|---|
| cantatgacn | tgattcgcca | acttggtacc | ngctcggatc | cctagtaacg | gncgccattg | 60 |
| tnctggaatn | cgnccttagc | gtggtcgcgg | ccgaggtact | tcttcntttt | nctnnaattt | 120 |

| | |
|---|---|
| tccataacct agtgccngnt tgatnccctc acatggntgg ttcacatncn cngtacagan | 180 |
| gcncggncac catgggganag ggcagcactc ntnccttctn angggatctt ggcctaanggg | 240 |
| tgtacnaagg gagangatgg antntcttct gncctcncta nggcctaggg aacccagnag | 300 |
| canatcccac nacnccttcn atntttnagc caaggagaag ccccttggtg acnttnagtt | 360 |
| ccaaccatta tacncagtgn gagaatggat nntcctggtc ccaaccatta cagggtgaag | 420 |
| atatnaacag ttaaggaaga tacagttttng atgaggcctc anganggagc agntnacacc | 480 |
| atcatannca tatgcaggga a | 501 |

<210> SEQ ID NO 182
<211> LENGTH: 830
<212> TYPE: DNA
<213> ORGANISM: Homo Sapien
<220> FEATURE:
<221> NAME/KEY: misc_feature
<222> LOCATION: (1)...(830)
<223> OTHER INFORMATION: n = A,T,C or G

<400> SEQUENCE: 182

| | |
|---|---|
| ggcccttnga ngcatgctcg acggccgcca tgtgatggat atctgcagaa ttcgcccttt | 60 |
| cgagcggccg cccgggcagg tacacgagaa gctccgagga tggctgaagt ccaacgtctc | 120 |
| tgatgcggtg gctcagagca cccgtatcat ttatggaggc tctgtgactg gggcaacctg | 180 |
| caaggagctg gccagccagc ctgatgtgga tggcttcctt gtgggtggtg cttccctcaa | 240 |
| gcccgaattc gtggacatca tcaatgccaa acaatgagcc ccatccatct tccctaccct | 300 |
| tcctgccaag ccagggacta agcagcccag aagcccagta actgcccttt ccctgcatat | 360 |
| gcttctgatg gtgtcatctg ctccttcctg tggcctcatc caaactgtat cttccttttac | 420 |
| tgtttatatc ttcaccctgt aatggttggg accaggccaa tcccttctcc acttactata | 480 |
| atggttggaa ctaaacgtca ccaaggtggc ttctccttgg ctgagagatg gaaggcgtgg | 540 |
| tgggatttgc tcctgggttc cctaggccct agtgagggca gaagagaaac catcctctcc | 600 |
| cttcttacac cgtgaggcca agatcccctc agaangcang agtgcttgcc cttcccatgg | 660 |
| tgcccgtgcc tcttgtgctg ngtatgtgaa ccaccccatg tgaggaata aacctggcac | 720 |
| tangtctttg aaaaaaanaa aaacntnaaa aaaantccct tcggccgnga ccacgctaag | 780 |
| gnccaattcc ancacaatgg gcgnncgtna ctantggatc caaccttnct | 830 |

<210> SEQ ID NO 183
<211> LENGTH: 484
<212> TYPE: DNA
<213> ORGANISM: Homo Sapien
<220> FEATURE:
<221> NAME/KEY: misc_feature
<222> LOCATION: (1)...(484)
<223> OTHER INFORMATION: n = A,T,C or G

<400> SEQUENCE: 183

| | |
|---|---|
| ttgacatgat acccaacttg taccgagctc ggatccacta gtaacggccg ccagtgtgct | 60 |
| ggaattcgcc ctttcnagcg gccgcccggg caggtacccc agcccgcccc actgagtttg | 120 |
| ccttctatcc gggatatccg ggaacctacc agcctatggc cagttacctg gacgtgtctg | 180 |
| tggtgcagac tctgggtgct cctggagaac cgcgacatga ctccctgttg cctgtgggca | 240 |
| gttaccagtc ttgggctctc gctggtggct ggaacagcca gatgtgttgc cagggagaac | 300 |
| agaacccacc angtccctt ttggaaggca gcatttgcag acttcaacgg gcaaaacctc | 360 |
| tgacgcctgc gcctttcgtc gcggncgcag aaaccatttc gnactttaan attgaatctt | 420 |

```
ctctaaggtt ganaatttct ggatcccttg anaactttta canntgnnct ttantccntt    480
taaa                                                                484
```

<210> SEQ ID NO 184
<211> LENGTH: 824
<212> TYPE: DNA
<213> ORGANISM: Homo Sapien
<220> FEATURE:
<221> NAME/KEY: misc_feature
<222> LOCATION: (1)...(824)
<223> OTHER INFORMATION: n = A,T,C or G

<400> SEQUENCE: 184

```
ggccttagag ctgctcgacg gccgccatgt gatggatatc tgcagaattc gcccttagcg     60
tggtcgcggc cgaggtacca gattggccac tctagggtag aacaccaggt agattcctaa    120
ggttcctgac tccaggccct ggctcccagt tggcatctct ggacctactt ggggtcacag    180
tgaactcact gccctgaagg gaagatgcct ggctggatat gccacctgct gattggagag    240
tccttggacc ttgagtgaac acaggtggta gccaggcagt gatcatcata ggccttgggt    300
gagccccagt gctgtgttgg cttcaggtct gacacagagc tgtcccagtg gtagtcgcca    360 cagggtgct tgtgtcatca tcccttctcc agctccaggc agctcagcac agagacatag    420
tgtccatttg tttgagtgaa agtaaaagaa gagaacaaga gtctccacct agtaatccag    480
ggaattctcc cagatcttac ccaagacaac caaggcaaga gacacagcat tactgggctg    540
gaggtgcccc ctaatgcagg tatggctgca gtgaacaaag acttagatca caacacccaa    600
atcccttcta atagttggaa agccttncca agaaggatgc cggacaaaca agcccaaact    660
gtgaagacta caacaaatac ctaactcttt caatgcccag acactgaaga atatcccaaa    720
ctttaagacc atccatgaaa acatgacctt accaacaagc taaataagac accagtgacc    780
aatcccagag agatagagat atgtgtcctt tcnnacagag aatt                     824
```

<210> SEQ ID NO 185
<211> LENGTH: 499
<212> TYPE: DNA
<213> ORGANISM: Homo Sapien
<220> FEATURE:
<221> NAME/KEY: misc_feature
<222> LOCATION: (1)...(499)
<223> OTHER INFORMATION: n = A,T,C or G

<400> SEQUENCE: 185

```
cacttgacnt gatacgccaa cttgtaccga ctcggatcca ctagtaacgg ccgccagtgt     60
gctggaattc gcccttagcg tggtcgcggc cgaggtactt tttcttttt nttntatttt    120 ttttttcgt ctccccaaag ctttatctgt cttgactttt taaaaaagtt tgggggcaga    180
ttctgaattg gctaaaagac atgcattttt aaaactagca actcttattt ctttcccttta   240 aaaatacata gcattaaatc ccaaatccta tttaaagccc tgacagcttg agaaggtcac    300
tactgcattt ataggacctt ctggtggttc tgctgttacg tttgaagtct gacaatcctt    360
gagaatcttt gcatgcagag gaggtaagag gtattggatt tcacagagg aagaacacag    420 ccgcanaatg aagggccagg cttactgagc tgccaatgga gggctcatgg gtgggacatg    480
gnaaagaagg cacctagcc                                                 499
```

<210> SEQ ID NO 186
<211> LENGTH: 504
<212> TYPE: DNA

<213> ORGANISM: Homo Sapien
<220> FEATURE:
<221> NAME/KEY: misc_feature
<222> LOCATION: (1)...(504)
<223> OTHER INFORMATION: n = A,T,C or G

<400> SEQUENCE: 186

| | | | | | |
|---|---|---|---|---|---|
| cacttgacnt | gatacgccaa | cttggtaccg | agctcggatc | cctagtaacg | gccgccagtg | 60 |
| tgctggaatt | cgcccttagc | gtggtcgcgg | ccgaggtacc | tcaggaggtc | tgcaagtgtg | 120 |
| tggttaggta | aaaactganc | tgtgcaaact | cactgtatcc | aagctcttct | catgagagag | 180 |
| cggaacaacc | tggcaagctt | aaaggcaagt | gttttcgttc | ttttaattaa | ataggctgtg | 240 |
| acaaaattaa | caataaaact | agcccagaac | caaccagccc | ggtaagtgtc | gtgcaaatct | 300 |
| tgcagtaaca | aaagaccatc | tgagagacta | cacgttggtc | tccagtccta | gcaagcgtcc | 360 |
| cattctctnc | acattcttat | caattgtagc | ttgacatgtt | atctccttgg | cacattccat | 420 |
| aggaaaccag | cctctttctn | catctcgtag | tcgntccccc | ttataccagc | catcgctgac | 480 |
| acgtttgata | gatgaagacg | acgt | | | | 504 |

<210> SEQ ID NO 187
<211> LENGTH: 822
<212> TYPE: DNA
<213> ORGANISM: Homo Sapien
<220> FEATURE:
<221> NAME/KEY: misc_feature
<222> LOCATION: (1)...(822)
<223> OTHER INFORMATION: n = A,T,C or G

<400> SEQUENCE: 187

| | | | | | |
|---|---|---|---|---|---|
| gggcctctna | gctgctcgnc | ggccgccatg | tgatggatat | ctgcagaatt | cgcccttcg | 60 |
| agcggccgcc | cgggcaggta | cgcggggact | gggttttttct | cctttttgtag | ccttttcctt | 120 |
| tagtctcctc | ttcccggtgg | ttggtaaaaa | gaggtgaatt | gacagcctat | gttgaagaca | 180 |
| ctgtgctttt | ctcaagaagg | acatccaaac | agcaagtcta | cttctttctc | tttaacgatg | 240 |
| tgctcattat | caccaagaag | aagagtgaag | aaagttacaa | cgtcaatgat | tattccttaa | 300 |
| gagatcagct | attggtggaa | tcttgtgaca | atgaagagct | taattcttct | ccagggaaga | 360 |
| acagctccac | aatgctctat | tcaagacaga | gctctgccag | tcacctcttt | actctgacag | 420 |
| tccttagtaa | ccacgcgaat | gagaaagtgg | agatgctact | aggagctgag | acgcagagcg | 480 |
| agcgagcccg | ctggataact | gccctgggac | acagcagcgg | gaagccgcct | gcagaccgaa | 540 |
| cctcactgac | ccaggtggaa | atcgttaggt | catttactgc | taagcagcca | gatgaactct | 600 |
| ccctgcaggt | ggctgacgtc | gtcctcatct | atcaacgtgt | cagcgatggc | tggtatgagg | 660 |
| gggaacgact | acgagatgga | gaaagaagct | ggtttcctat | ggaatgtgcc | aaggagataa | 720 |
| catgtcaagc | tacaattgat | aagaatgtgg | agagaatggg | accttgctag | gactggagac | 780 |
| caacgtgtag | tctctcaaan | gncttttggt | actgcaagat | tg | | 822 |

<210> SEQ ID NO 188
<211> LENGTH: 504
<212> TYPE: DNA
<213> ORGANISM: Homo Sapien
<220> FEATURE:
<221> NAME/KEY: misc_feature
<222> LOCATION: (1)...(504)
<223> OTHER INFORMATION: n = A,T,C or G

<400> SEQUENCE: 188

| | | | | | |
|---|---|---|---|---|---|
| tatgancatg | atacgccaac | ttggtaccga | gctcggatcc | actagtaacg | gccgccagt | 60 |

```
gtgctggaat tcgcccttag cgtggtcgcg gccgaggtac caaaaaagta acattgata      120 atatggcctg acaacaatca gatatgctaa gctctagaag caaaagcaag gtaggattgc     180
ctccaaatgt tgacaggtat tagccatacc acagtaacta gatctaatgt gagggctaaa    240
tgcctggaga ggcagaaccc taaaggatgc ttagttatag ctccatgctg ccgccgagtg    300
gcttgatgct ccattacacc ctccttggat ccaaccttcc attaaggctg aaggctctag    360
agggcagagt attcaagatg ttagatctgg tccaagccca aattctagag ttaaaagcag    420
aggggttctt agtggctgaa aaaaaacaaa acctgatgac atttgggact ccagttttga    480
ggaaaggctc tgatgatgag gctt                                           504

<210> SEQ ID NO 189
<211> LENGTH: 842
<212> TYPE: DNA
<213> ORGANISM: Homo Sapien
<220> FEATURE:
<221> NAME/KEY: misc_feature
<222> LOCATION: (1)...(842)
<223> OTHER INFORMATION: n = A,T,C or G

<400> SEQUENCE: 189
nnnnnnnntt tttgaaccgg ccctntnang catgctcgac ggccgccatg tgatggatat     60
ctgcagaatt cgccctttcg agcggccgcc cgggcaggta cccttctcgc ttttgccatt    120
agccaaggat agaagctgca gtggtattaa ttttgatata atctttcaaa ccagcttcat    180
gtggcttccc ttttctttgt tcaagatgag ggccaggagg ggaaacatca cacctgccct    240
aaaccctgtt cctggaggtc agcatttgat ctgttgcaag cccctctttc tgtcccctct    300
tcctaccctg cctcccatga ctttgctcct cacacttttg gaaccatgcc ttccgggggg    360
gcccatctct tctggccgtc cttgtctctg ggccacttgg agtgtgtgat aaatcagtca    420
agctgttgaa gtctcaggag tctctggtag cctgcagaag taagcctcat catcagagcc    480
tttcctcaaa actggagtcc caaatgtcat caggttttgt ttttttttcag ccactaagaa    540 cccctctgct tttaactcta gaatttgggc ttggaccaga tctaacatct tgaatactct    600
gccctctaga gccttcagcc ttaatggaag gttggatcca aggagggtgt aatggagcat    660
caagccactc ggcggcagca tggagctata actaagcatc ctttagggtt ctgcctctcc    720
aggcatttag cccctacatt agatctagtt actgtggtat ggctaatacc tgtcaacatt    780
tggaggcaat cctaccttgc ttttgcttct agagcttagc atatctgatg gttgcaggcc    840
cg                                                                   842

<210> SEQ ID NO 190
<211> LENGTH: 503
<212> TYPE: DNA
<213> ORGANISM: Homo Sapien
<220> FEATURE:
<221> NAME/KEY: misc_feature
<222> LOCATION: (1)...(503)
<223> OTHER INFORMATION: n = A,T,C or G

<400> SEQUENCE: 190
actatgacct gattacgcca agcttggtac cgagctcgga tccctagtaa cggccgccag     60
tgtgctggaa ttcgcccttt cgagcggccg cccgggcagg taccatgctg acttcttggt    120
atcttttaag gcctaatttt cccttccttg agattactgt agtgtgttcc agctaatttc    180
tatttggaaa cgagttggaa cagctgaaaa ctaggtatta ttgaaggcaa agcagcctca    240
```

```
cgtcagtttt ttatcagctc atttgggaag ttttttttttt ttttttttta ttaattagaa     300
agtaggctgg acacggtggc tcatgcctat aatcccagca cttggggagg ccgaggatct     360
cctctctggt ggatcacttg agggcaggag ttaagagacc atcctggcca acatgatgaa     420
accctgtctc tactaaaaat acaaaaagta nctgggcgtg gtggcatact cttacaatcc     480
cagctacttg ggaggctgag gca                                             503

<210> SEQ ID NO 191
<211> LENGTH: 829
<212> TYPE: DNA
<213> ORGANISM: Homo Sapien
<220> FEATURE:
<221> NAME/KEY: misc_feature
<222> LOCATION: (1)...(829)
<223> OTHER INFORMATION: n = A,T,C or G

<400> SEQUENCE: 191
gggcctctga gcatgctcga cggccgccat gtgatggata tctgcagaat tcgcccttag      60
cgtggtcgcg gccgaggtac ttttttttttt tctttttttta catctgattt taatgcttcg    120
ttaacttcaa aaggaactgg tagagttcag aaggtgagct gttgttttttc taaacctctt    180 cccaggaagg ggacattgac acttgaattt ttgtcacctt tttcctcatt agaaggaaag    240
tagaaagcct tactgtagga tttttaaaaa aaaatccatc tcaccccata ttggtcttaa    300
ataagtatag actaattaac ctaagctacc tttaacaacg tagaatttag atgggttcat    360
atatgtgaga aaacctgaa tataggacag gggtcctact ttttttcccca cctctgtcgc    420 ccaggctaga gtatagtggt gtgatcttgg cccactgcaa cctctgcttc ctaggttcaa    480
gtgattctcc tgcctcagcc tcccaagtag ctgggattgt aagagtatgc caccacgccc    540
agctactttt tgtatttta gtagagacag ggtttcatca tgttggccag gatggtctct    600
taactcctgc cctcaagtga tccaccagag aggagatcct cggcctncccc aagtgctggg    660 attataggca tgagccaccg tgtccagcct actttctaat taattaaaaa aaaaaaaaa    720 aaactttcca aatgagctga taaaaaactg acgtgaggct gctttgcctt caataatacc    780
tagttttcag ctgtccaact cgtttccaaa tagaaattaa gctgggang                829

<210> SEQ ID NO 192
<211> LENGTH: 503
<212> TYPE: DNA
<213> ORGANISM: Homo Sapien
<220> FEATURE:
<221> NAME/KEY: misc_feature
<222> LOCATION: (1)...(503)
<223> OTHER INFORMATION: n = A,T,C or G

<400> SEQUENCE: 192
ntatgaccat gattacgcca agcttggtac ccgagctcgg atccactagt aacggccgcc     60
agtgtgctgg aattcgccct tcgagcggc cgcccgggca ggtactgcct ttgggcttct    120
tctctctcct gttttctcct ctcgaattct ttactgttt aatacattgt tcttctggct    180
gaggctggtc aaagctacac tgatcttcaa ataaggctc gtcaatgcta cactgttctt    240
caagcaacgg ctggtgaact tgttctgaca aaggatggtc gacttttctt gcttgcttcc    300
tatgtctttc ctcttcagct aaatagagat gtttcagatt atctgggtat cgatctgtga    360
attgagattc cagtgacgtt tgagccttct tttccttccg tagcaatttc ttgtaacttt    420
gctgtatttt cagttttctt cgaaaagcaa agccttgtcc ctcgcgaacg ctccccacga    480
agcttgcggg tggttaggcc gca                                             503
```

<210> SEQ ID NO 193
<211> LENGTH: 834
<212> TYPE: DNA
<213> ORGANISM: Homo Sapien
<220> FEATURE:
<221> NAME/KEY: misc_feature
<222> LOCATION: (1)...(834)
<223> OTHER INFORMATION: n = A,T,C or G

<400> SEQUENCE: 193

| | | | | | |
|---|---|---|---|---|---|
| ancggctctc | tagagctgct | cgacggccgc | catgtgatgg | atatctgcag | aattcgccct | 60 |
| tagcgtggtc | gcggcncgag | gtacaattca | ttatgtgttt | cattaattac | ctttattaaa | 120 |
| aacaacacaa | ttatattaca | atagggacaa | aaaatgttta | agcaaatgaa | aacgaaacca | 180 |
| tgacataccc | aaactcagga | ggaggcaaca | aaggcagtgc | taaagggaag | cttacagctc | 240 |
| cagatgctta | aattaaaaag | aagaaagatc | tcaaacccat | gctaaaggga | agcttacagc | 300 |
| tacagatcct | taaattaaaa | agaagaaaga | tctcaaaccc | atgctaaagg | gaagcttaca | 360 |
| gctgcagatg | cttaaattaa | aagaagaaa | gatctgaaac | ccttgctaaa | gggaagctta | 420 |
| tagctgcagg | tgcttaaatt | aaaaagaaga | agatctcaa | atcaataacc | taacattaca | 480 |
| cctgaagggg | gggaaaaaaa | ctaatgacaa | accaagcaaa | aggaagaaaa | taacagatta | 540 |
| gagcagagat | aagcagaata | agaccagaaa | aaaggaaaaa | aacactgagt | ttgttttttt | 600 |
| aaagatcaat | aaaaattta | aaactcacag | ctatattaag | aaaaaagaga | aatctcaaat | 660 |
| actaaaatca | taagtaaaag | angtgacagt | acaggaataa | gaatgtgaga | cagaagacat | 720 |
| ggcggcctac | cacccgcaag | ccttcgtggg | gagcgttcgc | ganggacaag | gctttgctt | 780 |
| tcgaagaaaa | ctgaaaatnc | cgcaaagttc | cagaaattgt | tcngaagaaa | agaa | 834 |

<210> SEQ ID NO 194
<211> LENGTH: 502
<212> TYPE: DNA
<213> ORGANISM: Homo Sapien

<400> SEQUENCE: 194

| | | | | | |
|---|---|---|---|---|---|
| cacttgacct | gattcgccaa | gcttggtacc | gagctcggat | ccctagtaac | ggccgccagt | 60 |
| gtgctggaat | tcgccctttc | gagcggccgc | ccgggcagga | cgctgaggcc | tgggagtctc | 120 |
| ttgactccac | tacttaattc | cgtttagtga | gaaacctttc | aatttctttt | tattagaagg | 180 |
| gccagcttac | tgttggtggc | aaaattgcca | acataagtta | atagaaagtt | ggccaatttc | 240 |
| acccattt | ctgtggttg | ggctccacat | tgcaatgttc | aatgccacgt | gctgctgaca | 300 |
| ccgaccggag | tacctcggcc | gcgaccacgc | taaggcgaa | ttctgcagat | atccatcaca | 360 |
| ctggcggccg | ctcgagcatg | catctagagg | gcccaattcg | ccctatagtg | agtcgtatta | 420 |
| caattcactg | gccgtcgttt | tacaacgtcg | tgactgggaa | aaccctggcg | ttacccaact | 480 |
| taatcgcctt | gcagcacatc | cc | | | | 502 |

<210> SEQ ID NO 195
<211> LENGTH: 848
<212> TYPE: DNA
<213> ORGANISM: Homo Sapien
<220> FEATURE:
<221> NAME/KEY: misc_feature
<222> LOCATION: (1)...(848)
<223> OTHER INFORMATION: n = A,T,C or G

<400> SEQUENCE: 195

-continued

| | | | |
|---|---|---|---|
| gnnnnnnntt tnnaatgggc | ctctnnagca | tgctcgagcg | gccgccatgt gatggatatc | 60 |
| tgcagaattc gcccttagcg | tggtcgcggc | cgaggtactc | cggtcggtgt cagcagcacg | 120 |
| tggcattgaa cattgcaatg | tggagcccaa | accacagaaa | atgggggtgaa attggccaac | 180 |
| tttctattaa cttatgttgg | caattttgcc | accaacagta | agctggccct tctaataaaa | 240 |
| gaaaattgaa aggtttctca | ctaaacggaa | ttaagtagtg | gagtcaagag actcccaggc | 300 |
| ctcagcgtcc tgcccgggcg | ccgctcgaa | agggcgaatt | ccagcacact ggcggccgtt | 360 |
| actagtggat ccgagctcgg | taccaagctt | ggcgtaatca | tggtcatagc tgtttcctgt | 420 |
| gtgaaattgt tatccgctca | caattccaca | caacatacga | gccggaagca taaagtgtaa | 480 |
| agcctggggt gcctaatgag | tgagctaact | cacattaatt | gcgttgcgct cactgcccgc | 540 |
| tttccagtcg ggaaacctgt | cgtgccagct | gcattaatga | atcggccaac gcgcggggag | 600 |
| aggcggtttg cgtattgggc | gctcttccgc | ttcctcgctc | actgactcgc tgcgctcggt | 660 |
| cgttcggctg cggcgagcgg | tatcagctca | ctcaaaggcg | gtaataccgg tattcacaga | 720 |
| attcagggga taacgcagga | aagaacatgt | gagcaaaagg | ncagccaaag gccaggaacc | 780 |
| cgtnaaaagg ccgcgttgct | ggcgttnttc | cataggctcc | gcccccttga cgagcatnac | 840 |
| aaaaatct | | | | 848 |

<210> SEQ ID NO 196
<211> LENGTH: 511
<212> TYPE: DNA
<213> ORGANISM: Homo Sapien
<220> FEATURE:
<221> NAME/KEY: misc_feature
<222> LOCATION: (1)...(511)
<223> OTHER INFORMATION: n = A,T,C or G

<400> SEQUENCE: 196

| | | | |
|---|---|---|---|
| canntatgac ctgattacgc | caagcttggt | accgagctcg | gatccactag taacggccgc | 60 |
| cagtgtgctg gaattcgccc | ttagcgtggt | cgcggccgag | gtactttttt tttttttttt | 120 |
| tttttttttt ttttagggtt | ataaaagccc | ttttataaag | ccattttaa acaaaacaaa | 180 |
| aaaaagtttt acaaaagaaa | aaagatnca | gaaaagaat | aacttgcttc atatgtccca | 240 |
| aaaagagaaa aaaataaagg | ggacaatgcc | aacatgctca | acaataaagg cttcttttc | 300 |
| ttattttttt aatacaaaat | ncaagcaaag | gatacacata | cttaaaacag agctcaggag | 360 |
| canacacgca ntcctggaaa | cccttcaata | aaancaaagc | aggagtttgn tttttctttg | 420 |
| tctatgcana tacatacaga | gactgggata | tgtaaaaatt | aagtatnaca aaagaccatt | 480 |
| acacgattct accaatgcat | gttgcatctn | g | | 511 |

<210> SEQ ID NO 197
<211> LENGTH: 816
<212> TYPE: DNA
<213> ORGANISM: Homo Sapien
<220> FEATURE:
<221> NAME/KEY: misc_feature
<222> LOCATION: (1)...(816)
<223> OTHER INFORMATION: n = A,T,C or G

<400> SEQUENCE: 197

| | | | |
|---|---|---|---|
| gggcctctag agcatgctcg | acggccgcca | tgtgatggat | atctgcagaa ttcgcccttt | 60 |
| cgagcggccg cccgggcagg | tactaaggaa | gttaaagttt | gaatgtaacc actttattta | 120 |
| aaaggttttt ttcttaatt | taaatgaaat | ggggttgaag | tgaacatgat tttgttgacc | 180 |
| atgttcgtga attacagatg | caacatgcat | tggtagaatc | gtgtgatggt cttttgtgat | 240 |

```
acttaattttt tacatatccc agtctctgta tgtatctgca tagacaaaga aaaacaaac      300 tcctgctttg cttttattga agggtttcca ggactgcgtg tctgctcctg agctctgttt      360
taagtatgtg tatcctttgc ttgtattttg tattaaaaaa ataagaaaaa gaagccttta      420
ttgttgagca tgttggcatt gtccccttta ttttttttctc tttttgggac atatgaagca     480
agttattctt tttctgtatc ttttttttctt ttgtaaactt ttttttttgtt ttgtttaaaa    540 atggctttat aaaagggctt ttataaccct aaaaaaaaaa aannnnnnna aaaaaaaaa       600 gtcctcggcc gcgaccacgc taagggcgaa ttccagcaca ctggcggncg ttactagtgg      660
atccgagctc ggaccaagct tggcgtaatc atggncatag ctgttcctgt gtgaaatgtt     720
atccgctcac aattcccaca catacaaccc ggagcataaa gtgtaaacct ggggtgccta      780
atgagtgagc tactcaataa ttgcgttgcg ctcang                                816
```

<210> SEQ ID NO 198
<211> LENGTH: 498
<212> TYPE: DNA
<213> ORGANISM: Homo Sapien
<220> FEATURE:
<221> NAME/KEY: misc_feature
<222> LOCATION: (1)...(498)
<223> OTHER INFORMATION: n = A,T,C or G

<400> SEQUENCE: 198

```
tgattcgcca agcttggtac cgagctcgga tccactagta acggcccgcc agtgtgctgg       60
aattcgccct tcgagcggnc gnccgggcag gtacaattca gagcaggtgt ccatagaaac     120
aactaggntt gaaaaaactg taagacaatt cacagttgaa atcaaaccaa cactgtgaat    180
gtgttaaata cttgccatat aacaacactt taacattgat cttgctaaat aaggctatga    240
ttcataagat gcatggattt ccaaagctgn ttaacattct tataaattaa ttcacaggat    300
tcaaatagtt gcttttttagc ttcaactggg tattagcaaa aatnatacaa aatgatcccc   360
gtgcaagcac aaatttacct tccttctaaa taaaacatga cagattatat tacaacttga    420
tagcctctct tttaaaaagt ctgtgacatt attaagagg tgacggaatg cttgntttgc     480 aaacccaac acatcttt                                                    498
```

<210> SEQ ID NO 199
<211> LENGTH: 837
<212> TYPE: DNA
<213> ORGANISM: Homo Sapien
<220> FEATURE:
<221> NAME/KEY: misc_feature
<222> LOCATION: (1)...(837)
<223> OTHER INFORMATION: n = A,T,C or G

<400> SEQUENCE: 199

```
nnnnnnntnn cantgggcct ctagagctgc tcgacggccg ccatgtgatg gatatctgca      60
gaattcgccc ttagcctggt cgcggccgag gtaccttgag atctgagcaa ctgtgttaat    120
gaagtaatag caatggtcca cagtgaaaga tgtgttgggg tttgcaaaac aagcattccg    180
tcacctcttt aataatgtca cagacttttt aaaagagagg ctatcaagtt gtaatataat   240
ctgtcatgtt ttatttagga aggaaggtaa atttgtgctt gcacggggat cattttgtat   300
tatttttgct aatacccagt tgaagctaaa aagcaactat ttgaatcctg tgaattaatt    360
tataagaatg ttaaacagct ttggaaatac atgcatctta tgaatcatag ccttatttag   420
caagatcaat gttaaagtgt tgttatatgg caagtattta acacattcac agtgtttgtt   480
```

| | |
|---|---|
| tgatttcaac tgtgaattgt cttacagttt tttcaaacct agttgtttct atggacacct | 540 |
| gctctgaatt gtacctgccc gggcggccgc tcgaagggcg aattccagca cactggcggc | 600 |
| cgttactagt ggatccgagc tcggtaccaa gcttggcgta atcatggtca tagctgnttc | 660 |
| ctgtgtgaaa ttggtatccc gctcacaatt ccacacaaca tacgagccgg aagcataaag | 720 |
| tgtaaagcct ggggtgccta atgagtgagc taactccatt aattgcgttg cgctcactgg | 780 |
| cccgctttnc agtcnggaaa cctgtctgcc anctgcatta atgaatcggc caccccg | 837 |

<210> SEQ ID NO 200
<211> LENGTH: 506
<212> TYPE: DNA
<213> ORGANISM: Homo Sapien
<220> FEATURE:
<221> NAME/KEY: misc_feature
<222> LOCATION: (1)...(506)
<223> OTHER INFORMATION: n = A,T,C or G

<400> SEQUENCE: 200

| | |
|---|---|
| nnnnttgacc tgattacgcc aagcttggta ccgagctcgg atccactagt aacggccgcc | 60 |
| agtgtgctgg aattcgccct tagcgtggtc gcggccgagg tactgcatcc ataatttatc | 120 |
| gccatgtgca acagctttgc gttttctaag gcacaatttt taatgaaatg atgtgtagat | 180 |
| ttcaatctaa taacagctca tccaaatgac aaatatggtc gaaatccctc cagtggctga | 240 |
| ggaaatttct gcacctatat ggaacccaca tgcaaagaac ccatctagca tgtaataaat | 300 |
| aatcgctagc catactcaat aagacacgga aaaattattg cttacataac agaaaaacat | 360 |
| ctacttgacc ccctttttatg actacatcaa tctattagga gtgtatccat agtctacatt | 420 |
| cacaaaatgt catcttgact tatttgccat tgatttaagg cagaataaat agtccccctt | 480 |
| tccccagtct taacaacaaa aaacaa | 506 |

<210> SEQ ID NO 201
<211> LENGTH: 864
<212> TYPE: DNA
<213> ORGANISM: Homo Sapien
<220> FEATURE:
<221> NAME/KEY: misc_feature
<222> LOCATION: (1)...(864)
<223> OTHER INFORMATION: n = A,T,C or G

<400> SEQUENCE: 201

| | |
|---|---|
| ccnntanagc atgctcgacg gccgcccggg caggtacctt ggaagttatg tcattaatat | 60 |
| aggctggttc atcaaataaa gcaaaacctt gcaatatcag ctagatttac actccgggac | 120 |
| gttgcccaaa ggtaggaaga aagcagggg aaatatttca gtcatcattt ccaaagtcat | 180 |
| tatcaaaatc tgtgaggaag tttaatcttc caaagagtca atgtcagaca tcaggcctct | 240 |
| gttgcctgct tctctcgagg cactagatta ggagtcttca ataagagact taacatgagg | 300 |
| tatatggaag atgaggcacc gagataagtt catcattagg tgtgagcact gctcacccctt | 360 |
| gctggcaagt tctccttaag ggcctgaagc acaggtgtcc aaagaaaagc gttaagtcca | 420 |
| tcttaataga atctatgtgg tatatgatgt ggtcagcccc tggtctgtga tcagcaagaa | 480 |
| cctacagcac agattatgcc ctgcccactt caatgaatac ctactctcct ncattctcca | 540 |
| tcactttttt gctatcaaga ctccggacct tgcccatgga gaagtttaga gaggaactct | 600 |
| tgtggagagc tggttaattt tctgccctgt gcgacaagtt tcaacttggc caagaaaggg | 660 |
| agtcaagtta ttaaaaagca tcacaatgta gaatcttcca ggctgggttt tttggntttt | 720 |
| tnggtggttn aanactgggg gnaaaagggg ggacctattt aaattccngg cctttaaaat | 780 |

```
caaatgggcc aaaattaagt tcaaggaatg gaccattttt ngggnaaat ggttngaacc    840 ttntngggan ttcccncctt ccct                                         864

<210> SEQ ID NO 202
<211> LENGTH: 505
<212> TYPE: DNA
<213> ORGANISM: Homo Sapien
<220> FEATURE:
<221> NAME/KEY: misc_feature
<222> LOCATION: (1)...(505)
<223> OTHER INFORMATION: n = A,T,C or G

<400> SEQUENCE: 202
gnntnanacn nttnactaat antganttag tnccgactcg atccctctna ctncantnan    60
ancgntngaa ttgcccttnn tagcggccnt ccngncaggt acaaccagtt tggaaaacag   120
tntcacagtt tttttaaaaa ttacatatac aaccancaac tgacccagcc atttcactcc   180
taggtattta cccaagatna actgaagtgt agatacaagc anagacttgn gcacaagtgt   240
tcatggtaag ctttactngc antagctcca aactanggac aactcaaata gccaacangg   300
aaatggacaa attatgttac tttcatacag tggaatattc tcttgtgata aaaataantg   360
aacanttgat acatggatga atctcaaaat aattatgctg agtaaaagaa gccagacaaa   420
atgtacagtg catacagcta ttcatgtggg tgccagctcc atcccccagt gacctcttca   480
tacggncaga gggtggcatg gcanc                                        505

<210> SEQ ID NO 203
<211> LENGTH: 819
<212> TYPE: DNA
<213> ORGANISM: Homo Sapien
<220> FEATURE:
<221> NAME/KEY: misc_feature
<222> LOCATION: (1)...(819)
<223> OTHER INFORMATION: n = A,T,C or G

<400> SEQUENCE: 203
ggcctcngca gcatgctcga ncggccgcca tgtgatggat atctgcagaa ttcgccctta    60
gcgtggtcgc ggccgaggta cgcgggagag caggaccgga gcgcgggcca agctggagat   120
ggatgatgct gaccctgagg aaagaaacta tgacaacatg ctgaaaatgc tgtcagatct   180
gaataaggac ttggaaaagc tattagaaga gatggagaaa atctcagtgc aggcgacctg   240
gatggcctat gacatggtgg tgatgcgcac caaccctacg ctggccgatt ccatgcgtcg   300
gctggaggat gccttcgtca actgcaagga ggagatggag aagaactggc aagagctgct   360
gcatgagacc aagcaaaggc tgtaggcccc actggcccac cacagctgcc atgccaccct   420
ctgcccgtat gaagaggtca ctgggggatg gagctggcac ccacatgaat agctgtatgc   480
actgtacatt ttgtctggct tcttttactc agcataatta ttttgagatt catccatgta   540
tcaattgttc acttattttt atcacaagag aatattccac tgtatgaaag taacataatt   600
tgtccatttc cctgttggct atttgagttg tccctagttt ggagctattg cgagtaaagc   660
taccatgaac atttgtgcac aagtctttgc ttgtatctac acttcagttt atcttgggta   720
aatacctang agtgaaatgg cttgggtcaa tntgttggtt ggatatgtaa ttttttaaaa   780
aaaactgnga tactgttttc caaactgggt tgtccctct                         819

<210> SEQ ID NO 204
<211> LENGTH: 840
<212> TYPE: DNA
```

<213> ORGANISM: Homo Sapien
<220> FEATURE:
<221> NAME/KEY: misc_feature
<222> LOCATION: (1)...(840)
<223> OTHER INFORMATION: n = A,T,C or G

<400> SEQUENCE: 204

| | | | | | |
|---|---|---|---|---|---|
| gnnnnntttn | nnctnntgga | acccgttttg | nnaagctgct | cgacggccgc | catgtgatgg | 60 |
| atatctgcag | aattcgccct | tagcgtggtc | gcggccgagg | taccttnaga | tctgagcaac | 120 |
| tgtgttaatg | aagtaatagc | aatggtccac | agtgaaagat | gtgttggggt | ttgcaaaaca | 180 |
| agcattccgt | cacctcttta | ataatgtcac | agacttttt | aaaagagagg | ctatcaagtt | 240 |
| gtaatataat | ctgtcatgtt | ttatttagga | aggaaggtaa | atttgtgctt | gcacggggat | 300 |
| cattttgtat | tattttttgct | aatacccagt | tgaagctaaa | aagcaactat | ttgaatcctg | 360 |
| tgaattaatt | tataagaatg | ttaaacagct | ttggaaatac | atgcatctta | tgaatcatag | 420 |
| ccttatttag | caagatcaat | gttaaagtgt | tgttatatgg | caagtattta | acacattcac | 480 |
| agtgtttgtt | tgatttcaac | tgtgaattgt | cttacagttt | tttcaaacct | agttgttctt | 540 |
| atggacacct | gctctgaatt | gtacccctca | gtcaccagca | aaagcatttc | cacccctttc | 600 |
| aaccccccaat | cagaccactg | cattcagtgg | tattggagga | ctttcatcac | agcttccagt | 660 |
| aggtgggtct | tggcacaggc | agnctgactg | gtatangaac | tggtgctctt | ggactccctg | 720 |
| cagtgaataa | cgacccttt | gtacctgccc | gggcggccgc | taagggcgaa | ttccacacac | 780 |
| tggccggccg | ttactagtng | gatccnaact | cggtccaaan | cttggcgtat | tcatggtcnt | 840 |

<210> SEQ ID NO 205
<211> LENGTH: 497
<212> TYPE: DNA
<213> ORGANISM: Homo Sapien
<220> FEATURE:
<221> NAME/KEY: misc_feature
<222> LOCATION: (1)...(497)
<223> OTHER INFORMATION: n = A,T,C or G

<400> SEQUENCE: 205

| | | | | | |
|---|---|---|---|---|---|
| nnnnttgacc | tgattacgcc | aagcttggta | ccgagctcgg | atccactagt | aacggccgcc | 60 |
| agtgtgctgg | aattcgccct | tagcgtggtc | gcggccgagg | tacatttact | ataaaagctg | 120 |
| ttgcattttta | gacaacttgt | tgttttttatt | ttttactgtt | tctcagaggc | attttagaat | 180 |
| aaatacttta | aatgaaagtt | agtataaccg | atatagaaca | ctggcccacc | cagagcagta | 240 |
| acatcttttg | gacggactca | catatgaggt | ggatcatttc | agtttgttaa | atcttacact | 300 |
| gtgtatagat | aactataata | tgtattgcat | taatcacact | acatagaaag | gaaatgtcat | 360 |
| ggaagttcgc | tagtgaaaaa | caaaaagtta | cccattattt | ttattaaaga | gtagggacta | 420 |
| gcttttggag | tatgagaaaa | aaaatcagat | atacttcctc | aggaacaata | aatcactcac | 480 |
| ttgcctcacc | tgttttt | | | | | 497 |

<210> SEQ ID NO 206
<211> LENGTH: 820
<212> TYPE: DNA
<213> ORGANISM: Homo Sapien
<220> FEATURE:
<221> NAME/KEY: misc_feature
<222> LOCATION: (1)...(820)
<223> OTHER INFORMATION: n = A,T,C or G

<400> SEQUENCE: 206

| | | | | | |
|---|---|---|---|---|---|
| gggcctntag | aagcatgctc | gagcggccgc | cagtgtgatg | gatatctgca | gaattcgccc | 60 |

```
tttcgagcgg ccgcccgggc aggtacatgt attgaagcta gaatcgagtc aagaaaaata      120 aagcccatt  ctccaactgc aaaatgtgct ttcccataat gaacactagt caccagcaca      180
gaataatctc caacattttc taaattctaa ttgccaactg tttctattta tatttgattt      240
atatttcatt tggagtctgt tacatggcag cttaggcaga ctagatcttg tttttttccaa     300 tgcagcataa tgagtatgat ctatttcttt tcaaataatc tttgagatcc caggaaaaaa      360
aatgctctgc tccattgagc tataatgtaa atgtgtttgt ttaaaaaaca ggtgaggcaa      420
gtgagtgatt tattgttcct gaggaagtat atctgatttt ttttctcata ctccaaaagc      480
tagtccctac tctttaataa aaataatggg taactttttg ttttcacta  gcgaacttcc      540 atgacatttc ctttctatgt agtgtgatta atgcaataca tattatagtt atctatacac      600
agtgtaagat ttaacaaact gaatgatcc  acctcatatg tgagtccgtc caaaagatgt      660
tactgctctg ggtgggccag tgttctatat cgggtatact aactttcatt taaagtattt      720
attctaaaat gcctctgaga aacagtaaaa ataaaaacca caagttgcta aaatgcaaca      780
gcttttatag taaatgtcct tgggccgcga ccacgcttag                            820

<210> SEQ ID NO 207
<211> LENGTH: 496
<212> TYPE: DNA
<213> ORGANISM: Homo Sapien
<220> FEATURE:
<221> NAME/KEY: misc_feature
<222> LOCATION: (1)...(496)
<223> OTHER INFORMATION: n = A,T,C or G

<400> SEQUENCE: 207
cnnttgacct gattacgcca agcttggtac cgagctcgga tccactagta acggccgcca      60
gtgtgctgga attcgccctt agcgtggtcg cggcccgagg tacaaaagac aaaatcagag      120
ttcaatttca gcagcaagac ttatcaagaa tttaatcact atttgacatc aatggttggt      180
tgcctgtgga cgtccaaacc ctttgggaaa ggaatatata ttgaccctga atcctagaa       240 aaaactggag tggctgaata taaaaacagt ttaaatgtag tccatcatcc ttctttcttg      300
agttacgctg tttccttttt gctacaggaa agcccagaag aaaggacagt aaatgtgagc      360
tctattcngg gaaagaaatg gagctggtat ttggactatt tatttttcaca ngggttacaa     420 ggcttgaaac tttttataag aagtagtggt catcattctt ncattcccag agcagaaggc      480
ataaactgca caatca                                                      496

<210> SEQ ID NO 208
<211> LENGTH: 810
<212> TYPE: DNA
<213> ORGANISM: Homo Sapien
<220> FEATURE:
<221> NAME/KEY: misc_feature
<222> LOCATION: (1)...(810)
<223> OTHER INFORMATION: n = A,T,C or G

<400> SEQUENCE: 208
gcatgctcga cggcccgcca gtgtgatgga tatctgcaga aattcgccct tcgagcggc       60 cgcccgggca ggtactcctt gaggatggca gtctgtcagt gaaatgaaaa tgggaactca      120
agatgagcca ctttgctcta gcaatgagga gtgagtttag tccagtgtgt tcagtttatg     180
tcaacattca tttaatattg attgttgcag tttatgccct ctgctctggg aatggaagaa      240
tgatgaacac tacttcttat aaaaagtttc aagccttgta accctgtga aaataaatag      300
```

-continued

| | |
|---|---|
| tccaaatacc agctccattt ctttccccga atagagctca catttactgt cctttcttct | 360 |
| gggctttcct gtagcaaaaa ggaaacagcg taactcaaga aagaaggatg atggactaca | 420 |
| tttaaactgt ttttatattc agccactcca gttttttcta ggatttcagg gtcaatatat | 480 |
| attcctttcc caaagggttt ggacgtccac aggcaaccaa ccattgatgt caaatagtga | 540 |
| ttaaattctt gataagtctt gctgctgaaa ttgaactctg attttgtctt ttgtacctcg | 600 |
| gccgcgacca cgctaagggc gaattccagc acactggcgg ccggtactag tggatccgag | 660 |
| ctcggtccaa gcttggcgta atcatgggca tagctgtttc ctggtgtgaa attgntatcc | 720 |
| gctcacaatt ccacacaaca tacgaaccgg aagcattaag tgtaaagcct ggggtgccta | 780 |
| atgagtgagc taacttacat taattgcgnt | 810 |

<210> SEQ ID NO 209
<211> LENGTH: 495
<212> TYPE: DNA
<213> ORGANISM: Homo Sapien
<220> FEATURE:
<221> NAME/KEY: misc_feature
<222> LOCATION: (1)...(495)
<223> OTHER INFORMATION: n = A,T,C or G

<400> SEQUENCE: 209

| | |
|---|---|
| cnnttgacct gattacgcca agcttggtac cgagctcgga tccctagtaa cggccgccag | 60 |
| tgtgctggaa ttcgccctta gcgtggtcgc ggccgaggta caactctcca gggcacaata | 120 |
| cgtttacagc tgcctttcct tcacatactt ttctaattca gaactactca caattctaag | 180 |
| caaattccca ttcacgaagt ctgtccataa tgcgaccttc tcttttttta acatatacat | 240 |
| cttaaaaaac aaatatataa aaaattctta ttttgctgga atgctttcaa tttttcacat | 300 |
| tttacatgat catcacattt atttcttata ttgaaaggca tggtttctgt tgacatgtcg | 360 |
| tgcaaagcca aaaaaaaaaa anaaaaaaaa aagggctgga ttgcttttca attggtctaa | 420 |
| cacttttcct tgtctaggct ttggatttta aagttcatga cagccccacc accagtagaa | 480 |
| accccaaggc ttgca | 495 |

<210> SEQ ID NO 210
<211> LENGTH: 820
<212> TYPE: DNA
<213> ORGANISM: Homo Sapien
<220> FEATURE:
<221> NAME/KEY: misc_feature
<222> LOCATION: (1)...(820)
<223> OTHER INFORMATION: n = A,T,C or G

<400> SEQUENCE: 210

| | |
|---|---|
| gggcctcaga gctgctcgan cggccgccat gtgatggata tctgcagaat tcgccctttc | 60 |
| gagcggccgc ccgggcaggt acccacgttt tgctccacac tccttgaccg caggggctcg | 120 |
| gacacaaacc cctgtcacca ggagagtcag tcagcactac ttgggagggc taaagggaaa | 180 |
| tttgaaaata aaattccaaa gtttggagta aaaaaattca agtgttgatt ttatattctt | 240 |
| tcccttcctg acacagccta aagcgtaggg ggaacatgtg tttatctgtg ggagataaac | 300 |
| aagatggagt cccaaagact ttaacaaaat atttttttaa aaatccacta gaatagaaaa | 360 |
| tacattattt agatatactt tatgctgaga gtgagtatat atgcttgtcc tatttaaact | 420 |
| tgtgagaaaa agtggtatcc cttgatacat ttagaaatat gggggctatc ttgtttcatt | 480 |
| gtggggggtgg ggcagaagga gaataaatgc aggatgaccc tgttgaagga atcttancat | 540 |
| ggccaacagg ggacgtttcc agtcgattac caggaaatgc aagccttggg gtttctactg | 600 |

```
gtggtggggc tgtcatgaac tttaaaatcc aaagcctaga caaggaaaag tgttagacca      660
attgaaaagc aatccagccc ttttttttttt nnnntttttt tttggctttg cacgacatgt      720
caacagaaac catgccttc aatntaagga aataaatgtg atgatcatgt aaaatgtgaa       780
aaattgaaag cattncacca aataaggaat tttttatttn                            820
```

<210> SEQ ID NO 211
<211> LENGTH: 499
<212> TYPE: DNA
<213> ORGANISM: Homo Sapien
<220> FEATURE:
<221> NAME/KEY: misc_feature
<222> LOCATION: (1)...(499)
<223> OTHER INFORMATION: n = A,T,C or G

<400> SEQUENCE: 211

```
canttgactg attacgccaa gcttggtacc gagctcggat ccactagtaa cggccgccag       60
tgtgctggaa ttcgcccttα gcgtggtcgc ggcccgaggt acaactctcc agggcacaat      120
acgtttacag ctgcctttcc ttcacatact tttctaattc agaactactc acaattctaa     180
gcaaattccc attcacgaag tctgtccata atgcgacctt ctcttttttt aacatataca     240
tcttaaaaaa caaatatata aaaaattctt attttgctgg aatgctttca attttttcaca    300 ttttacatga tcatcacatt tatttcttat attgaaaggc atggtttctg ttgacatgtc     360
gtgcaaagcc aaaaaaaaaa aaaaaaaaaa aagggctgga ttgcttttca atngggtcta     420 acactttcc ttgtctaggc tttggatttt aaagttcatg acagccccac caccagtaga      480
aaccccaagg cttgcattt                                                   499
```

<210> SEQ ID NO 212
<211> LENGTH: 821
<212> TYPE: DNA
<213> ORGANISM: Homo Sapien
<220> FEATURE:
<221> NAME/KEY: misc_feature
<222> LOCATION: (1)...(821)
<223> OTHER INFORMATION: n = A,T,C or G

<400> SEQUENCE: 212

```
gggcccntan agcatgctcg agcggccgcc atgtgatgga tatctgcaga attcgccctt       60
tcgagcggcc gcccgggcag gtacccacgt tttgctccac actccttgac cgcaggggct     120
cggacacaaa cccctgtcac caggagagtc agtcagcact acttgggagg ctaaagggaa     180
aatttggaaa taaattcca aagtttggag taaaaaatt caagtgttga ttttatattc       240 tttcccttc tgacacagcc taaagcgtag ggggaacatg tgtttatctg tgggagataa      300
acaagatgga gtcccaaaga ctttaacaaa atatttttt aaaatccac tagaatagaa       360 aatacattat ttagatatac tttatgctga gagtgagtat atatgcttgt cctatttaaa    420
cttgtgagaa aaagtggtat cccttgatac atttagaaat atgggggcta tcttgtttca    480
ttgtgggggt gggcagaag gagaataaat gcaggatgac cctgttgaag gaatcttagc    540
atggccaaca ggggacgttt ccagtcgatt accaggaaat gcaagccttg gggtttctac     600
tggtggtggg gctgtcatga actttaaaat ccaaagccta dcaaggaaa agtgttagac     660 caattgaaaa gcaatccagc cctttttttt tttttttttt ttggctttgc acgacattgt    720
taacagaaac catgccttc aatattagaa ataaatgtga tgatcatgtt aaaatgtgaaa    780 aattggaagc cttcagcaaa ataagaattt ttatttnttt n                        821
```

<210> SEQ ID NO 213
<211> LENGTH: 497
<212> TYPE: DNA
<213> ORGANISM: Homo Sapien

<400> SEQUENCE: 213

| | | | | | |
|---|---|---|---|---|---|
| acttgacctg | attacgccaa | gcttggtacc | gagctcggat | ccactagtaa | cggccgccag | 60 |
| tgtgctggaa | ttcgccctta | gcgtggtcgc | ggccgaggta | caaaacaata | gtctaaacta | 120 |
| acacgaactg | ttacctggtc | tattaaagga | tacacggtat | ccactaaaca | gacagatcct | 180 |
| tatttccctg | cttgatgttg | caaagccctt | ggcaaccagg | ggcaaaggtc | actggggttt | 240 |
| gactaactgg | ggctgagtgg | cagctatgac | tgtccttcag | atttttgagt | tgttttttgaa | 300 |
| attaaaagct | tctaaaagtt | gcatcaacat | cctcctaagc | ccccatagga | ttgtaacacc | 360 |
| accacaaaag | gccaccaaca | cttttttaaac | aaagtgaaaa | ctgtctgaca | ccaatcatct | 420 |
| tgaaaactcc | atggcaagtg | cattagctat | gatttcatca | cttacaggta | gagaagctta | 480 |
| ctgtctactg | gtgtggg | | | | | 497 |

<210> SEQ ID NO 214
<211> LENGTH: 817
<212> TYPE: DNA
<213> ORGANISM: Homo Sapien
<220> FEATURE:
<221> NAME/KEY: misc_feature
<222> LOCATION: (1)...(817)
<223> OTHER INFORMATION: n = A,T,C or G

<400> SEQUENCE: 214

| | | | | | |
|---|---|---|---|---|---|
| ggccttanag | ctgctcgncg | gccgccatgt | gatggatatc | tgcagaattc | gcccttttcga | 60 |
| gcggccgccc | gggcaggtac | tctcagtcat | atgcagaaat | acttttttttt | taattaatag | 120 |
| ttacaggctt | gttggtccag | tgggatttgg | gtaggggggag | aaagatacct | tctaaaatgg | 180 |
| atcaatagaa | ccaaaataat | acagcatgtt | ctataaccac | aaggaaatca | atgatcctg | 240 |
| tcatgattcc | agttagtcat | aaccatgtta | gcagtgctaa | atgcatttta | gaaatggtga | 300 |
| cttctgtggt | tttcctagca | tttgtctcta | acaaatggtg | aaataattac | tcatggccct | 360 |
| ctctgccatt | gtctttcatt | ttttcacagt | gaaattagac | ccctttactt | caccattctg | 420 |
| ccactgcaaa | ttaagtataa | agaaaatagc | aagagtgtcc | acaccagtag | acagtaagct | 480 |
| tctctacctg | taagtgatga | aatcatagct | aatgcacttg | ccatggagtt | ttcaagatga | 540 |
| ttggtgtcag | acagttttca | ctttgtttaa | aaagtgttgg | tggccttttg | tggtggtgtt | 600 |
| acaatcctat | gggggcttan | gaggatgttg | atgcaacttt | tagaagcttt | taatttcaaa | 660 |
| aacaactcaa | aaatctgaag | gacagtcata | gctgccactc | agccccagtt | agtcaaaccc | 720 |
| cagtgacctt | tgcccctggt | tgccaagggc | tttgcaacat | caagcangga | aataaggatc | 780 |
| tgnctgttag | tgggataccg | ggtatccttt | aatagac | | | 817 |

<210> SEQ ID NO 215
<211> LENGTH: 495
<212> TYPE: DNA
<213> ORGANISM: Homo Sapien
<220> FEATURE:
<221> NAME/KEY: misc_feature
<222> LOCATION: (1)...(495)
<223> OTHER INFORMATION: n = A,T,C or G

<400> SEQUENCE: 215

| | | | | | |
|---|---|---|---|---|---|
| acttgacctg | attacgccaa | gcttggtacc | gagctcggat | ccactagtaa | cggccgccag | 60 |

```
tgtgctggaa ttcgcccrta gcgtggtccg gccgaggtac catgctgact tcttggtatc    120
ttttaaggcc taattttccc ttccttgaga ttactgtagt gtgttccagc taatttctat    180
ttggaaacga gttggaacag ctgaaaacta ggtattattg aaggcaaagc agcctcacgt    240
cagtttttta tcagctcatt tgggaagttt tttttttttt tttttaatt aattagaaag     300 taggctgggc acggtggctc atgcctataa tcccagcact ggggaggcc gaggatctcc     360 tctctggtgg atcacttgag ggcaggagtt aagagaccat cctggccaac atgatgaaac    420
cctgtctcta ctaaaaatac aaaaagtagc tgggcgtggt ggcatactct tacaatccca    480
gctacttggg aggcn                                                    495
```

```
<210> SEQ ID NO 216
<211> LENGTH: 823
<212> TYPE: DNA
<213> ORGANISM: Homo Sapien
<220> FEATURE:
<221> NAME/KEY: misc_feature
<222> LOCATION: (1)...(823)
<223> OTHER INFORMATION: n = A,T,C or G

<400> SEQUENCE: 216
gggcctcaga gcatgctcgn cggccgccag tgtgatggat atctgcagaa ttcgcccttt     60
cgagcggccg cccgggcagg tactttttt tctttttta catctgattt taatgcttcg     120
ttaacttcaa aaggaactgg tagagttcag aaggtgagct gttgttttc taaacctctt    180 cccaggaagg ggacattgac acttgaattt ttgtcacctt tttcctcatt agaaggaaag    240
tagaaagcct tactgtagga ttttttaaaaa aaaatccatc tcaccccata ttggtcttaa    300
ataagtatag actaattaac ctaagctacc tttaacaacg tagaatttag atgggttcat    360
atatgtgaga aaaacctgaa tataggacag gggtcctact ttttttcccca cctctgtcgc    420 ccaggctaga gtatagtggt gtgatcttgg cccactgcaa cctctgcttc ctaggttcaa     480
gtgattctcc tgcctcagcc tcccaagtag ctgggattgt aagagtatgc caccacgccc    540
agctactttt tgtatttttta gtagagacag ggtttcatca tgttggccag gatggtctct    600
taactcctgc cctcaagtga tccaccagag aggagatcct cggcctncc aagtgctggg     660 attataggca tgagccaccc gtgcccagcc tactttctaa ttaattaaaa aaaaaaaaa     720 aaaaacttnc caaatgagct gatnaaaaac tgacgtgang ctgctttgcc ttcaataata    780
cctagttttc actggtccaa ctcgtttcca aatagaaatt acg                      823
```

```
<210> SEQ ID NO 217
<211> LENGTH: 827
<212> TYPE: DNA
<213> ORGANISM: Homo Sapien
<220> FEATURE:
<221> NAME/KEY: misc_feature
<222> LOCATION: (1)...(827)
<223> OTHER INFORMATION: n = A,T,C or G

<400> SEQUENCE: 217
nnnnnnnggc ctntnnagca tgctcgacgg ccgccatgtg atggatatct gcagaattcg     60
ccctttcgag cggccgcccg ggcaggtact gtatcattgg cagatgtgac gtcaccgaca    120
accagagtga agtggcggac aaaactgagg attacctgtg gctgaagttg aaccaagtgt    180
gttttgacga cgatggcacc agctccccac aagacaggct cactctctca cagttccaga    240
agcagttgtt ggaagactat ggcgagtccc actttacggt gaaccagcaa cccttcctct    300
```

```
acttccaagt cctgttcctg acagcgcagt ttgaagcagc agttgccttt cttttccgca    360
tggagcggct gcgctgccat gctgtccatg tagcactggt gctgtttgag ctgaagctgc    420
ttttaaagtc ctctggacag agtgctcagc tcctcagcca cgagcctggt gaccctcctt    480
gcttgcggcg gctgaacttc gtgcggctcc tcatgctgta cctcggccgc gaccacgcta    540
agggcgaatt ccagcacact ggcggccgtt actagtggat ccgagctcgg taccaagctt    600
ggcgtaatca tggtcatagc tgtttcctgt gtgaaattgt tatccgctca caattccaca    660
caacatacga gccggaagca taaagtgtaa agcctgggg gcctaatgag tgagctaact    720
cacattaatt gcgttgcgct cactgcccgc ttttcaatcg ggaaacctgt cgtgccagct    780
gcattaatga atcggncaac gccccgggan aagcggtttg cgtattt              827
```

<210> SEQ ID NO 218
<211> LENGTH: 498
<212> TYPE: DNA
<213> ORGANISM: Homo Sapien

<400> SEQUENCE: 218

```
cacttgacct gattacgcca agcttggtac cgagctcgga tccactagta acggccgcca     60
gtgtgctgga attcgccctt tcgagcggcc gcccgggcag gtactttttt tttttttttt    120
taattcccac aacaacccat ttcaaaatga gaaaactagg ttgagtgact tgtccacagt    180
tccaaagcta ataaaaatga tgaggcatat ttctcttctg ggcccactgt attcagttct    240
ttgttcttta cactgagtgc cgaaaaaaaa aaatcagact attttgattc tagaaagtga    300
gataattgaa aatgttaaca tatttctcca aaactgatca gactgtggag tctgtcactt    360
ttttggtata ataaggagt ttgaagaaac aaatgacatc attcctgatg atggtagccc    420
actccaacaa aggcgtatat atgtaggcaa gtttgaagat atctataaga gcattaaaag    480
gcaagtgcac cattgtgg                                                498
```

<210> SEQ ID NO 219
<211> LENGTH: 818
<212> TYPE: DNA
<213> ORGANISM: Homo Sapien
<220> FEATURE:
<221> NAME/KEY: misc_feature
<222> LOCATION: (1)...(818)
<223> OTHER INFORMATION: n = A,T,C or G

<400> SEQUENCE: 219

```
ggcctntnga gctgctcgac ggccgccatg tgatggatat ctgcagaatt cgcccttagc     60
gtggcgcggc cgaggtacct agaaaacaga aacttgagta gacatggtaa tgaccagaaa    120
aggctatctt tatacatttc ttttgctacg cttcaaattc atgtcaccta aaagttgtga    180
agtgcacaaa acaaatctac ttaactgaaa attattttca atgaatggga tgtttagaac    240
tctgtgaggg ttttaaggt cttttcgaat agcaaattct aatgaggctt ttttaagttg    300
gcaatttaaa ctcatacaag aaataaaaac tcaccagtgt ggctgggcag aatatatata    360
ttttctcaaa tattgtttgt tgttttttc cctgcactgt atccatggtc ccatgatgaa    420
actgttatat tgctgatata tttattggaa tatgtgggcc aacttccttt ccactcaaca    480
tatggattgg tagtttaaaa taattccttt ctattaagca aatgtgtggc taaggcacat    540
ttaaatagcc cattaaacca atgagatgac aatgtgttac cctcagagaa agcttaattt    600
ttggagtaat caattacaca tatcacagaa tgtctcatga gaacattttt ggctaggtct    660
accaatttat catgcaaata attatagatt tcatttgag gcaaagatgc tgattcatca    720
```

```
ttagtaacat ggtcacaaat aatcatttat tttattttgg taacatctgt ctttcctgtg    780
gggaaactta ctatatgctc tacgttaatt aaattaaa                             818
```

<210> SEQ ID NO 220
<211> LENGTH: 497
<212> TYPE: DNA
<213> ORGANISM: Homo Sapien

<400> SEQUENCE: 220

```
cacttgacct gattacgcca agcttggtac cgagctcgga tccactagta acggccgcca     60
gtgtgctgga attcgccctt tcgagcggcc gcccgggcag gtacagccat gaaattgttg    120
ctactcatag aaagtcttag tatagtttgg tttaaacatt taaaattgc aaataaatat     180 agatagataa tatcatgatg agaaggtcac gggaagcctg gagatttcag ggtgctcttt    240
cataattgga gcgagaatca tgtaacagtt aagaaactaa actcttgagc cttcatagtc    300
tttgctttct ccccatttat ttatctgata ttatataccc tctttaatta tagactggac    360
tgaaatattt tattttgtt ttattataaa aaatcctact cgtctttaac atgttctctt    420
aaagagtgtt tcatatataa atactttccc cccaaaatat aaagaggcta accactatag    480
tattgaaaga ttgaaag                                                    497
```

<210> SEQ ID NO 221
<211> LENGTH: 831
<212> TYPE: DNA
<213> ORGANISM: Homo Sapien
<220> FEATURE:
<221> NAME/KEY: misc_feature
<222> LOCATION: (1)...(831)
<223> OTHER INFORMATION: n = A,T,C or G

<400> SEQUENCE: 221

```
cnnnanggg cctntanagc atgctcgacg gccgccatgt gatggatatc tgcagaattc      60
gcccttagcg tggtcgcggc cgaggtacaa tgaaagtatg agctacctct ctgaagtctg    120
gaaaccttga gagtattaag gttacatgca taaaatcttt aaaatggaag tgtcattaca    180
tggtaaacca attcaaatta aaaataatct catgctgtga aagcaaaata tataactggt    240
ttacccattc ataggtaatt gcacgtcttt gttacatctc aatagtttct ttgtatttgt    300
tgcaatcacc ctccttcttc tcaacactct tttctacctc catgtaactg ctgttgtgaa    360
ttctttataa tattctcatc aatgtttaaa gatgaagttt aaagtgctta caaggaagc    420 attttaactc ctcttagaac tgagccttta aatttggttt tagacaccct aggtctttct    480
ttcaatcttt caatactata gtggttagcc tctttatatt ttgggggaa agtatttata    540 tatgaaacac tctttaagag aacatgttaa agacgagtag gatttttat aataaaacaa    600 aaataaaata tttcagtcca gtctataatt aaagagggta tataatatca gataaataaa    660
tggggagaaa gcaaagacta tgaaggctca agagtttagt ttcttaactg gtacatgatt    720
ctcgctncaa ttatgaaaga gcaccctgaa atctncangc ttnccgtgac cttctcatca    780
tgatattatc tatctatatt tattgcaatt ttaaaatggt taaaccaaac n             831
```

<210> SEQ ID NO 222
<211> LENGTH: 497
<212> TYPE: DNA
<213> ORGANISM: Homo Sapien

<400> SEQUENCE: 222

-continued

```
cacttgacct gattacgcca agcttggtac cgagctcgga tccactagta acggccgcca      60
gtgtgctgga attcgccctt agcgtggtcg cggccgaggt actctttctc tcccctcctc     120
tgaatttaat tctttcaact tgcaatttgc aaggattaca catttcactg tgatgtatat     180
tgtgttgcaa aaaaaagtg tctttgttta aaattacttg gtttgtgaat ccatcttgct      240
ttttccccat tggaactagt cattaaccca tctctgaact ggtagaaaaa catctgaaga     300
gctagtctat cggcatctga caggtgaatt ggatggttct cagaaccatt tcacccagac     360
agcctgtttc catcctgttt aataaattag tttgggttct ctacatgcat aacaaaccct     420
gctccaatct gtcacataaa agtctgtgac ttgaagttta gtcagcaccc ccaccaaact     480
ttatttttct atgtgtt                                                    497
```

<210> SEQ ID NO 223
<211> LENGTH: 822
<212> TYPE: DNA
<213> ORGANISM: Homo Sapien
<220> FEATURE:
<221> NAME/KEY: misc_feature
<222> LOCATION: (1)...(822)
<223> OTHER INFORMATION: n = A,T,C or G

<400> SEQUENCE: 223

```
gggcctnaga gctgctcgnc ggccgccatg tgatggatat ctgcagaatt cgcccttcga      60
gcggccgccc gggcaggtac tttatttca aaaaactcat atgtcgcaaa aaacacatag     120
aaaaataaag tttggtgggg gtgctgacta aacttcaagt cacagacttt tatgtgacag     180
attggagcag ggtttgttat gcatgtagag aacccaaact aatttattaa acaggatgga     240
aacaggctgt ctgggtgaaa tggttctgag aaccatccaa ttcacctgtc agatgccgat     300
agactagctc ttcagatgtt tttctaccag ttcagagatg ggttaatgac tagttccaat     360
ggggaaaaag caagatggat tcacaaacca agtaatttta aacaaagaca cttttttttt     420
gcaacacaat atacatcaca gtgaaatgtg taatccttgc aaattgcaag ttgaaagaat     480
taaattcaga ggaggggaga gaaagagtac ctcggccgcg accacgctaa gggcgaattc     540
cagcacactg gcggccgtta ctagtggatc cgagctcggt accaagcttg gcgtaatcat     600
ggtcatagct gtttcctgtg tgaaattgtt atccgctcac aattccacac aacatacgag     660
ccggaagcat aaagtgtaaa gcctggggtg cctaatgagt gagctaactc acattaattg     720
cgttgcgctc actggccgct tttcagtcng gaaacctgtc gtgccagctg cattaatgaa     780
tcggccaacg cgcgggaga ngcngnttgc gtattgggcc cn                         822
```

<210> SEQ ID NO 224
<211> LENGTH: 494
<212> TYPE: DNA
<213> ORGANISM: Homo Sapien
<220> FEATURE:
<221> NAME/KEY: misc_feature
<222> LOCATION: (1)...(494)
<223> OTHER INFORMATION: n = A,T,C or G

<400> SEQUENCE: 224

```
cncttgacnt gattacgcca agcttggtac cgagctcgga tccctagtaa cggccgccag      60
tgtgctggaa ttcgcccta gcgtggtcgc ggccgaggta ctttttttttt ttttttttaac    120 caactcaata tgtgtttgat gatagtgaat tgataaaacc cgaagctttt ccctgtaaat     180
cttacatctt tgcctttaaa gaatgggtta caaccatcac tagatcacag tagtgcctaa     240
tgaaggttga gaaccgtagg agaggctctc atgctgtaaa taatgttgca ggctaataac     300
```

```
ctttcatcac ttcctttgtg cgcttcctgc cttaagtgac aagtagcaac atggcttggg      360
tcccctgtgc agcatcagct tatgctgcca caagtcagtt tgcaccctag gtgcccagga      420
gctagtatcc ttagatcttt ctatcgctaa cttaattctc ttcgttattt atctgaccct      480
ctaactccat gtct                                                        494
```

<210> SEQ ID NO 225
<211> LENGTH: 822
<212> TYPE: DNA
<213> ORGANISM: Homo Sapien
<220> FEATURE:
<221> NAME/KEY: misc_feature
<222> LOCATION: (1)...(822)
<223> OTHER INFORMATION: n = A,T,C or G

<400> SEQUENCE: 225

```
gggccttnga gctgctcgnc ggccgccagt gtgatggata tctgcagaat tcgcccttcg       60
agcggccgcc cgggcaggta ctttaatttt gcttgttcaa atgatctaca cttacatttt      120
gcaaatcttt ttttttaaat ttttttaaatt ttatattttt tttccagcca actcaaggcc     180
aaaaaaaatt tcttaatata gttattatgc gaggggaggg gaagcaaagg agcacaggta      240
gtccacagaa taagacacaa gaaacctcaa gctgtgaggt caatttgtaa ttaaaagaat      300
actaagatta gatgaacaca acactcagaa atactctagg agagctgaaa agaaggaac      360 agatgttaac aaaacaaatt aaggctgctg gggaacctga gtccatgtta agcttgggtt      420
gactgtaaag aattttttt tttaatgcaa gttagacatg gagttagagg gtcagataaa       480
taacgaagag aattaagtta gcgatagaaa gatctaagga tactagctcc tgggcaccta      540
gggtgcaaac tgacttgtgg cagcataagc tgatgctgca caggggaccc aagccatgtt      600
gctacttgtc acttaaggca ggaagcgcac aaaggaagtg atgaaaggtt attagcctgc      660
acattattta cagcatgaga gcctctccta cggttctcaa ccttcattag gcctactgtg      720
atctantgat ggntgtaccc attctttaaa ggcaaagatg taaggattta cagggaaaag      780
cttcgggttt tatcaattca ctatcatcaa acacatattg ng                         822
```

<210> SEQ ID NO 226
<211> LENGTH: 498
<212> TYPE: DNA
<213> ORGANISM: Homo Sapien
<220> FEATURE:
<221> NAME/KEY: misc_feature
<222> LOCATION: (1)...(498)
<223> OTHER INFORMATION: n = A,T,C or G

<400> SEQUENCE: 226

```
anntaaacta tgacctgatt acgccaactt ggtaccgagc tcggatccac tagtaacggc       60
cgccagtgtg ctggaattcg cccttcgag cggccgcccg ggcaggtacc ctctcatata      120
tgcaaacaaa tgcagactag gcctcaggca gagactaaag gacatctctt ggggtgtcct     180
gaagtgattt ggacccctga gggcagacac ctaagtagga atcccagtgg gaagcaaagc     240
cataaggaag cccaggattc cttgtgatca ggaagtgggc caggaaggtc tgttccagct     300
cacatctnat ctgcatgcag cacgaccgg atgcgcccac tgggtcttgg cttccctccc     360
atcttctcaa gcagtgtcct tgttgagcca tttgcatcct ggctccagg tggctccctc     420 agtctggact ctaccacttg ggtctccaga ttttctgtta cgtccttgtg ggtcaggata     480
tttctggaag tcactccg                                                   498
```

<210> SEQ ID NO 227
<211> LENGTH: 815
<212> TYPE: DNA
<213> ORGANISM: Homo Sapien
<220> FEATURE:
<221> NAME/KEY: misc_feature
<222> LOCATION: (1)...(815)
<223> OTHER INFORMATION: n = A,T,C or G

<400> SEQUENCE: 227

```
gggcctctna agctgctcga cggccgccat gtgatggata tctgcagaat tcgcccttag      60
cgtggtcgcg gccgaggtac attgatgggc tggagagcag ggtggcagcc tgttctgcac     120
agaaccaaga attacagaaa aaagtccagg agctggagag gcacaacatc tccttggtag     180
ctcagctccg ccagctgcag acgctaattg ctcaaacttc caacaaagct gcccagacca     240
gcacttgtgt tttgattctt ctttttttccc tggctctcat catcctgccc agcttcagtc     300
cattccagag tcgaccagaa gctgggtctg aggattacca gcctcacgga gtgacttcca     360
gaaatatcct gacccacaag gacgtaacag aaaatctgga gacccaagtg gtagagtcca     420
gactgaggga gccacctgga gccaaggatg caaatggctc aacaaggaca ctgcttgaga     480
agatgggagg gaagccaaga cccagtgggc gcatccggtc cgtgctgcat gcagatgaga     540
tgtgagctgg aacagacctt cctggcccac ttctgatcac aaggaatcct gggcttcctt     600
atggctttgc ttccactggg attcctactt aggtgtctgc cctcaggggt ccaaatcact     660
tcaggacacc ccaagagatg tcctttagtc tctgctgagg cctantctgc atttggttgc     720
atatatgaaa aggtacctgc ccgggccggc cgttcnaang gcgaatttca gcacactggc     780
ggncgntact agtggatccc aactcggtac caagc                                815
```

<210> SEQ ID NO 228
<211> LENGTH: 512
<212> TYPE: DNA
<213> ORGANISM: Homo Sapien
<220> FEATURE:
<221> NAME/KEY: misc_feature
<222> LOCATION: (1)...(512)
<223> OTHER INFORMATION: n = A,T,C or G

<400> SEQUENCE: 228

```
annnnntttn acctannact atgacctgat tacgccaact tggtaccgag ctcggatcca      60
ctagtaacgg ccgccagtgt gctggaattc gccctttcga gcggccgccc gggcaggtac     120
taggtttgca aaaccaatag catgcacatg tgttgggctg aggttcatgt gtcagagact     180
cagttgtaga aggaactttg aatctggcag gcacttaact gtggctgctc agaactaatg     240
tatctggggc tgcttgagca ggggctgagg tcagaggcag ggagtgagct ctccatcatc     300
cttgactcag acccagctcc gcaggagctc catggtcatc cctggagctc atgtggagtg     360
caaggtccgg gagtgggggc gctgacagaa acaaatctgg ggggatcagc cagggtcagc     420
aggggacaga gatcatgtct tttagaagaa tgtgggcttc ctgacctata gaagggcagc     480
tgttcacccc ctgcagatga tagcagggat ng                                   512
```

<210> SEQ ID NO 229
<211> LENGTH: 815
<212> TYPE: DNA
<213> ORGANISM: Homo Sapien
<220> FEATURE:
<221> NAME/KEY: misc_feature
<222> LOCATION: (1)...(815)
<223> OTHER INFORMATION: n = A,T,C or G

<400> SEQUENCE: 229

```
gggcctnaga gcatgctcga cggccgccat gtgatggata tctgcagaat tcgcccttag      60
cgtggtcgcg gccgaggtac tttttttttt tttttttttt ttcagagata ggttcttact     120
atgctgccct ggctggagtg cagtggcttt cttaggggca atcacagctc actgcagcct     180
ggaactcctg ggctcagcct cctaagtagt tgagactacc aatgcacgcc accatacctg     240
gccttagata cccctgtat cctggaactc actccttata agagacactg aatgtggaag      300
tcttcgcaga tattaagggc actgcccagt tcctgtcttt gaattattgg gccaacaaca     360
gaaaggcgct cctgaggccc cagatcatcc ctgctatcat ctgcaggggg tgaacagctg     420
cccttctata ggtcaggaag cccacattct tctaaaagac atgatctctg tccctgctg     480
accctggctg atcccccag atttgtttct gtcagcgccc ccactccgg accttgcact       540
ccacatgagc tccagggatg accatggagc tcctgcggag ctgggtctga gtcaaggatg     600
atggagagct cactccctgc ctntgacctc agccctgct caagcagccc cagatacatt      660
agttctgagc agcccagtta agtgcctgcc agattcaaag ttccttctac aactgagtct     720
ctgacacatg aaccttaagc ccaacacatg tgcatgctat tgggttttgc aaacctagta     780
cctgnccggg cgggccgttc gaaanggcga attct                                815
```

<210> SEQ ID NO 230
<211> LENGTH: 502
<212> TYPE: DNA
<213> ORGANISM: Homo Sapien
<220> FEATURE:
<221> NAME/KEY: misc_feature
<222> LOCATION: (1)...(502)
<223> OTHER INFORMATION: n = A,T,C or G

<400> SEQUENCE: 230

```
tnnanctana cttgacctga ttacgccaac ttggtaccga gctcggatcc actagtaacg      60
gccgccagtg tgctggaatt cgcccttcg agcggccgcc cgggcaggta cacagagatg     120
cggtccagct gcaggtcgct gtccccgtgg taggtgccgg tggggtcgat gccatgttca     180
tcactgatca cctcccagaa cttggcaccg atctggtagc cacactgacc agcctggatg     240
tgcacgattt ccctcatggt taaaatttaa ttttttttgct cgcctcaagg tatgtatggg    300
gcaagaaaat aagtaatttt ttttctccgc aggtcgcagg ctggaaggtt ggaatgcgcc     360
ccagaggctg gagcagcgag gtgcaaacgc gacggcagga aggttctgag agccccgcgt     420
acctcggccg cgaccacgct aagggcgaat tctgcagata tccatcacac tgcggccgct     480
cgagcatgca tctagagggc cc                                               502
```

<210> SEQ ID NO 231
<211> LENGTH: 817
<212> TYPE: DNA
<213> ORGANISM: Homo Sapien
<220> FEATURE:
<221> NAME/KEY: misc_feature
<222> LOCATION: (1)...(817)
<223> OTHER INFORMATION: n = A,T,C or G

<400> SEQUENCE: 231

```
nngggcctct nnagctgctc gacggccgcc atgtgatgga tatctgcaga attcgccctt      60
agcgtggtcg cggccgaggt acgcggggct ctcagaacct tctgccgtc gcgtttgcac      120
ctcgctgctc cagcctctgg ggcgcattcc aaccttccag cctgcgacct gcggagaaaa     180
```

-continued

| | |
|---|---|
| aaaattactt attttcttgc cccatacata ccttgaggcg agcaaaaaaa ttaaatttta | 240 |
| accatgaggg aaatcgtgca catccaggct ggtcagtgtg gctaccagat cggtgccaag | 300 |
| ttctgggagg tgatcagtga tgaacatggc atcgacccca ccggcaccta ccacggggac | 360 |
| agcgacctgc agctggaccg catctctgtg tacctgcccg ggcggccgct cgaaagggcg | 420 |
| aattccagca cactggcggc cgttactagt ggatccgagc tcggtaccaa gcttggcgta | 480 |
| atcatggtca tagctgtttc ctgtgtgaaa ttgttatccg ctcacaattc cacacaacat | 540 |
| acgagccgga agcataaagt gtaaagcctg gggtgcctaa tgagtgagct aactcacatt | 600 |
| aattgcgttg cgctcactgc ccgctttcca gtcgggaaac ctgtcgtgcc agctgcatta | 660 |
| atgaatcggc caacgcgcgg ggagaggcng nttgcgtatt gggcgctctt ccgcttnctc | 720 |
| gctcacttga ctcgcttgcg ctcggtcgtt cngcttgcgg cnanccggat tcagcttact | 780 |
| taaaggcggt aataccggtt atccaccaga attangg | 817 |

<210> SEQ ID NO 232
<211> LENGTH: 481
<212> TYPE: DNA
<213> ORGANISM: Homo Sapien

<400> SEQUENCE: 232

| | |
|---|---|
| actatgacct gattacgcca agcttggtac cgagctcgga tccactagta acggccgcca | 60 |
| gtgtgctgga attcgccctt tcgagcggcc gcccgggcag gtacaaattt gttgtgtttt | 120 |
| ttatgttcta ataatactga gacttctagg tcttaggtta attttttagga agatcttgca | 180 |
| tgccatcagg agtaaatttt attgtggttc ttaatctgaa gttttcaagc tctgaaattc | 240 |
| ataatccgca gtgtcagatt acgtagagga agatcttaca acattccatg tcaaatctgt | 300 |
| taccatttat tggcatttag ttttcattta agaattgaac ataattattt ttattgtagc | 360 |
| tatatagcat gtcagattaa atcatttaca acaaaagggg tgtgaaccta agactattta | 420 |
| aatgtcttat gagaaaattt cataaagcca ttctcttgtc attcaggtcc agaaacaaat | 480 |
| t | 481 |

<210> SEQ ID NO 233
<211> LENGTH: 809
<212> TYPE: DNA
<213> ORGANISM: Homo Sapien
<220> FEATURE:
<221> NAME/KEY: misc_feature
<222> LOCATION: (1)...(809)
<223> OTHER INFORMATION: n = A,T,C or G

<400> SEQUENCE: 233

| | |
|---|---|
| gggcctctnn agcatgctcg acggccgcca tgtgatggat atctgcagaa ttcgcccttu | 60 |
| gcgtggtcgc ggccgaggta caaaagatac tgtttcacccc attagagaac tgatttgaag | 120 |
| ttactcttcc ctgtgagggc tctgtcatct taactgtatt cacatacttt caactgttcc | 180 |
| ccttgctgct aacctcaggt tctttagttc atctatctgg cagagctgat ttggggaaaa | 240 |
| caagacaaac cttgtcaggt tttcttaata aataagcagt tgtcatgttt caagagtttt | 300 |
| agaaatgagc aataatcaag gaagaggaca acgattgcat acgtttataa tatttagaac | 360 |
| atcttttgcc acaataaaca ctggaaacca cccacttgtg gacaccaaac atttggattt | 420 |
| gtatattttg tggcattccc tcactctaat cctctcatcc ttaaaaattt tcagaaattt | 480 |
| ttgcagcaac aaacactgat tgcaacatat gatttagggt agatttatga accattttt | 540 |
| cactgaaata catcaacagg agtgagtagt ctgagtgacc accccagcat ggagaaaact | 600 |

```
gtagtttaca gattcttctg gagcattttt atttctagat tgcagtggaa gtctaacccc    660
ccttggagat gtctgcctta aagggtcttt ggccagggtc ctctgtagag ccatagtcca    720
gatctactct atttgngtgc tccttacaac atcagaacag caactctcaa tccggatcat    780
cccagaatgc cgctgagtca cagcgtggg                                      809
```

<210> SEQ ID NO 234
<211> LENGTH: 482
<212> TYPE: DNA
<213> ORGANISM: Homo Sapien
<220> FEATURE:
<221> NAME/KEY: misc_feature
<222> LOCATION: (1)...(482)
<223> OTHER INFORMATION: n = A,T,C or G

<400> SEQUENCE: 234

```
actatgacca tgattacgcc aagcttggta ccgagctcgg atccactagt aacggccgcc     60
agtgtgctgg aattcgccct tcgagcggcc gcccgggcag gtactgaaaa gaagatagtg    120
ccatttgaaa caacagatgc atcttttata cattttcaca agttngtttt tcatatttt     180 aaaggcccca tttatctgta acagtggtat ttttatttag agtatcggct acttaatata    240
tacatgcaac aatatatgct ttaatagtca tttaacttttt angaatattt catnacatta   300
agtggttaag catagcgtta aaagagtgga atataaggaa tannaanntn tngaaaatac    360
gctgctannt tcattngcan actatagtag aatggagatg cccataaaag tgatcattgc    420
ccaactgaat tcctacccng aactaacatg tgattctcaa gtggggganaa atattattaa   480 aa                                                                   482
```

<210> SEQ ID NO 235
<211> LENGTH: 474
<212> TYPE: DNA
<213> ORGANISM: Homo Sapien
<220> FEATURE:
<221> NAME/KEY: misc_feature
<222> LOCATION: (1)...(474)
<223> OTHER INFORMATION: n = A,T,C or G

<400> SEQUENCE: 235

```
acttgacctg attacgccaa gcttggtacc gagctcggat ccactagtaa cggccgccag     60
tgtgctggaa ttcgcccttA gcgtggtcgc ggccgaggta cattacttgg tgttaacatt    120
gttggcagtg gtagcccctt ttcagaaagc aacttgctgt aagtcagggt gtccgttcca    180
accttcagct agtgaaaagg tagtaacaaa tggtaaacaa gagaatgatt gtttaaacct    240
atctgtggac acttaatgca actgtttaaa aatgataatc acgagttatg tagcaacgtg    300
gaaatatatt tacagaacat taatggagaa gcagggacac gaagtatatt atactacagt    360
tataactcaa cagtcattat atgccggtca tttaccagtc atttaaccag ttcattataa    420
ctgtttaaaa atatatatgc ttatagtcaa aagctgttgt ggtgttgttg ttgn          474
```

<210> SEQ ID NO 236
<211> LENGTH: 819
<212> TYPE: DNA
<213> ORGANISM: Homo Sapien
<220> FEATURE:
<221> NAME/KEY: misc_feature
<222> LOCATION: (1)...(819)
<223> OTHER INFORMATION: n = A,T,C or G

<400> SEQUENCE: 236

```
gggccttnna gctgctcgnc ggccgccagt gtgatggata tctgcagaat tcgcccttc    60 gagcggccgc ccgggcaggt acttttttt ttttttttt tttttatttt taactttatt   120
tttattgntg acactattac agatagaatg accacaacca tattaacaaa ccaaaaacct   180
gtgcacagaa acaagatgaa gaaatatat caagatgtta aacacactct ttggatggtg   240
aaaacatggg tgagtttctc ttctacattt ctgtaacttc aaagtttcta taatgaacac   300
atttcatata taatggaaat atatgtagta aaggtggact accaaaacac tagaatgatg   360 accttttcaag gaaaccgaaa caaaataacc ataatcccac aacaaccaca caactatttc   420
ttgnttttca tctttcttcc catctttgac atttatgcat acttatcact aacaccctaa   480
taatcacaga ctagtgcaca gatcaagatg ttaacagtta attgttgttg ggtgttggga   540
atatgtgtga atttcttta ctgaatttcc aaagttttgt atgagtatgt attatatttg   600
taatggaaaa tacatacata aaatttatta ccaaaacacc aaagattatt taagggaatt   660
tgagacaaaa tatttaacca aattcccaca atgacaacac tattttagtt attttccaca   720
tcttttcatt taagacttta tgcacacata tttaacactg gtatcacaag cgtgggcact   780
gaaacaagga tngangggaac nggatcagga tgttagccg                         819

<210> SEQ ID NO 237
<211> LENGTH: 483
<212> TYPE: DNA
<213> ORGANISM: Homo Sapien
<220> FEATURE:
<221> NAME/KEY: misc_feature
<222> LOCATION: (1)...(483)
<223> OTHER INFORMATION: n = A,T,C or G

<400> SEQUENCE: 237
agcttgacct gattacgcca agcttggtac cgagctcgga tccactagta acggccgcca    60
gtgtgctgga attcgccctt agcgtggtcg cggccgaggt actaagctca gcatgtctca   120
tggtcaatta ctgcgtattt ccaaaaaatg tgttgtttgg tcttgagaaa attctttagc   180
cccttgacac cagaattatc tccactgtag aaaaaataga caattatagt ctaacaggta   240
aatcacaaaa attcttcagc cacacttcct gggttcaaat gtggttttc tactcagtaa   300 tattgtaacc ctgggcaagt tatttaactt gtctaagtct cagtttctcc atctgtaaaa   360
tgaggataat cacaatatct actacataat gttcttctga agatgtaatg agataatcca   420
tgtnaaatat tcanacagca cataggaatg ggtcatttaa tgtttatcat tacttgccta   480
ttt                                                                  483

<210> SEQ ID NO 238
<211> LENGTH: 815
<212> TYPE: DNA
<213> ORGANISM: Homo Sapien
<220> FEATURE:
<221> NAME/KEY: misc_feature
<222> LOCATION: (1)...(815)
<223> OTHER INFORMATION: n = A,T,C or G

<400> SEQUENCE: 238
gggcccntnn agctgctcgn cggccgccag tgtgatggat atctgcagaa ttcgcccttt    60
cgagcggccg cccgggcagg taccattatt tttcattcaa taccatatgt ctgaaaaata   120
ggcaagtaat gataaacatt aaatgaccca ttcctatgtg ctgtctgaat atttacatg   180 gattatctca ttcatcttc agaagaacat tatgtagtag atattgtgat tatcctcatt   240
ttacagatgg agaaactgag acttagacaa gttaaataac ttgcccaggg ttacaatatt   300
```

```
actgagtaga aaaaccacat ttgaacccag gaagtgtggc tgaagaattt ttgtgattta      360
cctgttagac tataattgtc tatttttcct acagtggaga taattctggt gtcaaggggc      420
taaagaattt tctcaagacc aaacaacaca ttttttggaa atacgcagta attgaccatg      480
agacatgctg agcttagtac ctcggccgcg accacgctaa gggcgaattc cagcacactg      540
gcggccgtta ctagtggatc cgagctcggt accaagcttg gcgtaatcat ggtcatagct      600
gtttcctgtg tgaaattgtt atccgctcac aattccacac aacatacgag ccggaagcat      660
aaagtgtaaa gcctggggtg cctaatgagt gagctaactc acattaattg cgttgcgctc      720
actgnccgct ttccagtcgg gaaacctgtc gtgccagctg cattaatgaa tcggncaacg      780
cgccggggag aggcngnttg cgtattgggc gctct                                815

<210> SEQ ID NO 239
<211> LENGTH: 483
<212> TYPE: DNA
<213> ORGANISM: Homo Sapien
<220> FEATURE:
<221> NAME/KEY: misc_feature
<222> LOCATION: (1)...(483)
<223> OTHER INFORMATION: n = A,T,C or G

<400> SEQUENCE: 239
actatgacct gattacgcca agcttggtac cgagctcgga tccactagta acggccgcca       60
gtgtgctgga attcgccctt agcgtggtcg cggccgaggt acttttttt tttttttttt      120 ttttttttta gcgagcaagt atggnttatt acggacaaat ggtagaaaaa tgttactaat      180
atccatagat aagttcctta agtcatgtag agagactgtt attaaaagtt tgctgcattt      240
ttctattgaa tcaagaacta gctaccagtt acagtgcctt ctaaacacac agttagcttt      300
gctttatcaa taaccaaata ataaactagg tcccaatggt tttgtccaca tntagattgt      360
tcaggtgatc aggaactctt ttatttgtgt gctttagctt ttagttcttg gttatatctc      420
caaatacgaa aaagctgaga ggctcctact gcccccacaa agaaattaac agcaaacaga      480
ctt                                                                    483

<210> SEQ ID NO 240
<211> LENGTH: 815
<212> TYPE: DNA
<213> ORGANISM: Homo Sapien
<220> FEATURE:
<221> NAME/KEY: misc_feature
<222> LOCATION: (1)...(815)
<223> OTHER INFORMATION: n = A,T,C or G

<400> SEQUENCE: 240
gggcctntna gctgctcgac ggccgccatg tgatggatat ctgcagaatt cgcccttcg       60 agcggccgcc cgggcaggta caaccatcca gcaggtccca gaacagtttt cttctgggct      120
ccaattatga aatgggggtt ggtgtgtgct ggattggctg atatggccag acctgcagaa      180
aaacttagca cagctcaatc tgctgttttg atggctacag ggtttatttg gtcaagatac      240
tcacttgtaa ttattccaaa aaattggagt ctgtttgctg ttaatttctt tgtggggca      300 gtaggagcct ctcagctttt tcgtatttgg agatataacc aagaactaaa agctaaagca      360
cacaaataaa agagttcctg atcacctgaa caatctagat gtggacaaaa ccattgggac      420
ctagtttatt atttggttat tgataaagca agctaactg tgtgtttaga aggcactgta      480
actggtagct agttcttgat tcaatagaaa aatgcagcaa acttttaata acagtctctc      540
```

```
tacatgactt aaggaactta tctatggata ttagtaacat ttttctacca tttgtccgta      600
ataaaccata cttgctcgct aaaaaaaaaa aannnnnaaa aaaaaaagta cctcggccgc      660
gaccacgcta agggcgaatt ccagcacact ggcggccgtt actagtggat ccagctcgg      720 taccaagctt ggcgtaatca tgggtcatag ctggttcctg tgtgaaatgg tatccgntca      780
caattncaca caacatacga accggaagcc ttaag                                 815
```

<210> SEQ ID NO 241
<211> LENGTH: 486
<212> TYPE: DNA
<213> ORGANISM: Homo Sapien
<220> FEATURE:
<221> NAME/KEY: misc_feature
<222> LOCATION: (1)...(486)
<223> OTHER INFORMATION: n = A,T,C or G

<400> SEQUENCE: 241

```
agctatgacc atgattacgc caagcttggt accgagctcg gatccactag taacggccgc       60
cagtgtgctg gaattcgccc ttagcggccg cccgggcagg tacttcccac cactggaaat      120
gttagcataa aagaacttgg agaggaaaaa agtattaaca aaactgcagt ctgcactctt      180
taaacctgtt taaggctctt catcctggtt agcaaaaggt gtgaatgtaa tgtgatggaa      240
tttaaaagtt ttatgagacc aggcacagtg gctcacgact gtaattccag cagtttagga      300
agccgaagtg tgcagatcac ctgaggtccg gagaccagcc tggccaacat ggtgaaaccc      360
tgtctctact agaaatacaa aaattagcca ggtgtggtgg cgggcgcctg taatcccaac      420
tactcaggag gctgaggcta gagaatcact tgaacccagc angcggaggt tgcggtgagt      480 cganat                                                                486
```

<210> SEQ ID NO 242
<211> LENGTH: 481
<212> TYPE: DNA
<213> ORGANISM: Homo Sapien
<220> FEATURE:
<221> NAME/KEY: misc_feature
<222> LOCATION: (1)...(481)
<223> OTHER INFORMATION: n = A,T,C or G

<400> SEQUENCE: 242

```
anttgacctg attacgccaa gcttggtacc gagctcggat ccctagtaac ggccgccagt       60
gtgctggaat tcgcccttcg agcggccgcc cgggcaggta catcagtgtt cattttatta      120
tttcttacac tgtcttcatg acttacacat aatatttgc tagttttaaa acataagatg       180
tgataataat ctaaacagac caaggaaat aaatgaatat gattaaaaaa agacagagaa       240
taagccctgt ctgatggaaa gcataacaaa gcaggtagaa caactgtcag gaatgcttga      300
tccaataaag ctaggtttgt gatccacaac acttcagcat tttaatgtga ttttttgatgt     360 tngcttttg caatggtgat tctcagttgc ctccctcctg tgtctttaca agctgaaatc       420
aagtgaagct acttctgact ttttctaaaa cttaaaccca acatgaaggt ctgcgtattc       480
t                                                                     481
```

<210> SEQ ID NO 243
<211> LENGTH: 824
<212> TYPE: DNA
<213> ORGANISM: Homo Sapien
<220> FEATURE:
<221> NAME/KEY: misc_feature
<222> LOCATION: (1)...(824)
<223> OTHER INFORMATION: n = A,T,C or G

<400> SEQUENCE: 243

```
cnanngggcc tntnnagcat gctcgacggc cgccatgtga tggatatctg cagaattcgc      60
ccttagcgtg gtcgcggccg aggtacataa tactttagat aaacattttt agaataactt     120
tattataact cgataagcaa ataatccaa accttttatac atttctacaa ggatagtcac     180
atatgtcaat ttttcggttt cctctcgtgc ctattttgtc tcctgagccg gccccttcc     240
agctgacacg tgtgctccgt gttctcccac aatagtgtga cctggcctga gtccatgccg     300
ccgtgagcct ccttctgtg cttacaacag cagcctgcct gatgtcagtt atggactatt     360
cttctttca gcctcatttc agggtcctct gcctcttaga gctgctgctg tagcttagct     420
agagacccgc tgctgttgca tcatggaaaa gtgccacata cgtgcacatg tgaaagaata     480
cgcagacctt catgttgggt ttaagttta gaaaagtca gaagtagctt cacttgattt     540
cagcttgtaa agacacagga gggaggcaac tgagaatcac cattgcaaaa agcaaacatc     600
aaaaatcaca ttaaaatgct gaagtgttgt ggatcacaaa cctagcttta ttggatcaag     660
cattcctgac agttgttcta cctgcttttg ttatgctttc catcagacag ggcttattct     720
ctgtcttttt taatcatatt catttatttc ctttggtctg tttagattat tatcacatct     780
tatgttttaa aactagcaaa atattatgtg taagtcatga agnt                      824
```

<210> SEQ ID NO 244
<211> LENGTH: 483
<212> TYPE: DNA
<213> ORGANISM: Homo Sapien
<220> FEATURE:
<221> NAME/KEY: misc_feature
<222> LOCATION: (1)...(483)
<223> OTHER INFORMATION: n = A,T,C or G

<400> SEQUENCE: 244

```
actatgacct gattacgcca agcttggtac cgagctcgga tccactagta acggccgcc      60
agtgtgctgg aattcgccct ttcgagcggc cgcccgggca ggtacgcggg ggcagggtgt     120
ttaatcgtcg ccaagcggga cttactgcaa gctatcaaat ctgaggtctt atttttgttga    180
gtcgaaagtg aaattttcct ttggccaacg tgacagggct ttgtttggtg gtaaaaaggg     240
ttactagaca ccctcattc cactgccact ggagggcgca tttctcagct cttgctcttc     300
aaacctgctg aaaggaattc ctagatctaa acaccagcat ttgacattgt gcagcaaana     360
aatggttatg ganaagccca gtccgctgct tgtanggcgg gagtttgtga ggcaatatta     420
tactttgctg aataaagctc cggaatattt acacaggttt tatggcagga attcttccta     480
tgt                                                                    483
```

<210> SEQ ID NO 245
<211> LENGTH: 822
<212> TYPE: DNA
<213> ORGANISM: Homo Sapien
<220> FEATURE:
<221> NAME/KEY: misc_feature
<222> LOCATION: (1)...(822)
<223> OTHER INFORMATION: n = A,T,C or G

<400> SEQUENCE: 245

```
ttgggcccnt nnagcatgct cgacggccgc catgtgatgg atatctgcag aattcgccct      60
tagcgtggtc gcggccgagg tacttcccct cgaaacataa tcggttttgc aattaagatt     120
ctctgaactg gttcagagtc atcaaaaacc acaaaaccaa aatttggaag ctttccccca     180
```

-continued

| | |
|---|---|
| acacccttgg tattgatgcg aagttccaca acgtttccaa aactcatgaa gaattccttt | 240 |
| agctcatttt catcaatatc atgtggcaag ttaccaacaa aaagttgatg actatctgga | 300 |
| tagcgaatta ttctacggtt gtcagagtca ttctgttcca tatctcctct gcctggtctt | 360 |
| ggtcctctag gaggaaaacc aggtcgttct ctaggtcgtt gttcacgcac acgaggtggc | 420 |
| tgagattgaa cttctggttt agcttcgact cttggctttg gtggttcttg tggcagagaa | 480 |
| acaggttctg ccggaggagg agtagtagat ttctcctcta gttcttctaa gttcttctcc | 540 |
| tccacttgtg gtttcagctc ttcagtcttt gtttcagatt ctggctcagg ttcaggttca | 600 |
| tgagaggatt cttccaaagg ctcctctatg ccattagtca cagggtgagc ttcatagtaa | 660 |
| ccactgttag cattttcttg cacaggttca ggagatggtt gnctttcttc ttggtcctct | 720 |
| tctacttcat cttctgattc ttcatcaaag ttcangctca gaatcaccaa acacttnatc | 780 |
| ttcataacga aacatatcat tgtgaacata aaatttattt gg | 822 |

<210> SEQ ID NO 246
<211> LENGTH: 482
<212> TYPE: DNA
<213> ORGANISM: Homo Sapien

<400> SEQUENCE: 246

| | |
|---|---|
| actatgacct gattacgcca agcttggtac cgagctcgga tccactagta acggccgcca | 60 |
| gtgtgctgga attcgccctt agcgtggtcg cggccgaggt actttttttt tttttttttt | 120 |
| aaccaactca atatgtgttt gatgatagtg aattgataaa acccgaagct ttccctgta | 180 |
| aatcttacat ctttgccttt aaagaatggg ttacaaccat cactagatca cagtagtgcc | 240 |
| taatgaaggt tgagaaccgt aggagaggct ctcatgctgt aaataatgtt gcaggctaat | 300 |
| aacctttcat cacttccttt gtgcgcttcc tgccttaagt gacaagtagc aacatggctt | 360 |
| gggtcccctg tgcagcatca gcttatgctg ccacaagtca gtttgcaccc taggtgccca | 420 |
| ggagctagta tccttagatc tttctatcgc taacttaatt ctcttcgtta tttatctgac | 480 |
| cc | 482 |

<210> SEQ ID NO 247
<211> LENGTH: 816
<212> TYPE: DNA
<213> ORGANISM: Homo Sapien
<220> FEATURE:
<221> NAME/KEY: misc_feature
<222> LOCATION: (1)...(816)
<223> OTHER INFORMATION: n = A,T,C or G

<400> SEQUENCE: 247

| | |
|---|---|
| gggccttnga gctgctcgan cggccgccat gtgatggata tctgcagaat tcgcccttc | 60 |
| gagcggccgc ccgggcaggt actttaattt tgcttgttca aatgatctac acttacatttt | 120 |
| tgcaaatctt ttttttaaat tttttaaatt ttatattttt tttccagcca actcaaggcc | 180 |
| aaaaaaaatt tcttaatata gttattatgc gaggggaggg gaagcaaagg agcacaggta | 240 |
| gtccacagaa taagacacaa gaaacctcaa gctgtgaggt caatttgtaa ttaaaagaat | 300 |
| actaagatta gatgaacaca acactcagaa atactctagg agggctgaaa agaaggaac | 360 |
| agatgttaac aaaacaaatt aaggctgctg gggaacctga gtccatgtta agcttgggtt | 420 |
| gactgtaaag aatttttttt tttttaatgc aagttagaca tggagttaga gggtcagata | 480 |
| aataacgaag agaattaagt tagcgataga aagatctaag gatactagct cctgggcacc | 540 |
| tagggtgcaa actgacttgt ggcagcataa gctgatgctg cacaggggac ccaagccatg | 600 |

```
ttgctacttg tcacttaagg caggaagcgc acaaaggaag tgatgaaagg ttattagcct      660
gcaacattat ttacagcatg agagcctctc ctacgggtct caaccttcat taggcactac      720
tgngatctag tgatggttgt acccattctt taaaggcaaa gatgtaagat ttacagggaa      780
aagcttcggg ttttatcaat cctatcatca acacng                                816

<210> SEQ ID NO 248
<211> LENGTH: 482
<212> TYPE: DNA
<213> ORGANISM: Homo Sapien

<400> SEQUENCE: 248
actatgacct gattacgcca agcttggtac cgagctcgga tccactagta acggccgcca       60
gtgtgctgga attcgccctt tcgagcggcc gcccgggcag gtactctttg ggcattaatg      120
ccttctctgt aattatatct cgttttttgct tggcagtgac ctacccagta attgcatcgt     180
gtattgccat gaaaggtaaa cacattgtga actgaactta ccaagcagat tctgtgagaa      240
agcactggtt ggggctgaac actgttgaca catcattttt attggaagag tattaactgg      300
tgcctcttct gaaacacacc aacccatatt cctctgctcc cccaaagctg tttctgatcc      360
tgctgggagc aactaactag ttattatgca catctgctcc agaccccagct ctttaacttc     420 atggttttac agcttgtttt ttctttttct tttcttttct ttttttttaa aaaagcacct      480
tt                                                                      482

<210> SEQ ID NO 249
<211> LENGTH: 821
<212> TYPE: DNA
<213> ORGANISM: Homo Sapien
<220> FEATURE:
<221> NAME/KEY: misc_feature
<222> LOCATION: (1)...(821)
<223> OTHER INFORMATION: n = A,T,C or G

<400> SEQUENCE: 249
ggcctctnag ctgctcgacg gccgccatgt gatggatatc tgcagaattc gcccttagcg       60
tggtcgcggc cgaggtactt tatgaatttg gggtaggtaa agtttgtatt ttatcttaaa      120
catgttttct atgatgaaaa ggaacaaaat tgtaaaaaat gaggatcttc cctctaaagg      180
tttcaaagcg ttagaggaca tgcaattaaa tgttgttaca ccttgaacaa tgagcctctt      240
gagtttgtag gaagggcaga ccggctccat taccaacaac tttggggtag aaagcacagc      300 tctcctctttt tacccagcac aaatgcaatc ctgattataa actatttgt gtttctaaat     360 acaaccaaag gaaatcttag agaaacataa attagaaacc tcttttatta aggggaaaca      420
acaaaaaaag gtgctttttt aaaaaaaaag aaaagaaaag aaaagaaaa aacaagctgt      480 aaaaccatga agttaaagag ctgggtctgg agcagatgtg cataataact agttagttgc      540
tcccagcagg atcagaaaca gctttggggg agcagaggaa tatgggttgg tgtgtttcag      600
aagaggcacc agtaatatct cttccaataa aaatgatgtg tcaacagtgt tcagccccaa      660
ccagtgcttt ctcacagaat ctgcttggta agttcagttc acaatgtgtt tacctttcat      720
ggcaatacac gatgcaatta ctgggtaggt cactgccaag caaaaaccga agatntaatt      780
tcccgagaag gcattaatgc ccaaagagta cctgccccgg n                          821

<210> SEQ ID NO 250
<211> LENGTH: 481
<212> TYPE: DNA
```

```
<213> ORGANISM: Homo Sapien

<400> SEQUENCE: 250
acttgacctg attacgccaa gcttggtacc gagctcggat ccactagtaa cggccgccag      60
tgtgctggaa ttcgccctta gcgtggtcgc ggccgaggta caacattgat gttttaatat     120
agaatgaagt gcttgctaca cagtcaagta aatcaacata tccattacca cacacacttt     180
tcttttctga ggagcggtaa gagtacttta attttgcagt tattgattaa ttaaaaaaca     240
cagttgtttt cagcatttcc tagttacagt agtgcatagg aaattccatt ctaaacaaag     300
aagtaattaa tgaaataaca acacacctta acatttaca ttgataggtt acagtttaca     360
aggtgctttc acatacatta tttcatttga ttcttacaac aagcagaaaa aacagtggga     420
aagattttttt ttttcaggct tacaatgagt attttcaggc caatgggcag ttaacacaag     480
g                                                                    481

<210> SEQ ID NO 251
<211> LENGTH: 803
<212> TYPE: DNA
<213> ORGANISM: Homo Sapien
<220> FEATURE:
<221> NAME/KEY: misc_feature
<222> LOCATION: (1)...(803)
<223> OTHER INFORMATION: n = A,T,C or G

<400> SEQUENCE: 251
gggccttnna gctgctcgnc ggccgccagt gtgatggata tctgcagaat tcgcccttc      60
gagcggccgc ccggcaggta cactaaatta gaatatttt aaagtatgta acattcccag     120
tttcagccac aatttagcca agaataagat aaaaacttga ataagaagta agtagcataa     180
atcagtattt aacctaaaat tacatatttg aaacagaaga tattatgtta tgctcagtaa     240
ataattaaga gatggcattg tgtaagaagg agccctagac tgaaagtcaa gacatctgaa     300
tttcaggctg gaaaactatc agtatgatct cagcctcagt tctcttgtct gtaaaatgga     360
agaactggat taggcagttt gtaagattcc tcctaacttt cacagtcgat gacaagattg     420
tcttttttatc tgatattttg aagggtatat tgctttgaag taagtctcaa taaggcaata     480
tattttaggg catctttctt cttatctctg acagtgttct taaaattatt tgaatatcat     540
aagagccttg gtgtctgtcc taattccttt ctcactcacc gatgctgaat acccagttga     600
atcaaactgt caacctacca aaacgatat tgtggcttat gggtattgct gtctcattct     660
tggtatattc ttgtgttaac tgcccatggc ctgaaaatac tcattgtaag cctgaaaaaa     720
aaaatctttc ccactggttt ttctgcttgg tgtaagaatc aaatgaaata tggatgtgaa     780
agcccttgta actgtaccta tcn                                             803

<210> SEQ ID NO 252
<211> LENGTH: 500
<212> TYPE: DNA
<213> ORGANISM: Homo Sapien
<220> FEATURE:
<221> NAME/KEY: misc_feature
<222> LOCATION: (1)...(500)
<223> OTHER INFORMATION: n = A,T,C or G

<400> SEQUENCE: 252
tacnccaann tttgacctga ttacgccaag cttggtaccg agctcggatc cactagtaac      60
ggccgccagt gtgctggaat tcgcccttag cgtggtcgcg gccgaggtac agatgaaaag     120
aagtggtgtt aatgacctac ctgcaccgat aataaagcaa atagaatgat tatatacatt     180
```

```
aagatcagct tgattaaaaa taaattttat atgcaggtaa attgatcatt aaaatgaacc      240
cagtttaact cttctcgtgt gttgttttaa ggtaggccac tgaaacgcag agataaaatc      300
anatggggaa aattaaaagc naagaaaaaa attacaaaac aagtgggtta agccatggat      360
tcttaaccaa accctggact aaatgtgcca aagtgctttg aaaatttcca ctgccagcna      420
tggntggtaa agtcantttg gcaaaaaaaa ggtggttnga aaaaaaactn acctttttaaa     480 ttcccacctt ggatctggcn                                                 500
```

```
<210> SEQ ID NO 253
<211> LENGTH: 831
<212> TYPE: DNA
<213> ORGANISM: Homo Sapien
<220> FEATURE:
<221> NAME/KEY: misc_feature
<222> LOCATION: (1)...(831)
<223> OTHER INFORMATION: n = A,T,C or G

<400> SEQUENCE: 253
gnnnnnnnnn gnnnnnnnnn ntttnnantg ggcctctnna gcatgctcga cggccgccat      60
gtgatggata tctgcagaat tcgcccttt c gagcggccgc ccgggcaggt actatatttg     120
tgagcctagg gtaggggcac tgctgcaact tctgctttca tcccatgcct catcaatgag     180
gaaagggaac aaagtgtata aaactgccac aattgtattt taattttgag gtatgatatt     240
ttcagatatt tcataatttc taacctctgt tctctcagta aacagaatgt ctgatcgatc     300
atgcagatac aatgttggta tttgagaggt tagttttttt tcctacactt ttttttgcca     360
actgacttaa caacattgct gtcaggtgga aatttcaagc acttttgcac atttagttca     420
gtgtttgttg agaatccatg gcttaaccca cttgttttgc tattttttttc tttgctttta     480 attttcccca tctgattta tctctgcgtt tcagtggcct accttaaaac aacacacgag      540
aagagttaaa ctgggttcat tttaatgatc aatttacctg catataaaat ttatttttaa     600
tcaagctgat cttaatgtat ataatcattc tatttgcttt attatcggtg caggtaggtc     660
attaacacca cttcttttca tctgtacctc ggccgcgacc acgctaaggg cgaattccag     720
cacactggcg gcccgttact agtggatccg agctcggtac caagcttggc gtaatcatgg     780
gtcatagctg tttcctgtgt gaaattggta tccgntcaca attcccacan g              831
```

```
<210> SEQ ID NO 254
<211> LENGTH: 514
<212> TYPE: DNA
<213> ORGANISM: Homo Sapien
<220> FEATURE:
<221> NAME/KEY: misc_feature
<222> LOCATION: (1)...(514)
<223> OTHER INFORMATION: n = A,T,C or G

<400> SEQUENCE: 254
cacttgacnt gatcgccaac ttggtaccga cntcgnntcc attattaccg gacacttgac      60
tgatacgcca ncttggtacc gactcggacc actagtaacg gncgccagtg tgctggaatt     120
cgcccttgag cggccgcccg ggcaggtacc tctaatgcag gctaataaat ttaagctaat     180
tatttatgct acctgtgctg tggtggtttc ctatcagcag ccaaatataa cctcacagtt     240
gttttgctgt ttttgctttc acaaagagc tattaaccaa cttaaaaatg ttttttgatt     300
gaaggatgct tagggatga gaggatatca acaatataag cccatgccaa atccccattt     360
cttatcatta aaactgacct gacattaaag caatgcttaa ttttttacca taagagtgaa     420
```

| | |
|---|---|
| attttgagat tataatttta aagtgtaaaa tatttacact taaattacac ttataatttt | 480 |
| aaagtgtata atatttacac agattaaaat aaaa | 514 |

<210> SEQ ID NO 255
<211> LENGTH: 830
<212> TYPE: DNA
<213> ORGANISM: Homo Sapien
<220> FEATURE:
<221> NAME/KEY: misc_feature
<222> LOCATION: (1)...(830)
<223> OTHER INFORMATION: n = A,T,C or G

<400> SEQUENCE: 255

| | |
|---|---|
| nnnnnngncn nnnnnnannn nnnnnnnant gggcctctnn agcntgctcg acggccgcca | 60 |
| tgtgatggat atctgcagaa ttcgccctta gcgtggtcgc ggccgaggta cttttttttt | 120 |
| ttttccagat gaagtcttgc tctgttgccc aggctggagc gcagtggcac aatctcagct | 180 |
| cactgaaacc ttcgccccct gggctcaagc tagccagtct tttagtaaac atttagtcaa | 240 |
| caaatctgca attataacgg aggtttgatt tttgtttgttt ttgttttgtttt ttaagtcact | 300 |
| ctgtgtttgt aatatcaatt tacttttcaa gtttagaatg ttttgcttca ttgtttccca | 360 |
| tattttattt taatctgtgt aaatattata cactttaaaa ttataagtgt aatttaagtg | 420 |
| taaatatttt acactttaaa attataatct caaaatttca ctcttatggt aaaaaattaa | 480 |
| gcattgcttt aatgtcaggt cagttttaat gataagaaat ggggatttgg catgggctta | 540 |
| tattgttgat atcctctcat cccctaagca tccttcaatc aaaaaacatt tttaagttgg | 600 |
| ttaatagctc ttttgtgaaa gcaaaaacag caaaacaact gtgaggttat atttggctgc | 660 |
| tgataggaaa ccaccacagc acaggtagca taaataatta gcttaaattt attagcctgc | 720 |
| attagaggta cctgcccggg cnggccgtca agggcgaatt ccagcacact ggcggccgtt | 780 |
| ctagtggatc cgactcggtc cagcttgcgt aatcatggtc atagctgttg | 830 |

<210> SEQ ID NO 256
<211> LENGTH: 524
<212> TYPE: DNA
<213> ORGANISM: Homo Sapien
<220> FEATURE:
<221> NAME/KEY: misc_feature
<222> LOCATION: (1)...(524)
<223> OTHER INFORMATION: n = A,T,C or G

<400> SEQUENCE: 256

| | |
|---|---|
| cnnnnnnnna ncntnanacn nnnnnntngn nnnnagnnn nnnnnnnnn nnnnnnnan | 60 |
| actatgactg attacgccan cttggtaccg actcggatcc actagtaacg gccgccagtg | 120 |
| tgctggaatt cgcccttagc gtggtcgcgg ccgaggtaca ttacttggtg ttaacattgt | 180 |
| tggcagtggt agccccttt cagaaagcaa cttgctgtaa gtcagggtgt ccgttccaac | 240 |
| cttcagccag tgaaaaggta gtaacaaatg gtaaacaaga gaatgattgt ttaaacctat | 300 |
| ctgtggacac ttaatgcaac tgtttaaaaa tgataatcac gagttatgta gcaacgtgga | 360 |
| aatatattta cagaacatta agtggagaaa gcaggacacg aaagtatatt tatactacag | 420 |
| ttataactca acagttcatt tatatgctgn tcatttaaca gttcatttaa acagttcatt | 480 |
| ataactgttt aaaatatat atgcttatag tcaaaagctg ttgg | 524 |

<210> SEQ ID NO 257
<211> LENGTH: 814
<212> TYPE: DNA
<213> ORGANISM: Homo Sapien
<220> FEATURE:
<221> NAME/KEY: misc_feature
<222> LOCATION: (1)...(814)
<223> OTHER INFORMATION: n = A,T,C or G

<400> SEQUENCE: 257

| | | | | |
|---|---|---|---|---|
| ntgggcctct agaagcatgc tcgagcggcc gccagtgtga tggatatctg cagaattcgc | | | | 60 |
| ccttgagcgg ccgcccgggc aggtactttt tttttttttt tttttttttt tttgatattt | | | | 120 |
| attttaact ttattttat tgntgacact attacagata gaatgaccac aaccatatta | | | | 180 |
| acaaaccaaa aacctgtgca cagaaacaag atgaagaaaa tatatcaaga tgttaaccac | | | | 240 |
| actctttgga tggtgaaaac atgggtgagt ttctcttcta catttctgta acttcaaagt | | | | 300 |
| ttctataatg aacacatttc atatataatg gaaatatatg tagtaaaggt ggactaccaa | | | | 360 |
| aacactagaa tgatgacctt tcaaggaaac cgaaacaaaa taaccataat cccacaacaa | | | | 420 |
| ccacacaact atttcttgct tttcatcttt cttcccatct ttgacattta tgcatactta | | | | 480 |
| tcactaacac cctaataatc acagactagt gcacagatca agatgttaac agttaattgt | | | | 540 |
| tgttgggtgt tgggaatatg tgtgaatttt ctttactgaa tttccaaagt tttgtatgag | | | | 600 |
| tatgtattat atttgtaatg gaaatacat acataaaatt tattaccaaa acaccaaaga | | | | 660 |
| ttatttaagg aatttgagac aaaatatta accaaattcc cacaatgaca acactatttt | | | | 720 |
| agttattttc cacatctttt catttaaaga ctttatgcac acatatttaa cactgntatc | | | | 780 |
| acaagcgtgt gcactgnaac aggattgagg aaan | | | | 814 |

<210> SEQ ID NO 258
<211> LENGTH: 474
<212> TYPE: DNA
<213> ORGANISM: Homo Sapien
<220> FEATURE:
<221> NAME/KEY: misc_feature
<222> LOCATION: (1)...(474)
<223> OTHER INFORMATION: n = A,T,C or G

<400> SEQUENCE: 258

| | | | | |
|---|---|---|---|---|
| acagctatga cctgattacg ccaagcttgg taccgagctc ggatccacta gtaacggccg | | | | 60 |
| ccagtgtgct ggaattcgcc cttagcgtgg tcgcggncga ngtacattat ttggaggact | | | | 120 |
| taaaatctgn atgtggacat ggtcccaact tantgtccgt taactagtta tccaaattgt | | | | 180 |
| aanagctaca gaaagcccag ttgaggggta antgtgcctg gntcacacag cctgcaccct | | | | 240 |
| gtcacctcgg caatgagcca gtgtgggca ctggggactt ctaacccttg gattgctctt | | | | 300 |
| tttgacctgt gcataccttc taattgnaaa atatatttca gaccgagagt acntgcccgg | | | | 360 |
| gcggccnctc aaaagggcga attctgcaaa tatccatcac atggcggccg ntngagcatg | | | | 420 |
| catctaggag ggcncaattc ccctatagng agtngtatta caattcactg gcnc | | | | 474 |

<210> SEQ ID NO 259
<211> LENGTH: 809
<212> TYPE: DNA
<213> ORGANISM: Homo Sapien
<220> FEATURE:
<221> NAME/KEY: misc_feature
<222> LOCATION: (1)...(809)
<223> OTHER INFORMATION: n = A,T,C or G

<400> SEQUENCE: 259

| | | | | |
|---|---|---|---|---|
| ntgggcccnt agangcatgc tcgncggccg ccatgtgatg gatatctgca gaattcgccc | | | | 60 |
| tttcgagcgg ccgcccgggc aggtactcac ggtctgaaat atattttaca attagaaggt | | | | 120 |

-continued

| | |
|---|---|
| atgcacaggt caaaaagagc aatccaaggg ttagaagtcc ccagtgcccc acactggctc | 180 |
| attgccgagg tgacagggtg caggctgtgt gagccaggca cacttacccc tcaactgggc | 240 |
| ttctgtagct ttacaatttg gataactagt tagcggacag tagttgggac atgtcacata | 300 |
| cagatttgag tcctccaata atgtacctcg gccgcgacca cgctaagggc gaattccagc | 360 |
| acactggcgg ccgttactag tggatccgag ctcggtacca agcttggcgt aatcatggtc | 420 |
| atagctgttt cctgtgtgaa attgttatcc gctcacaatt ccacacaaca tacgagccgg | 480 |
| aagcataaag tgtaaagcct ggggtgccta atgagtgagc taactcacat taattgcgtt | 540 |
| gcgctcactg cccgctttcc agtcgggaaa cctgtcgtgc cagctgcatt aatgaatcgg | 600 |
| ccaacgcgcg gggagaggcg gtttgcgtat tgggcgctct ccgcttcct cgctcactga | 660 |
| ctcgctgcgc tcggtcgttc ggctgcggcg agcggtatca gctactcaaa ggcggtaata | 720 |
| ccgttatnca cagaatcang ggatacgcag gaaagaacat gtgagcaaaa ngccacaaaa | 780 |
| ggccaggaac cgtaaaaagg ccgcgtttg | 809 |

<210> SEQ ID NO 260
<211> LENGTH: 713
<212> TYPE: DNA
<213> ORGANISM: Homo Sapien
<220> FEATURE:
<221> NAME/KEY: misc_feature
<222> LOCATION: (1)...(713)
<223> OTHER INFORMATION: n = A,T,C or G

<400> SEQUENCE: 260

| | |
|---|---|
| ctctttaaac gccagctcga ntccganntc tatccntgac aannnnngtn ccggnctgga | 60 |
| attcgncctt tcgagcggcc gcccgggcag gtacttgagt tcatgggcat ctctcccgcc | 120 |
| gcctctcagc ctatctgcac catgtctcac acgttcagtt gcagctctta ccgttttgaa | 180 |
| ggcgcacgtg ggcaagaagt cctgggcagc acaagaaagt caatcacgtt gagacagaga | 240 |
| gagcaggaga ggaagtgggc cccagtagaa gtgggcgaga gagcgttggg tgggaacgtg | 300 |
| gcacgagaga gagaaattat gagattgaga gagagagaga gagagagaga gagagagaga | 360 |
| gaaagagana ganagaggga aaganaaaga gacagagaaa agaaactatt gttggttaaa | 420 |
| atgccagcga aaagtccatg ggggtgaatg agtccggcaa tggncangga gttagcagct | 480 |
| tggcgtagtg tctttcactg ntttggctgt cttgagaata gcattcnacn ccgactgtgg | 540 |
| ttccccanca gactttagnc ngttgcccng ncttgaattg ccggaccaag gttaacatag | 600 |
| gcttttcggn tctnaatatt tttggggctn gaatantcgg aaccntttgg gctgggccat | 660 |
| ttacccgntn cnncntgggt nnnacatttt tnctggntaa tcccgccttt tng | 713 |

<210> SEQ ID NO 261
<211> LENGTH: 722
<212> TYPE: DNA
<213> ORGANISM: Homo Sapien
<220> FEATURE:
<221> NAME/KEY: misc_feature
<222> LOCATION: (1)...(722)
<223> OTHER INFORMATION: n = A,T,C or G

<400> SEQUENCE: 261

| | |
|---|---|
| acgcanttag gtaccgagct cggatcccta gtaacggccg ccagtgtgct ggaattcgcc | 60 |
| cttagcgtgg tcgcggcccg aggtactcct cagccatgcc gaaggtcctc ttccgggact | 120 |
| cttcgatggc agacagcagg gcattgtcct tctcattctt caggaagccc tgcagctctt | 180 |
| aaatttaagg agttacagaa cggtcgatgc tgncgatcac tgcagctctt ccaaaccttc | 240 |

```
ttatatgaga tgagctctgt cggaaccagt gctcaagttt ttcccacccc aaactgcctg    300
aattgaggga tggggggtggg gagaaggaca gagagaagag aaaaagagag aagaagana    360 aaggaaaaga acaacccctc tgcaagtgct gatgtgactg aagcactaaa gagtcaaatt    420
aaacaatgaa gattgcaggg tcccttaaa aagggtgcac tgcagncccc ngagcacanc    480
natcccattc gnttgngccg ctncacanat tctagagaan tcnnccatca tgtttgaaan    540
gcncaaaant gatgggannt cccgnntacg cggggactta attctgcctt gggaaatcaa    600
ggaanacttt gnttggangc ggcanttnaa anntggcctt aagaangnng tgngaatttg    660
ttggccaaac nantngaaag gtnttccggc cgatnggtcc ctgattttta aggattnnaa    720 ng                                                                   722
```

<210> SEQ ID NO 262
<211> LENGTH: 705
<212> TYPE: DNA
<213> ORGANISM: Homo Sapien
<220> FEATURE:
<221> NAME/KEY: misc_feature
<222> LOCATION: (1)...(705)
<223> OTHER INFORMATION: n = A,T,C or G

<400> SEQUENCE: 262

```
acgctttaaa cnccagcttg gtaccgagct cggatccta gtaacggccg ccagtgtgct    60
ggaattcgcc cttgccgccc gggcaggtac ctgatatttt gaacttttaa ttgctatcaa    120
atttcagctc tggttttatg cattgttgta atttctcagt gaatcccagt gcttctttcc    180
ttcttgaaaa atgccatttc gcccaggcgc ggtggctcat gcttgtaatc ccagcacttt    240
ggtaggccga ggtgggtgga tcagctgagg tctgtagttc aagaccagcc tggctaacat    300
gatgaaaccc tgtctctacc aaaatacaa aaaaaaacta gccaggcatg gtgttgtatg    360
cctgtaatcc cagctactca ggaggctgag acaggagaat cgcttgaacc tgggaggtgg    420
aggttgcagt gagccaagat cgcgccactg cactncaacc tgggcaacag agtgagactc    480
catctcaaaa naannaaaaa ggaaaatgcc atttcttggg cccantgcca atatgcacca    540
agaatgttng taggaactac tttggtctgg ctgcagaagt tcttaatcta gcattaaaaa    600
tccaacggtt gatttgatct cttaaaatgg ttttcnnant ttgganctga aattgagnat    660
aaattacctt tgcnnntnaa ttcaaaangt tnaacctnnt tnann                   705
```

<210> SEQ ID NO 263
<211> LENGTH: 656
<212> TYPE: DNA
<213> ORGANISM: Homo Sapien
<220> FEATURE:
<221> NAME/KEY: misc_feature
<222> LOCATION: (1)...(656)
<223> OTHER INFORMATION: n = A,T,C or G

<400> SEQUENCE: 263

```
acncgcttgt accgagctcg gatccctagt aacggccgcc agtgtgctgg aattcgccct    60
tagcgtggtc gcggcccgag gtaccgcggg ggagaacgcc agggagctgt gagagtgtgc    120
agtcgcgttc ctgctgtccg gacactttt tcctctactg agactcatct ggtagatccg    180
caggccagtc ctcccagggg ctgaagttgt gaaatatggg ttttctaaga agattaatct    240
atcggcgtag accaatgatc tatgtagaat cttctgagga gtccagtgat gagcaacctg    300
acgaagtgga atcaccaact caaagtcagg attctacacc tgctgaagag agagaggatg    360
```

```
agggagcatc tgcagctcaa gggcaggagc ctgaagctga tagccaggaa ctggttcagc      420
caaagactgg gtgtgagctt ggagatggtc ctgataccaa gagggtntgc ctgcgaaatg      480
aagagcagat gaaactgccc gnagaaggcc agacctgann cgatagcagg acagttcccc      540
gaaactggtg tagcgcgaat gtctgtgtca gagtggcctg ccaatcaagg agtgaaccct      600
gggaataagc atccagctta aagannccct ganggttagt gtctngtgaa ttncct          656
```

<210> SEQ ID NO 264
<211> LENGTH: 752
<212> TYPE: DNA
<213> ORGANISM: Homo Sapien
<220> FEATURE:
<221> NAME/KEY: misc_feature
<222> LOCATION: (1)...(752)
<223> OTHER INFORMATION: n = A,T,C or G

<400> SEQUENCE: 264

```
ggnttgaang tatacgactc nctanggcga attgggccct ctagatgcat gctcgagcgg       60
cccgccagtg tgatggatat ctgcagaatt cgcccttagc gtggtcgcgg ccgaggtacc      120
tttgataatt cctagacctc tattttcatt ctgtgtatta atgtgaataa cagatggata      180 tttaatatt taaggcagat ggtaaacttt cctataggtc ttgtgagact tcgtcttata       240
ggctgaacac cattcacaaa atgtaataat gcttcattcc ttcaggttga ggtaaagaac      300
ttgagcaact ggattagcaa agctgcaaag aatgaaatgt ggcctaagat gtaattatgt      360
tctctgccct tcctttgggc cagggtagtt ttgcacttga cacaatggaa aataggccat      420
aaagcctgaa aataaaatgt tctaaacccc aatctcacag cactttagta ggcttttcac      480
taggcatctt taaagtattt tcaacaaaat actaattaag ctaccacttc aaaagagctt      540
caaggaaaag ctctgctttc ttataaaatc ttttgagac agagtttccg ctcttgtcag       600
cacaggctgg agtgcaatgg ccgtgatctc gactnaaccg naaccttcgg cctgctgggt      660
tcaagtgatt ctctagncct caagcttctg agtaggttgg gattacaggc gcccggncaa      720
ccacacctgg gctaaatttt ggatttctan gn                                    752
```

<210> SEQ ID NO 265
<211> LENGTH: 747
<212> TYPE: DNA
<213> ORGANISM: Homo Sapien
<220> FEATURE:
<221> NAME/KEY: misc_feature
<222> LOCATION: (1)...(747)
<223> OTHER INFORMATION: n = A,T,C or G

<400> SEQUENCE: 265

```
gngntttcnc nnngcgctct anagcatgct cgagcggccg ccagtgtgat ggatatctgc       60
agaattcgcc cttagcgtgg tcgcggccga ggtaccttg atnattccta gacctctatt       120
ttcattctgt gtattaatgt gaataacaga tggatattgt aatatttaag gcagatggta      180
aactttccta taggtcttgt gagactncnt cttataggct gaacaccatt nacnanntgt     240
antaatgctt nattccttca ggcngaggtn nanaacttga gcacctggat tagcagcagc      300
tgcgaagaat gaaatgcngc ctaacatgta attatgnatc tctgnccttc ctttgggcca      360
gggtagtnat gcnctagaca cantggatga tangccatna agcctgannn tgnaatgatc      420
taaacccnaa tctnncagca ctttattagg ctantcacta ggcatcttta agagtnggtt      480
cccnttaata ctagncaacc nnccactcca aaanancttc aagganaagc tntgntntnt      540
tanaaaatct tttcgnnaca cantttnacn cttggcgcnc angctggant gcaatggccg     600
```

| | |
|---|---|
| tgatctctac tcacccgaan cctcngactg ctgagttcaa gtgattgtct gnccttanct | 660 |
| ctccgggacc angnttnggg attancaagc ctcgcgggca anncacaggtg nctaattgnt | 720 |
| tgcattngcn taaaatnagg acaccng | 747 |

<210> SEQ ID NO 266
<211> LENGTH: 738
<212> TYPE: DNA
<213> ORGANISM: Homo Sapien
<220> FEATURE:
<221> NAME/KEY: misc_feature
<222> LOCATION: (1)...(738)
<223> OTHER INFORMATION: n = A,T,C or G

<400> SEQUENCE: 266

| | |
|---|---|
| cgnnnntgaa ggntacgact cactataggg cgaattgggc cctctagatg catgctcgag | 60 |
| cggccgccag tgtgatggat atctgcagaa ttcgcccttt cgagcggccg cccgggcagg | 120 |
| tacagctgaa gtttgataac aaagaaatat atataagaca aaaatagaca agagttaaca | 180 |
| ataaaaacac aactatctgt tgacataaca tatggaaact ttttgtcaga aagctacatc | 240 |
| ttcttaatct gattgtccaa atcattaaaa tatggatgat tcagtgccat tttgccagaa | 300 |
| attcgtttgg ctggatcata gattaacatt tcgagagca atccaagcc attttcatcc | 360 |
| aagtttttga catgggatgc taggcttctg gtttccattt gggaaatgta ttcttatagt | 420 |
| cctgtaaaga ttccacttct ggccacactt cattattggg agtgcccaaa gctctgaaat | 480 |
| cctgaagagt tgatcaattc tgaatcccat ggaaaagtgg ttcttagtgc tagtcaacaa | 540 |
| atatnggngc ctatactcca aagtcactt ggagttgagt natggagctg acccccagcat | 600 |
| acttttggaa aactggacca agtggttgca ccaccnttaa aaaatttaaa accggnngta | 660 |
| ttttaaataa ggtggaagaa acctttcct tttttattta aggaattcac ttagcnctta | 720 |
| ctaaattcat ggtgggg | 738 |

<210> SEQ ID NO 267
<211> LENGTH: 731
<212> TYPE: DNA
<213> ORGANISM: Homo Sapien
<220> FEATURE:
<221> NAME/KEY: misc_feature
<222> LOCATION: (1)...(731)
<223> OTHER INFORMATION: n = A,T,C or G

<400> SEQUENCE: 267

| | |
|---|---|
| gngnntttgn aagggccctc tagatgcatg ctcgagcggc cgccagtgtg atggatatct | 60 |
| gcagaattcg ccctttcgag cggccgcccg ggcaggtaca gctgaagttt gataacaaag | 120 |
| aaatatatat aagacaaaaa tagacaagag ttaacaataa aaacacaact atctgttgac | 180 |
| ataacatatg gaactttttt gtcagaaagc tacatcttct taatctgatt gtccaaatca | 240 |
| ttaaaatatg gatgattcag tgccattttg ccagaaattc gtttggctgg atcatagatt | 300 |
| aacatttcg agagcaaatc caagccattt tcatccaagt tttgacatg ggatgctagg | 360 |
| cttcctggtt tccatttggg aaatgtattc ttatagtcct gtaaagattc cacttctggc | 420 |
| cacacttcat tattgggagt gcccaaagct ctgaaatcc tgaagagttg atcaatttct | 480 |
| gaatccccat ggaaaagtgg tttcttagtt gctagttcag caaatatggt gcctatactc | 540 |
| caaatgtcaa ctgagttga gtaatgagct gaccccagca atacttctgg agatctgtca | 600 |
| agtggttgca acaccattaa aaaatataaa agcagtagtt atattaaaat aatgttgaag | 660 |

-continued

| aaaacatatn cctatatatt tnaaggaatt tcactaagca ctactaaatt tcatgttgtt | 720 |
| gggangngtt a | 731 |

<210> SEQ ID NO 268
<211> LENGTH: 745
<212> TYPE: DNA
<213> ORGANISM: Homo Sapien
<220> FEATURE:
<221> NAME/KEY: misc_feature
<222> LOCATION: (1)...(745)
<223> OTHER INFORMATION: n = A,T,C or G

<400> SEQUENCE: 268

| gnnnnnntaa agnanacntc actatanngc gaattgggcc ctctagatgc atgctcgagc | 60 |
| ggccgccagt gtgatggata tctgcagaat tcgcccttg agcggccgcc cgggcaggta | 120 |
| cttcccacac aggtttgttg taaaaattaa gtgagctaat gtgtataaaa acttcagtg | 180 |
| ctgaataaat gttggctttt attatatatt gttaaaaaac aacacaggct gggtatgata | 240 |
| gctcacgcct ataatcctag catttaggga ggccaaggca ggaggattgc ttgagtccag | 300 |
| gggtttgaga ccagcctggg caacatagtg agaccctatc tctacaaaat aaaataaatt | 360 |
| agttgggcat ggtggcacat gcctgtagtc ccagctactc aggaggctga ggtgggagga | 420 |
| ttgcttgagc ccaggaggta gaggttgcag tgagctgtga tcacaccact gcactccagc | 480 |
| gtcggtgacg gagtgagaac ctatctcaaa caaacaaaca aaaaaaccca aaacaaacaa | 540 |
| aaaaatccag taaagacaga gattcctaaa attctacaat tctaaaaacc agtagggctc | 600 |
| actgaatata agagaggcaa gcaaaaaatt actccaatat tttgagtttg ggtaacctgg | 660 |
| aatatgggtc atttattgag taaatagtta ctgagtccta actatgtgcc acacactggg | 720 |
| ttaacacttg gcactgtctc ttatg | 745 |

<210> SEQ ID NO 269
<211> LENGTH: 730
<212> TYPE: DNA
<213> ORGANISM: Homo Sapien
<220> FEATURE:
<221> NAME/KEY: misc_feature
<222> LOCATION: (1)...(730)
<223> OTHER INFORMATION: n = A,T,C or G

<400> SEQUENCE: 269

| gntnnnnttt tnaanccggt cctnntgcat gctcgagcgg cccgccagtg tgatggatat | 60 |
| ctgcagaatt cgcccttga gcggccgcc gggcaggtac ttcccacaca ggtttgttgt | 120 |
| aaaaattaag tgagctaatg tgtataaaat acttcagtgc tgaataaatg ttggcttta | 180 |
| ttatatattg ttaaaaaaca acacaggctg gtatgatag ctcacgccta taatcctagc | 240 |
| atttagggag gccaaggcag gaggattgct tgagtccagg ggtttgagac cagcctgggc | 300 |
| aacatagtga gaccctatct ctacaaaata aaataaatta gttgggcatg gtggcacatg | 360 |
| cctgtagtcc cagctactca ggaggctgag gtgggaggat tgcttgagcc caggaggtag | 420 |
| aggttgcagt gagctgtgat cacaccactg cactccagcg tcggtgacgg agtgagaacc | 480 |
| tatctcaaac aaacaacaa aaaacccaa acaaacaaa aaaatccagt aaagacagag | 540 |
| attcctaaaa ttctacaatt ctaaaaacca gtagggctca ctgaatataa gagaggcaag | 600 |
| caaaaaatta ctccaatatt ttgagtttgg gtaacctgga atatggtcat tattgagtna | 660 |
| atagttactg agtcctacta tgtgcccaca ctgggtnaac acttgcactg tctcttatga | 720 |
| aatcttccan | 730 |

<210> SEQ ID NO 270
<211> LENGTH: 713
<212> TYPE: DNA
<213> ORGANISM: Homo Sapien
<220> FEATURE:
<221> NAME/KEY: misc_feature
<222> LOCATION: (1)...(713)
<223> OTHER INFORMATION: n = A,T,C or G

<400> SEQUENCE: 270

```
aattgggccc tctagatgca tgctcgagcg gccgccagtg tgatggatat ctgcagaatt      60
cgccctttcg agcggccgcc cgggcaggta caaaccaata gctcctattc tggaaggttt     120
tcttttatt taaaaaaat tcaaacaagg ttaaaagtca agcaagaagg gaagagagaa       180
actgggttct gagaaaaaaa tgtgccagta taaataaac tcctaaatgc gtgcttgtca     240
tcctctagtt ttttttttaa gttgaatttc ttttccactg taacttaaga tttgagattg     300
aggtttgcgg tccagaacat accctcagca gatacagtga ctaactggaa agtgcagttg     360
ttcaaggtct gtcatgctca atcacctaaa gctataattt gnttgatata ttaagcatgt     420
agacctagtg cagcatggga gccactcagg aagtttatgc aattaataaa ctttcagcat     480
aatttactat gaagtatgca gaatttcacc ctcttctcca cacttaacat ttagttgtat     540
atgtgaactc tcctttctta attggggaat gtagcattat atagaatgtt gntaaaggta     600
attttaatcc tttttgacat taaccttttt ttttttttggn aaaccaagtg atctgccttt    660
cagcaactgg cttattttgg gtctttgaaa ctgngatttt tatttcattn gnc            713
```

<210> SEQ ID NO 271
<211> LENGTH: 702
<212> TYPE: DNA
<213> ORGANISM: Homo Sapien
<220> FEATURE:
<221> NAME/KEY: misc_feature
<222> LOCATION: (1)...(702)
<223> OTHER INFORMATION: n = A,T,C or G

<400> SEQUENCE: 271

```
gnctcgagcg gccgccagtg tgatggatat ctgcagaatt cgccctttcg agcggccgcc      60
cgggcaggta caaaccaata gctcctattc tggaaggttt tcttttatt taaaaaaat      120
tcaaacaagg ttaaaagtca agcaagaagg gaagagagaa actgggttct gagaaaaaaa    180
tgtgccagta taaataaac tcctaaatgc gtgcttgtca tcctctagtt ttttttttaa     240
gttgaatttc ttttccactg taacttaaga tttgagattg aggtttgcgg tccagaacat    300
accctcagca gatacagtga ctaactggaa agtgcagttg ttcaaggtct gtcatgctca    360
atcaccctaa agctataatt tgtttgatat attaagcatg tagacctagt gcagcatggg    420
agccactcag gaagtttatg caattaataa actttcagca taatttacta tgaagtatgc    480
agaatttcac cctcttctcc acacttaaca tttagttgta tatgtgaact ctcctttctt    540
aattggggaa tgtncattat atagaatgtt ggtaaaggta attttaatcc tttttgacat    600
taaccttttt ttttttttgg taaaccaagt gatctgncttt ttaacaactg gcttattttgg   660
gtcctttgna actgggaatt ttatttcatt tgnncctcgg cc                       702
```

<210> SEQ ID NO 272
<211> LENGTH: 736
<212> TYPE: DNA
<213> ORGANISM: Homo Sapien
<220> FEATURE:

<221> NAME/KEY: misc_feature
<222> LOCATION: (1)...(736)
<223> OTHER INFORMATION: n = A,T,C or G

<400> SEQUENCE: 272

```
gnnntttgan nnnnnnnnnn ntatagggcg aattgggccc tctagatgca tgctcgagcg      60
gccgccagtg tgatggatat ctgcagaatt cgcccttcg agcggccgcc cgggcaggta      120
ctttttttta ttcctcagtt aaaacatgcc tgttattctt tttgtaatac ttaagcaatt     180
ttattttaaa gatatactac ttagttcatc cgtctccact tgttttttt ttttgnnant     240
annggttgg ttccnttaan nccacnggtt ttaaanccat nntngtcnnn ggnaaattan      300
nnttantnat taaanntnnn tnncntngca aanntccagn taaaatttta gtggggggg      360
ggggttantt acnggnaann aattaantnc nggnnaatan tttaannntt ggnaangnac     420
nntngnnnta annattattt nnttnannt tttaataann annaatttta ntttgnaacn     480
ntggtnttta ntaannggaa anncaatta attggttggt tgnattttc ccagnaaccn      540
ntccntgggc nggaacnncc ntangggnaa nttcnagnnn ntngngggcn gtncnnaggg    600
nnnccaacnt nggcccancn tggnggaann nnnggcnnna nnggttccn gggnaaatg      660
gtattcngtt cnaatccnnc aanttccaac ccggagnctt aanggtaan nccngggggg    720
cntanngagn gcctaa                                                     736
```

<210> SEQ ID NO 273
<211> LENGTH: 715
<212> TYPE: DNA
<213> ORGANISM: Homo Sapien
<220> FEATURE:
<221> NAME/KEY: misc_feature
<222> LOCATION: (1)...(715)
<223> OTHER INFORMATION: n = A,T,C or G

<400> SEQUENCE: 273

```
gngntttnac ganngnnnnn nnnnnctgct cgagcggccg ccagtgtgat ggatatctgc      60
agaattcgcc ctttcgagcg gccgcccggg caggtacttt ttttattcc tcagttaaaa     120
catgcctgtt attctttttg taatacttaa gcaattttat tttaaagata tactacttag    180
ttcatccgtc tccacttgtt tttttttttt gnnantanng ggttggttcc nttaanncna    240
cnggtnttaa anccannnnn gtcnnggna aattannntt antcnntaaa nntnnnnnc      300
ntggnaannn tccagntaaa atttnagtgg ggggggggg ttaattancg gnaannantt    360
aantnccgga naatanttta annttggna angnacnttn gnnntaagna ttatttnnt     420
canntttta atnantanna attttaattt gnaancntgg nntttannaa nnggaaannc    480
caattaattg gttggttgna ttttccag naaccnnncc ntgggcngga acanccntaa     540
ggncaaatcn accaantgnc ggccgtacna agggatcca acntggccc anctggnng      600
naataatggc cnaantggtt nccngggnna aatggnattc cgttcaaatt ccnccanntc    660
cnacccggag ccttaagngg taaacctggg ggcctaangg ggggcctaac tcaat         715
```

<210> SEQ ID NO 274
<211> LENGTH: 746
<212> TYPE: DNA
<213> ORGANISM: Homo Sapien
<220> FEATURE:
<221> NAME/KEY: misc_feature
<222> LOCATION: (1)...(746)
<223> OTHER INFORMATION: n = A,T,C or G

<400> SEQUENCE: 274

| | |
|---|---|
| gnnnntnnan gnntacgact cactataggg cgaattgggc cctctagatg catgctcgag | 60 |
| cggccgccag tgtgatggat atctgcagaa ttcgcccctta gcgtggtcgc ggccgaggta | 120 |
| ccaggtgggc tgacgcacat cccctaaaca ttctggatct cttactcatc gtgaaaggca | 180 |
| gacgctctaa gtctaaagtc tagggtagga gtttccattc tttggaaaac caaagatggt | 240 |
| tactcttctt aatgaaactg agaagaaggt atctacagaa aacactgaat ttaaacaaat | 300 |
| tatgaccttg tttgttgaag ccatcaagga cccaagatat atcaaagaac aacatctctg | 360 |
| tattggccta caggttcaga gtgttttgag gtctgtttaa gcactaatag gattttaggc | 420 |
| cagcatccag tcagaagaga tagttcacag actcagagtt ggaaacagat taaaaaaaaa | 480 |
| aagatgtcaa catagaaaat gatgatagag tttagttaaa aaaattcaca cataaaatta | 540 |
| cagttaaaaa aattcacaca taaatagag tgtttgcata gcaagacatt attgcccttc | 600 |
| agcctggcag aaaacataa actcaggtgt atattttata ataaacattg nattgaatgc | 660 |
| taagaatgat acactggtga acatctnctg aatggttgcc ttcttgtaaa tcataccaat | 720 |
| tggttagaca attgaaattn ccagct | 746 |

<210> SEQ ID NO 275
<211> LENGTH: 725
<212> TYPE: DNA
<213> ORGANISM: Homo Sapien
<220> FEATURE:
<221> NAME/KEY: misc_feature
<222> LOCATION: (1)...(725)
<223> OTHER INFORMATION: n = A,T,C or G

<400> SEQUENCE: 275

| | |
|---|---|
| gnnnttaann ccttccctnt anatgcatgc tcgagcggcc gccagtgtga tggatatctg | 60 |
| cagaattcgc cctttagcgtg gtcgcggccg aggtaccagg tgggctgacg cacatcccct | 120 |
| aaacattctg gatctcttac tcatcgtgaa aggcagacgc tctaagtcta aagtctaggg | 180 |
| taggagtttc cattctttgg aaaccaaag atggttactc ttcttaatga aactgagaag | 240 |
| aaggtatcta cagaaaacac tgaatttaaa caaattatga ccttgtttgt tgaagccatc | 300 |
| aaggacccaa gatatatcaa agaacaacat ctctgtattg gcctacaggt tcagagtgtt | 360 |
| ttgaggtctg tttaagcact aataggattt taggccagca tccagtcaga agagatagtt | 420 |
| cacagactca gagttggaaa cagattaaaa aaaaaagat gtcaacatag aaatgatga | 480 |
| tagagtttag ttaaaaaaat tcacacataa aattacagtt aaaaaaattc acacataaaa | 540 |
| tagagtgttt gcatagcaag acattattgc ccttcagcct ggcagaaaaa cataaactca | 600 |
| ggtgtatatt ttataataaa cattgnattg aatgctaaga atgatcactg ttgaacatct | 660 |
| cctgaatggt ttgccttctt gtaaatcata ccaatggtta gacaattgaa attccagctc | 720 |
| tttct | 725 |

<210> SEQ ID NO 276
<211> LENGTH: 744
<212> TYPE: DNA
<213> ORGANISM: Homo Sapien
<220> FEATURE:
<221> NAME/KEY: misc_feature
<222> LOCATION: (1)...(744)
<223> OTHER INFORMATION: n = A,T,C or G

<400> SEQUENCE: 276

| | |
|---|---|
| nnnnntgann gtatacgact cactataggg cgaattgggc cctctagatg catgctcgag | 60 |

```
cggccgccag tgtgatggat atctgcagaa ttcgccctta gcgtggtcgc ggccgaggta     120
cttctgctgt ggtaactcaa gtaaccctcc gtttaaacca ggacagacct atgctgacaa     180 ccattttat cactcttagt ggtattttct ttctttgaac atgaatgcat atttctgctc     240
tttaatggcc tttggtattt aagattacat tcagctagtc tccttattgc atgttgtttt     300
attccagtcc caccagcact cagaacaaca gcaagtgtgt gtaacagcgg gcacaggcgc     360
tccagacgga aggacctcac tgacgcagtt agctcaggta gagcttattt ctgtgttcaa     420
ttttcttgtc atgagaagca gtgaccccta agaatttgta tccctttgtt cacttctttg     480
ttttaggaga gaaacttcta aagcattact ctaaaggtg atagagacag agacgggcca     540
ttttcatcta ccccttgcag agttaagttt tattacagta agttgtgagg tgagacatga     600
tggctgcagg cacatagtca agatctaccc ttctaaggaa ataaaacggg gaaaagtggt     660
tgaatgtcca atatagaaaa tttaatcacc actttcccaa aaagaataa atggaggact     720 ncattggaat tatggaaatg aaan                                            744

<210> SEQ ID NO 277
<211> LENGTH: 724
<212> TYPE: DNA
<213> ORGANISM: Homo Sapien
<220> FEATURE:
<221> NAME/KEY: misc_feature
<222> LOCATION: (1)...(724)
<223> OTHER INFORMATION: n = A,T,C or G

<400> SEQUENCE: 277
gnnnnttncg antgggccct ctagatgcat gctcgagcgg ccgccagtgt gatggatatc      60
tgcagaattc gcccttagcg tggtcgcggc cgaggtactc ctgctgtggt aactcaagta     120
accctccgtt taaaccagga cagacctatg ctgacaacca tttttatcac tcttagtggt     180
attttctttt tttgaacatg aatgcatatt tctgctcttt aatggccttt ggtatttaag     240
attacattca gctagtctcc ttattgcatg ttgttttatt ccagtcccac cagcactcag     300
aacaacagca gtgtgtgta acagcgggca caggcgctcc agacgaagg acctcactga     360 cgcagttagc tcaggtagag cttatttctg tgttcaattt tcttgtcatg agaagcagtg     420
acccctaaga atttgtatcc ctttgttcac ttctttgttt taggagagaa acttctaaag     480
cattactcta aaaggtgata gagacagaga cgggccattt tcatctaccc cttgcagagt     540
taagttttat tacagtaagt tgtgaggtga gacatgatgg ctgcaggcac atagtcaaga     600
tctacccttc taaggaaata aaacggggaa agtggttga atgtccaata tagaaaattt     660
aatcaccact ttccaaaaaa gaataaatgg aggactncat tgtaattatg gaatgaaat     720 ttgg                                                                 724

<210> SEQ ID NO 278
<211> LENGTH: 748
<212> TYPE: DNA
<213> ORGANISM: Homo Sapien
<220> FEATURE:
<221> NAME/KEY: misc_feature
<222> LOCATION: (1)...(748)
<223> OTHER INFORMATION: n = A,T,C or G

<400> SEQUENCE: 278
gnnnntgaaa gtatacgact cactataggg cgaattgggc cctctagatg catgctcgag      60
cggccgccca gtgtgatgga tatctgcaga attcgccctt tcgagcggcc gcccgggcag     120
gtacagctgc ccaagggcgt tcgtaacggg aatgccgaag cgtgtgaaaa agggagcggt     180
```

-continued

```
ggcggaagac ggggatgagc tcaggacaga gccagaggcc aagaagagta agacggccgc    240
aaagaaaaat gacaaagagg cagcaggaga gggcccagcc ctgtatgagg accccccaga    300
tcagaaaacc tcacccagtg gcaaacctgc cacactcaag atctgctctt ggaatgtgga    360
tgggcttcga gcctggatta agaagaaagg attagattgg gtaaaggaag aagcccccaga   420 tatactgtgc cttcaagaga ccaaatgttc agagaacaaa ctaccagctg aacttcagga    480
gctgcctgga ctctctcatc aatactggtc agctccttcg gacaaggaag ggtactagca    540
actaaccatg gttaaaaggt cttagtcaga attacaaaaa caaacatttt agagtaaatac   600 ttatgaatac aagcataatt ggttcctcgc cttctacaaa taaccatctt gaaaatgata    660
aaagcaggtt tcaactgtgg tcttctctca ttgagaaggt gcagatacac atgggtgatc    720
tactgattta ccttcttgaa agtnctcg                                      748
```

<210> SEQ ID NO 279
<211> LENGTH: 727
<212> TYPE: DNA
<213> ORGANISM: Homo Sapien
<220> FEATURE:
<221> NAME/KEY: misc_feature
<222> LOCATION: (1)...(727)
<223> OTHER INFORMATION: n = A,T,C or G
<400> SEQUENCE: 279

```
gnnnnttcga ntgggccctc tngngcatgc tcgagcggca cgccagtgtg atggatatct    60
gcagaattcg ccctttcgag cggccgcccg ggcaggtaca gctgcccaag ggcgttcgta   120
acgggaatgc cgaagcgtgt gaaaaaggga gcggtggcgg aagacgggga tgagctcagg   180
acagagccag aggccaagaa gagtaagacg gccgcaaaga aaaatgacaa agaggcagca   240
ggagagggcc cagccctgta tgaggacccc ccagatcaga aaacctcacc cagtggcaaa   300
cctgccacac tcaagatctg ctcttggaat gtggatgggc ttcgagcctg gattaagaag   360
aaaggattag attgggtaaa ggaagaagcc ccagatatac tgtgccttca agagaccaaa   420
tgttcagaga acaaactacc agctgaactt caggagctgc ctggactctc tcatcaatac   480
tggtcagctc cttcggacaa ggaagggtac tagcaactaa ccatggttaa aaggtcttag   540
tcagaattac aaaaacaaaa catttagagt aatacttatg aatcaagcat aattggttcc   600
tcgccttcta caaataccat ctttgaaaat gatnaaaagc aggtttcaac tgtggttctt   660
ctctcanttg aaaaggtcag atcccatggg tgatctactg atttaccttc tgaaaagtac   720
ttggccg                                                              727
```

<210> SEQ ID NO 280
<211> LENGTH: 751
<212> TYPE: DNA
<213> ORGANISM: Homo Sapien
<220> FEATURE:
<221> NAME/KEY: misc_feature
<222> LOCATION: (1)...(751)
<223> OTHER INFORMATION: n = A,T,C or G
<400> SEQUENCE: 280

```
gnnnntgann gtatacgact cactataggg cgaattgggc cctctagatg catgctcgag    60
cggccgccag tgtgatggat atctgcagaa ttcgccctta gcgtggtcgc ggccgaggta   120
ctcatgtatt tttttttttt tccagatctc tttccccaag ttgctattgt aagagtattc   180
tgctgcgtgt ggatgcagtt atacacatta aagcagatct ggagtctgaa gtagctataa   240
```

-continued

```
agcagctata aaacagaaat acatgcatag ctgcagaaac catgataggt agaggacttt      300
tcttttggtt ttgttttgtt ttgttttgtt ttgtttttgg ttttacagag aagagatttt      360
tattacaaag aaaaaaattc cagtgaattg tgcagaaatg ctggttttta caccatccta      420
aagaaaaact ttacaagggt gttttggagt agaaaaaagg ttataaagtt ggaatcttaa      480
attgtaaaat taaccattga gtgtcaaagt tctaaaagca gaactcattt tgtgcaatga      540
acataaggaa agactactgn ataggttttt tttttctcct tttaaatgaa gaaaagcttt      600
gcttaagggt tgcatacttt tattggagta aatctgaatg atcctactcc tttgagtaa       660 aactagtgct taccagtttc caattggatt taacttctgg ggtggaattt ggaaaaaaaa      720
agaannnngg aaaaagaaaa cctaanttaa n                                      751

<210> SEQ ID NO 281
<211> LENGTH: 727
<212> TYPE: DNA
<213> ORGANISM: Homo Sapien
<220> FEATURE:
<221> NAME/KEY: misc_feature
<222> LOCATION: (1)...(727)
<223> OTHER INFORMATION: n = A,T,C or G

<400> SEQUENCE: 281
gnnnttcgan tgggccctct agatgcatgc tcgagcggcc gccagtgtga tggatatctg       60
cagaattcgc ccttagcgtg gtcgcggccg aggtactcat gtattttttt ttttttccag      120
atctctttcc ccaagttgct attgtaagag tattctgctg cgtgtggatg cagttataca      180
cattaaagca gatctggagt ctgaagtagc tataaagcag ctataaaaca gaaatacatg      240
catagctgca gaaccatga taggtagagg acttttcttt tggttttgtt ttgttttgtt       300
ttgttttgtt tttggttttta cagagaagag atttttatta caaagaaaaa aattccagtg      360
aattgtgcag aaatgctggt ttttacacca tcctaaagaa aaactttaca agggtgtttt      420
ggagtagaaa aaaggttata agttggaat cttaaattgt aaaattaacc attgagtgtc       480
aaagttctaa aagcagaact catttgtgc aatgaacata aggaaagact actgnatagg      540
tttttttttt ctccttttaa atgaagaaaa gctttgctta agggttgcat acttttattg      600
gagtaaatct gaatgatcct actccttgg agtaaaacta ngcttccag tttccaattg        660 gatttaactt ctggntggaa tttgnaaaaa aagaanaaa aggaaanga aaccctaant        720 naaatag                                                                 727

<210> SEQ ID NO 282
<211> LENGTH: 749
<212> TYPE: DNA
<213> ORGANISM: Homo Sapien
<220> FEATURE:
<221> NAME/KEY: misc_feature
<222> LOCATION: (1)...(749)
<223> OTHER INFORMATION: n = A,T,C or G

<400> SEQUENCE: 282
tnnaaagnaa gctctttact cactatnngg gcgaattggg ccctctagat gcatgctcga       60
gcggccgcca gtgtgatgga tatctgcaga attctnccctt cgagcggccg cccgggcagg     120
tacttttttt tttttttttt tttttttttt tttttnaaac tactaggatt tactgtagga      180
taaaagctnt acatgcccct gcntacaaac tttctgcata cttctgcaaa tttttatgcn      240
ttactnaatc cattaaaaat caccttggaa naaactgcaa acncantana aactaaatga      300
natagtcaca gagaacanca aaatagtaa ttnaagttcc catacaacat caagtgtgtn      360
```

```
cagtctatttt tnggttcttc gggttctctt taaaattgaa ttgagtttgn atatgcatat    420
gtatgtagga gtggaggatg gaattaatta tcccaaacat cctacantca ctcctctaat    480
atttctttng ttaacatgca aatctgttct cttcattacg gngatactgc atttacatta    540
caacacantt agagatcatt aactttctcc tttataatca gccatttttca caggcctttg   600 atatacaagc acctataata tattcttact catctcacac tttcatttac caaagtgtca    660
aaacaacatt tttacatcat tgatatttgg ttnantttct gcaanctggc tgttanaaaa    720
tgattacttc tnttaaatta cctttttanc                                     749

<210> SEQ ID NO 283
<211> LENGTH: 730
<212> TYPE: DNA
<213> ORGANISM: Homo Sapien
<220> FEATURE:
<221> NAME/KEY: misc_feature
<222> LOCATION: (1)...(730)
<223> OTHER INFORMATION: n = A,T,C or G

<400> SEQUENCE: 283
gtctntgaan cnggncctct ngatgcatgc tcgagcggcc gccagtgtga tggatatctg     60
cagaattcgc ccttcgagcg gccgcccggg caggtacttt tttttttttt tttttttttt    120
tttttttttc aaactactag gatttactgt aggataaaag ctntacatgg ccctgcatac    180
aaactttntg catacttntg caaatttttta tgcattactc aatccattaa aaatcacctt   240
ggaanaaact gcaaacncaa tagaaactaa atganatagt cacagagaac aacaaaaata    300
gtaatttaag ttcccataca acatcaagtg tgttcagtct attttttggtt cttcgggttc    360 tctttaaaat tgaattgagt ttgtatatgc atatgtatgt aggantggag gatggaatta    420
attatcccaa acatcctaca ctcactcctc taatatttct tttgttaaca tgcaaatctg    480
ttctcttcat tacggngata ctgcatttac attacaacac aattagagat cattaacttt    540
ctcctttata atcagccatt tcacaggcc tttgatatac aagcacctat aatatattct    600
tactcatctt acactttcat ttaccaaagt gtcaaaaaca acattttttac atcattggat   660 atttggttta gtttctgcaa nctggctttt anaaaatga ttacttctct taaattacct    720
tttaccctca                                                           730

<210> SEQ ID NO 284
<211> LENGTH: 739
<212> TYPE: DNA
<213> ORGANISM: Homo Sapien
<220> FEATURE:
<221> NAME/KEY: misc_feature
<222> LOCATION: (1)...(739)
<223> OTHER INFORMATION: n = A,T,C or G

<400> SEQUENCE: 284
gnnntnaaag tatacgactc actatagggc gaattgggcc ctctagatgc atgctcgagc     60
ggccgccagt gtgatggata tctgcagaat tcgcccttag cgtggtcgcg ccgaggtac    120 aacataaagc aacagagagg tcttcatgtt tgggaagtgg ctgggcagga tgccaaaccc   180
caaatgactt attgagcaat ttctaaacca aacagagagg taggaaaaga ggatgggggt    240
cagggtggga ggctgtggaa aggggagagc gagggctgaa gagaatggca gccatacagg    300
tgttttgttt ttatttccac atctgaggac tgagagtctg atttgctgcc tgtccatttc    360
cgccactcat tgactgtcca tagttcatca tgccattggc tccatagaag ttcatcccag    420
```

-continued

```
ccatctgctg ggtcatctga gtaaggttcc attgcagctg ctgagctggc tggaccccat      480
acacagtctg gggcatagct gccatgcctg ccatgtagcc agcctgctgg gtggtcatca      540
ttccattcgg cacacccatc attgatgcct gcatgccacc catatagcct gcaggcatgg      600
ccatgggggc aaccatccca gaactnctgc tgagcaacca tgcctactgg tggaagcatc      660
atgcttccca ttatgctgtt angangtgta ccccngggaa actggggtag ctgtgggata      720
tccatctgan ccggaccat                                                   739
```

<210> SEQ ID NO 285
<211> LENGTH: 721
<212> TYPE: DNA
<213> ORGANISM: Homo Sapien
<220> FEATURE:
<221> NAME/KEY: misc_feature
<222> LOCATION: (1)...(721)
<223> OTHER INFORMATION: n = A,T,C or G

<400> SEQUENCE: 285

```
gnnnttcgan tgggccctct ngatgcatgc tcgagcggcc gccagtgtga tggatatctg       60
cagaattcgc ccttagcgtg gtcgcggcac gaggtacaac ataaagcaac agagaggtct      120
tcatgtttgg gaagtggctg ggcaggatgc caaaccccaa atgacttatt gagcaatttc      180
taaaccaaac agagaggtag gaaaagagga tgggggtcag gggtggaggc tgtggaaagg      240
ggagagcgag ggctgaagag aatggcagcc atacaggtgt tttgttttta tttccacatc      300
tgaggactga gagtctgatt tgctgcctgt ccatttccgc cactcattga ctgtccatag      360
ttcatcatgc cattggctcc atagaagttc atcccagcca tctgctgggt catctgagta      420
aggttccatt gcagctgctg agctggctgg accccataca cagtctgggg catagctgcc      480
atgcctgcca tgtagccagc tgctgggtg gtcatcattc cattcggcac acccatcatt      540
gatgcctgca tgccacccat atagcctgca ngcatgcca tggggcaac catcccagaa      600 ctcctggctg agcaaccatg cctactggtg gangcatcat gcttcccatt atgctgttag      660
gangtgtacc ccggggaanc tggggtagct gtgggatatc catttaaccg gagccatgaa      720
c                                                                      721
```

<210> SEQ ID NO 286
<211> LENGTH: 757
<212> TYPE: DNA
<213> ORGANISM: Homo Sapien
<220> FEATURE:
<221> NAME/KEY: misc_feature
<222> LOCATION: (1)...(757)
<223> OTHER INFORMATION: n = A,T,C or G

<400> SEQUENCE: 286

```
gnnnnttaaa gnntacgact cactatuggg cgaattgggc cctctagatg catgctcgag       60
cggcccgcca gtgtgatgga tatctgcaga attcgccctt tcgagcggcc gcccgggcag      120
gacgcggggg ttgcaccatg gcgtccatgg ggaccctcgc cttcgatgaa tatgggcgcc      180
ctttcctcat catcaaggat caggaccgca gtcccgtct tatgggactt gaggccctca      240
agtctcatat aatggcagca aaggctgtag caaatacaat gagaacatca cttggaccaa      300
atgggcttga taagatgatg gtggataagg atggggatgt gactgtaact aatgatgggg      360
ccaccatctt aagcatgatg gatgttgatc atcagattgc caagctgatg gtggaactgt      420
ccaagtctca ggatgatgaa attggagatg gaaccacagg agtggtttgtc ctggctggtg      480 ccttgttaga agaagcggag caattgctag accgaggcat tcacccaatc agaatagccc      540
```

| | |
|---|---|
| gatggctatg agcaggctgc tcgcgttgct attgaacacc tggacaagat cagcgatagc | 600 |
| gtccttgttg acataaagga caccgaaccc ctgattcaga cagcaaaaaa ccacgctggg | 660 |
| cttncaaaag tggtcaacag ttgtcaccga cagatggctt gaaaattgct gtgaaatgcc | 720 |
| cgtccttact gtaaccagat atngaaccgg aaaagac | 757 |

<210> SEQ ID NO 287
<211> LENGTH: 726
<212> TYPE: DNA
<213> ORGANISM: Homo Sapien
<220> FEATURE:
<221> NAME/KEY: misc_feature
<222> LOCATION: (1)...(726)
<223> OTHER INFORMATION: n = A,T,C or G

<400> SEQUENCE: 287

| | |
|---|---|
| gnnnnactga tttctggctc gaagttgnat ntgcggncgc cagtgtgatg gatatctgca | 60 |
| gaattcgccc tttcgagcgg ccgcccgggc aggacgcggg ggttgcacca tggcgtccat | 120 |
| ggggaccctc gccttcgatg aatatgggcg cccttttcctc atcatcaagg atcaggaccg | 180 |
| caagtcccgt cttatgggac ttgaggccct caagtctcat ataatggcag caaaggctgt | 240 |
| agcaaataca atgagaacat cacttggacc aaatgggctt gataagatga tggtggataa | 300 |
| ggatggggat gtgactgtaa ctaatgatgg ggccaccatc ttaagcatga tggatgttga | 360 |
| tcatcagatt gccaagctga tggtggaact gtccaagtct caggatgatg aaattggaga | 420 |
| tggaaccaca ggagtggttg tcctggctgg tgccttgtta gaagaagcgg agcaattgct | 480 |
| agaccgaggc attcacccaa tcagaatagc ccgatggcta tgagcaggct gctcgcgttg | 540 |
| ctattgaaca cctggacaag atcagcgata gcgtccttgn tgacataaag gacaccgaac | 600 |
| ccctgattca gacagcaaaa accacgctgg gctccaaaag tggtcaacag ttgtcaccga | 660 |
| cagatggctg aaaatgctgt gaatgccgtc ctnctgtanc agatatngaa ccggaaaaga | 720 |
| ccttga | 726 |

<210> SEQ ID NO 288
<211> LENGTH: 743
<212> TYPE: DNA
<213> ORGANISM: Homo Sapien
<220> FEATURE:
<221> NAME/KEY: misc_feature
<222> LOCATION: (1)...(743)
<223> OTHER INFORMATION: n = A,T,C or G

<400> SEQUENCE: 288

| | |
|---|---|
| gnnntganng tatacgactc actatagggc gaattgggcc ctctagatgc atgctcgagc | 60 |
| ggccgccagt gtgatggata tctgcagaat tcgcccttcg gccgcccggg caggtacctt | 120 |
| ttacctaaaa ttctagccac tttaatttgg agagtttcca gagcaagggg cacagatccc | 180 |
| aggcataaca acgctttgcg tatacagcaa ccaatatctt gtcaacccaa gaaagttcct | 240 |
| ccattgatac ctagtagaaa tagcccagtt tttaaagtcc tcaaaactgt aacaaattac | 300 |
| ttgttttttaa aatttaactt aaattaatac aatcagattt ttgtgttatt tgggtattag | 360 |
| agtatgttaa agcacatata tcccagagac atagagtttc cgtttcaaaa agtcatgcat | 420 |
| tcatgtgtgc taatgacaat cctatcctga cccgctatgt gacttgtatc tctaaaccat | 480 |
| aggctttcct gaatttatc tgttaattta acctgatttt ctcagcagca gcttctcttt | 540 |
| gtaaatagac ttgcctcttc tgtgtctgac ctctgctcct cataatcaga ttaactcaga | 600 |

```
taaagctgct tcagggaaga ggtcaaaacc gttgccaaaa atagtagttg ccctacttca      660
gtctattttc aacagagtag cccaggagat ctgtcacacc aaagtccaat cagccctact      720
ggtagcactc tgntcacaag ccn                                              743

<210> SEQ ID NO 289
<211> LENGTH: 726
<212> TYPE: DNA
<213> ORGANISM: Homo Sapien
<220> FEATURE:
<221> NAME/KEY: misc_feature
<222> LOCATION: (1)...(726)
<223> OTHER INFORMATION: n = A,T,C or G

<400> SEQUENCE: 289
gnnnnnactc gcagtccgtc tagatgcatg ctcgagcggc cgccagtgtg atggatatct       60
gcagaattcg cccttcggcc gcccgggcag gtaccttta cctaaaattc tagccacttt      120
aatttggaga gtttccagag caaagggcac agatcccagg cataacaacg ctttgcgtat      180
acagcaacca atatcttgtc aacccaagaa agttcctcca ttgataccta gtagaaatag      240
cccagttttt aaagtcctca aaactgtaac aaattacttg tttttaaaat ttaacttaaa      300
ttaatacaat cagattttg tgttatttgg gtattagagt atgttaaagc acatatatcc      360
cagagacata gagtttccgt ttcaaaaagt catgcattca tgtgtgctaa tgacaatcct      420
atcctgaccc gctatgtgac ttgtatctct aaaccatagg ctttcctgaa ttttatctgt      480
taatttaacc ctgattctc agcagcagct tctctttgta aatagacttg cctcttctgt      540
gtctgacctc tgctcctcat aatcagatta actcagataa agctgcttca gggaagaggt      600
caaaaccgtt gccaaaaata gtagttgccc tacttcagtc tattttcaac agagtagcca      660
ggagatctgt tcacaccaaa gtccaatcag ccctactggt agcactctgc tcacaagcct      720 ncagtg                                                                 726

<210> SEQ ID NO 290
<211> LENGTH: 740
<212> TYPE: DNA
<213> ORGANISM: Homo Sapien
<220> FEATURE:
<221> NAME/KEY: misc_feature
<222> LOCATION: (1)...(740)
<223> OTHER INFORMATION: n = A,T,C or G

<400> SEQUENCE: 290
gnnnngaaag tatacgactc actatagggc gaattgggcc ctctagatgc atgctcgagc       60
ggccgccagt gtgatggata tctgcagaat tcgcccttag cgtggtcgcg gccgaggtac      120
ccagatgtct ttctcggtca ccttcccgag accatttaag acctccctag ctgctcgttc      180
tccagcctca actgcccctt ccatgtagcc gctccacttt gtggcagtct ctgtgcccgc      240
aaagaaaatc ctgcccacgg gttgacgaat caccctcca tattgagtca tgatcccagg      300
agggaagtag gccgtgtagc agcccccaga gtacctgccc gggcggccgc tcgaaagggc      360
gaattccagc acactggcgg ccgttactag tggatccgag ctcggtacca agcttggcgt      420
aatcatggtc atagctgttt cctgtgtgaa attgttatcc gctcacaatt ccacacaaca      480
tacgagccgg aagcataaag tgtaaagcct ggggtgccta atgagtgagc taactcacat      540
taattgcgtt gcgctcactg cccgctttcc agtcgggaaa cctgtcgtgc cagctgcatt      600
aatgaatcgg ccaacgcgcc ggggagaggc ggnttgcgta ttgggcgctc ttncgctttc      660
tngctcactg actcgctgcg ctcggtcgtt cggctgcggc nagcggtatc agctcattaa      720
```

```
angcggtaat acggtatccn                                                  740

<210> SEQ ID NO 291
<211> LENGTH: 724
<212> TYPE: DNA
<213> ORGANISM: Homo Sapien
<220> FEATURE:
<221> NAME/KEY: misc_feature
<222> LOCATION: (1)...(724)
<223> OTHER INFORMATION: n = A,T,C or G

<400> SEQUENCE: 291
gnnnnnncna ntgggccctc tngngcatgc tcgagcggcc gccagtgtga tggatatctg       60
cagaattcgc ccttagcgtg gtcgcggccg aggtacccag atgtctttct cggtcaccctt    120
cccgagacca tttaagacct ccctagctgc tcgttctcca gcctcaactg ccccttccat    180
gtagccgctc cactttgtgg cagtctctgt gcccgcaaag aaaatcctgc ccacgggttg    240
acgaatcacc cttccatatt gagtcatgat cccaggaggg aagtaggccg tgtagcagcc    300
cccagagtac ctgcccgggc ggccgctcga aagggcgaat tccagcacac tggcggccgt    360
tactagtgga tccgagctcg gtaccaagct tggcgtaatc atggtcatag ctgtttcctg    420
tgtgaaattg ttatccgctc acaattccac acaacatacg agccggaagc ataaagtgta    480
aagcctgggg tgcctaatga gtgagctaac tcacattaat tgcgttgcgc tcactgcccg    540
ctttccagtc gggaaacctg tcgtgccagc tgcattaatg aatcggccaa cgcgcgggga    600
gaggcggttt gcgtattggg cgctcttccg cttcctcgct cactgactcg ctgcgcttng    660
nccgtccggt tgcggcagcg gtataactna ctcaaaggcg gtaataccgg tatncacaga    720
atca                                                                  724

<210> SEQ ID NO 292
<211> LENGTH: 740
<212> TYPE: DNA
<213> ORGANISM: Homo Sapien
<220> FEATURE:
<221> NAME/KEY: misc_feature
<222> LOCATION: (1)...(740)
<223> OTHER INFORMATION: n = A,T,C or G

<400> SEQUENCE: 292
gnnnngnang tatacgactc actatagggc gaattgggcc ctctagatgc atgctcgagc       60
ggcccgccag tgtgatggat atctgcagaa ttcgccctta gcgtggtcgc ggccgaggta    120
cagaaagaat caaagaacat atatatatat taagtttcat tccaacctac aaagagcctg    180
cacttaaaag tcttaaaggt ttcctgaatc atggaatctc aacttacctg ccaattaatc    240
cagttctctc ttttttaaatg cagactccaa ccttaaacag aaggcatatt ctagctgact    300
tctaagtgtg tccaaagcat acctcagaga gccaagtggt ctgtgttcaa tacctattct    360
ttctatagaa tctcaaaagt ggcagtatga tgaaaagaaa agctacttt tctcctaaaa    420
atacccccct tcatcatcag tgtgttgtca tttttgcatc acaaagaata gacattctaa    480
atgttccctt ccacacagaa agacataaga gagaatgtga gtatgagtga gagtgtgtag    540
gtaagttgag ggatagtttg ctatccaaaa tgaatcattt tgaagatgac tttgtaaaga    600
agtaatatag ttaaaaatct caagacatga gattgangan ggcagggaaa taaggacct    660
angaatggaa aagagttaca gcccatgtga atacatacac aaacctacca ggttatttct    720
gngaattctc acacaggttg                                                 740
```

<210> SEQ ID NO 293
<211> LENGTH: 723
<212> TYPE: DNA
<213> ORGANISM: Homo Sapien
<220> FEATURE:
<221> NAME/KEY: misc_feature
<222> LOCATION: (1)...(723)
<223> OTHER INFORMATION: n = A,T,C or G

<400> SEQUENCE: 293

| | | | | | |
|---|---|---|---|---|---|
| gnnnnnnncn | anngccctc | tagatgcatg | ctcgagcggc | cgccagtgtg | atggatatct | 60 |
| gcagaattcg | cccttagcgt | ggtcgcggcc | gaggtacaga | aagaatcaaa | gaacatatat | 120 |
| atatattaag | tttcattcca | acctacaaag | agcctgcact | taaaagtctt | aaaggtttcc | 180 |
| tgaatcatgg | aatctcaact | tacctgccaa | ttaatccagt | tctctctttt | taaatgcaga | 240 |
| ctccaacctt | aaacagaagg | catattctag | ctgacttcta | agtgtgtcca | aagcatacct | 300 |
| cagagagcca | agtggtctgt | gttcaatacc | tattctttct | atagaatctc | aaaagtggca | 360 |
| gtatgatgaa | agaaaagct | acttttctc | ctaaaaatac | ccccttcat | catcagtgtg | 420 |
| ttgtcatttt | tgcatcacaa | agaatagaca | ttctaaatgt | tcccttccac | acagaaagac | 480 |
| ataagagaga | atgtgagtat | gagtgagagt | gtgtaggtaa | gttgagggat | agtttgctat | 540 |
| ccaaaatgaa | tcattttgaa | gatgactttg | taaagaagta | atatagttaa | aaatctcaag | 600 |
| agcatgagat | tganganggc | agggaaataa | angcctagga | atggaaaaga | gttaacagcc | 660 |
| catgtgaata | catagcacaa | acctaccagg | ttatttctgg | gaatctnacc | agtttgctgg | 720 |
| aaa | | | | | | 723 |

<210> SEQ ID NO 294
<211> LENGTH: 736
<212> TYPE: DNA
<213> ORGANISM: Homo Sapien
<220> FEATURE:
<221> NAME/KEY: misc_feature
<222> LOCATION: (1)...(736)
<223> OTHER INFORMATION: n = A,T,C or G

<400> SEQUENCE: 294

| | | | | | |
|---|---|---|---|---|---|
| gnnnnnnnna | gaccgactca | ctatagggcg | aattgggccc | tctagatgca | tgctcgagcg | 60 |
| gccgccagtg | tgatggatat | ctgcagaatt | cgcccttcg | agcggccgcc | cgggcaggta | 120 |
| cctgggatta | caggcaccca | ccaccacgcc | tggctaattt | tttttttgtat | ctttagtagg | 180 |
| gttttgccat | gttggccagg | ctggtcttta | actcctacct | cgtgatccac | ccgcctcggc | 240 |
| ccccaaagt | gctaggacca | caggcgtgag | ccaccacgcc | cagcccctg | tctctttttt | 300 |
| taaaacacaa | tttaaaagca | gaagaaaaa | atctgtgctg | tttagactca | gattcttaat | 360 |
| tagctagtat | ttcttaattc | aatcaataaa | ttattaagac | cttttcactg | ctcccttttt | 420 |
| aaagtcttct | ttggagtgat | ttaagtgctt | cttattacca | agctctcaaa | gagaagataa | 480 |
| aattaaaatc | tgatgggtaa | ccatttaaat | aagacaactg | gggtaaccca | tttctccagg | 540 |
| acccctctct | gcaacagaga | gctattctct | ttctttggcc | tagtaaacct | ctgctcttaa | 600 |
| cctttaaaaa | aaaaaaaaaa | gtacctcggc | cgcgaccacg | ctaanggcga | attccagcac | 660 |
| actggcggcc | gttactagtg | gatccgaact | cggtccaact | tggcgtaatc | atggcatagt | 720 |
| ggttcctgng | tgaaan | | | | | 736 |

<210> SEQ ID NO 295
<211> LENGTH: 725

```
<212> TYPE: DNA
<213> ORGANISM: Homo Sapien
<220> FEATURE:
<221> NAME/KEY: misc_feature
<222> LOCATION: (1)...(725)
<223> OTHER INFORMATION: n = A,T,C or G

<400> SEQUENCE: 295
gnnnnnnnnn anngngccct ctagatgcat gctcgagcgg ccgccagtgt gatggatatc      60
tgcagaattc gcccttttcga gcggccgccc gggcaggtac ctgggattac aggcacccac   120
caccacgcct ggctaattttt tttttgtatc tttagtaggg ttttgccatg ttggccaggc    180
tggtctttaa ctcctacctc gtgatccacc cgcctcggcc ccccaaagtg ctaggaccac    240
aggcgtgagc caccacgccc agcccccctgt ctctttttttt aaaacacaat ttaaaagcag   300
aaagaaaaaa tctgtgctgt ttagactcag attcttaatt agctagtatt cttaattca     360
atcaataaat tattaagacc ttttcactgc tcccttttta aagtcttctt tggagtgatt    420
taagtgcttc ttattaccaa gctctcaaag agaagataaa attaaaatct gatgggtaac    480
catttaaata agacaactgg ggtaacccat ttctccagga cccctctctg caacagagag    540
ctattctctt tctttggcct agtaaacctc tgctcttaac ctttaaaaaa aaaaaaaaag    600
tacctcggcc gcgaccacgc taagggcgaa ttccagcaca ctggcggccg ttactagtgg   660
atccgaactc ggtaccaagc ttgcgtaatc atggcatagc tggttcctgt gtgaaatggt   720
atccg                                                                725

<210> SEQ ID NO 296
<211> LENGTH: 742
<212> TYPE: DNA
<213> ORGANISM: Homo Sapien
<220> FEATURE:
<221> NAME/KEY: misc_feature
<222> LOCATION: (1)...(742)
<223> OTHER INFORMATION: n = A,T,C or G

<400> SEQUENCE: 296
gnnnnnnnnn nnacaaanct gggtagggcg aattgggccc tctagatgca tgctcgagcg      60
gccgccagtg tgatggatat ctgcagaatt cgcccttttcg agcggccgcc cgggcaggta   120
ccatgctgac ttcttggtat cttttaaggc ctaattttcc cttccttgag attactgtag    180
tgtgttccag ctaatttcta tttggaaacg agttggaaca gctgaaaact aggtattatt    240
gaaggcaaag cagcctcacg tcagtttttt atcagctcat ttgggaagtt ttttttttt     300
tttttttta attaattaga aagtaggctg ggcacggtgg ctcatgccta taatcccagc    360
acttggggag gccgaggatc tcctctctgg tggatcactt gagggcagga gttaagagac    420
catcctggcc aacatgatga aaccctgtct ctactaaaaa tacaaaaagt agctgggcgt    480
ggtggcatac tcttacaatc ccagctactt gggaggctga ggcaggagaa tcacttgaac   540
ctaggaagca gaggttgcag tgggccaaga tcacaccact atactctagc ctgggcgaca   600
gaagtgggga aaaagtagg accctgtcc tatattcang gttttctcac atatatgaac     660
ccatctaaat tctacgttgg taaaaggaac ctaaggttaa ttagnctata cttatttaag    720
aaccattntg gggnggagat gg                                             742

<210> SEQ ID NO 297
<211> LENGTH: 728
<212> TYPE: DNA
<213> ORGANISM: Homo Sapien
<220> FEATURE:
```

<221> NAME/KEY: misc_feature
<222> LOCATION: (1)...(728)
<223> OTHER INFORMATION: n = A,T,C or G

<400> SEQUENCE: 297

| tnnnntttga anncnacnct ctagngcatg ctcgagcggc cgccagtgtg atggatatct | 60 |
| gcagaattcg cccttttcgag cggccgcccg ggcaggtacc atgctgactt cttggtatct | 120 |
| tttaaggcct aatttttccct tccttgagat tactgtagtg tgttccagct aatttctatt | 180 |
| tggaaacgag ttggaacagc tgaaaactag gtattattga aggcaaagca gcctcacgtc | 240 |
| agttttttat cagctcattt gggaagtttt tttttttttt tttttttaat taattagaaa | 300 |
| gtaggctggg cacggtggct catgcctata atcccagcac ttggggaggc cgaggatctc | 360 |
| ctctctggtg gatcacttga gggcaggagt taagagacca tcctggccaa catgatgaaa | 420 |
| ccctgtctct actaaaaata caaaaagtag ctgggcgtgg tggcatactc ttacaatccc | 480 |
| agctacttgg gaggctgagg caggagaatc acttgaacct aggaagcaga ggttgcagtg | 540 |
| ggccaagatc acaccactat actctagcct gggcgacaga agtggggaaa aaagtaggac | 600 |
| ccctgtccta tattcangtt tttctcacat atatgaaccc atctaaattc tacgttggta | 660 |
| aaggtancttt aagttaatta gnctatactt atttaaganc aatatgggt gaaaatggat | 720 |
| ttttttttn | 728 |

<210> SEQ ID NO 298
<211> LENGTH: 745
<212> TYPE: DNA
<213> ORGANISM: Homo Sapien
<220> FEATURE:
<221> NAME/KEY: misc_feature
<222> LOCATION: (1)...(745)
<223> OTHER INFORMATION: n = A,T,C or G

<400> SEQUENCE: 298

| gnnnnnttna nnnnatacga ctcactatat agggcgaatt gggccctcta gatgcatgct | 60 |
| cgagcggccg ccagtgtgat ggatatctgc agaattcgcc cttagcgtgg tcgcggccga | 120 |
| ggtacccacg ttttgctcca cactccttga ccgcaggggc tcggacacaa accctgtca | 180 |
| ccaggagagt cagtcagcac tacttgggag ggctaaaggg aaatttggaa ataaaattcc | 240 |
| aaagtttgga gtaaaaaaat tcaagtgttg attttatatt ctttccttt ctgacacagc | 300 |
| ctaaagcgta gggggaacat gtgtttatct gtgggagata acaagatgg agtcccaaag | 360 |
| actttaacaa aatattttt taaaaatcca ctagaataga aatacatta tttagatata | 420 |
| ctttatgctg agagtgagta tatatgcttg tcctatttaa acttgtgaga aaagtggta | 480 |
| tcccttgata catttagaaa tatgggggct atcttgtttc attgtggggg tggggcagaa | 540 |
| ggagaataaa tgcaggatga ccctgttgaa ggaatcttag catggccaac aggggacgtt | 600 |
| tccagtcgat taccaggaaa tgcaagcctt ggggtttcta ctggtggtgg ggctgtcatg | 660 |
| aactttaaaa tccaaagcct agacaaggaa aagtgttaga ccaattgaaa agcaatccac | 720 |
| cctttttttt ttttttttt ggctt | 745 |

<210> SEQ ID NO 299
<211> LENGTH: 733
<212> TYPE: DNA
<213> ORGANISM: Homo Sapien
<220> FEATURE:
<221> NAME/KEY: misc_feature
<222> LOCATION: (1)...(733)
<223> OTHER INFORMATION: n = A,T,C or G

<400> SEQUENCE: 299

```
gnnnnnnnnn nnnnnnncct ctagatgctg ctcgaacggc cgccagtgtg atggatatct    60
gcagaattcg cccttagcgt ggtcgcggcc gaggtaccca cgttttgctc cacactcctt   120
gaccgcaggg gctcggacac aaaccctgt caccaggaga gtcagtcagc actacttggg   180
agggctaaag ggaaatttgg aaataaaatt ccaaagtttg gagtaaaaaa attcaagtgt   240
tgattttata ttctttccct ttctgacaca gcctaaagcg tagggggaac atgtgtttat   300
ctgtgggaga taaacaagat ggagtcccaa agactttaac aaaatatttt tttaaaaatc   360
cactagaata gaaaatacat tatttagata tactttatgc tgagagtgag tatatatgct   420
tgtcctattt aaacttgtga gaaaaagtgg tatcccttga tacatttaga aatatggggg   480
ctatcttgtt tcattgtggg ggtggggcag aaggagaata aatgccagga tgaccctgtt   540
gaaggaatct tancatggcc aacagggac gtttccagtc gattaccagg aaatgcaagc   600
cttggggttt ctactggtgg tggggctgtc atgaacnttt aaaatccaaa gcctagacca   660
aggaaaagtg ttaganccan tggaaaagcc attccagccc ttttttttn nnnttttttg   720
gcttttcacc aca                                                    733
```

<210> SEQ ID NO 300
<211> LENGTH: 741
<212> TYPE: DNA
<213> ORGANISM: Homo Sapien
<220> FEATURE:
<221> NAME/KEY: misc_feature
<222> LOCATION: (1)...(741)
<223> OTHER INFORMATION: n = A,T,C or G

<400> SEQUENCE: 300

```
gnnnntgann gtatacgaac tcactatagg gcgaattggg ccctctagat gcatgctcga    60
gcggccgcca gtgtgatgga tatctgcaga attcgcccctt tcgagcggcc gcccgggcag   120
gtacgtagtc taggccatat gtgttggaga ttgagactag tagggctagg cccaccgctg   180
cttcgcaggc ggcaaagact agtatggcaa taggcacaat attggctaag agggagtggg   240
tgttgagggt tatgagagta gctataatga acagcgatag tattattcct tctaggcaca   300
gtagggagga tatgaggtgt gagcgatata ctagtattcc tagaagtgag atggtaaatg   360
ctagtataat atttatgtaa atgaggggcc ccgcgtactc aagtgggtct ctgcctctca   420
gtggtggcct tggtcttcaa gtttcagcaa ttctgggaag ccaaggacac ctccatctcc   480
tcctccctga tctgcaactc atctaagagc agctttctca ctggaatgtc ttgtgtttaa   540
ggaacaagaa tccctgtttc cggtttgggt gcccaagtgc acctactgga tccaacccag   600
gattggagat actttgcaga acacaacatc atctggcaca tgaccagcca tggtgtttca   660
cttttcacaat ttcagcttnc ttcactgatt gcagcataat cgnggtcaac accttcaaga   720
ccaaggctga tgtgggccgc t                                             741
```

<210> SEQ ID NO 301
<211> LENGTH: 724
<212> TYPE: DNA
<213> ORGANISM: Homo Sapien
<220> FEATURE:
<221> NAME/KEY: misc_feature
<222> LOCATION: (1)...(724)
<223> OTHER INFORMATION: n = A,T,C or G

<400> SEQUENCE: 301

| | |
|---|---|
| gnnnnntncn antgggccct ctngngcatn gctcgagcgg cacgccagtg tgatggatat | 60 |
| ctgcagaatt cgcccttttcg agcggccgcc cgggcaggta cgtagtctag gccatatgtg | 120 |
| ttggagattg agactagtag ggctaggccc accgctgctt cgcaggcggc aaagactagt | 180 |
| atggcaatag gcacaatatt ggctaagagg gagtgggtgt tgagggttat gagagtagct | 240 |
| ataatgaaca gcgatagtat tattccttct aggcacagta gggaggatat gaggtgtgag | 300 |
| cgatatacta gtattcctag aagtgagatg gtaaatgcta gtataatatt tatgtaaatg | 360 |
| aggggccccg cgtactcaag tgggtctctg cctctcagtg gtggccttgg tcttcaagtt | 420 |
| tcagcaattc tgggaagcca aggacacctc catctcctcc tccctgatct gcaactcatc | 480 |
| taagagcagc tttctcactg gaatgtcttg tgtttaagga acaagaatcc ctgtttccgg | 540 |
| tttgggtgcc caagtgcacc tactggatcc aacccaggat tggagatact ttgcagaaca | 600 |
| caacatcatc tggcacatga ccagccatgg tgtttcactt tcacaatttc agcttncttc | 660 |
| actgattgca cataatcgtg gtcaacacct tcaagaccan ggctgatgtn ggccgntaca | 720 |
| ngga | 724 |

<210> SEQ ID NO 302
<211> LENGTH: 745
<212> TYPE: DNA
<213> ORGANISM: Homo Sapien
<220> FEATURE:
<221> NAME/KEY: misc_feature
<222> LOCATION: (1)...(745)
<223> OTHER INFORMATION: n = A,T,C or G

<400> SEQUENCE: 302

| | |
|---|---|
| gnnnntgaaa gtntanacga ctcactatag ggcgaattgg gccctctaga tgcatgctcg | 60 |
| agcggccgcc agtgtgatgg atatctgcag aattcgccct tcgagcggc cgcccgggca | 120 |
| ggtactattc cggatataca agatcactgg gagatgttga tgatggagac acagtgacag | 180 |
| atttcatggc ccaagagcga gaaagaggca ttactattca atcagctgct gttacatttg | 240 |
| attggaaagg ttatagagtc aatctaattg atacaccagg tcatgtggac tttaccttgg | 300 |
| aggttgagcg gtgcctaaga gtgttggatg gtgcagtggc tgtatttgat gcctctgctg | 360 |
| gtgtagaggc ccagactctc acagtatgga ggcaagctga taaacacaat atacctcgaa | 420 |
| tctgtttttt aaacaagatg gacaaaactg gagcaagctt taagtatgca gttgaaagca | 480 |
| tcagagagaa gttaaaggca aagcctttgc ttttacagtt accaattggt gaagccaaaa | 540 |
| cttttcaaagg agtggtggat gtagtaatga agaaaaact tctttggaat tgcaattcaa | 600 |
| atgatggaaa agactttgag agaaagcccc tcttggaaat gaatgatcct gaattgctga | 660 |
| aggaaacaac tgaagcaagg aatgccttaa ttgaacaagt tgcagaattt ggatgatgaa | 720 |
| ttgctgactt gggtttanaa naaat | 745 |

<210> SEQ ID NO 303
<211> LENGTH: 724
<212> TYPE: DNA
<213> ORGANISM: Homo Sapien
<220> FEATURE:
<221> NAME/KEY: misc_feature
<222> LOCATION: (1)...(724)
<223> OTHER INFORMATION: n = A,T,C or G

<400> SEQUENCE: 303

| | |
|---|---|
| gnnnttcgan tgggcccttc tagatgcatg ctcgagcggc cgccagtgtg atggatatct | 60 |
| gcagaattcg cccttttcgag cggccgcccg ggcaggtact attccggata tacaagatca | 120 |

```
ctgggagatg ttgatgatgg agacacagtg acagatttca tgcccaaga gcgagaaaga      180 ggcattacta ttcaatcagc tgctgttaca tttgattgga aaggttatag agtcaatcta      240
attgatacac caggtcatgt ggactttacc ttggaggttg agcggtgcct aagagtgttg      300
gatggtgcag tggctgtatt tgatgcctct gctggtgtag aggcccagac tctcacagta      360
tggaggcaag ctgataaaca caatatacct cgaatctgtt ttttaaacaa gatggacaaa      420
actggagcaa gctttaagta tgcagttgaa agcatcagag agaagttaaa ggcaaagcct      480
ttgcttttac agttaccaat tggtgaagcc aaaactttca aaggagtggt ggatgtagta      540
atgaaagaaa aacttctttg gaattgcaat tcaaatgatg gaaaagactt tgagagaaag      600
cccctcttgg aaatgaatga tcctgaattg ctgaaggaaa caactgaagc aaggaatgcc      660
ttaattgaca agttgcagat ttggatgatg aatttgctga cttggtttta aagaattan      720 tgag                                                                   724

<210> SEQ ID NO 304
<211> LENGTH: 741
<212> TYPE: DNA
<213> ORGANISM: Homo Sapien
<220> FEATURE:
<221> NAME/KEY: misc_feature
<222> LOCATION: (1)...(741)
<223> OTHER INFORMATION: n = A,T,C or G

<400> SEQUENCE: 304
gnnnnnngaa agtntacgac tcactatagg gcgaattggg ccctctagat gcatgctcga      60
gcggccgcca gtgtgatgga tatctgcaga attcgcccct agcgtggtcg cggccgaggt     120
actttataaa tggaattttc ttctacttgt atccatttcc cggggcttat ggacccattc     180
atactctcca tatttagaat caaaggttcc tttctgaaga gaccttaatt ttaaggtaaa     240
acgtggtcca agttcctgaa ttcccacttt cttttcactc ctgaatatgt atctgtgaaa     300
tctgaagaat atgtaatccc gttgattgtg aatgtggca acctgccttc cgataaattg      360
aggattatga ggaaagagag atgcaaacat acgtccaatt gaatgaccca gccgtgttgt     420
aaaattattc agaattattt caggtatgtg ttctgtgggg tccttgcctc ttctcttaat     480
ttctttacga agacgaacac tgctcatttt aaaatgagca gttgggccat ttggcaagtg     540
actcaaaata agtccatttg gggttttacg atcttcatta ataacaatca ggtctgtgaa     600
atctcttgcg atgcactgtg gaataatttt tttcagaacc agcctcttct gtaataaaca     660
tgtgagtttg gtataactgt gganagctgt cacagagtcg taccagtata ccaaccatac     720
caactntgtt gtagagcaaa a                                                741

<210> SEQ ID NO 305
<211> LENGTH: 719
<212> TYPE: DNA
<213> ORGANISM: Homo Sapien
<220> FEATURE:
<221> NAME/KEY: misc_feature
<222> LOCATION: (1)...(719)
<223> OTHER INFORMATION: n = A,T,C or G

<400> SEQUENCE: 305
gnnnttncaa ntgggccctc tngatgcatg ctcgagcggc cgccagtgtg atggatatct      60
gcagaattcg cccttagcgt ggtcgcggcc gaggtacttt ataaatggaa ttttcttcta     120
cttgtatcca tttcccgggg cttatggacc cattcatact ctccatattt agaatcaaag     180
```

| | |
|---|---|
| gttcctttct gaagagacct taatttaag gtaaaacgtg gtccaagttc ctgaattccc | 240 |
| actttcttt cactcctgaa tatgtatctg tgaaatctga agaatatgta atcccgttga | 300 |
| ttgtggaatg tggcaacctg ccttccgata aattgaggat tatgaggaaa gagagatgca | 360 |
| aacatacgtc caattgaatg acccagccgt gttgtaaaat tattcagaat tatttcaggt | 420 |
| atgtgttctg tggggtcctt gcctcttctc ttaatttctt tacgaagacg aacactgctc | 480 |
| atttaaaat gagcagttgg gccatttggc aagtgactca aataagtcc atttggggtt | 540 |
| ttacgatctt cattaataac aatcaggtct gtgaaatctc ttgcgatgca ctgtggaata | 600 |
| atttttcag agccagtcct cttctgtaat aaacatgtga agtttggtat actgtggana | 660 |
| gctgtcacag agtcgacagt ataccaacca taccaactct gttgnagaac anaacccat | 719 |

<210> SEQ ID NO 306
<211> LENGTH: 746
<212> TYPE: DNA
<213> ORGANISM: Homo Sapien
<220> FEATURE:
<221> NAME/KEY: misc_feature
<222> LOCATION: (1)...(746)
<223> OTHER INFORMATION: n = A,T,C or G

<400> SEQUENCE: 306

| | |
|---|---|
| gnnnnntgaa agtatacgac tcactatagg gcgaattggg ccctctagat gcatgctcga | 60 |
| gcggccgcca gtgtgatgga tatctgcaga attcgcccct tcgagcggcc gcccgggcag | 120 |
| gtactccagc ccaggcgaca gagtgagact cagtctcaaa aaaaaaaaaa atttgggcaa | 180 |
| gttatagtcc atctcatagt gttgttagga ctaatttctt catgtgctta gaaaatgcc | 240 |
| tggcagatag gaaatggtca atattattat tattgataag atgaccattt tggagtttag | 300 |
| aaaaccattt tcaatgccta tgaaataaca actccataag ccattcccctt aaatccagta | 360 |
| gactgaattc tcacaagtcc tcatcactca tcatttctac atcctgctga tttacaaata | 420 |
| cttcttcata ccatggttta tgtctttgct taatatcaag gaggatggat tccatggtag | 480 |
| agccaaactc aatgatacta cgagtctcat tttggtaagt ataagcaaag ccagcagcat | 540 |
| gcatggccac caatgaacct tttgaatcaa acacaggga gcccggaagc cccaaagaaa | 600 |
| aattcagtgt cataggtaat cacatcangg ttgtgaacta ttttctggaa acttctttga | 660 |
| gtatacatat ggacatactc tggactttct gctttttag actgaacacg ttcctgacat | 720 |
| ttctttgctc gctgaccctg anggat | 746 |

<210> SEQ ID NO 307
<211> LENGTH: 725
<212> TYPE: DNA
<213> ORGANISM: Homo Sapien
<220> FEATURE:
<221> NAME/KEY: misc_feature
<222> LOCATION: (1)...(725)
<223> OTHER INFORMATION: n = A,T,C or G

<400> SEQUENCE: 307

| | |
|---|---|
| gnnnnntncn antggccctc tagatgcatg ctcgagcggc cgccagtgtg atggatatct | 60 |
| gcagaattcg ccctttcgag cggccgcccg ggcaggtact ccagcccagg cgacagagtg | 120 |
| agactcagtc tcaaaaaaaa aaaaatttg gcaagttat agtccatctc atagtgttgt | 180 |
| taggactaat ttcttcatgt gcttagaaaa atgcctggca gataggaaat ggtcaatatt | 240 |
| attattattg ataagatgac catttggag tttagaaaac cattttcaat gcctatgaaa | 300 |
| taacaactcc ataagccatt cccttaaatc cagtagactg aattctcaca agtcctcatc | 360 |

| | |
|---|---|
| actcatcatt tctacatcct gctgatttac aaatacttct tcataccatg gtttatgtct | 420 |
| ttgcttaata tcaaggagga tggattccat ggtagagcca aactcaatga tactacgagt | 480 |
| ctcattttgg taagtataag caaagccagc agcatgcatg gccaccaatg aacctttga | 540 |
| atcaaacaca ggggagccgg aagccccaaa gaaaaattca gtgtcatagg taatcacatc | 600 |
| anggttgtga actattttct ggaaacttct ttgagtatac atatggacat actctggact | 660 |
| ttctgctttt ttagactgac acgttcctga catttctttg ctcgctgacc ctgagggatc | 720 |
| acang | 725 |

<210> SEQ ID NO 308
<211> LENGTH: 744
<212> TYPE: DNA
<213> ORGANISM: Homo Sapien
<220> FEATURE:
<221> NAME/KEY: misc_feature
<222> LOCATION: (1)...(744)
<223> OTHER INFORMATION: n = A,T,C or G

<400> SEQUENCE: 308

| | |
|---|---|
| gnnnntgaaa gtaatacgac tcactatagg gcgaattggg ccctctagat gcatgctcga | 60 |
| gcggccgcca gtgtgatgga tatctgcaga attcgccctt tcgagcggcc gcccgggcag | 120 |
| gtacgcgggg tgacaagtag caacatggct tgggtcccct gtgcagcatc agcttatgct | 180 |
| gccacaagtc agtttgcacc ctaggtaccc aggagctagt atccttagat cttctatcg | 240 |
| ctaacttaat tctcttcgtt atttatctga ccctctaact ccatgtctaa cttgcattaa | 300 |
| aaaaaaaaaa attctttaca gtcaacccaa gcttaacatg gactcaggtt ccccagcagc | 360 |
| cttaatttgt tttgttaaca tctgttcctt ctttttcagc tctcctagag tatttctgag | 420 |
| tgttgtgttc atctaatctt agtattcttt taattacaaa ttgacctcac agcttgaggt | 480 |
| ttcctgtgtc ttattctgtg gactacctgt gctcctttgc ttccctccc ctcgcataat | 540 |
| aactatatta agaaattttt tttggccttg agttggctgg aaaaaaaata taaaatttaa | 600 |
| aaaaaaaan nnnnnnnaa aaaaaaaag tacctnggcc gggaccacgc taanggcgaa | 660 |
| ttccagcaca ctggcggccg ttactaagtg gatccgaact cggtaccaac ttggcgtaat | 720 |
| catggcatag ctggttcctg ngga | 744 |

<210> SEQ ID NO 309
<211> LENGTH: 746
<212> TYPE: DNA
<213> ORGANISM: Homo Sapien
<220> FEATURE:
<221> NAME/KEY: misc_feature
<222> LOCATION: (1)...(746)
<223> OTHER INFORMATION: n = A,T,C or G

<400> SEQUENCE: 309

| | |
|---|---|
| gnnnntncga ntgggccctc tagatgcatg ctcgagcggc cgccagtgtg atggatatct | 60 |
| gcagaattcg ccctttcgag cggccgcccg ggcaggtacg cggggtgaca agtagcaaca | 120 |
| tggcttgggt cccctgtgca gcatcagctt atgctgccac aagtcagttt gcaccctagg | 180 |
| tacccaggag ctagtatcct tagatctttc tatcgctaac ttaattctct tcgttattta | 240 |
| tctgaccctc taactccatg tctaacttgc attaaaaaaa aaaaaattct ttacagtcaa | 300 |
| cccaagctta acatggactc aggttcccca gcagccttaa tttgttttgt taacatctgt | 360 |
| tccttctttt tcagctctcc tagagtattt ctgagtgttg tgttcatcta atcttagtat | 420 |

| | |
|---|---|
| tcttttaatt acaaattgac ctcacagctt gaggtttcct gtgtcttatt ctgtggacta | 480 |
| cctgtgctcc tttgcttccc ctcccctcgc ataataacta tattaagaaa ttttttttgg | 540 |
| ccttgagttg gctggaaaaa aaatataaaa tttaaaaaaa aaannnnnnn nnnnaaaaaa | 600 |
| aaaagtcctt ggccgggacc acnctaangg cgaaattcca gcacaactgg gcggnccgtt | 660 |
| actaagggga atcccnaact tnggnacccn aaacttgggc gtaaaacaat gggncaataa | 720 |
| gctggnnncc ctggnggtga aaaatt | 746 |

<210> SEQ ID NO 310
<211> LENGTH: 751
<212> TYPE: DNA
<213> ORGANISM: Homo Sapien
<220> FEATURE:
<221> NAME/KEY: misc_feature
<222> LOCATION: (1)...(751)
<223> OTHER INFORMATION: n = A,T,C or G

<400> SEQUENCE: 310

| | |
|---|---|
| gnnnntgana gtaatacgac tcactatagg gcgaattggg ccctctagat gcatgctcga | 60 |
| gcggccgcca gtgtgatgga tatctgcaga attcgcccct tcgagcggcc gcccgggcag | 120 |
| gtacttaatg cctttctcct cctggacatc agagagaaca cctgggtatt ctggcagaag | 180 |
| tttatatttc tccaaatcaa tttctggaaa aaacgtgtca ctttcaaagt cttgcatgat | 240 |
| ccttgtcaca aatagtttaa gatggcctgg gtgattcatg gcttccttat aaacagaact | 300 |
| gccaccaact atccagacca tgtctacttt atttgctaat tctggttgtt cagtaagttt | 360 |
| taaggcatca tctagacttc tggaaagaaa atgagctcct tgtggaggtt ccttgagttc | 420 |
| tctgctgaga actaaattaa ttctacccct taaaggtcga ttcttctcag gaatggagaa | 480 |
| ccaggtcttc ttacccataa tcaccagatt ctgnttacct tctactgaag aagttgtggt | 540 |
| cattctctgg aaatatctga attcattcct gagcggtggc caaggcangt ncccgttctt | 600 |
| gccgatgccc atgttctggg acacagcgac gatgcagttt agcgaaccaa ccatgacagc | 660 |
| aaccgggang accttcgagc cccgttcgnt acaagccccc gcgtaccttn gggccgngaa | 720 |
| cacgcttaag ggcgaattnc aacacactgg c | 751 |

<210> SEQ ID NO 311
<211> LENGTH: 724
<212> TYPE: DNA
<213> ORGANISM: Homo Sapien
<220> FEATURE:
<221> NAME/KEY: misc_feature
<222> LOCATION: (1)...(724)
<223> OTHER INFORMATION: n = A,T,C or G

<400> SEQUENCE: 311

| | |
|---|---|
| gnnttncnan tgggccctct agatgcatgc tcgagcggcc gccagtgtga tggatatctg | 60 |
| cagaattcgc cctttcgagc ggccgcccgg gcaggtactt aatgcctttc tcctcctgga | 120 |
| catcagagag aacacctggg tattctggca gaagtttata tttctccaaa tcaatttctg | 180 |
| gaaaaaacgt gtcactttca agtcttgca tgatccttgt cacaaatagt ttaagatggc | 240 |
| ctgggtgatt catggcttcc ttataaacag aactgccacc aactatccag accatgtcta | 300 |
| ctttatttgc taattctggt tgttcagtaa gttttaaggc atcatctaga cttctggaaa | 360 |
| gaaaatgagc tccttgtgga ggttccttga gttctctgct gagaactaaa ttaattctac | 420 |
| cctttaaagg tcgattcttc tcaggaatgg agaaccaggt cttcttaccc ataatcacca | 480 |
| gattctgttt accttctact gaagaggttg tggtcattct ctggaaatat ctgaattcat | 540 |

```
tcctgagcgg tggccaaggc angtccccgt tcttgccgat gcccatgttc tgggacacag    600
cgacgatgca gtttancgaa ccacccatga cagcagcggg aggaccttcg agcccgctcg    660
ttacaagccc ccgcgtacct tnggccgcga acaccttang gcgaaattca acacactggc    720
ggcc                                                                  724
```

<210> SEQ ID NO 312
<211> LENGTH: 738
<212> TYPE: DNA
<213> ORGANISM: Homo Sapien
<220> FEATURE:
<221> NAME/KEY: misc_feature
<222> LOCATION: (1)...(738)
<223> OTHER INFORMATION: n = A,T,C or G

<400> SEQUENCE: 312

```
nnnntttgaa gnctacnact cactataggg cgaattgggc cctctagatg catgctcgag     60
cggccgccag tgtgatggat atctgcagaa ttcgcccttt gagcggccgc ccgggcaggt    120 acgcggggg cagacatggc gacattgaca gtggtccagc cgctcaccct ggacagagat    180
gttgcaagag caattgaatt actggaaaaa ctacaggaat ctggagaagt acgttcacta    240
attatctaca aggacaaaat cagttgtatt tacaaaactc tacttcagtg tttgttttag    300
tttttttttt actgaaactt gttttttgtga atactctgtg cttagaatta aatatcactt    360
tcttatgaac aacataactt cttcagattg tgtatatgaa acattagca agtcttgttt     420 tttctatgaa gcaaacacaa ttggtgacaa aggttgtcaa tcatttcttc aaaattataa    480
tgcagttcta atggtcagca tattttgata ttaaatttaa agatcaccctc tctgcatttg   540 tttttaaatt atgctaatac accacacatt atgttggtat gttttggtct gtcctcggcc    600
gcgaccacgc ttanggcgaa ttccagcaca ctggcgggcc gttactagtg gatccgagct    660
cggtccaagc tggcgtaatc atggtcatag ctggttcctg tgtgaaatgg tatccgttac    720
aattcccaca catacgan                                                   738
```

<210> SEQ ID NO 313
<211> LENGTH: 720
<212> TYPE: DNA
<213> ORGANISM: Homo Sapien
<220> FEATURE:
<221> NAME/KEY: misc_feature
<222> LOCATION: (1)...(720)
<223> OTHER INFORMATION: n = A,T,C or G

<400> SEQUENCE: 313

```
gnnttncaan tgggccctct agatgcatgc tcgagcggcc gccagtgtga tggatatctg     60
cagaattcgc cctttgagcg gccgcccggg caggtacgcg gggggcagac atggcgacat    120
tgacagtggt ccagccgctc accctggaca gagatgttgc aagagcaatt gaattactgg    180
aaaaactaca ggaatctgga agtacgtt cactaattat ctacaaggac aaaatcagtt     240
gtatttacaa aactctactt cagtgtttgt tttagttttt ttttactga aacttgtttt     300 tgtgaatact ctgtgcttag aattaaatat cactttctta tgaacaacat aacttcttca    360
gattgtgtat atgaaaacat tagcaagtct tgttttttct atgaagcaaa cacaattggt    420
gacaaaggtt gtcaatcatt tcttcaaaat tataatgcag ttctaatggt cagcatattt    480
tgatattaaa tttaaagatc accctctctg catttgtttt aaattatgct aatacaccac    540
acattatgtt ggtatgtttt gntctgtacc tcggccgcga ccacgctaan ggcgaattca    600
```

| | |
|---|---|
| ncacactggc ngncgttact agtggatccg agctcggacc aaacttggcg taatcatngn | 660 |
| catagctggt tcctgtgtga aatggtatc cgttacaatt tcacacacat acgagccgga | 720 |

<210> SEQ ID NO 314
<211> LENGTH: 740
<212> TYPE: DNA
<213> ORGANISM: Homo Sapien
<220> FEATURE:
<221> NAME/KEY: misc_feature
<222> LOCATION: (1)...(740)
<223> OTHER INFORMATION: n = A,T,C or G

<400> SEQUENCE: 314

| | |
|---|---|
| gnnnnttnaa gnctacgact cactataggg cgaattgggc cctctagatg catgctcgag | 60 |
| cggccgccag tgtgatggat atctgcagaa ttcgcccta gcgtggtcgc ggccgaggta | 120 |
| cttttttttt tttttttttt ttagtgcttt ctactttatt aaacatcaaa gcccaaatag | 180 |
| atgttccctg tggaggagga cttaaggaca ctaggggagg agaaagggac acctgggaag | 240 |
| agaatcacac cacagagacc aatcttcaca aaaagggtcc aatattgatt tctagggagg | 300 |
| agcagggcat ggtcagctca aatttggtga taacgtcagg atgaaggacc ccaagcttcc | 360 |
| cgacgctttg accctggca aagatctctg cacatcgccc ggggaagaaa gcaggccctt | 420 |
| ctgatgcttt gatcacatat ccccccttgt cttcaccagg aggcacatcg agcaactgca | 480 |
| taattctgtc cagcagccca tgaatgatct caaacccagg attcttgntg taataaacag | 540 |
| cactgagatg tctgtagttt tttgcaccta catctgnatt agaatctttt attacaatgt | 600 |
| cagagatttc aaacagtttc agtggaaggg gcatcttacg attgctgcta tggcttcagg | 660 |
| angccaggaa gaagggtagt gcgtgccacc tgaaattcac tggtttagga tacttatgtg | 720 |
| gactggcttt gttgcaaaan | 740 |

<210> SEQ ID NO 315
<211> LENGTH: 722
<212> TYPE: DNA
<213> ORGANISM: Homo Sapien
<220> FEATURE:
<221> NAME/KEY: misc_feature
<222> LOCATION: (1)...(722)
<223> OTHER INFORMATION: n = A,T,C or G

<400> SEQUENCE: 315

| | |
|---|---|
| gnnnnnnnnn nnnnnnntnn atgctgctcg agcggccgcc agtgtgatgg atatctgcag | 60 |
| aattcgccct tagcgtggtc gcggccgagg tacttttttt tttttttttt ttttagtgct | 120 |
| ttctacttta ttaaacatca aagcccaaat agatgttccc tgtggaggag gacttaagga | 180 |
| cactaggga ggagaaaggg acacctggga agagaatcac accacagaga ccaatcttca | 240 |
| caaaaagggt ccaatattga tttctaggga ggagcagggc atggtcagct caaatttggt | 300 |
| gataacgtca ggatgaagga ccccaagctt cccgacgctt tgaccctgg caaagatctc | 360 |
| tgcacatcgc ccggggaaga aagcaggccc ttctgatgct ttgatcacat atccccccttt | 420 |
| gtcttcacca ggaggcacat cgagcaactg cataattctg tccagcagcc catgaatgat | 480 |
| ctcaaaccca ggattcttgt tgtaataaac agcactgaga tgtctgtagt ttttgcacc | 540 |
| tacatctgna ttagaatctt ttattacaat gtcagagatt tcaaacagtt tcagtggaaa | 600 |
| ggggcatctt acgatttgct gctatggnct tcangaggnc angaaaaagg gtantgcntg | 660 |
| cccctgaaat tcanctggtt taggattacc tatgtggact ggctttgntg caaaaaaatn | 720 |
| cn | 722 |

<210> SEQ ID NO 316
<211> LENGTH: 753
<212> TYPE: DNA
<213> ORGANISM: Homo Sapien
<220> FEATURE:
<221> NAME/KEY: misc_feature
<222> LOCATION: (1)...(753)
<223> OTHER INFORMATION: n = A,T,C or G

<400> SEQUENCE: 316

| | | | | | |
|---|---|---|---|---|---|
| gnnnnttna | nagtnnnnac | gactcactat | agggcgaac | nctctncatg | catgctcnan | 60 |
| cggncnncan | ngtgatggat | atntgctgan | ttcgcccta | ccntgcntn | ggccgaggcg | 120 |
| cagntcccac | gtntngctcc | ncactncnnn | accgcagggg | cncgacncn | gaccngngnn | 180 |
| ncnnngngag | tnccncagca | ctacttggga | nggctanagg | gaagnttgga | aataaaattc | 240 |
| caaannttgg | agtaaaagca | atncangcgn | ngattatata | tgntnnccct | ttctgacacn | 300 |
| ncctagagcg | taggggaac | atgngtntat | ctgtgggana | tnaacaagat | ggagtcccaa | 360 |
| agactttaac | aaagntattt | cttaannatc | cnctacaatn | nanaatncat | tattcatatn | 420 |
| tactntatgc | tgnnagtgag | tatntatgct | ngtcctattt | aaacttgnga | gaanaagtgg | 480 |
| tntcccttga | tacattnaga | aatatgggg | ctatcttgnt | ncattgtggg | ggtgggcan | 540 |
| aagganaatn | aatgcangat | gaccctgttg | aangaatctt | aacatggcca | acanggggac | 600 |
| ngtttacagt | cgattaccag | gaaangcaag | ccttggggtt | tctactgcng | gtggggctg | 660 |
| tcatgaactt | naaaatccan | agnctatacc | aggaaaaagt | gttangaccc | aattgaaang | 720 |
| ctntccaccc | tttctttnn | tttgttccng | cnc | | | 753 |

<210> SEQ ID NO 317
<211> LENGTH: 893
<212> TYPE: DNA
<213> ORGANISM: Homo Sapien
<220> FEATURE:
<221> NAME/KEY: misc_feature
<222> LOCATION: (1)...(893)
<223> OTHER INFORMATION: n = A,T,C or G

<400> SEQUENCE: 317

| | | | | | |
|---|---|---|---|---|---|
| gtgnnntntn | cnaaatggnc | cntttnaatg | cctncctcga | gcgggccgcc | agtgtgatgg | 60 |
| atntntaatt | cgnccttagc | gtggtcgcgg | ccgnngtacn | aangaaataa | aantnacagt | 120 |
| ntcaaagaac | caaantaagt | cggacacaaa | ccctgtcac | cannagagtc | ccatanacat | 180 |
| aannggntg | ntgtcaagna | ggattnaaat | taactttaac | aacnttntat | ataatgctac | 240 |
| attccccaat | taataaagga | nagttcacat | atacanctaa | ntgntaattg | tggaaanaag | 300 |
| ggtgaaantn | tgcatantta | atannaaana | atgctgaang | cttttncata | nnattnnctt | 360 |
| aaaaatncac | ttncnatgca | gcantangtn | tacatgctta | atntatcntg | cnagtgattn | 420 |
| ntatgcttgt | cctacatgac | ntaccttgaa | caactggnac | tncccagatt | catactgaaa | 480 |
| tatgggncg | ntaantatnt | tgggancggn | annacntgaa | tcctcaaagg | atannnnntn | 540 |
| tccagntgga | tgaaaccnat | nattnaaang | gatatnntna | accatnggan | cgaatgnncg | 600 |
| nngtctttt | tcaatnntnc | gngaagntnc | cnnttnnata | nccgngggc | cncattgngg | 660 |
| ggnntatntn | ncaatcaann | ccnngagntg | tntnntcntt | cntcnaccgc | ataaccttt | 720 |
| gccataggga | accttnttn | aacccctttg | gnttatnggg | aaanaannnn | nnttttaaat | 780 |
| tcnccaaaat | ngggaaaaan | aaccctntc | actctaaaaa | nttanccnta | gacctanttn | 840 | tngngncata tttgntaaac nctatggncc ctcnagnggg gnnctgggnc nnc    893

<210> SEQ ID NO 318
<211> LENGTH: 744
<212> TYPE: DNA
<213> ORGANISM: Homo Sapien
<220> FEATURE:
<221> NAME/KEY: misc_feature
<222> LOCATION: (1)...(744)
<223> OTHER INFORMATION: n = A,T,C or G

<400> SEQUENCE: 318
gnnnngattg tatacgactc actatagggc gaattgggcc ctctagatgc atgctcgagc    60
ggccgccagt gtgatggata tctgcagaat tcgcccttc gagcggccgc ccgggcaggt    120
acctcattag taattgtttt gttgtttcat ttttttctaa tgtctcccct ctaccagctc    180
acctgagata acagaatgaa aatggaagga cagccagatt tctcctttgc tctctgctca    240
ttctctctga agtctaggtt acccattttg gggacccatt ataggcaata aacacagttc    300
ccaaagcatt tggacagttt cttgttgtgt tttagaatgg ttttccttt tcttagcctt    360
ttcctgcaaa aggctcactc agtcccttgc ttgctcagtg gactgggctc cccagggcct    420
aggctgcctt cttttccatg tcccacccat gagccctcca ctggacagct cagtaagcct    480
ggcccttcat tctgcgctgt gttcttcctc tgtgaaaatc caatacctct tacctcctct    540
gcatgcaaag attctcaagg attgtcagac ttcaaacgta acagcagaac caccagaagg    600
tcctataaat gcagtagtga ccttctcaag ctgtcanggc tttaaatagg atttgggatt    660
taatgctatg tattttttaaa ggaaagaaat aagagttgct agttttaaaa atgcatgtct    720
tttaccaatt canaatctgg cccc    744

<210> SEQ ID NO 319
<211> LENGTH: 720
<212> TYPE: DNA
<213> ORGANISM: Homo Sapien
<220> FEATURE:
<221> NAME/KEY: misc_feature
<222> LOCATION: (1)...(720)
<223> OTHER INFORMATION: n = A,T,C or G

<400> SEQUENCE: 319
gngtttaaac cttcttanng ctgctcgagc ggccgccagt gtgatggata tctgcagaat    60
tcgcccttc gagcggccgc ccgggcaggt acctcattag taattgtttt gttgtttcat    120
ttttttctaa tgtctcccct ctaccagctc acctgagata acagaatgaa aatggaagga    180
cagccagatt tctcctttgc tctctgctca ttctctctga agtctaggtt acccattttg    240
gggacccatt ataggcaata aacacagttc ccaaagcatt tggacagttt cttgttgtgt    300
tttagaatgg ttttccttt tcttagcctt ttcctgcaaa aggctcactc agtcccttgc    360
ttgctcagtg gactgggctc cccagggcct aggctgcctt cttttccatg tcccacccat    420
gagccctcca ctggacagct cagtaagcct ggcccttcat tctgcgctgt gttcttcctc    480
tgtgaaaatc caatacctct tacctcctct gcatgcaaag attctcaagg attgtcagac    540
ttcaaacgta acagcagaac caccagaagg tcctataaat gcagtagtga ccttctcaag    600
ctgtcanggc tttaaatagg atttgggatt taatgctatg tattttttaaa ggaaagaaat    660
agagttgcta gttttaaaaa tgcatgtctt ttaccaatt cagaatctgg ccccnaactt    720

<210> SEQ ID NO 320
<211> LENGTH: 694

<212> TYPE: DNA
<213> ORGANISM: Homo Sapien
<220> FEATURE:
<221> NAME/KEY: misc_feature
<222> LOCATION: (1)...(694)
<223> OTHER INFORMATION: n = A,T,C or G

<400> SEQUENCE: 320

| | | | | | |
|---|---|---|---|---|---|
| atgctcgagc | ggncggcant | gtgatggatn | tctgcagaat | tcgcccttc | gagcggccgc | 60 |
| ccgggcaggt | actattccgg | atatacaaga | tcactggag | atgttgatga | tggagacaca | 120 |
| gtgacagatt | tcatggccca | agagcgagaa | agaggcntta | ctattcaatc | agctgctgtt | 180 |
| acatttgatt | ggaaaggtta | tagagtcaat | ctaattgata | caccaggtca | tgtggacttt | 240 |
| accttggagg | ttgagcggtg | cctaagagtg | ttggatggtg | cantggctgt | atttgatgcc | 300 |
| tctgctggtg | tagaggccca | gactntcaca | gtatggaggc | aagctgataa | acacaatata | 360 |
| cctcgaatct | gtttttaaa | caagatggac | aaaactggag | caagctttaa | gtatgcagtt | 420 |
| gaaagcatca | gagagaagtt | aaaggcaaag | cctttgcttt | tacagttacc | aattggtgaa | 480 |
| gccaaaactt | tcaaggagt | ggtggatgta | gtaatgaang | aaaaacttct | ttgggaattg | 540 |
| caattcaana | tgatggaaaa | gactttgaga | gaaagcccct | cttggaaatg | aatgatcctg | 600 |
| aattgctgaa | ggaaacaact | gaacaaggaa | tgccttaatt | gaacaaagtt | gcagatttgg | 660 |
| atgatgaatt | tgctgacttg | gttttaagaa | gaat | | | 694 |

<210> SEQ ID NO 321
<211> LENGTH: 781
<212> TYPE: DNA
<213> ORGANISM: Homo Sapien
<220> FEATURE:
<221> NAME/KEY: misc_feature
<222> LOCATION: (1)...(781)
<223> OTHER INFORMATION: n = A,T,C or G

<400> SEQUENCE: 321

| | | | | | |
|---|---|---|---|---|---|
| gngttnacna | ntgggccctc | tngatgctgc | tcgagcggcc | gncagtgtga | tggatntctg | 60 |
| cagaatncgc | cctncgggcg | ccgnccggg | caggtactat | nccggatata | caagatcact | 120 |
| gggagatgtt | gatgatggag | acncagngac | agatttcatg | gcccaagagc | gagaaagagg | 180 |
| cnttactatn | caatcagctg | ctgttacatt | cgattggaaa | ggttatngag | tcaatctaat | 240 |
| tgatncacca | ngtnatgtgg | actttaccct | ggaggttgag | cggtgcctaa | nagtgttgga | 300 |
| tggtgcanng | gctgtatttg | atgcctctgc | tggtgtagag | gcccagactc | tcacagtatg | 360 |
| gatgcaagct | gataaacaca | atatacctng | aatctgtgtt | ttaaacaaga | tggacaaaac | 420 |
| tggagcaagc | tttaaagtnt | gcagttgaaa | gcatcagaga | gangttnaag | gcanagcctt | 480 |
| tgcttttaca | gttcccaat | tgggtgaaac | ccaaaacttt | tcaaagggag | ttggttggat | 540 |
| tgtaagtaat | gaaaggaaaa | acttctttgg | gaaantggca | atttcaanat | gattggaaaa | 600 |
| ngactttgg | gagaaaagcc | ccttcttggg | aaaatngaaa | tgatncctga | aatttgcngt | 660 |
| aaanngaaaa | cnaacntgna | atccaangga | attnccctt | aanttggaac | aaaggnttgc | 720 |
| naantttng | attgaatnga | atttgncnga | cntttnggtt | ttangaaaga | aattaaagng | 780 |
| g | | | | | | 781 |

<210> SEQ ID NO 322
<211> LENGTH: 744
<212> TYPE: DNA
<213> ORGANISM: Homo Sapien
<220> FEATURE:

<221> NAME/KEY: misc_feature
<222> LOCATION: (1)...(744)
<223> OTHER INFORMATION: n = A,T,C or G

<400> SEQUENCE: 322

| gnnntganag tatcgactca ctatagggcg aattgggccc tctagatgca tgctcgagcg | 60 |
| gcccgccagt gtgatggata tctgcagaat tcgcccttc gagcggccgc ccgggcaggt | 120 |
| acgcggggac tgggtttttc ccttttgta gccttttcct ttagtctcct cttcccggtg | 180 |
| gttggtaaaa agaggtgaat tgacagccta tgttgaagac actgtgcttt tctcaagaag | 240 |
| gacatccaaa cagcaagtct acttctttct ctttaacgat gtgctcatta tcaccaagaa | 300 |
| gaagagtgaa gaaagttaca acgtcaatga ttattcctta agagatcagc tattggtgga | 360 |
| atcttgtgac aatgaagagc ttaattcttc tccagggaag aacagctcca caatgctcta | 420 |
| ttcaagacag agctctgcca gtcacctctt tactctgaca gtccttagta accacgcgaa | 480 |
| tgagaaagtg gagatgctac taggagctga gacgcagagc gagcgagccc gctggataac | 540 |
| tgccctggga cacagcagcg ggaagccgcc tgcagaccga acctnactga cccaggtgga | 600 |
| aatcgttagg tcatttactg ctaagcagcc agatgaactc ttcctgcagt ggctgacgtc | 660 |
| gtcctcatct atcaacgtgt cagcgatggc tggtatgaag gggaacgact tcgagatgga | 720 |
| gaaagaagnt gggttcctat ggaa | 744 |

<210> SEQ ID NO 323
<211> LENGTH: 723
<212> TYPE: DNA
<213> ORGANISM: Homo Sapien
<220> FEATURE:
<221> NAME/KEY: misc_feature
<222> LOCATION: (1)...(723)
<223> OTHER INFORMATION: n = A,T,C or G

<400> SEQUENCE: 323

| gtgtttcaan cggtcctcta gatgctgctc gagcggccgc cagtgtgatg gatatctgca | 60 |
| gaattcgccc tttcgagcgg ccgcccgggc aggtacgcgg ggactgggtt ttttctccttt | 120 |
| tgtagccttt tcctttagtc tcctcttccc ggtggttggt aaaagaggt gaattgacag | 180 |
| cctatgttga agacactgtg cttttctcaa gaaggacatc caaacagcaa gtctacttct | 240 |
| ttctctttaa cgatgtgctc attatcacca agaagaagag tgaagaaagt tacaacgtca | 300 |
| atgattattc cttaagagat cagctattgg tggaatcttg tgacaatgaa gagcttaatt | 360 |
| cttctccagg gaagaacagc tccacaatgc tctattcaag acagagctct gccagtcacc | 420 |
| tctttactct gacagtcctt agtaaccacg cgaatgagaa agtggagatg ctactaggag | 480 |
| ctgagacgca gagcgagcga gcccgctgga taactgccct gggacacagc agcgggaagc | 540 |
| cgctgcagac cgaacctcac tgacccaggt ggaaatcgtt aggtcattta ctgctaagca | 600 |
| gccagatgaa ctcttcctgc angtggctga cgtcgtcctc atctatcaac gtgtcancga | 660 |
| tggtggtatg aagggaacg actacnagat ggagaaagaa gctggtttcc tatggaatgt | 720 |
| gcc | 723 |

<210> SEQ ID NO 324
<211> LENGTH: 746
<212> TYPE: DNA
<213> ORGANISM: Homo Sapien
<220> FEATURE:
<221> NAME/KEY: misc_feature
<222> LOCATION: (1)...(746)
<223> OTHER INFORMATION: n = A,T,C or G

<400> SEQUENCE: 324

```
gggnttgaag ncncgactca ctatagggcg aattgggccc tctagatgca tgctcgagcg      60
gcccgccagt gtgatggata tctgcagaat tcgcccttag cgtggtcgcg gccgaggtac     120
cttgagatct gagcaactgt gttaatgaag taatagcaat ggtccacagt gaaagatgtg     180
ttggggtttg caaaacaagc attccgtcac ctctttaata atgtcacaga ctttttttaaa    240
agagaggcta tcaagttgta atataatctg tcatgttttta tttaggaagg aaggtaaatt    300
tgtgcttgca cggggatcat tttgtattat ttntgctaat acccagttga agctaaaaag    360
caactatttg aatcctgtga attaatttat aagaatgtta aacagctntg gaaatacatg    420
catcttatga atcatagcct tatttagcaa gatcaatgtt aaagtgttga tatatggcaa    480
gtatttaaca cattcacagt gntagtttga tttcaactgt gaattgtctt acagtttttt    540
caaacctagt gtntctatgg acacctgctc tgaattgtac ccctcagtca ccaccaaagc    600
atttncaccc ctttcaaccc ccaatcagac cantgctttc agtggtattg gaggacttnt    660
atcacagctt catnangtgg tcttggcaca ggcagnctga ctngcttngg aactggtgct    720
tttggactcc cttcaanngn aatant                                         746
```

<210> SEQ ID NO 325
<211> LENGTH: 742
<212> TYPE: DNA
<213> ORGANISM: Homo Sapien
<220> FEATURE:
<221> NAME/KEY: misc_feature
<222> LOCATION: (1)...(742)
<223> OTHER INFORMATION: n = A,T,C or G

<400> SEQUENCE: 325

```
gtgtttcann cggccctcta gatgcatgct cgagcggccc gccagtgtga tggatatctg      60
cagaattcgc ccttagcgtg gtcgcggccg aggtaccttg agatctgagc aactgtgtta    120
atgaagtaat agcaatggtc cacagtgaaa gatgtgttgg ggtttgcaaa acatgcattc    180
cgtcacctct ttaataatgt cacagacttt tttaanagag aggctatcaa gttgtnatat    240
aatctgtcat gtattattta agaaggaagg taaatntgtg cttgcacggg gatcattttg    300
nattattnct gctnataccc agctgaagct nanaancnac tntttgnatc ctgtgantta    360
atncatanna atgttanaca gctntggaaa tccatgcctc ttatgaatca tngcctttat    420
tancangatc aatgttaaag ntgttgatat nnggcaagtn tntaacacat tnacantgct    480
agtntgattt caactgngaa ttgncttacc gtntttnnaa acctananga atntatngac    540
acctnctctn aatngnnncc ctcaancacc acnaaanctt ttncnncect tncaacccce    600
natcngaccn cngcattcag tngnaancng aangactttc atcacaactg gncaanatnt    660
nggactttgg cgccatgcnn accctcttgg nctttgaac nnggttgcct tttnggactt    720
tncnectgng ngataaccac cn                                             742
```

<210> SEQ ID NO 326
<211> LENGTH: 747
<212> TYPE: DNA
<213> ORGANISM: Homo Sapien
<220> FEATURE:
<221> NAME/KEY: misc_feature
<222> LOCATION: (1)...(747)
<223> OTHER INFORMATION: n = A,T,C or G

<400> SEQUENCE: 326

```
atgntttaag tatacgactc actatagggc gaattgggcc ctctagatgc atgctcgagc      60
ggccgccagt gtgatggata tctgcagaat tcgcccttc  gagcggccgc ccgggcaggt     120
actgtatcat tggcagatgt gacgtcaccg acaaccagag tgaagtggcg acaaaactg     180 aggattacct gtggctgaag ttgaaccaag tgtgttttga cgacgatggc accagctccc     240
cacaagacag gctcactctc tcacagttcc agaagcagtt gttggaagac tatgcgagt     300 cccactttac ggtgaaccag caaccttcc  tctacttcca agtcctgttc ctgacagcgc     360
agtttgaagc agcagttgcc tttcttttcc gcatggagcg gctgcgctgc catgctgtcc     420
atgtagcact ggtgctgttt gagctgaagc tgcttttaaa gtcctctgga cagagtgctc     480
aactcctcag ccacgaacct ggtgacccct cttgcttgcg cgggctgaac ttcgtgcggc     540
tcctcatgct gtacctcggc cgngaccacg ctaagggcga attccagcac actggcggnc     600
gttactagtg gatccgagct cggtaccaaa cttggcgtaa tcatggncat agctggttcc     660
tgtgtgaaat ggtatccgtt acaatttcac acaacatacg agccgggaag catnaagtgt     720
naaacctggg gtgcctnatg agtgacn                                        747
```

<210> SEQ ID NO 327
<211> LENGTH: 724
<212> TYPE: DNA
<213> ORGANISM: Homo Sapien
<220> FEATURE:
<221> NAME/KEY: misc_feature
<222> LOCATION: (1)...(724)
<223> OTHER INFORMATION: n = A,T,C or G

<400> SEQUENCE: 327

```
gtnatgaaac cnttctntng ngcatgctcg agcggccgcc agtgtgatgg atatctgcag      60
aattcgccct ttcgagcggc cgcccgggca ggtactgtat cattggcaga tgtgacgtca     120
ccgacaacca gagtgaagtg gcggacaaaa ctgaggatta cctgtggctg aagttgaacc     180
aagtgtgttt tgacgacgat ggcaccagct ccccacaaga caggctcact ctctcacagt     240
tccagaagca gttgttggaa gactatgcg  agtcccactt tacggtgaac cagcaaccct     300
tcctctactt ccaagtcctg ttcctgacag cgcagtttga agcagcagtt gcctttcttt     360
tccgcatgga gcggctgcgc tgccatgctg tccatgtagc actggtgctg tttgagctga     420
agctgctttt aaagtcctct ggacagagtg ctcagctcct cagccacgag cctggtgacc     480
ctccttgctt gcgcggctg  aacttcgtgc ggctcctcat gctgtacctc ggccgcgacc     540
acgctaaggg cgaattccag cacactggcg gccgttacta gtggatccga gctcggtacc     600
aagcttggcg taatcatggt catagctgtt tcctgtgtga aattgtatcc gctcacaatt     660
ncacacaaca tacgagccgg aagcataaag tgtaaaacct ggggtgccta atgagtgaac     720 taan                                                                 724
```

<210> SEQ ID NO 328
<211> LENGTH: 747
<212> TYPE: DNA
<213> ORGANISM: Homo Sapien
<220> FEATURE:
<221> NAME/KEY: misc_feature
<222> LOCATION: (1)...(747)
<223> OTHER INFORMATION: n = A,T,C or G

<400> SEQUENCE: 328

```
tgnntgttag atacgactca ctatagggcg aattgggccc tctagatgca tgctcgagcg      60
gcccgccagt gtgatggata tctgcagaat tcgcccttag cgtggtcgcg gccgaggtac     120
```

```
tttttttttt tttttttaaag acagagtctt gctctgtcac ccaggctgga gtgcagtggc      180
acgatctcgg ctcactgcaa gctctgcctc ccgggttcac gccattctcc tgcctcagcc      240
tcccgagtag ctgggactac aggtgcccgc caccatgccc ggctgatttc ttttttgtatt    300 tttagtagag acggagtttc accgtgttag ccaggatggt ctcgatctcc tgacctcgtg      360
atccgcccgc cttggcctcc aaagtgctgg gattacaggt gtgagctacc gcgcccggcc      420
tattatcttg tactttctaa ctgagccctc tattttcttt attttaataa tatttctccc      480
cacttgagaa tcacttgtta gttcttggta ggaattcagt tgggcaatga taacttttat      540
gggcaaaaac attctattat agtgaacaaa tgaaataac agcgtatttt caatattttc       600
ttattcctta aattccactc ttttaacact atgcttaacc acttaatgtg atgaaatatt      660
cctaaaagtt aaatgactat taaagcatat attggtgcat gnatatatta aagtacccga     720
tactctaaat aaaaatccac tggtccn                                          747

<210> SEQ ID NO 329
<211> LENGTH: 725
<212> TYPE: DNA
<213> ORGANISM: Homo Sapien
<220> FEATURE:
<221> NAME/KEY: misc_feature
<222> LOCATION: (1)...(725)
<223> OTHER INFORMATION: n = A,T,C or G

<400> SEQUENCE: 329
gcgtttcaan tgggccctct ngngcatgct cgagcggccg ccagtgtgat ggatatctgc      60
agaattcgcc cttagcgtgg tcgcggccga ggtactttt tttttttttt taaagacaga     120
gtcttgctct gtcacccagg ctggagtgca gtggcacgat ctcggctcac tgcaagctct     180
gcctcccggg ttcacgccat tctcctgcct cagcctcccg agtagctggg actacaggtg    240
cccgccacca tgcccggctg atttcttttt gtattttag tagagacgga gtttcaccgt     300
gttagccagg atggtctcga tctcctgacc tcgtgatccg cccgcttgg cctccaaagt     360 gctgggatta caggtgtgag ctaccgcgcc cggcctatta tcttgtactt tctaactgag    420
ccctctattt tctttatttt aataatattt ctccccactt gagaatcact tgttagttct     480
tggtaggaat tcagttgggc aatgataact tttatgggca aaacattct attatagtga     540 acaaatgaaa ataacagcgt attttcaata ttttcttatt ccttaaattc cactcttta     600 acactatgct taaccactta atgtgatgaa atattcctaa aagttaaatg actattaaag     660
catatattgg tgcatgtata tattaagtag cccgatctct naataaaaat ccactggtac    720
agata                                                                 725

<210> SEQ ID NO 330
<211> LENGTH: 741
<212> TYPE: DNA
<213> ORGANISM: Homo Sapien
<220> FEATURE:
<221> NAME/KEY: misc_feature
<222> LOCATION: (1)...(741)
<223> OTHER INFORMATION: n = A,T,C or G

<400> SEQUENCE: 330
gnnntganag atacgactca ctatagggcg aattgggccc tctagatgca tgctcgagcg      60
gcccgccagt gtgatggata tctgcagaat tcgcccttag cgtggtcgcg gccgaggtac     120
tttttttttt tttttttttt tttttttttt ggaagtttaa tttactcaca gttcaacatg     180
```

-continued

```
gctggggagg cctcaggaaa tttacaatta taacagaagg caaagggaa gccagatacc    240 ttcttcacaa ggtggcagga aggagaagag ccgagagaag gcggaagaat cccttataaa    300
accatcagat ctcgtgagaa ctcacttgct atcaggagaa cagcatgggg gaaccgcccc    360
caggattcaa tgacctncac ctggtctctc ccttgacacg tgaggattat ggggattaca    420
attccagatg agatttgggt ggggacacaa agccaaacca tatcaactgt gactaccttg    480
ggtaagggcc atccaggcag aggcagggg aacattctgg gcaaaggcct tggggcaggg    540
gcctggtatg ttcagatagc ancaagtagg ccagantggc cggaggggag taagtgtggg    600
gaggccagtg ganagatgag ggtagggaag ggatggatca gatcatgcag ggccccgggg    660
gccacaggaa ngacctnagc atttactgca agtaangtgg gaaccatcga atgtctaagc    720
naggaggaat ccctgtgact c                                              741
```

<210> SEQ ID NO 331
<211> LENGTH: 727
<212> TYPE: DNA
<213> ORGANISM: Homo Sapien
<220> FEATURE:
<221> NAME/KEY: misc_feature
<222> LOCATION: (1)...(727)
<223> OTHER INFORMATION: n = A,T,C or G

<400> SEQUENCE: 331

```
gtnnnncgan ngggccctct agatgcatgc tcgagcggcc gccagtgtga tggatatctg     60
cagaattcgc ccttagcgtg gtcgcggccg aggtactttt tttttttttt tttttttttt    120 tttttggaa gtttaattta ctcacagttc aacatggctg ggaggcctc aggaaattta    180 caattataac agaaggcaaa ggggaagcca gatacttct tcacaaggtg gcaggaagga    240
gaagagccga gagaaggcgg aagaatccct tataaaacca tcagatctcg tgagaactca    300
cttgctatca ggagaacagc atgggggaac cgccccagg attcaatgac ctccacctgg    360 tctctcccctt gacacgtgag gattatgggg attacaattc cagatgagat ttgggtgggg    420
acacaaagcc aaaccatatc aactgtgact accttgggta agggccatcc aggcagaggc    480 aggggaaca ttctgggcaa aggccttggg gcaggggcct ggtatgttca gatagcagca    540
agtaggccag antggccgga ggggagtaag tgtgggagg ccagtggaaa atgangg ta    600 gggaaggga tggatcagat catgcaggc ccgggggcc acangaagga cctnacattt    660
actgcaagta angtgggagc catcgaatgt tctaagcana ngangaatcc ctgngactca    720 ngtgttn                                                              727
```

<210> SEQ ID NO 332
<211> LENGTH: 734
<212> TYPE: DNA
<213> ORGANISM: Homo Sapien
<220> FEATURE:
<221> NAME/KEY: misc_feature
<222> LOCATION: (1)...(734)
<223> OTHER INFORMATION: n = A,T,C or G

<400> SEQUENCE: 332

```
gnntganagt atacgactca ctataggcg aattgggccc tctagatgca tgctcgagcg     60
gcccgccagt gtgatggata tctgcagaat tcgccctttc gagcggccgc ccgggcaggt    120 accccttctcg cttttgccat tagccaagga tagaagctgc agtggtatta attttgatat    180
aatctttcaa accagcttca tgtggcttcc cttttctttg ttcaagatga gggccaggag    240
gggaaacatc acacctgccc taaaccctgt tcctggaggt cagcatttga tctgttgcaa    300
```

```
gcccctcttt ctgtcccctc ttcctaccct gcctcccatg actttgctcc tcacactttt      360
ggaaccatgc cttccgggggg ggcccatctc ttctggccgt ccttgtctct gggccacttg    420
gagtgtgtga taaatcagtc aagctgttga agtctcagga gtctctggta gcctgcagaa    480
gtaagcctca tcatcagagc ctttcctcaa aactggagtc ccaaatgtca tcaggttttg    540 ntttttttc aaccactaag aacccctctg cttttaactc tagaatttgg gcttggacca     600
gatctaacat cttgaatact ctgccctcta gaccttcacc ttaatggaan gtggatccca    660
nganggtgta atggacatca agccactcgc ggcagcatgg agctatacta agcatcctta   720
nggtctgcct ctcn                                                                 734
```

<210> SEQ ID NO 333
<211> LENGTH: 710
<212> TYPE: DNA
<213> ORGANISM: Homo Sapien
<220> FEATURE:
<221> NAME/KEY: misc_feature
<222> LOCATION: (1)...(710)
<223> OTHER INFORMATION: n = A,T,C or G

<400> SEQUENCE: 333

```
ntgggccctc tngngctgct cgagcggccg ccagtgtgat ggatatctgc agaattcgcc      60
ctttcgagcg gccgcccggg caggtaccct tctcgctttt gccattagcc aaggatagaa    120
gctgcagtgg tattaatttt gatataatct ttcaaaccag cttcatgtgg cttcccttt     180 ctttgttcaa gatgagggcc aggagggggaa acatcacacc tgccctaaac cctgttcctg   240
gaggtcagca tttgatctgt tgcaagcccc tctttctgtc ccctcttcct acctgcctc    300 ccatgacttt gctcctcaca cttttggaac catgccttcc ggggggggccc atctcttctg   360 gccgtccttg tctctgggcc acttggagtg tgtgataaat cagtcaagct gttgaagtct   420
caggagtctc tggtagcctg cagaagtaag cctcatcatc agagcctttc ctcaaaactg   480
gagtcccaaa tgtcatcagg ttttgttttt ttttcagcca ctaagaaccc ctctgctttt   540
aactctagaa tttgggcttg gaccagatct aacatcttga atactctgcc ctctagagcc    600
ttcagcctta atggaagggt ggatccaang anggtgtaat ggaacatcaa gccactcgcg    660
gcagcatgga gctatactaa gcatccttta nggtctgcct cttcagcatt                 710
```

<210> SEQ ID NO 334
<211> LENGTH: 2051
<212> TYPE: DNA
<213> ORGANISM: Homo sapien
<220> FEATURE:
<221> NAME/KEY: misc_feature
<222> LOCATION: (1)...(2051)
<223> OTHER INFORMATION: n = A,T,C or G

<400> SEQUENCE: 334

```
gcccttgcct cagcctaccc agtagctggt gatggccatc ctttataaa tgcaacgtcc        60 ttcgttcctg ttaagtcatg ggggaggaag gccttttctc tcttcagtct aataatcaac    120
tgttcactat tcacaatagc aacatcatgg gctgaaccta tgtgtccatc aacagatgat    180
tagattttaa aatgtgcata tataccatgg aatacatacg caaccatcaa aataatgaa     240 atcacatctt ttgcagcaat atggatggaa ctggaagccc ttatcgtaag tgaaatgact   300
cagagacaga aagtcagaaa ctgcatgttc tcatttggaa actgaaaatc acacacacat   360
aaatctaata aagacatggg tactttattt tcaaaacact catatgttgc aaaaaacaca   420
```

-continued

| | |
|---|---|
| tagaaaaata aagtttggtg ggggtgctga ctaaacttca agtcacagac ttttatgtga | 480 |
| cagattggag cagggtttgt tatgcatgta gagaacccaa actaatttat taaacaggat | 540 |
| agaaacaggc tgtctggtg aaatggttct gagaaccatc caattcacct gtcagatgct | 600 |
| gatagactag ctcttcagat gttttctac cagttcagag atgggttaat gactagttcc | 660 |
| aatggggaaa aagcaagatg gattcacaaa ccaagtaatt ttaaacaaag acactttttt | 720 |
| tttttttgc aacacaatat acatcacagt gaaatgtgta atccttgcaa attgcaagtt | 780 |
| gaaagaatta aattcagagg aggggagaga aagagtactc agtagggact gagcactaaa | 840 |
| tgcttatttt aaaagaaatg taaagagcag aaagcaattc aggctaccct gccttttgtg | 900 |
| ctggctagta ctccggtcgg tgtcagcagc acgtggcatt gaacattgca atgtggagcc | 960 |
| caaaccacag aaaatggggt gaaattggcc aactttctat taacttatgt tggcaatttt | 1020 |
| gccaccaaca gtaagctggc ccttctaata aagaaaatt gaaaggtttc tcactaaacg | 1080 |
| gaattaagta gtggagtcaa gagactccca ggcctcagcg tacctcatta gtaattgttt | 1140 |
| tgttgtttca ttttttttcta atgtctcccc tctaccagct cacctgagat aacagaatga | 1200 |
| aaatggaagg acagccagat ttctcctttg ctctctgctc attctctctg aagtctaggt | 1260 |
| tacccatttt gggacccat tataggcaat aaacacagtt cccaaagcat ttggacagtt | 1320 |
| tcttgttgtg ttttagaatg gttttccttt ttcttagcct tttcctgcaa aaggctcact | 1380 |
| cagtcccttg cttgctcagt ggactgggct ccccagggcc taggctgcct tcttttccat | 1440 |
| gtcccaccca tgagccctcc actggacagc tcagtaagcc tggcccttca ttctgcgctg | 1500 |
| tgttcttcct ctgtgaaaat ccaatacctc ttacctcctc tgcatgcaaa gattctcaag | 1560 |
| gattgtcaga cttcaaacgt aacagcagaa ccaccagaag gtcctataaa tgcagtagtg | 1620 |
| accttctcaa gctgtcaggt ctttaaatag gatttgggat ttaatgctat gtattttaa | 1680 |
| aggaaagaaa taagagttgc tagtwttaaa aatgcatgtc ttttagccaa ttcagaatct | 1740 |
| gcccccaaac ttttttaaaa agtcaagaca gataaagctt tggggagacg gaaaaaaaaa | 1800 |
| aaaaaaaaaa aacaagtacc tcggccgcga ccacgctaag ggcgaattcc agcacactgg | 1860 |
| cggccgttac tagtgggttc nanncccggt acnaaccctt gggggtttaa caagggcnaa | 1920 |
| ancnggttnc cggggntnaa aattgttacc cgcnaaaaat tccanaaaaa natncgaacc | 1980 |
| cggaaancca taanttntn aancccnggn ggccnaaggg agngnnnaac cccnaataaa | 2040 |
| tggnttggnc c | 2051 |

<210> SEQ ID NO 335
<211> LENGTH: 1312
<212> TYPE: DNA
<213> ORGANISM: Homo sapien

<400> SEQUENCE: 335

| | |
|---|---|
| acctagaaaa cagaaacttg agtagacatg gtaatgacca gaaaaggcta tctttataca | 60 |
| tttcttttgc tacgcttcaa attcatgtca cctaaaagtt gtgaagtgca caaacaaat | 120 |
| ctacttaact gaaaattatt ttcaatgaat gggatgttta gaactctgtg agggttttta | 180 |
| aggtcttttc gaatagcaaa ttctaatgag gcttttttaa gttggcaatt taaactcata | 240 |
| caagaaataa aaactcacca gtgtggctgg gcagaatata tatattttct caaatattgt | 300 |
| ttgtttgttt ttttccctgca ctgtatccat ggtcccatga tgaaactgtt atattgctga | 360 |
| tatatttatt ggaatatgtg ggccaacttc cttttccactc aacatatgga ttggtagttt | 420 |
| aaaataattc ctttctatta agcaaatgtg tggctaaggc acatttaaat agcccattaa | 480 |

| | |
|---|---|
| accaatgaga tgacaatgtg ttaccctcag agaaagctta attttttggag taatcaatta | 540 |
| cacatatcac agaatgtctc atgagaacat ttttggctag gtctaccaat ttatcatgca | 600 |
| aataattata gattttcatt tgaggcaaag atgctgattc atcattagta acatggtcac | 660 |
| aaataatcat ttatttatt tttgttaaca tctgtctttc ctgtggggaa acttactata | 720 |
| tgctctacgt ttatttaatt taaaaagtca attggttatt ctgaatttt aaaaataaca | 780 |
| taaaactgtt gttctaaatc acagcacctg ctttctttt tttagtgaaa ttatataagc | 840 |
| atttagagaa tgaaagtgta agacttgtgg tttctggtct cttttactg tttgtaagcc | 900 |
| tactcgtcat gatattccac aatggtgcac ttgccttta atgctcttat agatatcttc | 960 |
| aaacttgcct acatatatac gcctttgttg gagtgggcta ccatcatcag gaatgatgtc | 1020 |
| atttgtttct tcaaactcct ttattatacc aaaaagtga cagactccac agtctgatca | 1080 |
| gttttggaga aatatgttaa cattttcaat tatctcactt tctagaatca aaatagtctg | 1140 |
| attttttttt ttcggcactc agtgtaaaga acaagaact gaatacagtg ggcccagaag | 1200 |
| agaaatatgc ctcatcattt ttattagctt tggaactgtg gacaagtcac tcaacctagt | 1260 |
| tttctcattt tgaaatgggt tgttgtggga attaaaaaaa aaaaaaaaaa gt | 1312 |

<210> SEQ ID NO 336
<211> LENGTH: 787
<212> TYPE: DNA
<213> ORGANISM: Homo sapien

<400> SEQUENCE: 336

| | |
|---|---|
| acagccatga aattgttgct actcatagaa agtcttagta tagtttggtt taaacatttt | 60 |
| aaaattgcaa ataaatatag atagataata tcatgatgag aaggtcacgg gaagcctgga | 120 |
| gatttcaggg tgctctttca taattggagc gagaatcatg taacagttaa gaaactaaac | 180 |
| tcttgagcct tcatagtctt tgctttctcc ccatttattt atctgatatt atataccctc | 240 |
| tttaattata gactggactg aaatatttta ttttgtttt attataaaaa atcctactcg | 300 |
| tctttaacat gttctcttaa agagtgtttc atatataaat actttccccc caaaatataa | 360 |
| agaggctaac cactatagta ttgaaagatt gaaagaaaga cctagggtgt ctaaaaccaa | 420 |
| atttaaaggc tcagttctaa gaggagttaa aatgcttcct ttgtaagcac tttaaacttc | 480 |
| atctttaaac attgatgaga atattataaa gaattcacaa cagcagttac atggaggtag | 540 |
| aaaagagtgt tgagaagaag gagggtgatt gcaacaaata caaagaaact attgagatgt | 600 |
| aacaaagacg tgcaattacc tatgaatggg taaaccagtt atatattttg ctttcacagc | 660 |
| atgagattat ttttaatttg aattggttta ccatgtaatg acacttccat tttaaagatt | 720 |
| ttatgcatgt aaccttaata ctctcaaggt ttccagactt cagagaggta gctcatactt | 780 |
| tcattgt | 787 |

<210> SEQ ID NO 337
<211> LENGTH: 772
<212> TYPE: DNA
<213> ORGANISM: Homo sapien

<400> SEQUENCE: 337

| | |
|---|---|
| acatcagtgt tcattttatt atttcttaca ctgtcttcat gacttacaca taatatttg | 60 |
| ctagttttaa aacataagat gtgataataa tctaaacaga ccaaaggaaa taatgaata | 120 |
| tgattaaaaa aagacagaga ataagccctg tctgatggaa agcataacaa agcaggtaga | 180 |

-continued

| | |
|---|---|
| acaactgtca ggaatgcttg atccaataaa gctaggtttg tgatccacaa cacttcagca | 240 |
| ttttaatgtg attttttgatg tttgcttttt gcaatggtga ttctcagttg cctccctcct | 300 |
| gtgtctttac aagctgaaat caagtgaagc tacttctgac tttttctaaa acttaaaccc | 360 |
| aacatgaagg tctgcgtatt ctttcacatg tgcacgtatg tggcactttt ccatgatgca | 420 |
| acagcagcgg gtctctagct aagctacagc agcagctcta agaggcagag gaccctgaaa | 480 |
| tgaggctgaa agaaagaata gtccataact gacatcaggc aggctgctgt tgtaagcaca | 540 |
| gaaaggaggc tcacggcggc atggactcag gccaggtcac actattgtgg gagaacacgg | 600 |
| agcacacgtg tcagctggaa aggggccggc tcaggagaca aaataggcac gagaggaaac | 660 |
| cgaaaaattg acatatgtga ctatccttgt agaaatgtat aaaggtttgg attattttgc | 720 |
| ttatcgagtt ataataaagt tattctaaaa atgtttatct aaagtattat gt | 772 |

<210> SEQ ID NO 338
<211> LENGTH: 1383
<212> TYPE: DNA
<213> ORGANISM: Homo sapien

<400> SEQUENCE: 338

| | |
|---|---|
| ttactcacta tagggctcga gcggccgccc gggcaggtgt aaaaataaaa tgacagtttg | 60 |
| aacatacaaa acccacccca ttcctataga gcctagtact acactacccc ctcccaactt | 120 |
| tagcctccac atatagtaat gtgcttggaa cacaaaaaac acttcataaa ttgtgctgaa | 180 |
| tgaaatcatt tccatgagtg tttatggatt ttgagttcat ttgtacctttt tacctaaaat | 240 |
| tctagccact ttaatttgga gagtttccag agcaaaggac cttttaccta aaattctagc | 300 |
| cactttaatt tggagagttt ccagagcaaa gggcacagat cccaggcata acaacgcttt | 360 |
| gcgtatacag caaccaatat cttgtcaacc caagaaagtt cctccattga tacctagtag | 420 |
| aaatagccca gttttttaaag tcctcaaaac tgtaacaaat tacttgtttt taaaatttaa | 480 |
| cttaaattaa tacaatcaga ttttttgtgtt atttgggtat tagagtatgt taaagcacat | 540 |
| atatcccaga gacatagagt ttccgtttca aaaagtcatg cattcatgtg tgctaatgac | 600 |
| aatcctatcc tgacccgcta tgtgacttgt atctctaaac cataggcttt cctgaatttt | 660 |
| atctgttaat ttaaccctga tttctcagca gcagcttctc tttgtaaata gacttgcctc | 720 |
| ttctgtgtct gacctctgct cctcataatc agattaactc agataaagct gcttcaggga | 780 |
| agaggtcaaa accgttgcca aaaatagtag ttgccctact tcagtctatt ttcaacagag | 840 |
| tagccaggag atcctgttca caccaaagtc caatcagccc tactgttagc actctgctca | 900 |
| caagcctcca gtggcttccg acctcactca cagtaaaagc caagtcatcc tttagcctat | 960 |
| gatgtcctac atgatttgaa ttcccttcca ttgattttttg tcactgattt ttaaaaatcc | 1020 |
| aaattcattc tcatacagct gaattgtcct ctttgcttta agtatgccag gattattttct | 1080 |
| acctcagggc ctttgcactt gatattccct tcaccttttc caagatagtt attccctcac | 1140 |
| ctcagtcaag cctttatttta gatgccccct tctcatcaag gcattctctg atctccttat | 1200 |
| ttaaatgtat gacaccccttt ctttgcttta catttaatca gaacatgtgt cactatctag | 1260 |
| catataatac atttgcttga cctcttttttgt ttactgtcta tgcctcctga atactgtgta | 1320 |
| agctccacga tacaggcact tttctctatt tcgagcactg ttgtattaca gagccttaaa | 1380 |
| agt | 1383 |

<210> SEQ ID NO 339
<211> LENGTH: 1815

<212> TYPE: DNA
<213> ORGANISM: Homo sapien

<400> SEQUENCE: 339

```
acttttttgtt catttttgatt tttggataat gcaaaattat agattttttta aaaattatat    60
tcaaagaata ctgagtgcaa gacaatcttt ctaggttaaa aaatatctta taaacctgaa   120
ttgtcaatta ttattgtatc ccagatgtat ggaagttaat ggatagtcag taacatacag   180
gactagcaga aggtttgttg ttataggtaa tctggagaga agccaggtaa gtggaatttg   240
ggatttgctg ctgttgccag aaagcagcac agagacatgg taagtggcaa gacccaggta   300
actaaaacaa ccatgtctta gtccttttat gctgctgtaa cagaatatca cagactgagt   360
aatttataat gaacagaact ttatttgtct tctggttctg gagactggga aatctaagag   420
cgtggcattg acatatggtg agggcatttg tgcctcatca tcccatgaca gaagatggaa   480
atgcaagaga gctcaaaagc aagagagcaa atggggccaa acttgctttt tataacaagc   540
cactcttgtg ataatgaacc aactcaaaca ataaagacat aaatccattc atgagggcag   600
agccctcaag gatgaatcac ttcacttctt aatggcctca gcttctaata ccatcacaat   660
agtaattcag tttcaacatg gttttatag ggacgttgga accacagcaa actgtaacca   720
ttttgatttc cttatttgca ccatttttaaa aaaacctatt tatttaacga ctgtttattc   780
agtgcctatt ctgttgtgtt ggggactaga ggtaattaca aagggaataa gacaaacagt   840
cacccactct ggtgatgctt cccttatctt cataatgcat ttgatcctgt gattctttgg   900
cacatgagtc cattgcatct tgcatattag tgtccagtaa gttttttcctg accaattgat   960
aatatagata tacattggta gcagttttgt gtatattttt atagttagat gttgttggca  1020
catgtgactt gtgtctcaga aaaatacaga aaatggttaa agacaggagg atactaccct  1080
gatttctctg ttcattaaag aacagctatt tgggggggaaa acctgataca attatttgag  1140
catgtggctt aaagattaga cctataaaca attcaggagc atcttccagc aaactgtgtg  1200
agaattcaca gaaataaaacc tggtaggttt gtgctatgtt attcacatgg gctgttaact  1260
cttttccatt cctaggtcct ttatttccct gccctcctca atctcatgct cttgagattt  1320
ttaactatat tacttcttta caaagtcatc ttcaaaatga ttcattttgg atagcaaact  1380
atccctcaac ttacctacac actctcactc atactcacat tctctcttat gtctttctgt  1440
gtggaaggga acatttagaa tgtctattct ttgtgatgca aaaatgacaa cacactgatg  1500
atgaagggggg gtattttttag gagaaaaagt agcttttctt ttcatcatac tgccactttt  1560
gagattctat agaaagaata ggtattgaac acagaccact tggctctctg aggtatgctt  1620
tggacacact tagaagtcag ctagaatatg ccttctgttt aaggttggag tctgcattta  1680
aaaagagaga actggattaa ttggcaggta agttgagatt ccatgattca ggaaaccttt  1740
aagactttta agtgcaggct ctttgtaggt tggaatgaaa cttaatatat atatatgttc  1800
tttgattctt tctgt                                                   1815
```

<210> SEQ ID NO 340
<211> LENGTH: 22
<212> TYPE: PRT
<213> ORGANISM: Homo sapiens

<400> SEQUENCE: 340

Cys Gly Pro Arg Leu Pro Ser Phe Pro Cys Pro Thr His Glu Pro Ser
 1               5                  10                  15

Thr Gly Gln Leu Ser Lys

-continued

```
<210> SEQ ID NO 341
<211> LENGTH: 23
<212> TYPE: PRT
<213> ORGANISM: Homo sapiens

<400> SEQUENCE: 341

Cys Lys Asp Ser Gln Gly Leu Ser Asp Phe Lys Arg Asn Ser Arg Thr
 1               5                  10                  15

Thr Arg Arg Ser Tyr Lys Cys
            20
```